(12) United States Patent
Cook et al.

(10) Patent No.: US 9,213,043 B2
(45) Date of Patent: Dec. 15, 2015

(54) CLINICAL DIAGNOSTIC SYSTEM INCLUDING INSTRUMENT AND CARTRIDGE

(71) Applicant: Wellstat Diagnostics, LLC, Gaithersburg, MD (US)

(72) Inventors: Richard Alan Cook, Derwood, MD (US); Sang Cho, Rockville, MD (US); Charles Quentin Davis, Frederick, MD (US); Kevin E Dorsey, Germantown, MD (US); Jason Charles Harley, Gaithersburg, MD (US); Jonathan Leland, Gaithersburg, MD (US); Rober Krikor Matikyan, Potomac, MD (US); Sjef Otten, Gaithersburg, MD (US); Jeffrey Howard Peterman, Silver Spring, MD (US); Brian B Thomas, Frederick, MD (US)

(73) Assignee: WELLSTAT DIAGNOSTICS, LLC, Gaithersburg, MD (US)

( * ) Notice: Subject to any disclaimer, the term of this patent is extended or adjusted under 35 U.S.C. 154(b) by 0 days.

(21) Appl. No.: 14/401,275

(22) PCT Filed: May 15, 2013

(86) PCT No.: PCT/US2013/041252
§ 371 (c)(1),
(2) Date: Nov. 14, 2014

(87) PCT Pub. No.: WO2013/173524
PCT Pub. Date: Nov. 21, 2013

(65) Prior Publication Data
US 2015/0132860 A1    May 14, 2015

Related U.S. Application Data

(63) Continuation-in-part of application No. 13/844,450, filed on Mar. 15, 2013, and a continuation-in-part of (Continued)

(51) Int. Cl.
*G01N 21/00* (2006.01)
*G01N 35/10* (2006.01)

(Continued)

(52) U.S. Cl.
CPC ........ *G01N 35/1079* (2013.01); *B01L 3/50273* (2013.01); *B01L 3/502715* (2013.01);

(Continued)

(58) Field of Classification Search
CPC ...... G01N 33/50; G01N 21/66; F04B 49/065; F04B 49/106; H05B 1/025
USPC ......... 422/52, 73, 82.01, 82.05, 82.06, 82.07, 422/82.08, 82.09, 82.11, 407, 501, 502, 422/503, 504, 507; 436/17, 43, 63, 94, 149, 436/164, 172, 174, 177, 517, 518, 805, 436/809; 435/4, 6.1, 6.11, 6.12, 7.1, 7.92, 435/29, 288.5
See application file for complete search history.

(56) References Cited

U.S. PATENT DOCUMENTS 3,705,100 A    12/1972    Blatt et al.
4,212,742 A    7/1980    Solomon et al.

(Continued)

FOREIGN PATENT DOCUMENTS

EP    486059    1/1997
EP    1489303 B1    12/2004

(Continued)

OTHER PUBLICATIONS

Notice of Allowance and Fees Due, dated Mar. 3, 2015, from co-pending U.S. Appl. No. 13/844,450.

(Continued)

*Primary Examiner* — Dennis M White

(57) ABSTRACT

In embodiments disclosed herein, a diagnostic system is provided having a cartridge comprising at least one needle; at least one reservoir; at least one fluidic seal; and at least one fluidic channel of a fluidic pathway, wherein the cartridge is configured to store at least one reagent and at least one waste material on the cartridge. The diagnostic system is provided also having a diagnostic instrument comprising the fluidic pathway; an electrochemiluminescence (ECL) detection system; and a pump, wherein the fluidic pathway begins and ends in the cartridge and has a substantially single direction of flow in a pathway fluidically connecting the diagnostic instrument and the cartridge.

55 Claims, 77 Drawing Sheets

Related U.S. Application Data application No. 13/844,527, filed on Mar. 15, 2013, now Pat. No. 9,075,042, and a continuation-in-part of application No. PCT/US2012/067041, filed on Nov. 29, 2012.

(60) Provisional application No. 61/647,272, filed on May 15, 2012.

(51) Int. Cl.

| | | |
|---|---|---|
| *G01N 35/00* | (2006.01) | |
| *G01N 33/58* | (2006.01) | |
| *G01N 21/76* | (2006.01) | |
| *F04B 49/06* | (2006.01) | |
| *F04B 49/10* | (2006.01) | |
| *G01N 27/327* | (2006.01) | |
| *G01N 33/536* | (2006.01) | |
| *G01N 33/543* | (2006.01) | |
| *B01L 3/00* | (2006.01) | |

(52) U.S. Cl.
CPC ............. *F04B49/065* (2013.01); *F04B 49/106* (2013.01); *G01N 21/76* (2013.01); *G01N 27/3273* (2013.01); *G01N 33/536* (2013.01); *G01N 33/543* (2013.01); *G01N 33/58* (2013.01); *G01N 33/582* (2013.01); *G01N 35/0098* (2013.01); *G01N 35/00722* (2013.01); *B01L 2200/025* (2013.01); *B01L 2200/027* (2013.01); *B01L 2200/0605* (2013.01); *B01L 2200/0689* (2013.01); *B01L 2200/10* (2013.01); *B01L 2300/0645* (2013.01); *B01L 2300/0672* (2013.01); *B01L 2300/0681* (2013.01); *B01L 2300/087* (2013.01); *B01L 2300/0809* (2013.01); *B01L 2300/0816* (2013.01); *B01L 2300/0861* (2013.01); *B01L 2300/0864* (2013.01); *B01L 2300/0867* (2013.01); *B01L 2300/0887* (2013.01); *B01L 2300/105* (2013.01); *B01L 2400/049* (2013.01); *B01L 2400/0487* (2013.01); *G01N 2035/0091* (2013.01); *Y10T 436/25* (2015.01); *Y10T 436/2575* (2015.01)

(56) References Cited

U.S. PATENT DOCUMENTS

| | | |
|---|---|---|
| 4,225,410 A | 9/1980 | Pace |
| 4,228,015 A | 10/1980 | De Vries et al. |
| 4,301,412 A | 11/1981 | Hill et al. |
| 4,301,414 A | 11/1981 | Hill et al. |
| 4,336,121 A | 6/1982 | Enzer et al. |
| 4,381,775 A | 5/1983 | Nose et al. |
| 4,397,725 A | 8/1983 | Enzer et al. |
| 4,436,610 A | 3/1984 | Enzer et al. |
| 4,540,492 A | 9/1985 | Kessler |
| 4,548,498 A | 10/1985 | Folestad et al. |
| 4,631,130 A | 12/1986 | Watanabe |
| 4,675,300 A | 6/1987 | Zare et al. |
| 4,735,718 A | 4/1988 | Peters |
| 4,735,776 A | 4/1988 | Yamamoto et al. |
| 4,762,594 A | 8/1988 | Guruswamy |
| 4,786,394 A | 11/1988 | Enzer et al. |
| 4,799,393 A | 1/1989 | Uffenheimer |
| 4,820,129 A | 4/1989 | Magnussen, Jr. |
| 4,833,087 A | 5/1989 | Hinckley |
| 4,835,477 A | 5/1989 | Polaschegg et al. |
| 4,887,458 A | 12/1989 | Baker et al. |
| 4,929,426 A | 5/1990 | Bodai et al. |
| 4,965,049 A | 10/1990 | Lillig et al. |
| 5,023,054 A | 6/1991 | Sato et al. |
| 5,061,445 A | 10/1991 | Zoski et al. |
| 5,068,088 A | 11/1991 | Hall et al. |
| 5,074,977 A | 12/1991 | Cheung et al. |
| 5,093,268 A | 3/1992 | Leventis et al. |
| 5,096,582 A | 3/1992 | Lombardi et al. |
| 5,130,254 A | 7/1992 | Collier et al. |
| 5,139,328 A | 8/1992 | Baker et al. |
| 5,139,685 A | 8/1992 | de Castro et al. |
| 5,143,084 A | 9/1992 | Macemon et al. |
| 5,147,806 A | 9/1992 | Kamin et al. |
| 5,155,039 A | 10/1992 | Chrisope et al. |
| 5,208,163 A | 5/1993 | Charlton et al. |
| 5,223,219 A | 6/1993 | Subramanian et al. |
| 5,223,718 A | 6/1993 | Taboada |
| 5,238,808 A | 8/1993 | Bard et al. |
| 5,247,243 A | 9/1993 | Hall et al. |
| 5,279,797 A | 1/1994 | Burns et al. |
| 5,288,646 A | 2/1994 | Lundsgaard et al. |
| 5,296,191 A | 3/1994 | Hall et al. |
| 5,298,224 A | 3/1994 | Plum |
| 5,302,348 A | 4/1994 | Cusack et al. |
| 5,310,687 A | 5/1994 | Bard et al. |
| 5,316,730 A | 5/1994 | Blake et al. |
| 5,372,946 A | 12/1994 | Cusack et al. |
| 5,399,486 A | 3/1995 | Cathey et al. |
| 5,405,510 A | 4/1995 | Betts et al. |
| 5,416,026 A | 5/1995 | Davis |
| 5,453,356 A | 9/1995 | Bard et al. |
| 5,466,416 A | 11/1995 | Ghaed et al. |
| 5,487,870 A | 1/1996 | McKinney et al. |
| 5,500,187 A | 3/1996 | Deoms et al. |
| 5,504,011 A | 4/1996 | Gavin et al. |
| 5,506,142 A | 4/1996 | Mahaffey et al. |
| 5,522,255 A | 6/1996 | Neel et al. |
| 5,525,518 A | 6/1996 | Lundsgaard et al. |
| 5,527,710 A | 6/1996 | Nacamulli et al. |
| 5,534,226 A | 7/1996 | Gavin et al. |
| 5,543,112 A | 8/1996 | Ghead et al. |
| 5,558,838 A | 9/1996 | Uffenheimer |
| 5,567,869 A | 10/1996 | Hauch et al. |
| 5,575,977 A | 11/1996 | McKinney et al. |
| 5,591,403 A | 1/1997 | Gavin et al. |
| 5,591,581 A | 1/1997 | Massey et al. |
| 5,593,638 A | 1/1997 | Davis |
| 5,597,910 A | 1/1997 | Gudibande et al. |
| 5,599,447 A | 2/1997 | Pearl et al. |
| 5,601,727 A | 2/1997 | Bormann et al. |
| 5,602,037 A | 2/1997 | Ostgaard et al. |
| 5,610,075 A | 3/1997 | Stahl-Rees |
| 5,624,637 A | 4/1997 | Ghaed et al. |
| 5,627,041 A | 5/1997 | Shartle |
| 5,629,209 A | 5/1997 | Braun, Sr. et al. |
| 5,635,347 A | 6/1997 | Link et al. |
| 5,641,623 A | 6/1997 | Martin |
| 5,643,713 A | 7/1997 | Liang et al. |
| 5,653,243 A | 8/1997 | Lauks et al. |
| 5,660,993 A | 8/1997 | Cathey et al. |
| 5,665,238 A | 9/1997 | Whitson et al. |
| 5,665,315 A | 9/1997 | Robert et al. |
| 5,666,967 A | 9/1997 | Lauks et al. |
| 5,679,519 A | 10/1997 | Oprandy |
| 5,686,244 A | 11/1997 | Gudibande et al. |
| 5,698,406 A | 12/1997 | Cathey et al. |
| 5,700,427 A | 12/1997 | Ghaed et al. |
| 5,705,402 A | 1/1998 | Leland et al. |
| 5,714,089 A | 2/1998 | Bard et al. |
| 5,716,781 A | 2/1998 | Massey et al. |
| 5,720,922 A | 2/1998 | Ghaed et al. |
| 5,731,147 A | 3/1998 | Bard et al. |
| 5,736,404 A | 4/1998 | Yassinzadeh et al. |
| 5,743,861 A | 4/1998 | Columbus et al. |
| 5,744,367 A | 4/1998 | Talley et al. |
| 5,746,974 A | 5/1998 | Massey et al. |
| 5,747,666 A | 5/1998 | Willis |
| 5,770,459 A | 6/1998 | Massey et al. |
| 5,779,650 A | 7/1998 | Lauks et al. |
| 5,779,976 A | 7/1998 | Leland et al. |
| 5,795,543 A | 8/1998 | Poto et al. |
| 5,798,083 A | 8/1998 | Massey et al. |
| 5,800,781 A | 9/1998 | Gavin et al. |

(56) References Cited

U.S. PATENT DOCUMENTS

| | | |
|---|---|---|
| 5,804,400 A | 9/1998 | Martin et al. |
| 5,821,399 A | 10/1998 | Zelin |
| 5,827,481 A | 10/1998 | Bente et al. |
| 5,846,485 A | 12/1998 | Leland et al. |
| 5,851,488 A | 12/1998 | Saul et al. |
| RE36,054 E | 1/1999 | Blake et al. |
| 5,858,676 A | 1/1999 | Yang et al. |
| 5,882,602 A | 3/1999 | Savage et al. |
| 5,885,533 A | 3/1999 | Savage et al. |
| 5,888,826 A | 3/1999 | Ostgaard et al. |
| 5,912,134 A | 6/1999 | Shartle |
| 5,914,042 A | 6/1999 | Ball et al. |
| 5,919,711 A | 7/1999 | Boyd et al. |
| 5,922,210 A | 7/1999 | Brody et al. |
| 5,935,779 A | 8/1999 | Massey et al. |
| 5,945,344 A | 8/1999 | Hayes et al. |
| 5,962,218 A | 10/1999 | Leland et al. |
| 5,968,329 A | 10/1999 | Anderson et al. |
| 5,980,830 A | 11/1999 | Savage et al. |
| 5,981,294 A | 11/1999 | Blatt et al. |
| 5,983,734 A | 11/1999 | Mathur et al. |
| 6,016,712 A | 1/2000 | Warden et al. |
| 6,048,687 A | 4/2000 | Kenten et al. |
| 6,057,151 A | 5/2000 | Greenwood et al. |
| 6,069,014 A | 5/2000 | Schrier et al. |
| 6,078,782 A | 6/2000 | Leland et al. |
| 6,082,185 A | 7/2000 | Saaski |
| 6,087,476 A | 7/2000 | Kenten et al. |
| 6,096,500 A | 8/2000 | Oprandy et al. |
| 6,099,760 A | 8/2000 | Jameison et al. |
| 6,112,888 A | 9/2000 | Sauro et al. |
| 6,120,986 A | 9/2000 | Martin |
| 6,132,648 A | 10/2000 | Zhang et al. |
| 6,132,955 A | 10/2000 | Talley et al. |
| 6,140,138 A | 10/2000 | Bard et al. |
| 6,146,838 A | 11/2000 | Williams et al. |
| 6,165,708 A | 12/2000 | Liang et al. |
| 6,165,729 A | 12/2000 | Leland et al. |
| 6,174,709 B1 | 1/2001 | Kenten et al. |
| 6,187,267 B1 | 2/2001 | Taylor et al. |
| 6,193,864 B1 | 2/2001 | Leader et al. |
| 6,200,531 B1 | 3/2001 | Liljestrand et al. |
| 6,214,552 B1 | 4/2001 | Heroux et al. |
| 6,217,744 B1 | 4/2001 | Crosby |
| 6,271,041 B1 | 8/2001 | Leland et al. |
| 6,274,087 B1 | 8/2001 | Preston et al. |
| 6,312,591 B1 | 11/2001 | Vassarotti et al. |
| 6,312,896 B1 | 11/2001 | Heroux et al. |
| 6,316,180 B1 | 11/2001 | Martin |
| 6,316,607 B1 | 11/2001 | Massey et al. |
| 6,319,670 B1 | 11/2001 | Sigal et al. |
| 6,319,719 B1 | 11/2001 | Bhullar et al. |
| 6,325,973 B1 | 12/2001 | Leland et al. |
| 6,379,969 B1 | 4/2002 | Mauze et al. |
| 6,387,290 B1 | 5/2002 | Brody et al. |
| 6,391,541 B1 | 5/2002 | Petersen et al. |
| 6,398,956 B1 | 6/2002 | Coville et al. |
| 6,403,384 B1 | 6/2002 | Lea |
| 6,406,672 B1 | 6/2002 | Bhullar et al. |
| 6,432,720 B2 | 8/2002 | Chow |
| 6,438,498 B1 | 8/2002 | Opalsky et al. |
| 6,440,725 B1 | 8/2002 | Pourahmadi et al. |
| 6,448,091 B1 | 9/2002 | Massey et al. |
| 6,451,225 B1 | 9/2002 | Leland et al. |
| 6,468,741 B1 | 10/2002 | Massey et al. |
| 6,475,372 B1 | 11/2002 | Ohara et al. |
| 6,479,233 B1 | 11/2002 | Bard et al. |
| 6,488,896 B2 | 12/2002 | Weigl et al. |
| 6,495,104 B1 | 12/2002 | Unno et al. |
| 6,517,777 B2 | 2/2003 | Liljestrand et al. |
| 6,524,513 B1 | 2/2003 | Pearl et al. |
| 6,524,865 B1 | 2/2003 | Martin et al. |
| 6,534,137 B1 | 3/2003 | Vadhar |
| 6,537,501 B1 | 3/2003 | Holl et al. |
| 6,554,788 B1 | 4/2003 | Hunley et al. |
| 6,559,096 B1 | 5/2003 | Smith et al. |
| 6,613,280 B2 | 9/2003 | Myrick et al. |
| 6,613,286 B2 | 9/2003 | Braun, Sr. et al. |
| 6,613,583 B1 | 9/2003 | Richter et al. |
| 6,635,418 B2 | 10/2003 | Heroux et al. |
| 6,656,428 B1 | 12/2003 | Clark et al. |
| 6,664,104 B2 | 12/2003 | Pourahmadi et al. |
| 6,676,902 B2 | 1/2004 | Baugh et al. |
| 6,699,718 B1 | 3/2004 | Bruegger |
| 6,702,986 B1 | 3/2004 | Leland et al. |
| 6,740,240 B2 | 5/2004 | Coville et al. |
| 6,748,332 B2 | 6/2004 | Chen |
| 6,750,053 B1 | 6/2004 | Widrig Opalsky et al. |
| D494,589 S | 8/2004 | Liljestrand et al. |
| 6,776,965 B2 | 8/2004 | Wyzgol et al. |
| 6,783,736 B1 | 8/2004 | Taylor et al. |
| 6,794,877 B2 | 9/2004 | Blomberg et al. |
| 6,808,939 B2 | 10/2004 | Sigal et al. |
| D499,035 S | 11/2004 | Cook et al. |
| 6,818,185 B1 | 11/2004 | Petersen et al. |
| 6,824,663 B1 | 11/2004 | Boone |
| 6,831,733 B2 | 12/2004 | Pettersson et al. |
| 6,846,629 B2 | 1/2005 | Sigal et al. |
| 6,852,284 B1 | 2/2005 | Holl et al. |
| 6,852,502 B1 | 2/2005 | Martin |
| 6,861,259 B2 | 3/2005 | Columbus |
| 6,866,823 B2 | 3/2005 | Wardlaw |
| 6,869,570 B2 | 3/2005 | Wardlaw |
| 6,878,540 B2 | 4/2005 | Pourahmadi et al. |
| 6,880,384 B2 | 4/2005 | Hvidtfeldt et al. |
| 6,881,536 B1 | 4/2005 | Shah et al. |
| 6,881,541 B2 | 4/2005 | Petersen et al. |
| 6,881,589 B1 | 4/2005 | Leland et al. |
| 6,887,693 B2 | 5/2005 | McMillan et al. |
| 6,893,879 B2 | 5/2005 | Petersen et al. |
| 6,919,173 B2 | 7/2005 | Tsionsky et al. |
| 6,926,834 B2 | 8/2005 | Coville et al. |
| 6,929,953 B1 | 8/2005 | Wardlaw |
| 6,949,377 B2 | 9/2005 | Ho |
| 6,969,450 B2 | 11/2005 | Taniike et al. |
| 6,977,722 B2 | 12/2005 | Wohlstadter et al. |
| D515,220 S | 2/2006 | Miller et al. |
| 7,004,184 B2 | 2/2006 | Handique et al. |
| 7,008,796 B2 | 3/2006 | Wohlstadter et al. |
| 7,011,794 B2 | 3/2006 | Kagan et al. |
| 7,018,353 B2 | 3/2006 | Hunley et al. |
| 7,036,917 B2 | 5/2006 | Mü-Chorus et al. |
| 7,041,206 B2 | 5/2006 | Gephart et al. |
| 7,061,595 B2 | 6/2006 | Cabuz et al. |
| 7,111,503 B2 | 9/2006 | Brumboiu et al. |
| 7,115,421 B2 | 10/2006 | Grzeda et al. |
| 7,135,547 B2 | 11/2006 | Gengrinovitch |
| 7,205,116 B2 | 4/2007 | Salamone et al. |
| 7,235,213 B2 | 6/2007 | Mpock et al. |
| 7,238,246 B2 | 7/2007 | Peters et al. |
| 7,247,488 B2 | 7/2007 | Ghai et al. |
| 7,277,166 B2 | 10/2007 | Padmanabhan et al. |
| 7,282,179 B2 | 10/2007 | Iwaki et al. |
| 7,285,425 B2 | 10/2007 | Shareef et al. |
| 7,288,195 B2 | 10/2007 | Coville et al. |
| 7,299,081 B2 | 11/2007 | Mace et al. |
| 7,306,727 B2 | 12/2007 | Perreault |
| 7,314,711 B2 | 1/2008 | Richter et al. |
| 7,329,538 B2 | 2/2008 | Waieright et al. |
| 7,335,339 B2 | 2/2008 | Brendtsson |
| 7,378,270 B2 | 5/2008 | Azarnia et al. |
| 7,384,409 B2 | 6/2008 | Fischer et al. |
| 7,399,637 B2 | 7/2008 | Wright et al. |
| 7,419,821 B2 | 9/2008 | Davis et al. |
| 7,422,903 B2 | 9/2008 | Conlon et al. |
| 7,422,905 B2 | 9/2008 | Clague et al. |
| 7,438,853 B2 | 10/2008 | Zen et al. |
| 7,439,017 B2 | 10/2008 | Heroux et al. |
| 7,439,069 B2 | 10/2008 | Nippoldt et al. |
| 7,471,394 B2 | 12/2008 | Padmanabhan et al. |
| 7,481,787 B2 | 1/2009 | Gable et al. |
| 7,485,153 B2 | 2/2009 | Padmanabhan et al. |
| 7,494,819 B2 | 2/2009 | Bahatt et al. |
| 7,497,997 B2 | 3/2009 | Glezer et al. |

(56) References Cited

U.S. PATENT DOCUMENTS

| | | |
|---|---|---|
| 7,521,247 B2 | 4/2009 | De Haan |
| 7,523,649 B2 | 4/2009 | Corey et al. |
| 7,547,384 B2 | 6/2009 | Keenan |
| 7,553,448 B2 | 6/2009 | Kumar et al. |
| 7,553,453 B2 | 6/2009 | Gu et al. |
| 7,569,346 B2 | 8/2009 | Petersen et al. |
| 7,569,393 B2 | 8/2009 | Sin |
| 7,595,169 B2 | 9/2009 | Swaim et al. |
| 7,604,777 B2 | 10/2009 | Columbus |
| 7,608,042 B2 | 10/2009 | Goldberger et al. |
| 7,630,063 B2 | 12/2009 | Padmanabhan et al. |
| 7,641,856 B2 | 1/2010 | Padmanabhan et al. |
| 7,666,355 B2 | 2/2010 | Alavie et al. |
| 7,682,511 B2 | 3/2010 | de Los Reyes et al. |
| 7,682,788 B2 | 3/2010 | Sigal et al. |
| 7,723,099 B2 | 5/2010 | Miller et al. |
| 7,736,901 B2 | 6/2010 | Opalsky et al. |
| 7,767,794 B2 | 8/2010 | Salamone et al. |
| 7,771,658 B2 | 8/2010 | Larsen |
| 7,776,583 B2 | 8/2010 | Billadeau et al. |
| 7,781,226 B2 | 8/2010 | McDevitt et al. |
| 7,816,124 B2 | 10/2010 | Samsoondar |
| 7,820,102 B2 | 10/2010 | Myrick et al. |
| 7,822,510 B2 | 10/2010 | Paik et al. |
| RE41,946 E | 11/2010 | Anderson et al. |
| 7,824,925 B2 | 11/2010 | Wohlstadter et al. |
| 7,833,746 B2 | 11/2010 | Brendtsson et al. |
| 7,838,631 B2 | 11/2010 | Yamashita et al. |
| 7,859,670 B2 | 12/2010 | Kim et al. |
| 7,887,750 B2 | 2/2011 | Blatt et al. |
| 7,888,125 B2 | 2/2011 | Gibbons et al. |
| 7,901,629 B2 | 3/2011 | Calatzis et al. |
| 7,911,617 B2 | 3/2011 | Padmanabhan et al. |
| 7,914,994 B2 | 3/2011 | Petersen et al. |
| 7,923,256 B2 | 4/2011 | Widrig Opalsky et al. |
| 7,928,718 B2 | 4/2011 | Larsen |
| 7,932,098 B2 | 4/2011 | Childers et al. |
| 7,939,021 B2 | 5/2011 | Smith et al. |
| 7,952,069 B2 | 5/2011 | Shiokawa et al. |
| 7,977,106 B2 | 7/2011 | Widrig Opalsky et al. |
| 7,978,329 B2 | 7/2011 | Padmanabhan et al. |
| 7,981,362 B2 | 7/2011 | Glezer et al. |
| 7,985,589 B2 | 7/2011 | Garner et al. |
| 8,003,060 B2 | 8/2011 | Cracauer et al. |
| 8,007,670 B2 | 8/2011 | Connors, Jr. |
| 8,008,034 B2 | 8/2011 | Gibbons et al. |
| 8,012,744 B2 | 9/2011 | Gibbons et al. |
| 8,012,745 B2 | 9/2011 | Glezer et al. |
| 8,017,382 B2 | 9/2011 | Davis et al. |
| 8,021,873 B2 | 9/2011 | Johnson et al. |
| 8,028,566 B2 | 10/2011 | Larsen |
| 8,034,296 B2 | 10/2011 | Cox et al. |
| 8,046,175 B2 | 10/2011 | Kuo et al. |
| 8,071,051 B2 | 12/2011 | Padmanabhan et al. |
| 8,101,404 B2 | 1/2012 | Samsoondar |
| 8,101,431 B2 | 1/2012 | McDevitt et al. |
| 8,105,783 B2 | 1/2012 | Handique |
| 8,105,849 B2 | 1/2012 | McDevitt et al. |
| 8,137,626 B2 | 3/2012 | Maltezos et al. |
| 8,236,555 B2 | 8/2012 | Stromgren et al. |
| 8,273,566 B2 | 9/2012 | Billadeau et al. |
| 8,343,526 B2 | 1/2013 | Billadeau et al. |
| 8,394,595 B2 | 3/2013 | Jung et al. |
| 8,394,608 B2 | 3/2013 | Ririe et al. |
| 8,481,901 B2 | 7/2013 | Bedingham et al. |
| 8,585,279 B2 | 11/2013 | Rida |
| 8,623,638 B2 | 1/2014 | Solomon |
| 8,747,779 B2 | 6/2014 | Sprague et al. |
| 8,772,017 B2 | 7/2014 | Battrell et al. |
| 8,778,665 B2 | 7/2014 | Gibbons et al. |
| 8,846,310 B2 | 9/2014 | Johnson et al. |
| 8,870,446 B2 | 10/2014 | Rida |
| 8,895,295 B2 | 11/2014 | Ririe et al. |
| 8,940,230 B2 | 1/2015 | Kuhnl et al. |
| 2002/0019060 A1 | 2/2002 | Petersen et al. |
| 2002/0098116 A1 | 7/2002 | Sugaya et al. |
| 2002/0143297 A1 | 10/2002 | Francavilla et al. |
| 2002/0155033 A1 | 10/2002 | Strand et al. |
| 2003/0029254 A1 | 2/2003 | Hvidtfeldt et al. |
| 2003/0035758 A1 | 2/2003 | Buechler et al. |
| 2003/0052054 A1 | 3/2003 | Pearl et al. |
| 2003/0073089 A1 | 4/2003 | Mauze et al. |
| 2003/0185707 A1 | 10/2003 | Iwaki et al. |
| 2003/0224523 A1 | 12/2003 | Thornberg et al. |
| 2004/0035792 A1 | 2/2004 | Rauch et al. |
| 2004/0086872 A1 | 5/2004 | Childers et al. |
| 2004/0096368 A1 | 5/2004 | Davis et al. |
| 2004/0176704 A1 | 9/2004 | Stevens et al. |
| 2004/0228765 A1 | 11/2004 | Witty et al. |
| 2004/0228766 A1 | 11/2004 | Witty et al. |
| 2004/0248284 A1 | 12/2004 | Van Beuningen |
| 2004/0259268 A1 | 12/2004 | Jacobs et al. |
| 2005/0014279 A1 | 1/2005 | Nguyen et al. |
| 2005/0042137 A1 | 2/2005 | Petersen et al. |
| 2005/0074900 A1 | 4/2005 | Morgan et al. |
| 2005/0181443 A1 | 8/2005 | Sun et al. |
| 2005/0220668 A1 | 10/2005 | Coville |
| 2005/0227370 A1 | 10/2005 | Ramel et al. |
| 2005/0245844 A1 | 11/2005 | Mace et al. |
| 2005/0250173 A1 | 11/2005 | Davis et al. |
| 2006/0094028 A1 | 5/2006 | Danna et al. |
| 2006/0165558 A1 | 7/2006 | Witty et al. |
| 2006/0177347 A1 | 8/2006 | Larsen et al. |
| 2006/0218010 A1 | 9/2006 | Michon et al. |
| 2006/0228259 A1 | 10/2006 | Samsoondar |
| 2006/0257854 A1 | 11/2006 | McDevitt et al. |
| 2006/0257941 A1 | 11/2006 | McDevitt et al. |
| 2006/0257991 A1 | 11/2006 | McDevitt et al. |
| 2006/0263818 A1 | 11/2006 | Scherer et al. |
| 2006/0275841 A1 | 12/2006 | Blankfard et al. |
| 2007/0003434 A1 | 1/2007 | Padmanabhan et al. |
| 2007/0009386 A1 | 1/2007 | Padmanabhan et al. |
| 2007/0031283 A1 | 2/2007 | Davis et al. |
| 2007/0036026 A1 | 2/2007 | Laibinis et al. |
| 2007/0116600 A1 | 5/2007 | Kochar et al. |
| 2007/0166195 A1 | 7/2007 | Padmanabhan et al. |
| 2007/0166196 A1 | 7/2007 | Bardell et al. |
| 2007/0166725 A1 | 7/2007 | McBride et al. |
| 2007/0172388 A1 | 7/2007 | Padmanabhan et al. |
| 2007/0178514 A1 | 8/2007 | Van Beuningen |
| 2007/0178521 A1 | 8/2007 | Sakaino et al. |
| 2007/0248497 A1 | 10/2007 | Robillot |
| 2007/0292941 A1 | 12/2007 | Handique et al. |
| 2008/0021296 A1 | 1/2008 | Creaven |
| 2008/0025872 A1 | 1/2008 | Dykes et al. |
| 2008/0057572 A1 | 3/2008 | Petersen et al. |
| 2008/0131322 A1 | 6/2008 | Kheiri et al. |
| 2008/0149840 A1 | 6/2008 | Handique et al. |
| 2008/0153078 A1 | 6/2008 | Braman et al. |
| 2008/0188732 A1 | 8/2008 | Mace et al. |
| 2008/0227219 A1 | 9/2008 | Gamez |
| 2008/0311002 A1 | 12/2008 | Kirby et al. |
| 2009/0018411 A1 | 1/2009 | Mace et al. |
| 2009/0047713 A1 | 2/2009 | Handique |
| 2009/0065357 A1 | 3/2009 | Glezer et al. |
| 2009/0081078 A1 | 3/2009 | Caramuta |
| 2009/0098541 A1 | 4/2009 | Southern et al. |
| 2009/0130658 A1 | 5/2009 | Barlag et al. |
| 2009/0130719 A1 | 5/2009 | Handique |
| 2009/0148882 A1 | 6/2009 | Goldstein |
| 2009/0151792 A1 | 6/2009 | Noda |
| 2009/0181864 A1 | 7/2009 | Nguyen et al. |
| 2009/0215072 A1 | 8/2009 | McDevitt et al. |
| 2009/0221059 A1 | 9/2009 | Williams et al. |
| 2009/0246076 A1 | 10/2009 | Kumar et al. |
| 2009/0253130 A1 | 10/2009 | Yoo |
| 2009/0311736 A1 | 12/2009 | Ciotti et al. |
| 2009/0325276 A1 | 12/2009 | Battrell et al. |
| 2010/0029011 A1 | 2/2010 | Sin |
| 2010/0081144 A1 | 4/2010 | Holmes et al. |
| 2010/0112723 A1 | 5/2010 | Battrell et al. |
| 2010/0117666 A1 | 5/2010 | Wada et al. |
| 2010/0158756 A1 | 6/2010 | Taylor et al. |
| 2010/0159556 A1 | 6/2010 | Rida |

(56) References Cited

U.S. PATENT DOCUMENTS

| | | |
|---|---|---|
| 2010/0173394 A1 | 7/2010 | Colston, Jr. et al. |
| 2010/0197522 A1 | 8/2010 | Liu et al. |
| 2010/0203521 A1 | 8/2010 | Klapperich et al. |
| 2010/0203550 A1 | 8/2010 | Miller et al. |
| 2010/0227412 A1 | 9/2010 | Cerda |
| 2010/0240022 A1 | 9/2010 | McNeely |
| 2010/0261292 A1 | 10/2010 | Glezer et al. |
| 2010/0262304 A1 | 10/2010 | Gonnella et al. |
| 2010/0282609 A1 | 11/2010 | Pollack et al. |
| 2010/0285578 A1 | 11/2010 | Selden et al. |
| 2010/0290952 A1 | 11/2010 | Koike et al. |
| 2010/0291588 A1 | 11/2010 | McDevitt et al. |
| 2010/0303722 A1 | 12/2010 | Jin et al. |
| 2011/0008908 A1 | 1/2011 | Biesbrouck |
| 2011/0016691 A1 | 1/2011 | Alden et al. |
| 2011/0039298 A1 | 2/2011 | Berndtsson et al. |
| 2011/0067489 A1 | 3/2011 | Haberstroh et al. |
| 2011/0091357 A1 | 4/2011 | Blatt et al. |
| 2011/0100101 A1 | 5/2011 | Zenhausern et al. |
| 2011/0143378 A1 | 6/2011 | Putnam |
| 2011/0171754 A1 | 7/2011 | Redmond et al. |
| 2011/0192218 A1 | 8/2011 | Miyamura et al. |
| 2011/0192219 A1 | 8/2011 | Miyamura et al. |
| 2011/0194977 A1 | 8/2011 | Miyamura et al. |
| 2011/0195490 A1 | 8/2011 | Kang et al. |
| 2011/0195495 A1 | 8/2011 | Selden et al. |
| 2011/0201099 A1 | 8/2011 | Anderson et al. |
| 2011/0201909 A1 | 8/2011 | Emery et al. |
| 2011/0203924 A1 | 8/2011 | Wohlstadter et al. |
| 2011/0259091 A1 | 10/2011 | Laubscher et al. |
| 2011/0269159 A1 | 11/2011 | Campbell et al. |
| 2011/0269222 A1 | 11/2011 | Miller et al. |
| 2011/0290669 A1 | 12/2011 | Davis et al. |
| 2011/0294224 A1 | 12/2011 | Liu |
| 2011/0312553 A1 | 12/2011 | Silverbrook et al. |
| 2011/0312661 A1 | 12/2011 | Silverbrook et al. |
| 2011/0312742 A1 | 12/2011 | Silverbrook et al. |
| 2011/0318774 A1 | 12/2011 | Larsen |
| 2012/0003730 A1 | 1/2012 | Padmanabhan et al. |
| 2012/0009667 A1 | 1/2012 | Peterson et al. |
| 2012/0034624 A1 | 2/2012 | Miller et al. |
| 2012/0034645 A1 | 2/2012 | Billadeau et al. |
| 2012/0043202 A1 | 2/2012 | Miyamura et al. |
| 2012/0045375 A1 | 2/2012 | Miyamura et al. |
| 2012/0051972 A1 | 3/2012 | Joseph |
| 2012/0053335 A1 | 3/2012 | Liu et al. |
| 2012/0115213 A1 | 5/2012 | Hofstadler et al. |
| 2012/0141337 A1 | 6/2012 | Maltezos et al. |
| 2012/0177537 A1 | 7/2012 | Aota et al. |
| 2012/0190128 A1 | 7/2012 | Nikbakht et al. |
| 2012/0190589 A1 | 7/2012 | Anderson et al. |
| 2012/0252138 A1 | 10/2012 | Sasso, Jr. et al. |
| 2013/0137172 A1 | 5/2013 | Ririe et al. |
| 2014/0017709 A1 | 1/2014 | Lowe et al. |
| 2014/0186935 A1 | 7/2014 | Yoo |
| 2014/0329301 A1 | 11/2014 | Handique |

FOREIGN PATENT DOCUMENTS

| | | |
|---|---|---|
| EP | 2007905 B1 | 12/2008 |
| EP | 2281631 B1 | 2/2011 |
| EP | 2419217 B1 | 2/2012 |
| GB | 2112293 | 7/1983 |
| JP | 2010-237050 | 10/2010 |
| WO | 8706706 | 11/1987 |
| WO | 9005302 | 5/1990 |
| WO | 9419683 | 9/1994 |
| WO | 9419684 | 9/1994 |
| WO | 9508644 | 3/1995 |
| WO | 9621154 | 7/1996 |
| WO | 9635697 | 11/1996 |
| WO | 9635812 | 11/1996 |
| WO | 9641177 | 12/1996 |
| WO | 9915694 | 4/1999 |
| WO | 2005095954 A1 | 10/2005 |
| WO | 2007002579 A2 | 1/2007 |
| WO | 2007005626 | 1/2007 |
| WO | 2011027092 A1 | 3/2011 |
| WO | 2011113569 | 9/2011 |
| WO | 2012024543 A1 | 2/2012 |
| WO | 2012058632 A1 | 5/2012 |
| WO | 2012136695 A1 | 10/2012 |
| WO | 2013082273 A1 | 6/2013 |
| WO | 2013136115 A1 | 9/2013 |
| WO | 2013173524 A2 | 11/2013 |
| WO | 2013173525 A1 | 11/2013 |
| WO | 2014043388 A1 | 3/2014 |

OTHER PUBLICATIONS

Notice of Allowance and Fees Due, dated Mar. 3, 2015, from co-pending U.S. Appl. No. 13/844,527.

Ascoli, et al., "Drug Binding to Human Serum Albumin: Abridged Review of Results Obtained with High-Performance Liquid Chromatography and Circular Dichroism", Chirality, vol. 18:667-679 (2006).

Bertino, et al., "5-Fluorouracil Drug Management: Pharmacokinetics and Pharmacogenomics Workshop Meeting Summary; Orlando, Florida; Jan. 2007", Clinical Colorectal Cancer, vol. 6(6):407-422 (2007).

Bertucci, et al., "The Binding of 5-fluorouracil to Native and Modified Human Serum Albumin: UV, CD, and 1H and 19F NMR Investigation", Journal of Pharmaceutical and Biomedical Analysis, vol. 13:1087-1093 (1995).

Beumer, et al., "A Rapid Nanoparticle Immunoassay to Quantitate 5-Fluorouracil (5-FU) in Plasma", ASCO GI 2008 Meeting (Poster).

Crowley, et al., "Isolation of Plasma from Whole Blood Using Planar Microfilters for Lab-on-a-Chip Applications", Lab Chip, vol. 5(9):922-929 (2005).

Jaffrin, M.Y. (1995). Biological Flows. M.Y. Jaffrin and Colin Caro (Eds.). Plenum Press, New York, pp. 199-226.

Joseph, et al., "Evaluation of Alternatives to Warfarin as Probes for Sudlow Site I of Human Serum Albumin Characterization by High-Performance Affinity Chromatography", J. Chromatogr. A., vol. 1216(16):3492-3500 (2009).

Lukas, et al., "Binding of Digitoxin and Some Related Cardenolides to Human Plasma Proteins", The Journal of Clinical Investigation, vol. 48:1041-1053 (1969).

Madsen, et al., "Cooperative Interaction of Warfarin and Phenylbutazone with Human Serum Albumin", Biochemical Pharmacology, vol. 30(11):1169-1173 (1981).

Means, et al. (1982). Modification of Proteins: Food, Nutritional, and Pharmacological Aspects. Robert E. Feeny and John R. Whitaker (Eds.). American Chemical Society. pp. 325-346.

Olympus UK Ltd—Diagnostics Laboratory News Directory, http://www.labnewsdirectory.co.uk/company/Olympus-UK-Ltd-Diagnostics/2232, (Oct. 1, 2009).

Peters, T., Jr., "Serum Albumin", Adv. Protein Chem., vol. 37:161-246 (1985).

Peyrin, et al., "Characterization of Solute Binding at Human Serum Albumin Site II and its Geometry Using a Biochromatographic Approach", Biophysical Journal, vol. 77:1206-1212 (1999).

Saif, et al. "Pharmacokinetically Guided Doe Adjustment of 5-Fluorouracil: A Rational Approach to Improving Therapeutic Outcomes", J. Natl. Cancer Inst., vol. 101:1543-1552 (2009).

Salamone, et al., "Novel Monoclonal Antibodies for Measuring 5-Fluorouracil Concentrations in Biological Fluids", Journal of Clinical Oncology, 2006 ASCO Annual Meeting Proceedings (Post-Meeting Edition); vol. 24(18S):2055 (2006).

Salamone, et al., "A Multi-Center Evaluation of a Rapid Immunoassay to Quantitate 5-Fluorouracil in Plasma", 2008 HOPA Conference—Anaheim, California (Poster).

Sulkowska, et al., "Competitive Binding of Phenylbutazone and Colchicine to Serum Albumin in Multidrug Therapy: A Spectroscopic Study", Journal of Molecular Structure, vol. 881:97-106 (2008).

(56) References Cited

OTHER PUBLICATIONS

Vandelinder, V. and A. Groisman, "Separation of Plasma from Whole Human Blood in a Continuous Cross-Flow in a Molded Microfluidic Device", Anal. Chem., vol. 78:3765-3771 (2006).

Villamor, J. and A. Zatón, "Data Plotting of Warfarin Binding to Human Serum Albumin", J. Biochem. Biophys. Methods, vol. 48:33-41 (2001).

Vos, et al., "Use of the Enzyme-Linked Immunosorbent Assay (ELISA) in Immunotoxicity Testing", Environmental Health Perspectives, vol. 43:115-121 (1982).

Yamashita, et al., "5-Fluorouracil Derivatives with Serum Protein Binding Potencies", Chem. Pharm. Bull., vol. 37 (10):2861-2863 (1989).

Yamashita, et al., "Possible Role of Serum Protein Binding to Improve Drug Disposition", International Journal of Pharmaceutics, vol. 108:241-247 (1994).

Zsila, et al., "Evaluation of Drug-Human Serum Albumin Binding Interactions with Support Vector Machine Aided Online Automated Docking", Bioinformatics, vol. 27(13):1806-1813 (2011).

Notice of Allowance and Fees Due, dated Jan. 5, 2015, from co-pending U.S. Appl. No. 13/844,450.

Notice of Allowance and Fees Due, dated Jan. 9, 2015, from co-pending U.S. Appl. No. 13/844,527.

International Search Report and the Written Opinion from International PCT Application No. PCT/US2013/041252, Dec. 20, 2013.

International Search Report and the Written Opinion from International PCT Application No. PCT/US2013/041255, Oct. 8, 2013.

International Search Report and the Written Opinion from International PCT Application No. PCT/US2012/067041, Feb. 11, 2013.

Restriction Requirement, dated Jun. 27, 2014, from co-pending U.S. Appl. No. 13/844,450.

Response to Jun. 27, 2014 Restriction Requirement, from co-pending U.S. Appl. No. 13/844,450, Mar. 15, 2013.

Restriction Requirement, dated Jul. 2, 2014, from co-pending U.S. Appl. No. 13/844,527.

Response to Jul. 2, 2014 Restriction Requirement, from co-pending U.S. Appl. No. 13/844,527, Mar. 15, 2013.

Notice of Allowance and Fees Due, dated Oct. 22, 2014, from co-pending U.S. Appl. No. 13/844,450.

Notice of Allowance and Fees Due, dated Oct. 30, 2014, from co-pending U.S. Appl. No. 13/844,527.

Australian Examination Report, dated Jun. 19, 2015, from AU Application No. 2013262816 (a co-pending application to U.S. Appl. No. 14/401,278).

Office Action, dated May 28, 2015, from co-pending U.S. Appl. No. 14/401,278.

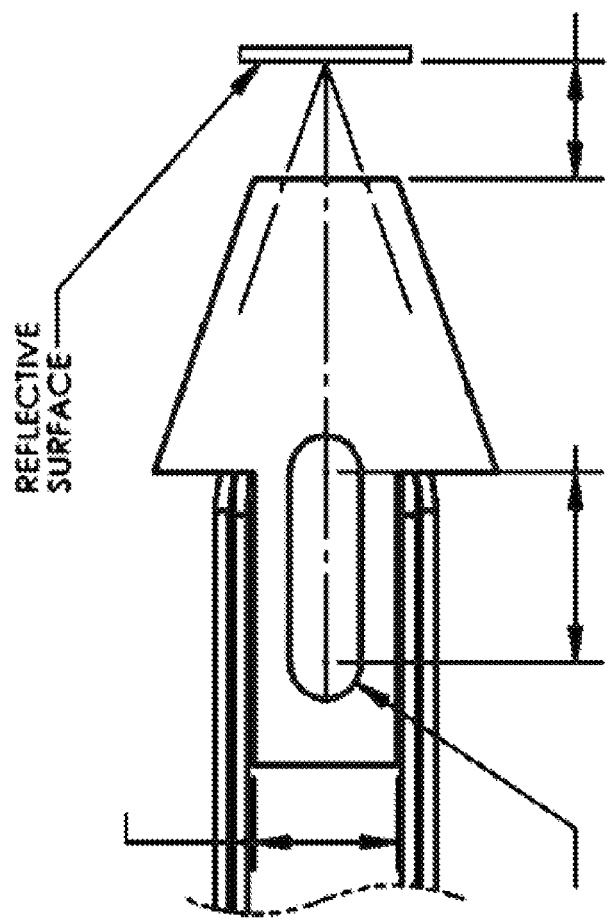

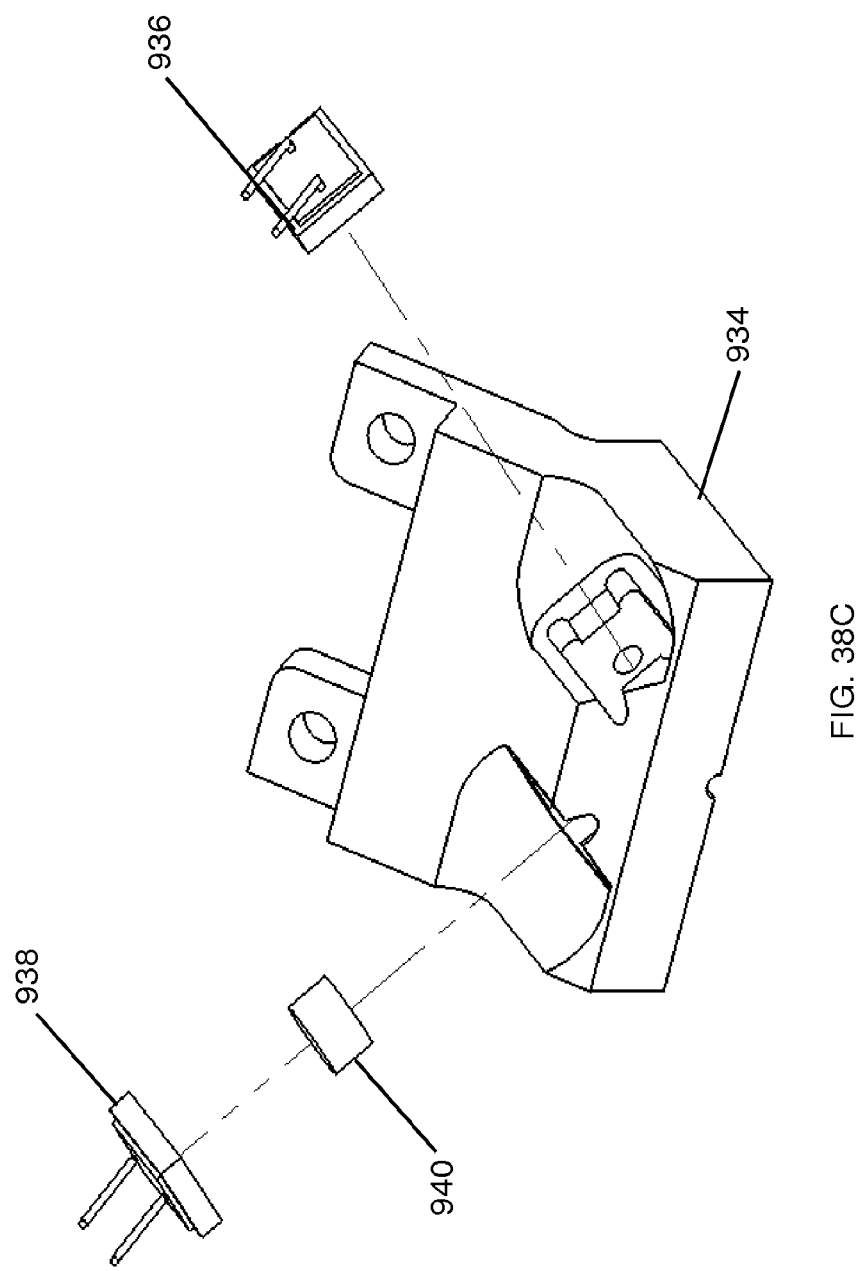

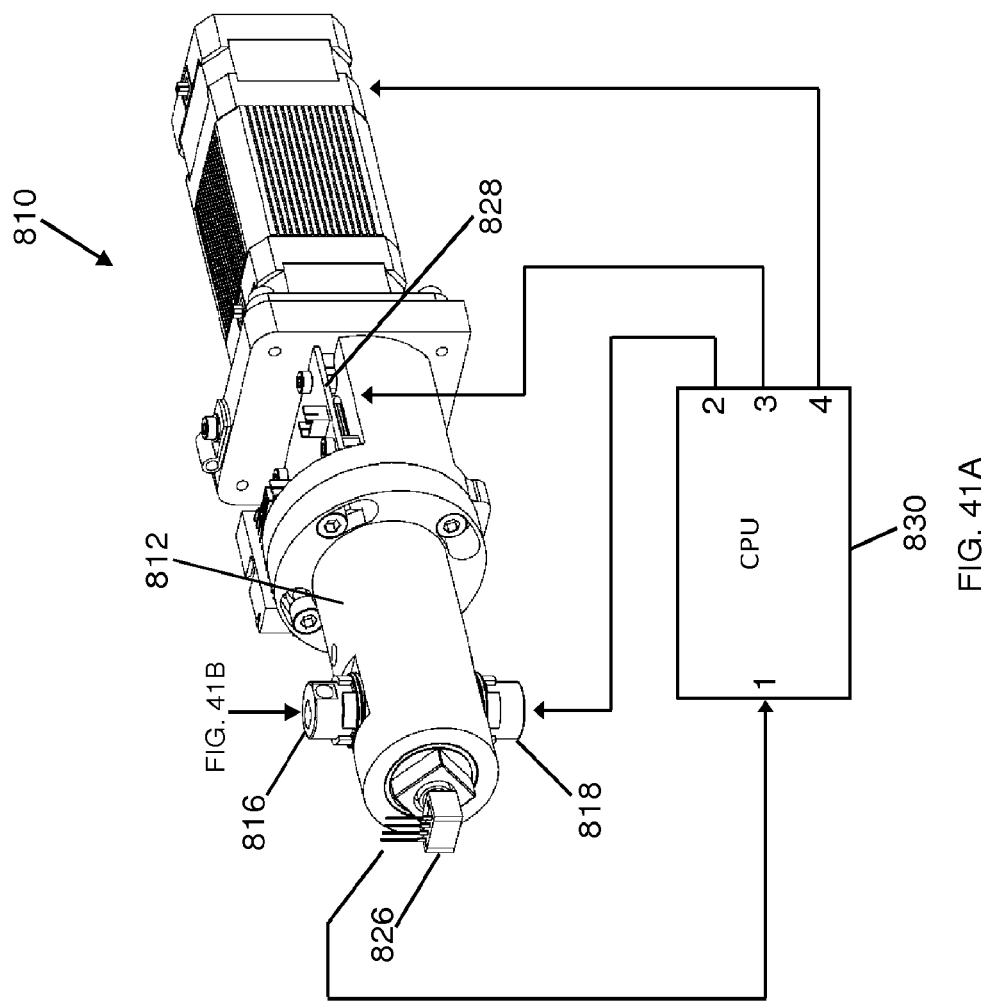

CLINICAL DIAGNOSTIC SYSTEM INCLUDING INSTRUMENT AND CARTRIDGE

CROSS-REFERENCE TO RELATED APPLICATIONS

This is a national stage application of International Application No. PCT/US2013/041252, filed internationally on May 15, 2013, which claims priority to U.S. Provisional Patent Application No. 61/647,272, filed May 15, 2012, which is herein incorporated by reference in its entirety. International PCT Application No. PCT/US2013/041252 is a continuation-in-part of each of International PCT Application No. PCT/US2012/067041, filed Nov. 29, 2012; and U.S. patent application Ser. Nos. 13/844,450 and 13/844,527, both filed Mar. 15, 2013; each of which is herein incorporated by reference in its entirety.

BACKGROUND

In the healthcare industry, diagnostic testing is essential for properly diagnosing medical issues. Accuracy and precision are necessary to provide proper diagnoses. In order to provide convenience, diagnostic systems have been created to analyze samples in laboratories, clinics, hospitals, physicians offices, etc. with accuracy and precision.

Providing clinical point-of-care diagnostic systems, as well as other diagnostic systems also requires ease of use and fail safe mechanisms in order to decrease the frequency and intensity of user errors, which may lead to inaccurate diagnoses.

Furthermore, the size and scale of the diagnostic systems is also important. In order to be able to use diagnostic systems in certain settings, compactness may also be needed. To this end, the system may include an instrument and separate cartridges, which can be used to provide samples to the instrument in the diagnostic systems. The cartridges may also be designed to assist in the compactness of the instrument.

Additionally, the cartridges used to provide samples to the diagnostic systems may also be designed to require less biological sample for testing, as well as be designed with ease of use and with fail safe mechanisms to further assist in the accuracy of diagnoses.

SUMMARY

Diagnostic systems with associated diagnostic instruments and cartridges are disclosed herein, which can provide accuracy and precision, ease of use with fail safe mechanism, and compactness of scale. As disclosed herein, embodiments of diagnostic systems may include clinical diagnostic systems that can be configured to accept samples via cartridges, process samples within the cartridges and instruments, conduct tests on the samples while the sample remain within the cartridges, and provide diagnostic results.

Also disclosed herein, embodiments of cartridges may include self-contained sample accepting reservoirs, and self-contained testing reagents for analyzing samples and detecting certain information. Additionally, the diagnostic instrument contains all of the components necessary to run a diagnostic test with the cartridge. The cartridge is configured to store dry and liquid reagents together without the need for separate packaging. The diagnostic system is also designed to collect substantially all waste materials from the diagnostic test, including processed regents and biological samples, within the cartridge for proper waste disposal. In this way, the self-contained diagnostic system can be very convenient for POC clinical settings.

Furthermore, as disclosed herein, embodiments of diagnostic systems may include electrochemiluminescence (ECL) detectors to accurately and precisely analyze samples provided via cartridges. The use of ECL technology as a platform for diagnostic tests, such as assays, can provide the desired sensitivity and specificity of results.

Also disclosed herein, diagnostic systems may be configured to require little to no end-user maintenance for over at least ten years from manufacture. Decreased need for maintenance can reduce overall costs. Additionally, the diagnostic system provides automated operation, meaning that with minimal input from a user, the diagnostic system can run a diagnostic test to completion on its own. Automated operation can be beneficial due to the increased reliability, decrease incidence of human error and lower costs for multiple tests or processing steps.

Furthermore, diagnostic systems disclosed herein may be configured to include features that are U.S. Food and Drug Administration (FDA) approved and can be designed to qualify for and obtain a Clinical Laboratory Improvement Amendments (CLIA)-waived categorization.

In embodiments disclosed herein, a diagnostic system is provided having a cartridge comprising at least one needle; at least one reservoir; at least one fluidic seal; and at least one fluidic channel of a fluidic pathway, wherein the cartridge is configured to store at least one reagent and at least one waste material on the cartridge. The diagnostic system is provided also having a diagnostic instrument comprising the fluidic pathway; an electrochemiluminescence (ECL) detection system; and a pump, wherein the fluidic pathway begins and ends in the cartridge and has a substantially single direction of flow in a pathway fluidically connecting the diagnostic instrument and the cartridge.

In embodiments disclosed herein, a cartridge is provided having a body and a cover, wherein the body and the cover mate together; a sample collection tube mount to secure a sample collection tube to the cartridge, wherein the sample collection tube mount includes the at least one needle to engage the sample collection tube and form a fluidic connection between the cartridge and the sample collection tube; a filtration module in fluidic communication with the sample collection tube mount; a sample cache in fluidic communication with the filtration module; at least one reagent handling station formed from the body; a multi-layer fluidic seal to establish a liquid and air-tight seal of the at least one reagent handling station and to establish a fluidic connection with at least one probe of the diagnostic instrument in the diagnostic system; the at least one fluidic channel formed from the body and sealed by a bottom seal, wherein the bottom seal defines in part the volume of the fluidic channels.

In embodiments disclosed herein, a diagnostic instrument is provided having a non-ECL detection system; a first probe fluidically connected to the non-ECL detection system by the fluidic pathway; the ECL detection system fluidically connected to the non-ECL detection system by the fluidic pathway; the pump fluidically connected to the ECL detection system by the fluidic pathway and fluidically connected to a waste probe by the fluidic pathway; and a motion assembly having two axes mechanically connected to the first probe and waste probe.

In example embodiments, a method of performing a diagnostic test, which can include the steps of introducing a sample into a cartridge; introducing the cartridge into a diagnostic instrument; mixing the sample with at least one reagent to form a detectable complex, wherein the at least one reagent is stored on the cartridge; analyzing the detectable complex with an electrochemiluminescence (ECL) detection apparatus in the diagnostic instrument; providing detection results through a user interface on the diagnostic instrument. The method of performing a diagnostic test can also include incubating the sample-reagent mixture within the cartridge with an incubator in the diagnostic instrument and washing the sample-reagent mixture to obtain a detectable complex.

This summary of the embodiments does not necessarily describe all features or necessary features of the embodiments. The embodiments may also reside in a sub-combination of the described features.

BRIEF DESCRIPTION OF THE DRAWINGS

The accompanying tables and figures are incorporated in, and constitute a part of this specification. For the purpose of illustrating the subject matter, there are depicted in the drawings certain embodiments of the subject matter. However, the present disclosure is not limited to the precise arrangements and instrumentalities of embodiments depicted in the drawings.

FIG. 26A is an illustration of an example mechanical outline of a sensor;

FIG. 38C is an illustration of an exploded perspective view of example components of an IS module;

FIG. 41A is an illustration of an example pump of a diagnostic system;

DETAILED DESCRIPTION

The following detailed description refers to the accompanying drawings. The same reference numbers in different drawings may identify the same or similar elements. Also, the following detailed description describes embodiments of the invention and is not intended to limit the invention. Instead, the scope of the invention is defined by the appended claims and equivalents.

The section headings used herein are for organizational purposes only and are not to be construed as limiting the subject matter described in any way.

Overview

Provided herein is a clinical diagnostic system that includes a cartridge and an instrument. The diagnostic system can provide accuracy and precision of test results, ease of system use, including fail safe mechanism, and compactness in terms of scale. By providing a robust system that utilizes ECL technology with an efficient and accurate instrument and cartridge, users of the diagnostic system can be assured precise results with very little training or set up.

In embodiments disclosed herein, a clinical diagnostic system can provide rapid, real-time test results for a variety of clinically important analytes. Example clinical diagnostic system embodiments can perform immunoassays using ECL-based detection technology with assays available in disposable cartridges, which may contain all the reagents required to perform a test.

DEFINITIONS

The following are definitions of terms related to a diagnostic system in general.

The term "assay construction" as used herein is intended to include a step by step process of conducting an assay whether manual or automated. Assay construction typically involves laboratory operations such as pipetting, dispensing, metering, washing, free-bound separations, dialyzing, filtering, collecting, fractionating, diluting, mixing, incubating, and the like.

The term "assay composition" as used herein is intended to include a complete set or subset of the necessary reagents or substances useful for an assay when combined. An assay composition may be the initial composition prior to assay construction, the composition immediately after initiating assay construction, the final mixture after assay construction, or the composition at any intermediate step of assay construction.

The term "bead(s)" as used herein is intended to include microscopic particles, such superparamagnetic particles, magnetic microparticles, and magnetic nanoparticles. A bead may typically be spherical, though the shape is not limited to that of a sphere and may include other shapes like spheroid, irregular particles, cubes, irregular cubes, and disks. The size range may cover from 1 nanometer to 10 microns in diameter.

The term "boost" as used herein is intended to include an initial application of temperature for a certain time and at a certain location on an incubator that can be used to heat up the cartridge.

Figure 37:
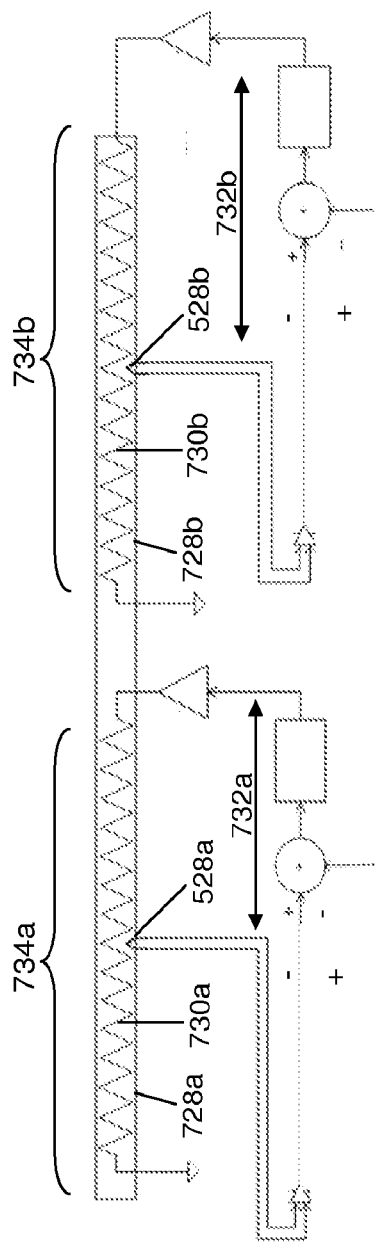
FIG. 37 is an illustration depicting example components and feedback control loops of a multi-zone incubation system.

The term "closed loop control" as used herein is intended to include a control module with one or more sensors to modulate a diagnostic system response. For example, a temperature control module portion of example diagnostic systems, such as the one discussed in FIG. 37, is an example of a closed loop control. A temperature sensor may be provided to send a feedback signal to a temperature control module to modulate the temperature of the example diagnostic systems.

The term "open loop control" is contrast with "closed loop control" and "open loop control" includes modules that do not provide a feedback signal to modulate a system response.

The term "conventional heating time" as used herein is intended to include a time that is proportional to the difference in temperature between the target temperature and starting cartridge temperature.

The term "dead volume" as used herein is intended to include a volume of a liquid trapped within a designated compartment, such as a sample receptacle or a reservoir, which is unrecoverable. It is advantageous to reduce the amount of dead volume when working with limited amounts of liquids to avoid waste.

The term "fluidic communication" as used herein is intended to include fluidic elements that are in fluidic communication if connected a channel, passageway, pathway, conduit, flow path or other fluidic element. Further, fluidic elements are in fluidic communication if connectable or transferable by a pipette or other transferrable means for example. Further, fluidic communication includes adjacent or nearby fluidic elements which liquid may be dispensed or transferred by pipette between or from one to the other. For example any two wells of a 96 well microtiter plate are in fluidic communication.

The term "fluidic element" as used herein is intended to include a structure to hold, carry, or allow transport of a fluid. A fluidic element includes a pipe, channel, well, reservoir, conduit, valve, vent, flow path, disperser, pipette, funnel, filter, and passageway.

The term "fluorescence" as used herein is intended to include any emission of electromagnetic radiation, including ultraviolet or visible light, stimulated in a substance by the absorption of incident radiation and persisting only as long as the stimulating radiation is continued.

The term "fluorophore" as used herein is intended to include a substance that is fluorescent.

The term "fluorescent label" as used herein is intended to include a fluorophore used in the detection or measurement of fluorescence. A substance which is fluorescent yet detected by another detection method, such as ECL, is not a fluorescent label. A fluorescent label is only operative when measuring fluorescence. Fluorescent beads are the same as fluorescent labeled beads.

The term "point of care" as used herein is intended to include places or people that include laboratories, clinics, hospitals, physicians' offices, etc., as well as, health care providers, clinicians, or others who may deliver healthcare products and services to patients at the time of care.

The term "precise" as used herein is intended to include situations when reproducibility and repeatability of a characteristic may occur. The term "highly precise" as used herein is intended to include situations when a characteristic variation is small over many observations of the characteristic.

The term "processed" as used herein is intended to include materials that may have been altered from their original or unused state (in relation to a diagnostic system), such as, for example, combined or mixed with other materials, reagents, samples or a combination thereof.

The term "standardized quantity" as used herein is intended to include a known amount of a substance, where the amount might be mass, concentration, volume, number, or other physical quantity. The known amount may have been determined or traceable to a reference method, golden standard, National Institute of Standards and Technology (NIST) traceable standard or other. A known amount of a substance may also be determined by comparing an analytical result to a calibrator.

The term "starting temperature" as used herein is intended to include an initial temperature of the bottom of a cartridge the instant the cartridge is inserted into a diagnostic instrument.

Diagnostic System Overview

A diagnostic system can perform diagnostic tests in a convenient and efficient manner. Embodiments of a diagnostic system described herein can include a diagnostic instrument that is portable and contains all the necessary mechanical and electronic components to operate with minimal end-user input. Embodiments of a diagnostic instrument can be used with a cartridge that can store and carry all necessary reagents and materials for a particular diagnostic test to be run on the diagnostic instrument. Embodiments of a cartridge can be compact, self-contained and disposable, and can maintain the portable convenience of the diagnostic system. Each of the cartridge and diagnostic instrument will be described in further detail below.

In operation, a sample (also referred to as "biological sample") collected from a patient can be introduced into the cartridge. The cartridge can be introduced into the diagnostic instrument where the sample can be processed within the cartridge in cooperation with the components of the diagnostic instrument. Analysis can be completed and waste materials can be collected in the cartridge for disposal. Results can be provided to the user through an interface, such as a display screen.

The diagnostic systems described herein can provide the high precision and accuracy of results that can be obtained in a central laboratory, but with the convenience of performing the tests and receiving the results in a clinical point of care setting. With such a diagnostic system, health care providers can access clinically actionable and relevant results to discuss with patients and develop appropriate treatment options at the time and point of care. The portability of the diagnostic system provides flexibility in reaching patients and providing care in alternative locations other than a traditional physician's office or hospital setting, or a laboratory setting.

Figure 1A:
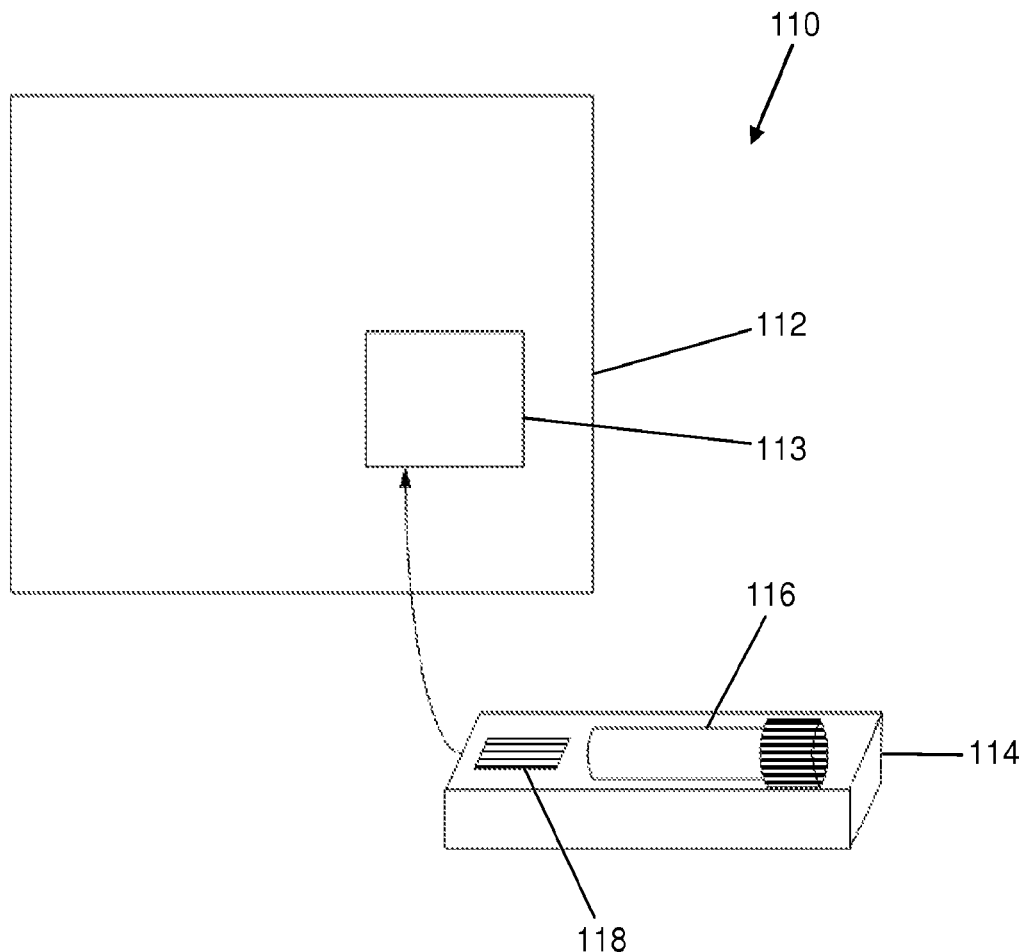
FIG. 1A is an illustration of an example diagnostic system.
Figure 1B:
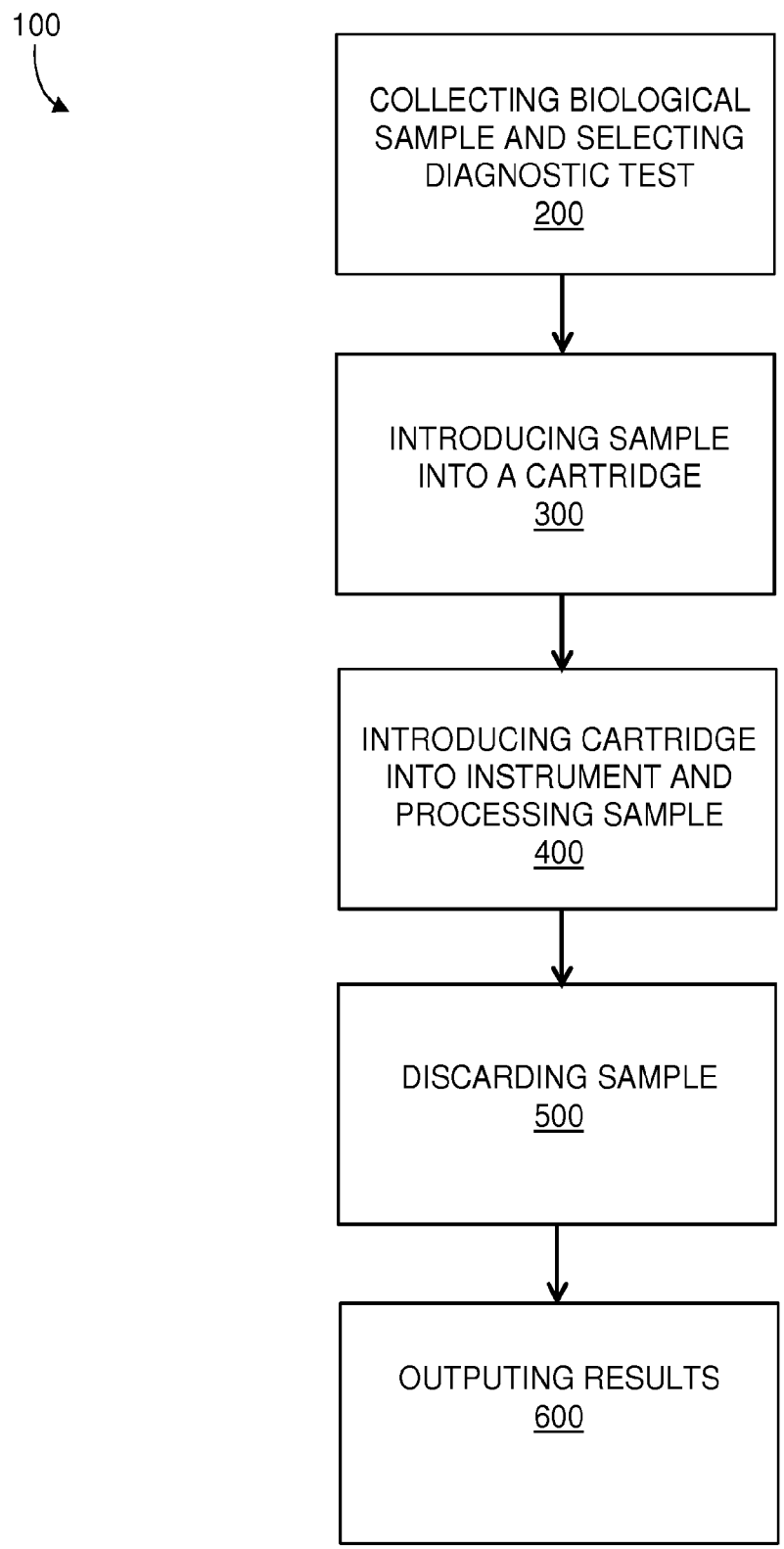
FIG. 1B is an overview illustration of an example method by which diagnostic system operates to perform a diagnostic test.

FIG. 1A is an illustration of an example diagnostic system. Various embodiments as described herein contemplate diagnostic systems that incorporate a diagnostic instrument 112 and a cartridge 114 to process diagnostic tests and to produce precise and accurate results in a clinical point of care setting. For example, FIG. 1B illustrates an example method 100 by which a diagnostic system may operate to perform a diagnostic test. Each step presented in method 100 can include additional or fewer methods and steps and sub-steps than those listed below.

Method 100 can include collecting a biological sample and selecting a diagnostic test in step 200.

Figure 2:
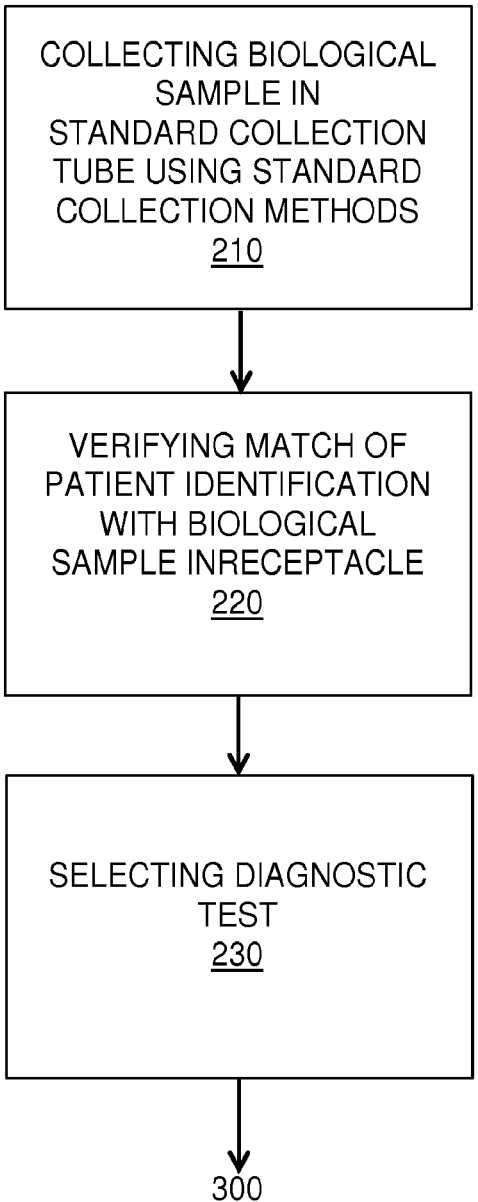
FIG. 2 is an overview illustration of an example method by which a biological sample is collected and an diagnostic test selected.

FIG. 2 illustrates the example method of step 200 (hereinafter "method 200") by which a biological sample is collected and a diagnostic test selected. FIG. 2 is an overview illustration of an example method 200 by which an example diagnostic system 100 may be used. As illustrated in FIG. 2, method 200 may include the step of collecting a biological sample 210. Example procedures for collecting a biological sample 210 may include any method available for gathering biological samples, such as venipuncture, cannulation, etc. The biological samples may be gathered into a vial, receptacle or tube, for example.

The step of collecting a biological sample 210 can also include verifying sample-patient identification. Verification can be confirmed by comparing sample identification with patient identification. For example, identification can be performed by comparing a label placed on a collection tube with a patient identification card or wrist band.

Method 200 can include collecting a biological sample in a standard receptacle using standard collection methods in step 210.

Method 200 can also include verifying sample collected with patient identification in step 220. Verification can be confirmed by comparing labels placed on the receptacle, such as a standard sample receptacle, containing information from the patient against a patient identification card or wrist band for example. Visual inspection by the user can be used to confirm identification. Optical machine-readable labels are often used to store such information on labels or ID cards. Information about the cartridge 114 and the test protocol to be applied (enabling the same diagnostic instrument to be able to process different types of cartridges) could be encoded on the barcode 118 along with the unique identifier for the specific cartridge, such as Lot Number and a Serial Number. The information can be scanned or read by a machine using known standard methods. Examples of optical machine-readable labels include standard UPC bar codes or Quick Response Codes (QR codes).

Method 200 can also include selecting the diagnostic or diagnostic test and verifying it is the correct test for the presently collected biological sample in step 230. As previously described, a cartridge 114 used in the diagnostic system 110 can contain all necessary reagents and materials for a particular diagnostic test. Each cartridge 114 can be labeled based on the diagnostic test contents contained within for proper identification. Here again visual inspection by the user or optical machine-readable labels can be used to verify the contents of cartridge for use with the biological sample collected. After verification, the sample can be introduced into the cartridge as described in step 300 of method 100.

Figure 3:
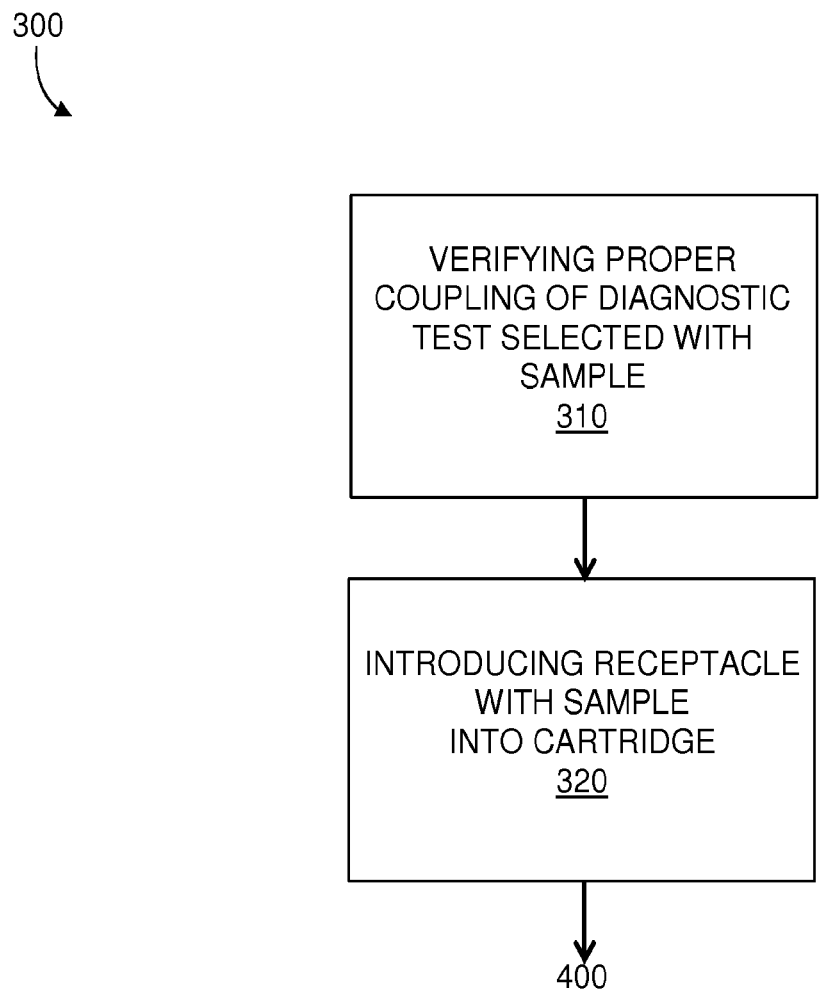
FIG. 3 is an overview illustration of an example method by which a sample is introduced into a cartridge.

Method 100 can include introducing a sample into a cartridge in step 300. FIG. 3 is an overview illustration of an example method of step 300 (hereinafter "method 300") by which a sample is introduced into a cartridge.

Method 300 can include verifying that the diagnostic test selected is properly coupled with the biological sample collected in step 310. For example, visual inspection by the user or optical machine-readable labels can also be used to verify that the cartridge with the appropriate designated diagnostic test is selected.

Method 300 can also include, after verification, the receptacle containing the sample can be introduced into the cartridge in step 320. Example procedures for introducing a sample into a cartridge 300 may include any method available for introducing a sample into a cartridge 114, such as inserting a blood vial into a preconfigured area of a cartridge 114. The cartridge can then be introduced into the diagnostic instrument for processing of the sample in the diagnostic system in step 400 of method 100.

Figure 4:
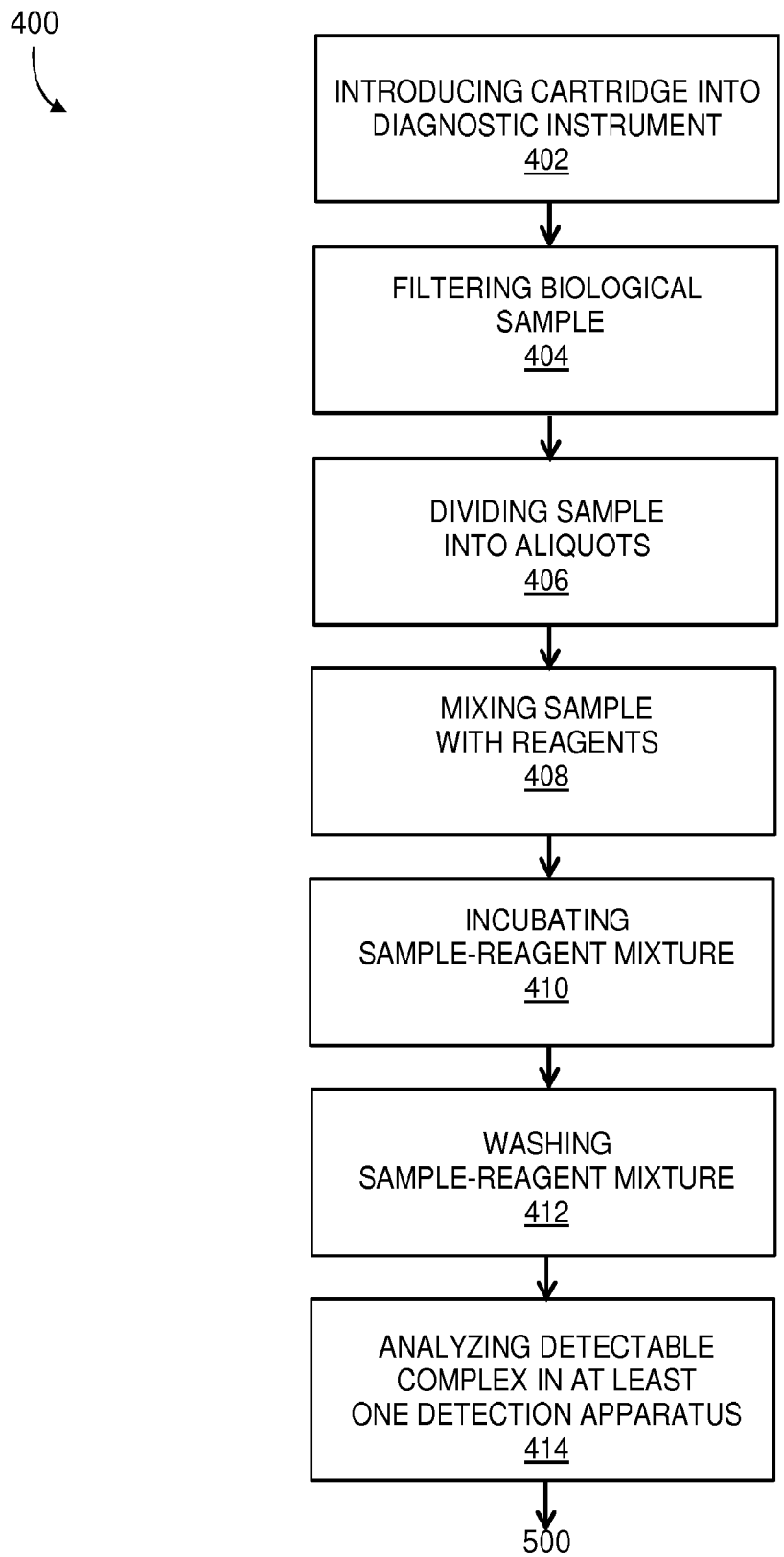
FIG. 4 is an overview illustration of an example method by which a biological sample is processed in a diagnostic system.

Method 100 can include introducing a cartridge into a diagnostic instrument and processing a sample within the cartridge in step 400. FIG. 4 is an overview illustration of an example method of step 400 (hereinafter "method 400") by which a biological sample is processed in a diagnostic system.

Method 400 can include introducing a cartridge into the diagnostic instrument in step 402. Example procedures for introducing a cartridge 114 into a diagnostic instrument 112 may include any method available for introducing a cartridge 114 into a diagnostic instrument 112, such as inserting a cartridge 114 into a preconfigured area of a diagnostic instrument 112. In embodiments discussed further below, the introducing a cartridge into diagnostic instrument 112 may be provided as illustrated in FIG. 1A, wherein cartridge 114 is configured to fit within a preconfigured section of instrument 112. For example, as illustrated in FIG. 1A, cartridge 114 may be inserted into slot 113 in instrument 112 of system 110. The cartridge 114 is shown as holding a standard receptacle 116, such as a blood collection tube, containing the sample. The cartridge 114 may also include an optical machine-readable label 118, such as a bar code, to assist in step 220. It is contemplated that the diagnostic instrument 112 and the cartridge 114 can be configured into various sizes and shapes depending on the overall design and model of the diagnostic system.

Figure 5A:
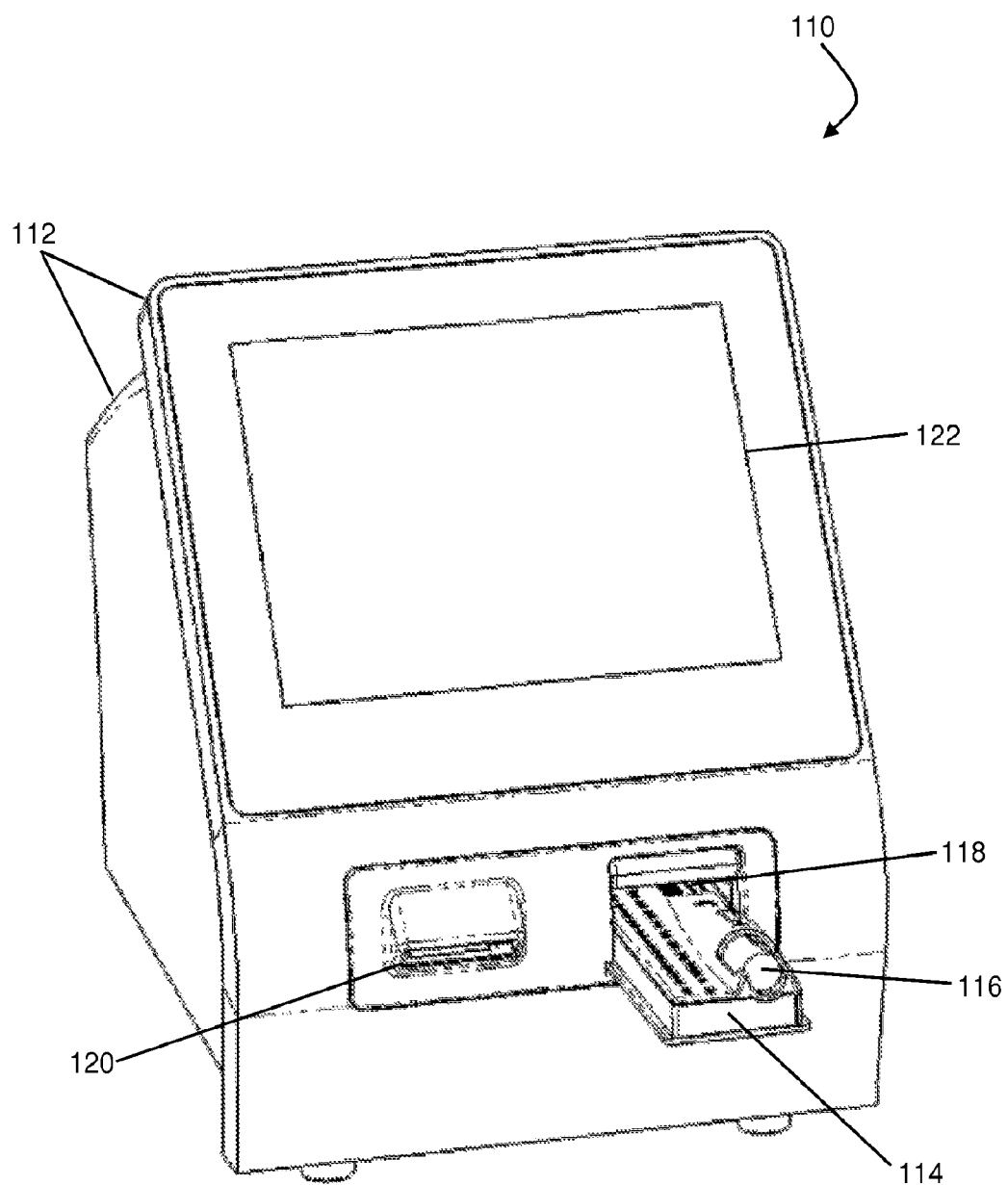
FIG. 5A is an illustration of a perspective view of an example diagnostic system.

For example, FIG. 5A, illustrates an embodiment of a diagnostic system 110 depicted as having a diagnostic instrument 112 and a cartridge 114. The diagnostic instrument 112 may include a user interface 122 in the form of a display screen for input and output of information and operation of the diagnostic system 110. It is contemplated that other user interfaces can be used for data input/output exchange with the diagnostic instrument 112. An external scanner 120 is also shown on the diagnostic instrument 112. The external scanner 120 can be used to read one or more of the optical machine-readable labels 118 previously discussed regarding step 220. The information gathered from the test scanner 120 can be stored and processed by the diagnostic instrument 112 for output with the diagnostic test results.

The cartridge 114 can be partially inserted into the diagnostic instrument 112 to allow for easier insertion and removal. The cartridge 114 may hold a receptacle 116, such as a blood collection tube, which may include an optical machine-readable label 118 on its surface.

Method 400 can also include filtering the biological sample. For example, filtering the sample may include separating plasma from a whole blood sample in step 404. In many diagnostic tests, it is preferred or necessary to use a particular form of a biological sample, such as using plasma instead of whole blood. It is contemplated that samples can be processed in numerous ways to achieve the desired form of the sample, for example, filtering the biological sample can be a useful method of obtaining the desired form of the sample. In particular, various embodiments of the diagnostic system 110 contemplate that a specialized filtration module can be used to separate plasma from a whole blood sample. Examples of suitable filtration modules and methods of filtration are described in co-pending International PCT Application No. PCT/US2012/067041 (hereinafter referred to as the "'041 PCT application"), herein incorporated by reference in its entirety.

Figure 6:
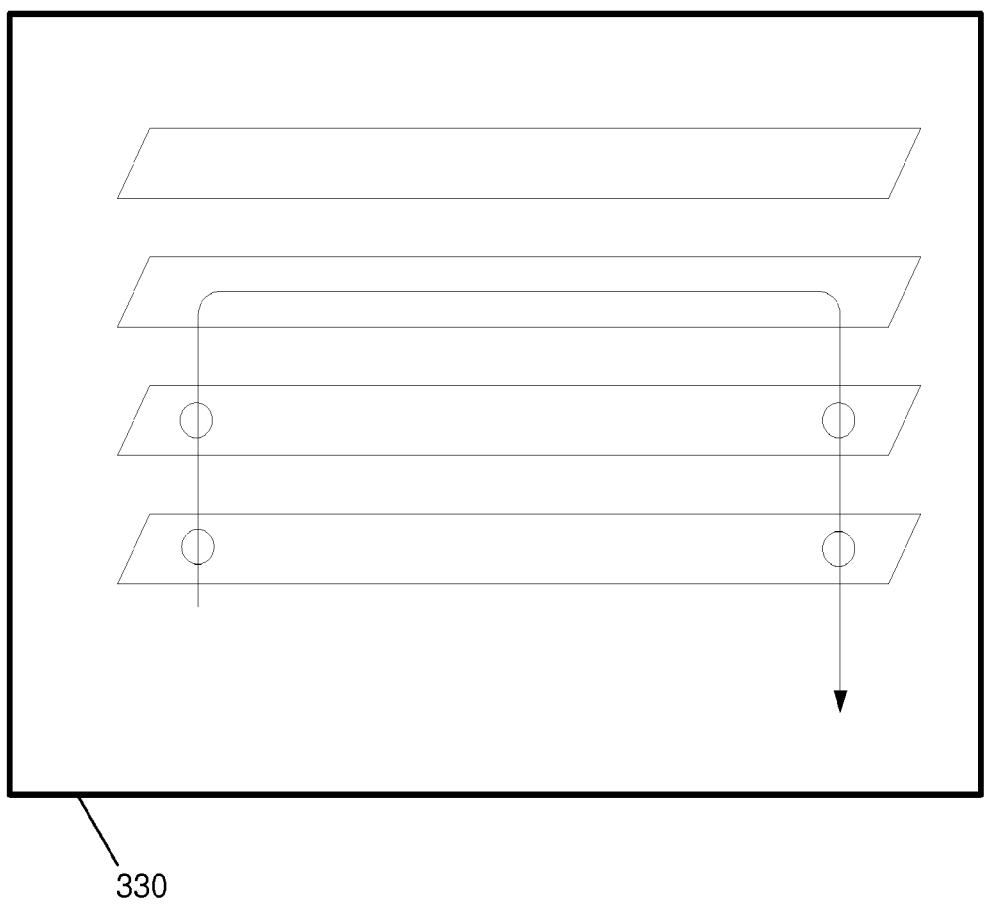
FIG. 6 is an illustration of an exploded view of an example filtration module used to filter a biological sample.

FIG. 6 illustrates an exploded view of an example multi-layered filtration module 330 that can be used to filter a biological sample. The filtration module 330 can utilize tangential flow filtration. Tangential flow filtration is advantageous for filtering liquids, such as blood, which contain a high proportion of small size particles. With sufficiently high wall shear, tangential flow can have high efficiency. Tangential flow filtration can also avoid the use of high surface area filter elements common with dead stop filtration.

It is contemplated that the filtration module 330 can be configured to have more than or less than the number of layers shown in FIG. 6, depending on the targeted filtrate, the design and configuration of the cartridge 114 and/or the diagnostic system 110. It is further contemplated that the shape of the filtration module 330 can be adapted to fit the design of the cartridge 114 within which it is situated.

Some embodiments of the diagnostic system 110 contemplate that a filtration module 330 can be situated within the cartridge 114. In such a cartridge 114, the plasma can be filtered from whole blood previously collected all while within the cartridge and without the need for centrifugation of the sample, for example. Once the sample is in the desired form for use, for example, as filtered plasma, the sample with the desired form can be collected in a storage area (not shown), such as a cache, on the cartridge 114, and then divided into volumes for further processing.

Method 400 can also include dividing the sample into aliquots in step 406. Aliquoting a sample into multiple volumes is a typical component of clinical testing, particularly when conducting a panel of assays or when conducting replicate measurements. Various embodiments of the diagnostic system 110 contemplate dividing the filtered sample or plasma into equal volumes within the cartridge 114 for further processing.

Figure 7:
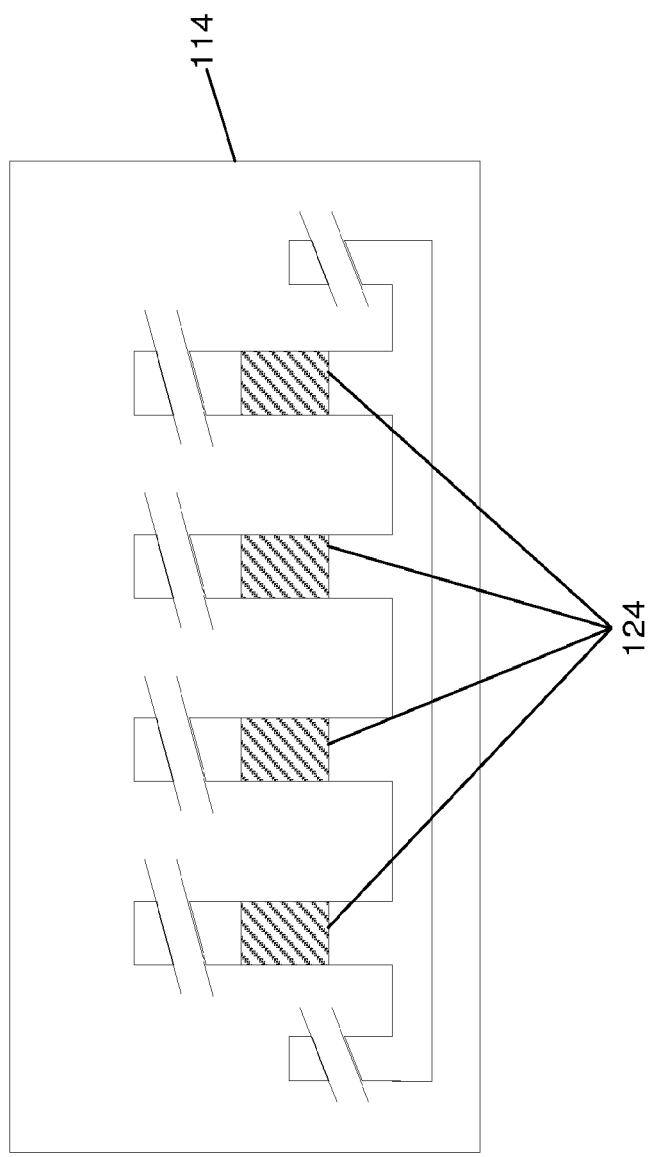
FIG. 7 is an illustration of an example of an aliquoted biological sample within a cartridge of a diagnostic system.

FIG. 7 is an illustration of an example sample (shaded) that has been divided into equal volumes within a portion of the cartridge 114. The method of dividing of the sample 124 into equal or non-equal volumes can involve the use of a pump (not shown) that may be a component of the diagnostic instrument 112 to assist in controlling the movement of the sample 124 into the aliquoted volumes within the cartridge 114. For example, the pump can create a vacuum within a portion of the cartridge 114 that can drive the motion of the sample 124 into the aliquoted volumes. If a diagnostic test requires equal divisions of the sample, the pump can also function to control the accuracy and precision of the aliquots to ensure that the divisions are equal for more accurate results of the diagnostic tests. In particular, in some embodiments, it may be important for the sample to be divided equally so that when the sample is mixed with reagents that have been premeasured prior to storage on the cartridge, there is an appropriate ratio of the sample to reagent when they are combined.

It is contemplated that a sensor (not shown), such as an optical sensor, can be used in conjunction with the pump to accurately position and divide the volumes within the cartridge 114. The sensor can be a component of the diagnostic instrument 112 and may be positioned in such a way that it can detect the location of a sample within the cartridge 114. One way the sensor may accomplish this, for example, may be to detect the transition between the presence of a fluid or sample as compared to the presence of air or the lack of presence of a fluid. Through standard electrical components that may be included in the diagnostic instrument 112, the feedback from the sensor can be translated into directions to tell the pump to stop or move the sample as needed.

Method 400 can also include mixing the sample with reagents stored in the cartridge in step 408. Various embodiments of the diagnostic system 110 contemplate that the cartridge 114 can hold and store all of the necessary reagents for a particular diagnostic test. The reagents may be selected and measured into appropriate amounts depending on the intended purpose or goal of the diagnostic test. Pre-measured volumes of reagents can be situated in various designated portions of a cartridge 114 for storage and use, such as in compartments, wells, and channels.

With the assistance of a pump, which may be the same or different from the other pumps discussed herein, the reagents can be mixed with the filtered sample or plasma within the cartridge 114. For example, aliquoted volumes of plasma can be moved into a portion of the cartridge 114 holding the reagents, such as mixing well or a channel, so that a sample-reagent mixture 125 is formed upon mixing. It is important that the sample and reagents are mixed thoroughly to create a homogeneous mixture to ensure proper processing of the diagnostic test.

Figure 8A:
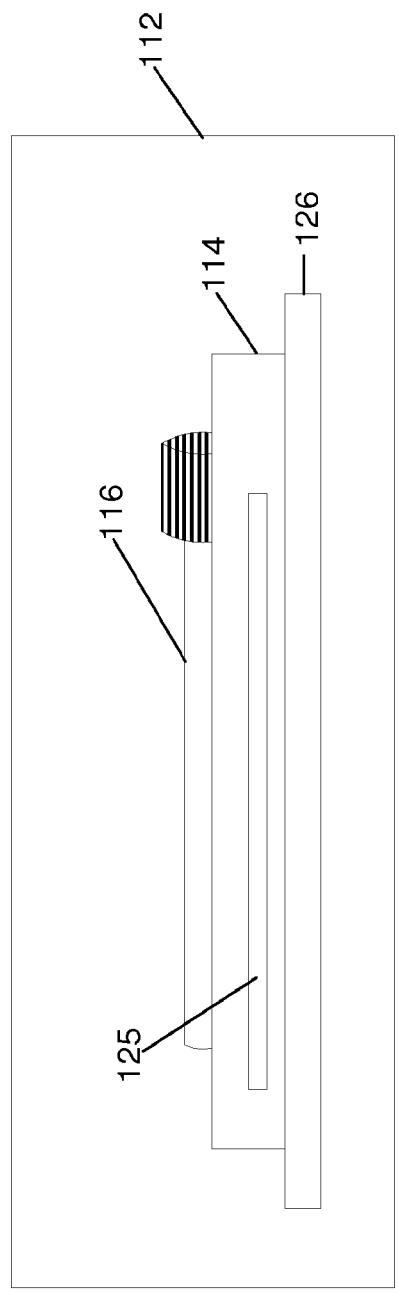
FIG. 8A is an illustration of an example cartridge positioned on an incubator within a diagnostic instrument of a diagnostic system.
Figure 8B:
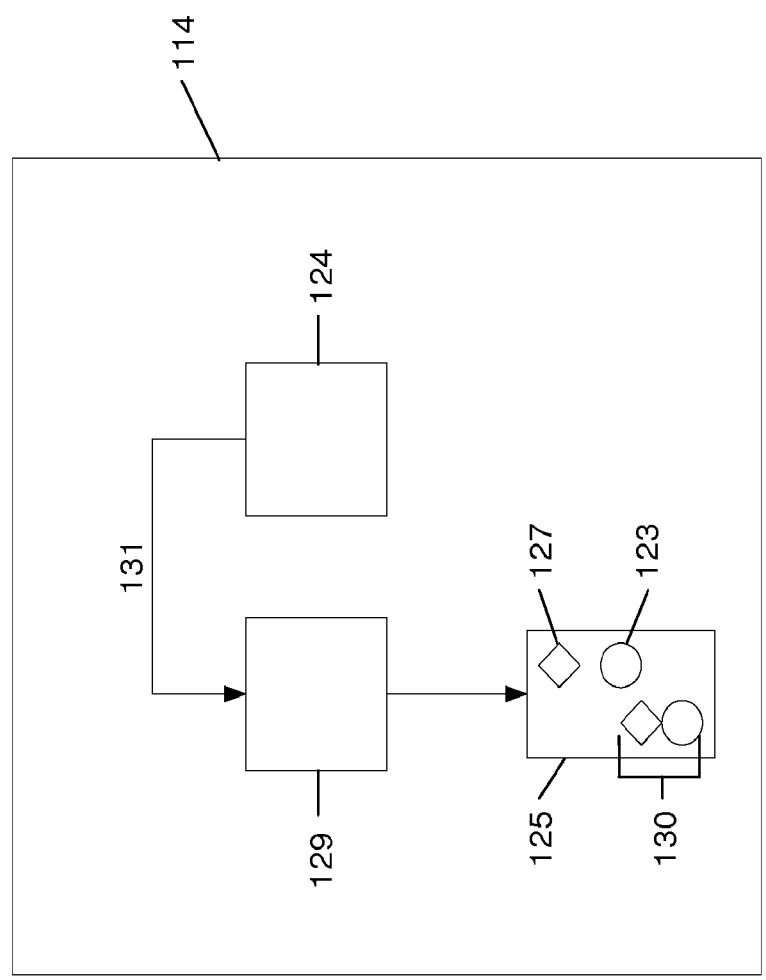
FIG. 8B is an illustration of example components used in mixing and washing the sample with reagents within a cartridge.

FIG. 8B is an illustration of example components used in mixing the testing sample with reagents within a cartridge. In FIG. 8B, the testing sample-reagent mixture 125 can optionally include a reagent-reacted sample, or "detectable complex" 130, unreacted sample 123, and unreacted reagent 127. The detectable complex 130 can form in the mixing step 408 and/or the incubating step 410. The detectable complex 130 can have a labeled analyte attached, directly or indirectly, to a solid phase medium, such as a bead. The detectable complex 130 may include a detection label that can be read for analysis of the diagnostic test. For example, an ECL detection unit in a diagnostic system 110 may detect information about a detectable complex 130 by detecting a detection unit attached to an analyte. The unreacted sample 123 and the unreacted reagent 127 remain in the sample-reagent mixture 125 until removed or reacted.

In embodiments herein, the sample 124 and reagents 129 are preferably mixed thoroughly to create a homogeneous sample-reagent mixture 125 for diagnostic test accuracy. A homogeneous mixture can refer to a sample-reagent mixture 125 that includes a maximum amount of analyte or antigen present in the sample or plasma has bound to the reagents with which the sample is mixed. The pump can assist in agitating the combined sample-reagent mixture 125 within the cartridge by creating back and forth movements to produce a homogeneous mixture.

Method 400 can also include incubating the sample-reagent mixture in step 410. Various embodiments of a diagnostic system 110 contemplate a method of incubating the sample-reagent mixture 125 once a homogeneous mixture is achieved. The sample-reagent mixture 125 can be incubated by an incubator apparatus that may be a component of the diagnostic instrument 112. FIG. 8A is an illustration of a cartridge 114 with a receptacle 116, positioned adjacent to an incubator 126 within a diagnostic instrument 112 (not shown) of a diagnostic system 110. The cartridge 114 can be positioned on the incubator apparatus of the diagnostic instrument 112 so that the bottom of the cartridge 114 is adjacent to the incubator 126.

Incubation of the sample-reagent mixture 125 can assist in providing optimal temperatures for the antigens and reagents to react and/or bind with one another. The incubator 126 can include one or more sensors that can provide feedback on the temperature of the sample-reagent mixture 125 to ensure that the temperature is maintained at a predetermined temperature, for example. In particular, an optimal temperature can range from about 25° C. to about 42° C., for example, at about 37° C. It is contemplated that the predetermined temperature can be adjusted depending on the diagnostic test being run, as well as the reagents and sample being used. The time of the incubation can also be adjusted depending on the diagnostic test, reagents and sample being used.

Method 400 can also include washing the sample-reagent mixture to expose a targeted analyte with a biomarker detection label in step 412. Various embodiments of the diagnostic system 110 contemplate a method of washing away the unbound sample or plasma and any unreacted reagents from the mixture to expose a detectable complex that may include a solid phase medium, such as a bead, to which a desired analyte or antigen can be attached directly or indirectly. A biomarker or detection label can be coupled to either the analyte or the solid phase medium, directly or indirectly.

The washing method described herein can be similar to a washing step in a common assay, where excess materials and samples are washed away to expose a detectable component that can be analyzed in a detection step. By washing away the sample and unbound reagents, the sensitivity and accuracy of the detection and analysis of the diagnostic test can be increased because, for example, background noise can be substantially reduced during the detection step, as compared to a sample that is not washed. It is contemplated that substantially all of the sample and unbound reagents are washed away, collected and contained within the cartridge so that substantially none of the sample is introduced into the detection apparatus of the diagnostic instrument, thereby reducing contamination between diagnostic tests.

In some embodiments, it is contemplated that the reagents can include a biomarker or detection label that can attach directly or indirectly to an analyte or a solid phase medium for detection and analysis. Thus, the resultant complex can have a labeled analyte of interest attached, directly or indirectly, to a solid phase medium. The detection label on the resultant complex can then be read such as, with a detection apparatus within the instrument 112 for analysis of a diagnostic test.

In some embodiments, it is contemplated that the reagent can include a solid phase medium. An example solid phase medium can have a paramagnetic quality so that a magnet can be used to hold the detectable complex in place while a rinsing fluid 131, such as a buffer, can be moved over the detectable complex for the washing step.

Figure 9:
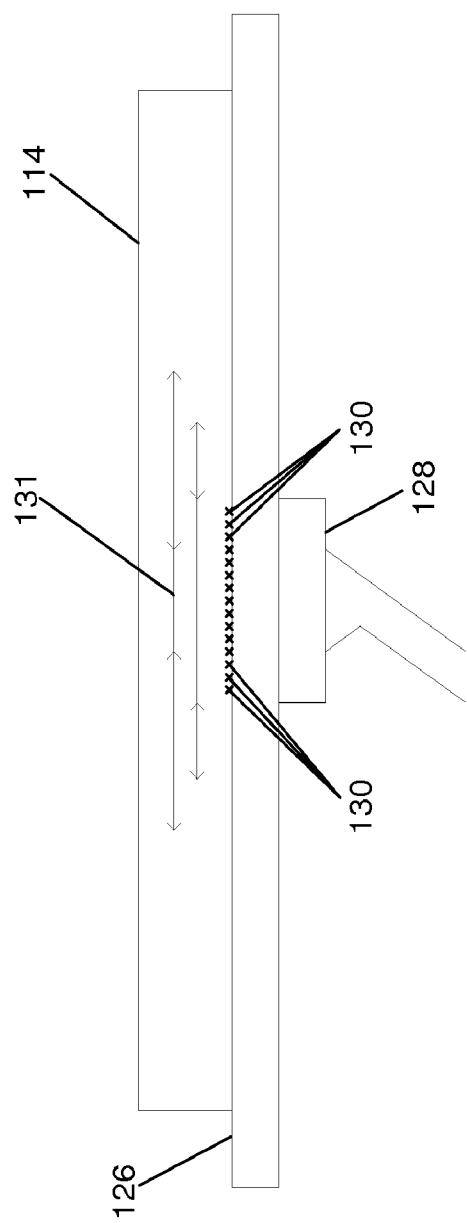
FIG. 9 is an illustration of an example magnet holding a detectable complex in place within a cartridge during a washing step.

For example, FIG. 9 illustrates an arrangement where a magnet 128 of the diagnostic instrument 112 can be used to hold a detectable complex 130 in place within a cartridge 114 while a rinsing fluid 131, such as a buffer, is allowed to wash over the detectable complex 130 to wash away the sample and unbound reagents. The magnet 128 can be a component of the diagnostic instrument 112 and can come in close proximity to a portion of the cartridge 114 where the mixture may be located. When the magnet 128 is positioned closely to the mixture in the cartridge 114, the detectable complex 130 may be held in place and the fluid can wash over the detectable complex 130.

The pump (not shown) of the diagnostic instrument 112 can play an integral role in washing away the unbound sample and unbound reagents by moving the sample-reagent mixture 125 within the cartridge 114 and introducing additional fluids stored on the cartridge 114 to assist in rinsing. The sensor (not shown) may also assist in displacing and positioning fluids within the cartridge 114 in order to wash away the sample and unbound reagents. It is also contemplated that during the washing of the sample-reagent mixture 125, incubation can continue.

Figure 10:
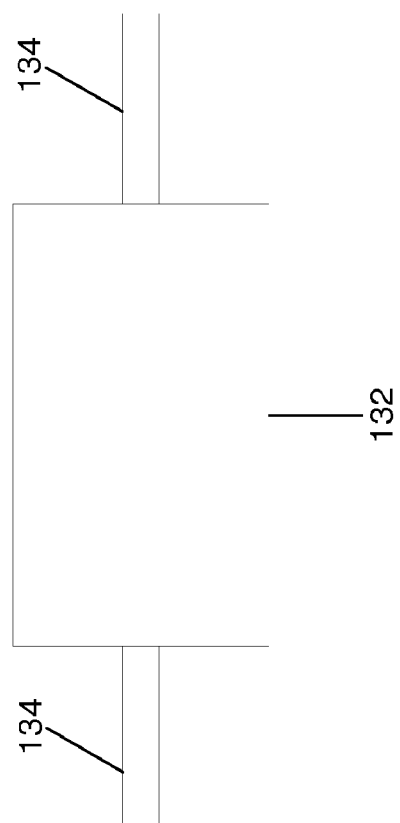
FIG. 10 is an illustration of an example detection apparatus.

Method 400 can also include detecting and/or analyzing the detectable complex in at least one detection apparatus in step 414. Various embodiments of the diagnostic system 110 contemplate a method of detecting and/or analyzing a detectable complex using a detection apparatus. FIG. 10 illustrates a detection apparatus 132 within a diagnostic instrument (not shown) connected to a pathway 134 that fluidically connects a cartridge (not shown) to the diagnostic instrument. A detectable complex prepared on the cartridge through processing steps, such as those previously discussed, can travel through the pathway 134 to the detection apparatus 132, which can be a component of the diagnostic instrument.

It is contemplated that there may be more than one detection apparatuses in a single diagnostic instrument or within a diagnostic system. The diagnostic systems can be configured to meet different desired detection and analytical goals and to accommodate the diagnostic test being run. The type of detection and analysis can also vary depending on many factors, including, but not limited to, the diagnostic test being run and the desired specificity and sensitivity for the component being detected. The detection apparatus can use many different types of detection including electrochemiluminescence, chemiluminescence, [expand list of possible detection methods the system can use].

For example, electrochemiluminescence (ECL) is a quick and sensitive technique. ECL has been described in detail in the following U.S. Pat. Nos. 5,714,089, 6,165,729, 6,316,607, 6,312,896, 6,808,939, 6,881,589, 6,881,536, and 7,553,448, each of which is herein incorporated by reference in its entirety. It is contemplated that a label is an ECL label that may be bound to a magnetic bead, and the presence of the bound labeled molecule is detected by ECL. ECL signals are generated by a redox reaction between an ECL label with a substrate. In certain embodiments the electrochemiluminescence label is a ruthenium-containing reagent. One example of a suitable ECL label is Tris(bypyridine)ruthenium(II) [Ru(bipy)3]2+, also referred to as TAG. In certain other embodiments, the substrate is tripropylamine (TPA). Some advantages of the method of using ECL-based assays is they are rapid and sensitive. It is contemplated that for other detection methods, the detection label and reagents can be varied as necessary to satisfy the requirements of the detection method.

Figure 11:
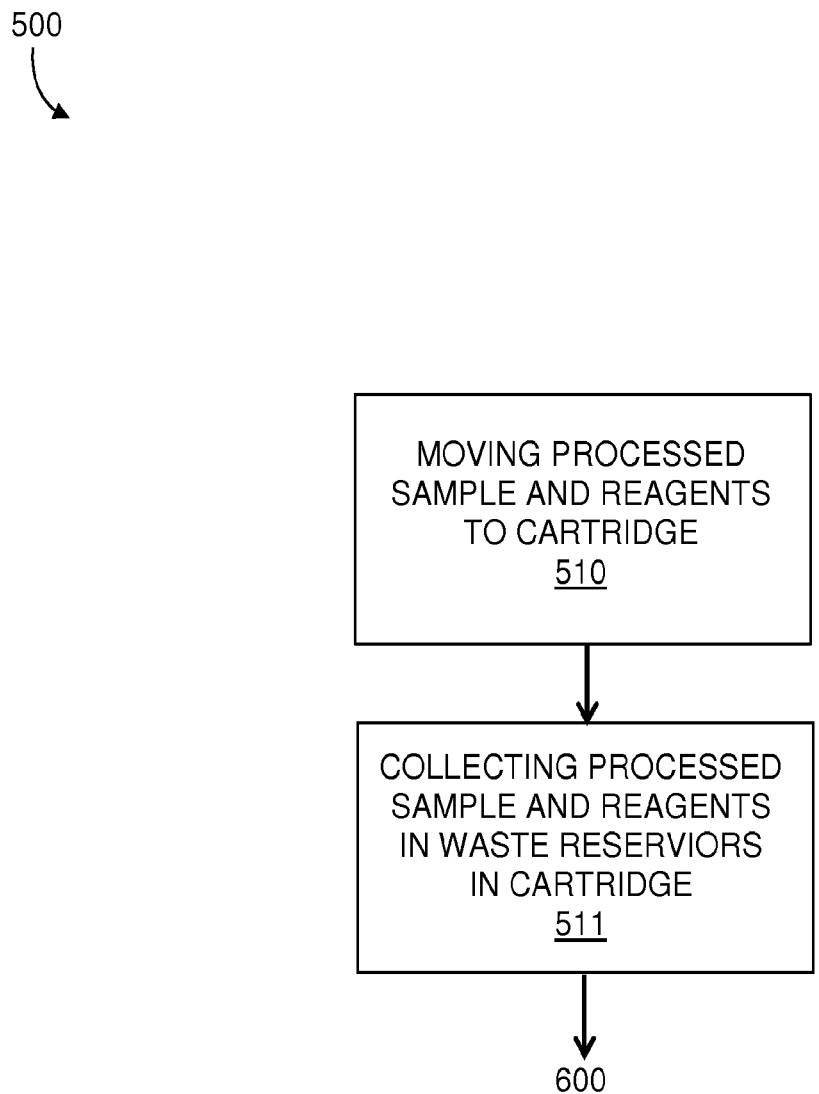
FIG. 11 is an overview illustration of an example method by which a processed biological sample is discarded in a diagnostic system.

Method 100 can include discarding a sample in step 500. FIG. 11 is an overview illustration of an example method of step 500 (hereinafter "method 500") by which a biological sample after it has been processed is discarded into a cartridge 114 in a diagnostic system 110. Method 500 can include discarding the processed filtered plasma or sample and reagents along with detectable complexes 130 used in the diagnostic test into the cartridge 114 of the diagnostic instrument in step 510. Various embodiments of the diagnostic system 110 contemplate that once the diagnostic test has been completed, substantially all of the sample along with substantially all of reagents that were originally stored on the cartridge 114, processed and analyzed, are returned to the cartridge 114 for disposal.

Figure 12:
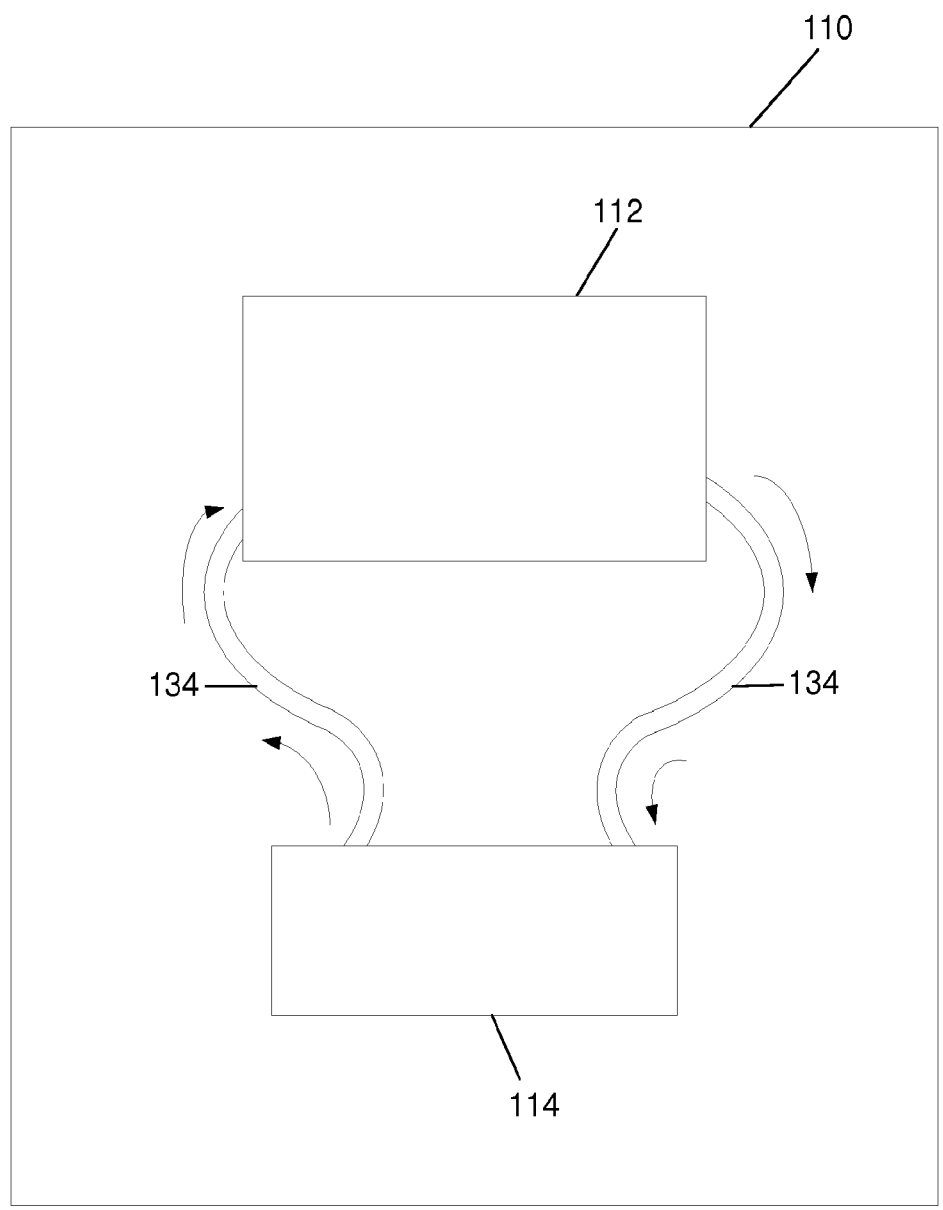
FIG. 12 is an illustration of an example fluidic pathway within a diagnostic system having a substantially single direction of flow.

FIG. 12 is an illustration of a diagnostic system 110 having a diagnostic instrument 112 fluidically connected to a cartridge 114 by way of fluidic pathways 134. The arrows indicate an example of a substantially single direction of flow for the materials travelling through the diagnostic system 110. In some embodiments, the disposal of processed materials can be returned to the cartridge without cross-contamination between tests run on the diagnostic instrument due to a substantially single direction of flow that the fluids in the diagnostic test follow.

Figure 13:
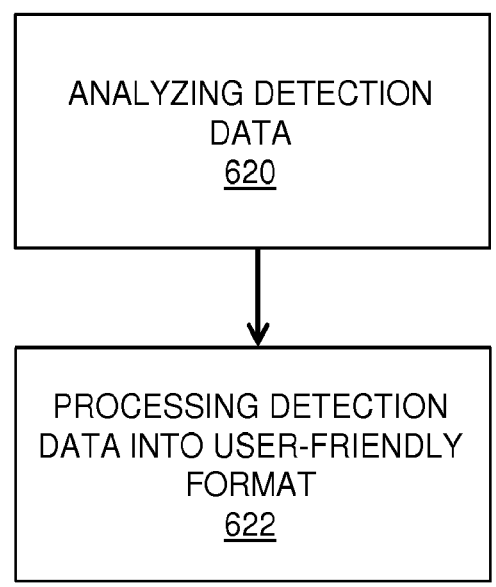
FIG. 13 is an overview illustration of an example method by which a diagnostic system outputs results from a diagnostic test.

Method 100 can include outputting results in step 600. FIG. 13 is an overview illustration of an example method of step 600 (hereinafter "method 600") by which a diagnostic system outputs results from a diagnostic test. Method 600 can include analyzing detection data received from a detection apparatus of the diagnostic instrument 112 in step 620. Further discussion regarding analyzing detection data can be found below.

Method 600 can also include processing the detection data into a user-friendly format that can be interfaced by a user in step 622. For example, the data can be formatted and outputted on a display screen or be printed on a paper receipt, or both. Alternatively, the detection data may be outputted via any output device or portion of the diagnostic instrument 112, as discussed further above and below.

Cartridge Overview

The diagnostic system 110 can include a cartridge 114 that is self-contained and compact, as previously shown in FIG. 5A. Various embodiments of the diagnostic system 110 contemplate that a sample can be introduced into a cartridge 114 where the sample can be processed within the cartridge 114 during a diagnostic test. The cartridge 114 can be introduced into a diagnostic instrument 112 having the mechanical and electrical components necessary to run the diagnostic test and detect results using detection technology contained within the diagnostic instrument 112. The components and methods associated with the cartridge 114 will be described in more detail in the following disclosure.

Example embodiments of cartridge 114 can be configured to perform steps of an example diagnostic test completely within a diagnostic system 110 in conjunction with a diagnostic instrument 112 of the diagnostic system 110. For example, a cartridge 114 can be loaded and configured to store and hold all necessary reagents and materials necessary to perform a particular diagnostic test, such as an assay. The cartridge 114 can also be configured to store the reagents and materials in separate compartments, and can provide air-tight and liquid-tight seals that can assist in diagnostic test functions, which will be described in further detail herein.

The cartridge 114 can also be configured to receive a biological sample for processing and analysis during the diagnostic test. Through cooperative mechanisms with the diagnostic instrument 112, a biological sample can be prepared and processed completely within the diagnostic system 110 without the requirement for end-user input, once the sample is collected and introduced into the cartridge 114. The cooperative mechanisms between the cartridge and the diagnostic instrument 112 of the diagnostic system also will be described in further detail in the following disclosure.

The cartridge 114 can also be configured to retain and collect substantially all of the processed sample, reagents, and materials used in the diagnostic test for disposal once a diagnostic test is completed. By collecting processed sample-reagents and materials for disposal, an added convenience of being self-contained is provided, along with a prevention and/or reduction of cross-over or contamination between different diagnostic tests run on the same diagnostic instrument. The mechanisms involved in collecting the processed sample-reagents and materials also will be described in further detail in the following disclosure.

Cartridge Industrial Design

Examples of industrial designs of certain embodiments of a cartridge 114 are disclosed in co-pending U.S. Design application Nos. 29/420,961 and 29/420,967, both filed on May 15, 2012, and each of which is herein incorporated by reference in its entirety. Images contained within those disclosures prescribe example diagnostic cartridges of the diagnostic system 110, and designs thereof, which relay both the function and form, and the connection between the product, the user, and the environment. Such images merely represent example cartridges 114, diagnostic systems 110, and the present disclosure is not limited to these particular designs.

Cartridge Body and Components

Figure 14A:
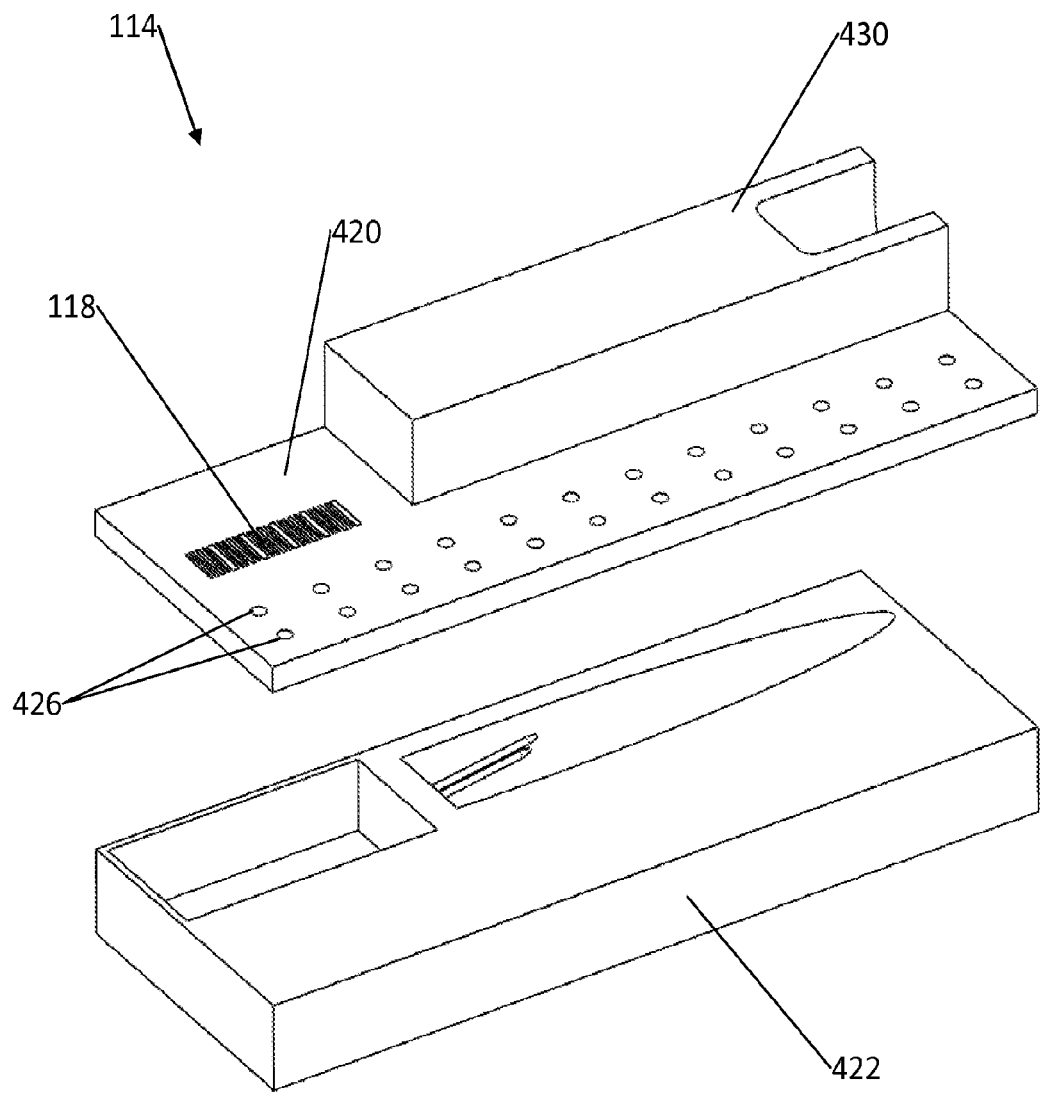
FIG. 14A is an illustration of an exploded perspective view of an example body and a cover of a cartridge.

FIG. 14A is an illustration of an exploded perspective view of an example body and cover of a cartridge 114 of a diagnostic system 110. Various embodiments of a cartridge 114 contemplate having a cover 420 and a body 422 that fit together to form the cartridge 114.

Figure 14B:
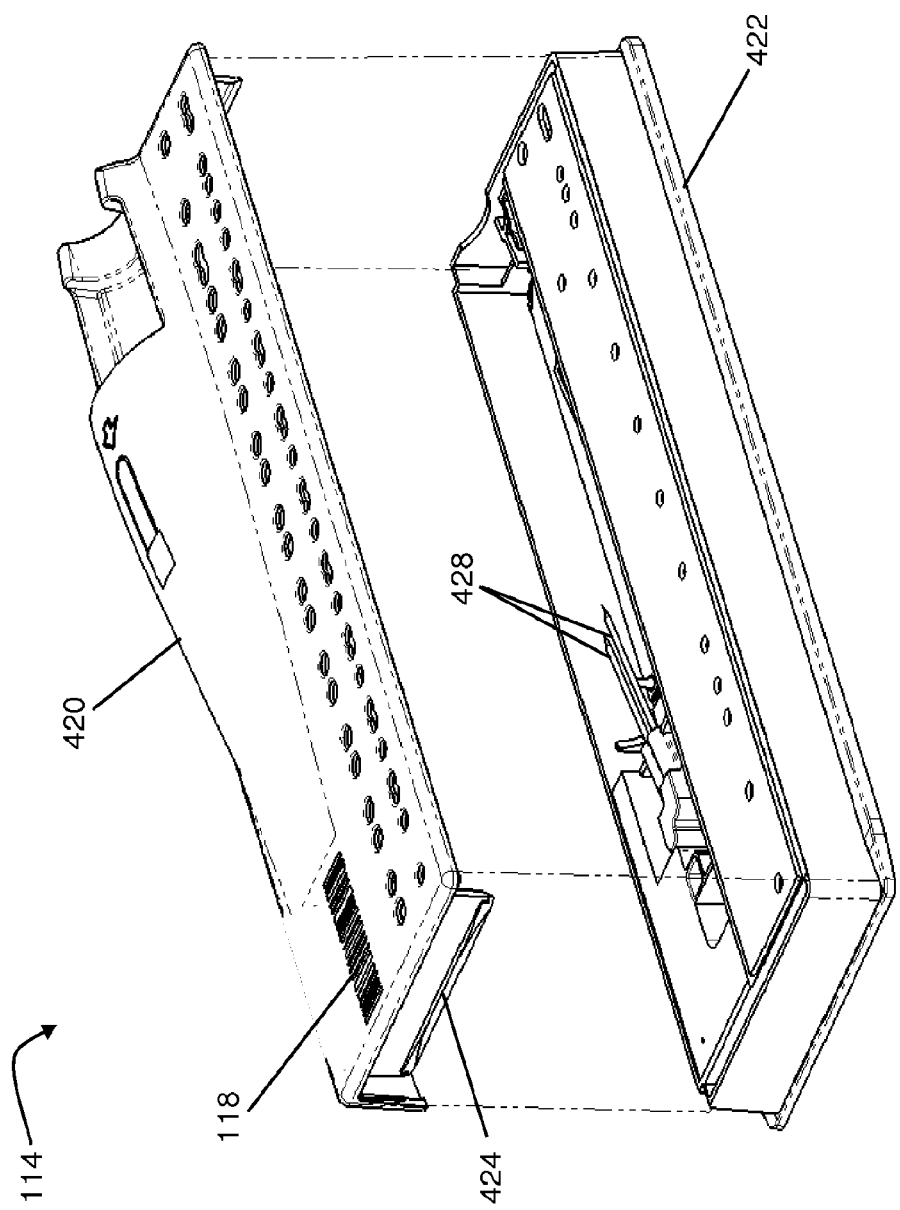
FIG. 14B is an illustration of an exploded perspective view of an example cartridge.

FIG. 14B is an illustration of an exploded perspective view of an example cartridge 114 of a diagnostic system 110. The cover 420 can have at least one retaining feature 424 to facilitate connecting the cover 420 to the body 422. For example, the at least one retaining feature 424 can include a snap fit, friction fit, etc., on one or both ends of the cover 420.

Various embodiments of the cartridge 114 contemplate that the cover 420 can have a flat area to make contact with and cover the body 422 to effectively cover and protect the components of the body 422. No liquid or air tight seals are needed between the cover 420 and the rest of the cartridge 114. An optical machine-readable label 118 can be positioned on a portion of the flat area of the cover 420 for identification as previously discussed and as part of one of many failsafe mechanisms incorporated into the diagnostic system 110.

Some embodiments of the cover 420 contemplate being formed with at least two rows of a plurality of perforations 426, for example, as shown in FIG. 14A. The at least two rows of a plurality of perforations 426 can be formed in areas of the cover 420 through which at least one probe 712, 714 of a diagnostic instrument can interface with internal portions of the cartridge 114. One of the rows of the plurality of perforations, or first probe perforations 426a, can interface with a first probe (see first probe 712 in FIG. 27, for example), and the other row of perforations, waste probe perforations 426b, can interface with a waste probe 714 of the diagnostic instrument 112. The waste probe perforations 426b can be sized larger than the first probe to provide a greater tolerance in position variation of the waste probe (see waste probe 714 of FIG. 27) as it interfaces with the cartridge 114. For example, waste probe perforations may be 0.015 in. larger in diameter (0.095 in. vs. 0.080 in.) than the waste probe.

The cover 420 may also make the cartridge 114 be more unitary and possibly more aesthetically pleasing. The cover 420 can be injected molded out of a variety of materials, such as structural polymers like, poly(methyl methacrylate) (PMMA), polycarbonate (PC), and polycarbonate/Acrylonitrile butadiene styrene (PC/ABS) blends. It is contemplated that other materials may be used to form the cover 420 depending on desired specifications and manufacturing goals for the disposable cartridge 114, such as, for example, a polycarbonate/acrylonitrile butadiene styrene such as GE Cycoloy HC 1204HF, a polycarbonate such as Sabic Lexan™ (PC) EXL9134, polyethylene terephthalate (PET), polypropylene (PP), polyvinyl chloride (PVC), and Teflon™. It is contemplated that other known methods of forming the cover 420 can be employed, including, but not limited to casting, rotational molding, thermoforming, compression molding, and injection molding.

With reference to FIG. 14B, functionally, the cover 420 can be shaped or molded to assist in guiding a sample receptacle (not shown) into the cartridge 114. The sample receptacle, such as a commercially available VACUTAINER® sample receptacle, can be guided toward at least one needle 428 integrated into the body 422 such that the sample in the sample receptacle may be accessed by the cartridge 114 via the at least one needle 428 and used during processing of a diagnostic test. The cover 420 also serves to protect an operator from the sharp point of the at least one needle 428.

Various embodiments of the cartridge 114 can also have structural and functional features useful for filtration of a sample, assay processing regions (each region also referred to as a cartridge assay replicate (CAR)), probe wash areas and draw reservoirs filled with ECL read buffer (can also be referred to as a read buffer filled reagent handling station (RHS)), and a pump storage fluid filled RHS. Certain embodiments contemplate that some components of the cartridge 114 can be attached to the body 422, including, for example, the cover 420, a filtration module 330, at least one needle 428, and multiple seals (see, e.g., FIGS. 14B, 18, and 21B).

The body 422 can be injection molded out of a variety of materials such as polymers that may have a low moisture vapor transmission rate (MVTR). For example, Topas grade AS 5013 (MVTR=0.03 g mm/(m$^2$ day) at 23° C. and 85% RH), Topas grade 8007 (MVTR=0.025 g mm/(m$^2$ day) at 23° C. and 85% RH), or Zeonor 1420R (MVTR=0.029 g mm/(m$^2$ day) at 25° C. and 90% RH) may be used to form the body 422 of the cartridge 114. It is contemplated that other materials may be used to form the body 422 depending on desired specifications and manufacturing goals for the disposable cartridge 114, including, but not limited to, high density polyethylene (HPDE), polypropylene (PP), and polyethylene terephthalate (PET). It is contemplated that other known methods of forming the body 422 can be employed, including, but not limited to, casting, rotational molding, thermoforming, pressure forming, compression molding, and injection molding.

The body 422 also can have at least one notch 454 (see, e.g., FIG. 21A) on at least one side of the body 422 to assist in motion control of the cartridge 114 by holding the cartridge 114 in place during operation within the diagnostic instrument 112. Other features can be incorporated into the cartridge body 422 that coordinate with components of the diagnostic instrument 112 to ensure proper spatial arrangement and function between the cartridge 114 and diagnostic instrument 112 within the diagnostic system 110. The cartridge 114 may have several additional features and components in relation to the functional aspect of each feature and component, which may include features disclosed below.

Figure 15A:
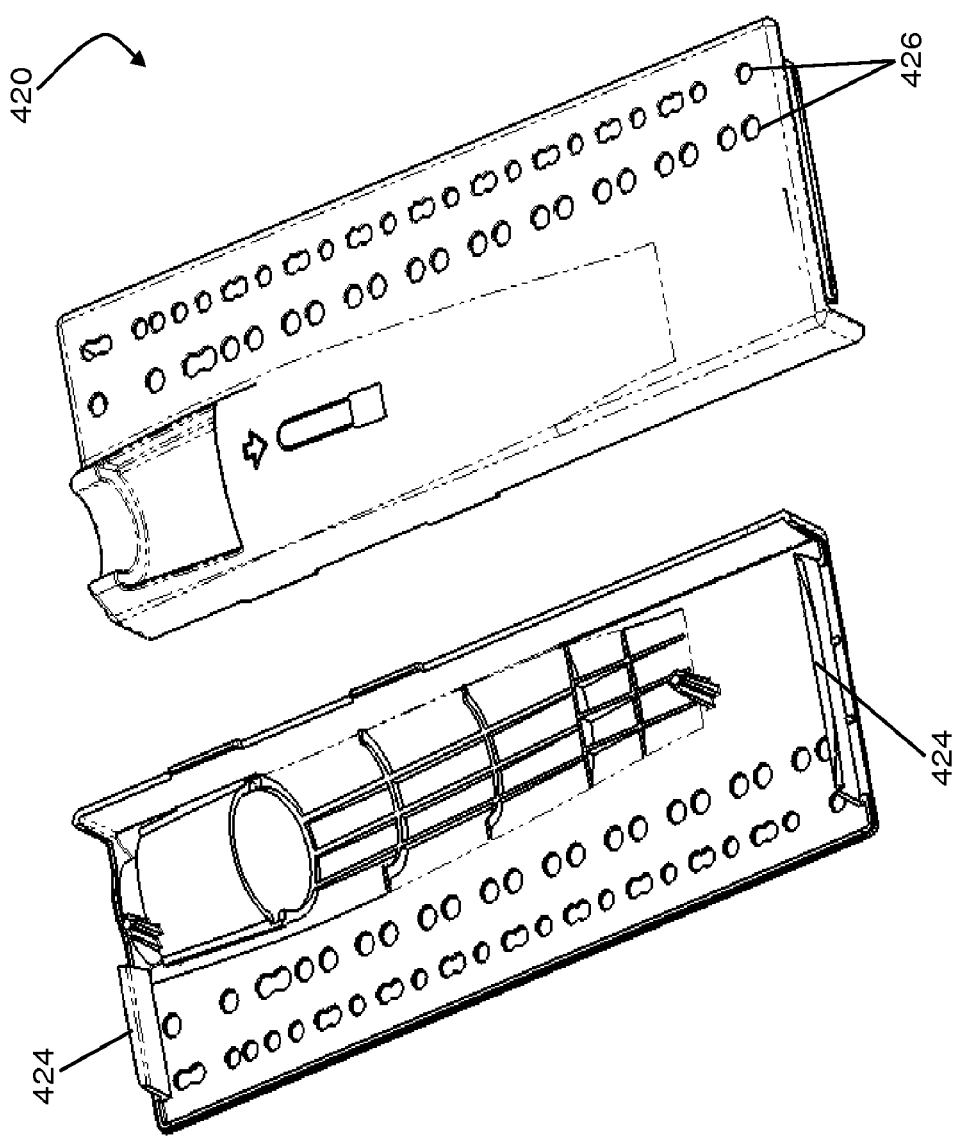
FIG. 15A is an illustration of a perspective view of an example of the front and back of a cartridge cover.
Figure 15B:
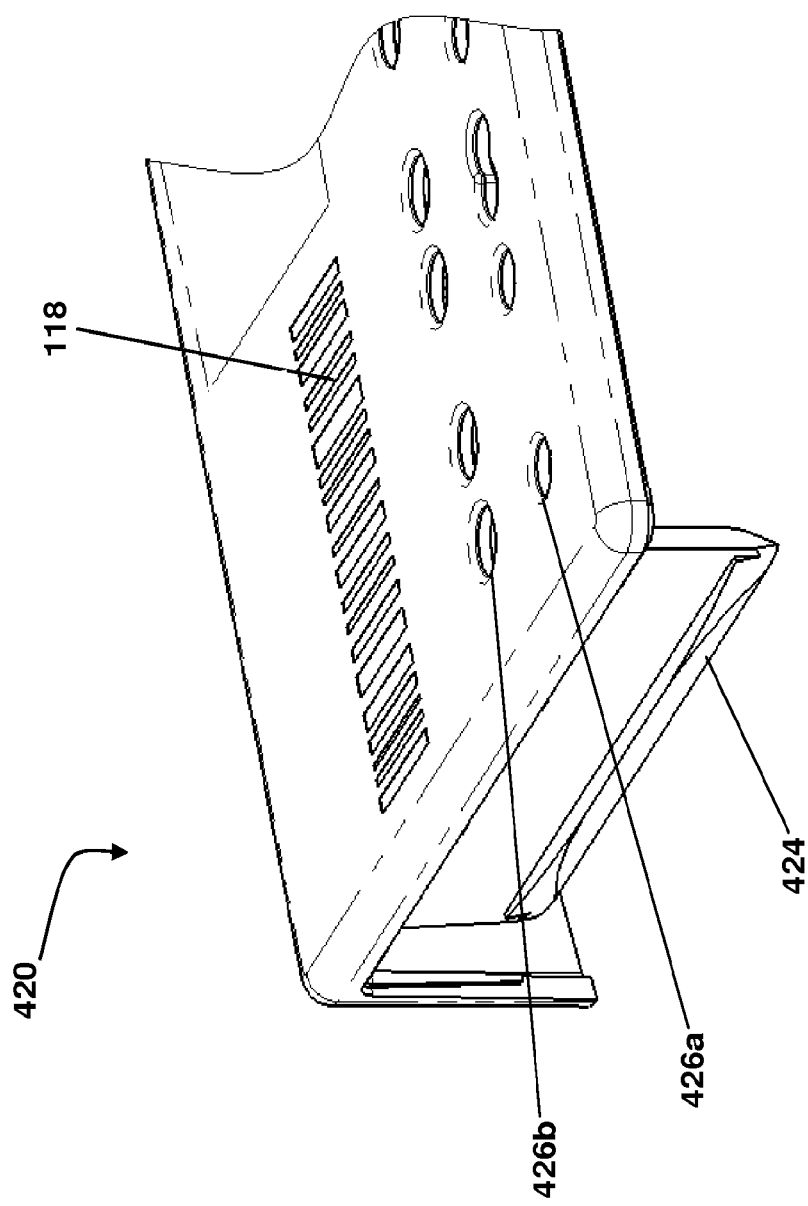
FIG. 15B is an illustration of a perspective view of an example of a portion of a cartridge cover.

FIGS. 15A and 15B illustrate the at least one retaining feature 424, and also show examples of a cover 420. By providing the at least one retaining feature 424, a pull on each end of the cover 420 can be provided to ensure a secure fit to the body 422. It is contemplated that additional retaining features known in the art can be designed and included in the cover 420 to assist in securing the cover 420 to the body 422, including, but not limited to, press fits, tabs, spring locks, and over-molded magnets.

Sample Receptacle Mount

The cartridge 114 depicted in FIG. 14A, illustrates an example of a cartridge 114 having a sample receptacle mount 430 in a diagnostic system 110. Various embodiments of a cartridge 114 of the diagnostic system 110 contemplate having a sample receptacle mount 430 and having a sample receptacle 116. For example, the body 422 can be configured with a sample receptacle mount 430 to accommodate the mounting of an industry standard sample receptacle (i.e., VACUTAINER®), or similar sample receptacle 116, which can connect to a fluidic pathway of the diagnostic system 110. As previously described, the sample can be a biological sample such as blood, plasma, urine or sputum.

Figure 16A:
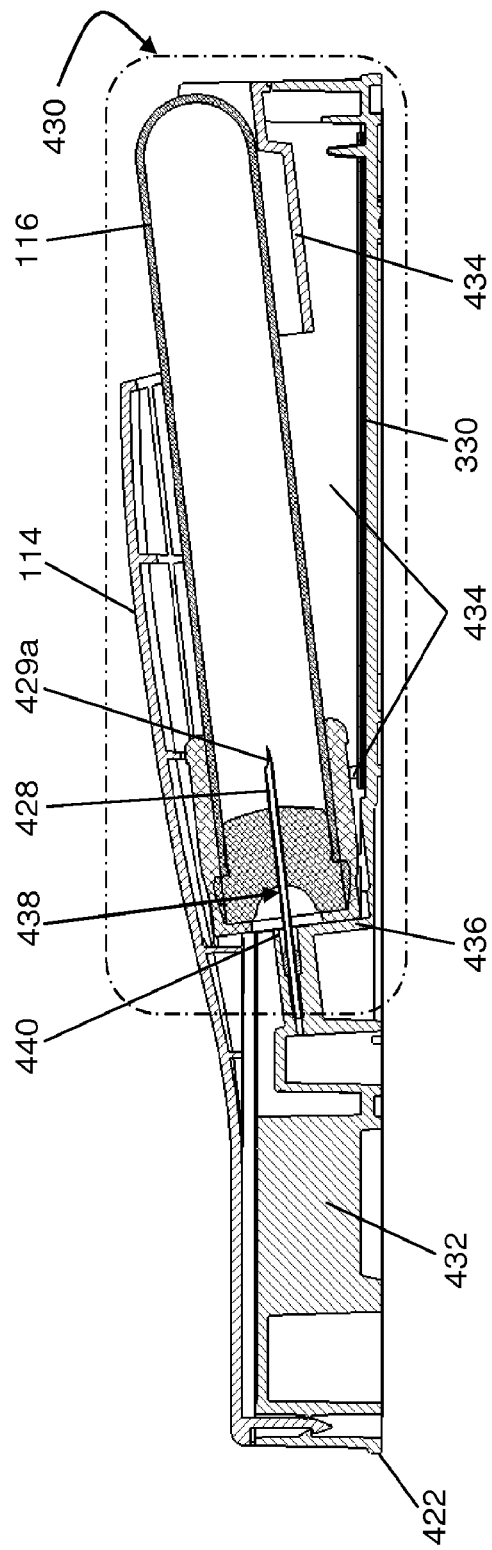
FIG. 16A is an illustration of a cross-section of an example sample receptacle mount in an example cartridge.

FIG. 16A illustrates a cross-section of an embodiment of a sample receptacle mount 430 within a cartridge 114 of a diagnostic system 110. As illustrated, sample receptacle mount 430 may have a framework 432 that can be formed as part of the body 422 out of injection molded or machined plastic or other material(s) of appropriate physical and chemical characteristics, as the remaining portions of the body 422.

The framework 432 can incorporate structures or be shaped or configured to form supports 434 and guide features 434 to mount and hold a sample receptacle 116 at an angle between, for example, the horizontal and 45° from horizontal, which facilitates extraction of a predetermined amount of sample from the sample receptacle 116. The framework 432 can incorporate structures that form supports 434 and guide features 434 to mount and hold a sample receptacle 116 at an angle between, for example, the horizontal and 45° from horizontal, which facilitates extraction of a predetermined minimum amount of blood from said tube.

In some embodiments, the configuration of the sample receptacle mount 430 can increase the efficiency of extraction of the sample from the sample receptacle 116. By increasing the efficiency of extraction, a majority or substantially all of the sample can be accessible for extraction from the sample receptacle 116. Additionally, the configuration of the sample collection tube mount 430 can allow for the sample collection tube 116 to maintain a low profile within the cartridge 114.

In certain embodiments, the sample receptacle mount 430 can be configured to hold a sample receptacle 116 to increase sample extraction from the tube. For example, in certain embodiments, the sample receptacle mount 430 has an angle sufficient to facilitate sample extraction from the sample receptacle 116, wherein the angle can range from about less than 90° to about 0° from the horizontal. In other embodiments, the angle can range from about 45° to 0° from the horizontal. In other embodiments, the angle can range from less than 90° to about 45°, from about 45° to about 0°, from about 30° to about 0°, from about 20° to about 0°, from about 10° to about 0°, from about 7° to about 0°, from about 45° to about 20, from about 45° to about 15°, from about 45° to about 10°, from about 35° to about 15°, from about 35° to about 10°, from about 35° to about 5°, from about 25° to about 15°, from about 25° to about 10°, from about 25° to about 5°, from about 15° to about 10°, from about 15° to about 5°, from about 10° to about 5°, from about 10° to about 7°, or from about 7° to about 5°, or from about 5° to about 0° from the horizontal. In still other embodiments, the angle can be about 45°, about 30°, about 25°, about 20°, about 15°, about 10°, about 8°, about 7°, about 6°, about 5°, about 0° from the horizontal. By way of a non-limiting example, the position at 7° can minimize the profile of the blood tube-cartridge arrangement, preserving space in the diagnostic instrument 112 and cartridge 114.

The configurations of the cartridge 114 can be adapted or designed to accommodate different diagnostic system and instrument configurations depending on use, function and manufacturing needs and costs. A cartridge with a configuration having a smaller angle, such as about 7°, can be advantageous over existing designs which have a sample receptacle arranged at an angle of less than 90° but that still may require tipping or additional maneuvering to get the sample out, resulting in excess dead volume due to the larger angle from the horizontal (e.g., the higher the angle from the horizontal, the more dead volume in the sample receptacle).

In some embodiments, the sample receptacle mount 430 can also be configured to hold a sample receptacle 116 at a desired angle using ribs or other support structures 434 which constrain the tube axially along the desired angle. Certain features may be incorporated into the sample receptacle mount 430 to prevent or inhibit removal of a sample receptacle 116 after insertion into the sample receptacle mount 430, such as, for example, a shroud or tang (not depicted) may be molded in the cover 420 that inhibits gripping the sample receptacle 116.

In certain embodiments, the sample receptacle mount 430 can be configured to provide an indication that the sample receptacle 116 is properly seated with the sample receptacle mount 430. For example, a wall 436 may be formed from the framework 432 and molded into the body 422 to provide a positive stop for the sample receptacle 116, as well as provide feedback that the sample receptacle 116 in fully inserted. Other indications may include, for example, a user feeling or hearing a slight pop or click after the sample collection tube 116 reaches a designated location in the sample receptacle mount 430. Alternatively, confirmation may be provided by looking through a viewing window in the cover 420 for visual confirmation. The framework 432 can also include features that can prevent, inhibit and/or deter removal of a sample receptacle 116 from the cartridge 114 after insertion onto the framework 432, such as a tang (not depicted).

In certain embodiments, the sample receptacle mount 430 can be configured to guide a sample receptacle 116 onto at least one needle 428 to establish fluidic communication, such as, for example, with a diagnostic instrument 112. The guide features or supports 434 can also facilitate the piercing of the desired portion of the sample receptacle's septum 438 by physically constraining the radial motion of the sample receptacle 116. The at least one needle 428 can be mounted on the framework 432 to facilitate its insertion into the septum 438 of a sample receptacle 116, which would thereby facilitate, establish and maintain the fluidic connections between the at least one needle 428 and a diagnostic instrument 112. In some embodiments, the sample receptacle mount 430 can have a first needle 428a and a second needle 428b, such as that depicted in FIG. 16B.

The sample receptacle mount 430 can also be formed in part within the cover 420, where a portion of the cover 420, may be shaped, for example, as a domed region, and can assist in guiding the sample receptacle 116 into place. The cover 420 can also assist in securing the sample receptacle 116 in place after insertion.

Figure 16B:
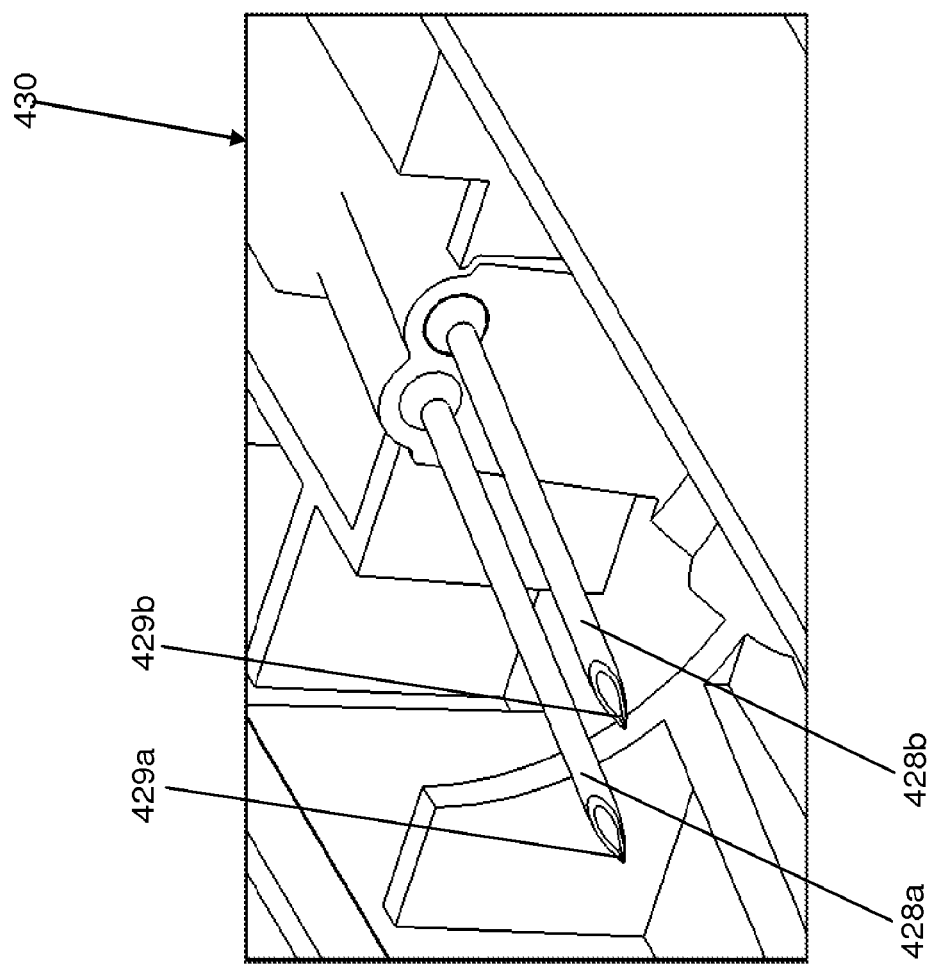
FIG. 16B is an illustration of a perspective view of a portion of an example sample receptacle mount.

FIG. 16B is an illustration of a portion of an example of a sample receptacle mount 430 having two needles 428a, 428b. The needles 428a, 428b can be mounted to the framework 432 to establish connections between fluidic pathways (not shown) molded into the framework 432 and the fluidic channels formed from the needles 428a, 428b. Alternately, the fluidic pathways may be formed out of tubes or a separate material from the framework 432. In such a configuration, the fluidic pathways may connect to the needles 428a, 428b directly or indirectly, and the framework 432 can be designed to support the mounting of the needles 428a, 428b as they are connected to the fluidic pathways.

The two-needle configuration can be designed to prevent or minimize undesired communication of gasses between the needles 428a, 428b during sample extraction. The sample receptacle mount 430 can be configured to use a pressure differential between the inside of a sample receptacle 116 and fluidic pathways as the means to extract sample from the sample receptacle 116. Alternatively, any number of needles and corresponding fluidic pathways may be contemplated to provide more or less fluidic pathways. Additionally, the gauge of the needles may be chosen to increase or decrease fluid flow.

To facilitate a secure connection, the first and second needles 428a, 428b can be incorporated into the sample receptacle mount 430 by being fitted into at least one recess (not shown) per needle configured to receive one end of a designated needle. The first and second needles 428a, 428b can be permanently attached to the framework 432 so that the exterior surface of the first and second needles 428a, 428b are sealed airtight to the framework 432 by means of an adhesive, gasket or other seal, or by insert molding the needles into the framework 432. Examples of suitable adhesives include, but are not limited to, an epoxy resin, acrylic cements, silicones, LOCTITE™ 3924, and hot-melt adhesive. The adhesive may be set with a heat treatment or cured with a UV light. It is contemplated that the at least one recess may be designed to snuggly fit the at least one needle 428 so that the need for an adhesive is not necessary. It is further contemplated that any combination of the fitted size of the recess and an adhesive may be used to secure the needle 428.

In an embodiment where two needles are present, the first needle 428a can be mounted such that its terminal end 429a is physically separated from, and not below, the terminal end 429b of the second needle 428b within the sample receptacle 116 such that air introduced into the tube to pressurize the tube does not communicate with the second needle 428b causing an unwanted reduction in the flow of sample out of the sample receptacle 116. Thus, the terminal end of the second needle 429b may be located below the terminal end of the first needle 429a, as the first needle is mounted to the framework 432 on a level above that of the second needle 428b. In other words, the first needle 428a protrudes outward from the framework farther than the second needle 428b protrudes from the framework.

In the case of a positively pressurized sample receptacle 116 (e.g., a tube with higher than atmospheric pressure therein), the needle 428a by which a pressure differential is established can be mounted in a position where it will not easily communicate gasses with the needle 428b used for sample extraction assuming they are separate entities. Thus, the needle 428a by which a pressure differential is established is mounted such that its terminal end 429a is physically separated from, and not below, the terminal end 429b of the needle 428b used for sample extraction.

Alternatively, in the case of a negatively pressurized sample receptacle 116 (e.g., a tube with lower than atmospheric pressure therein), the needle 428a by through which sample is extracted can be mounted in a position where it will not easily communicate gasses with the needle 428b used for pressure normalization assuming they are separate entities. Thus, the needle 428a by which sample is extracted can be mounted such that its terminal end 429a is physically separated from, and not above, the terminal end 429b of the needle 428b used for pressure normalization.

Various embodiments of the diagnostic system 110 contemplate a method of extracting a sample from a sample receptacle 116 within a cartridge 114. The method can include positioning the sample receptacle 116 containing a sample on a cartridge 114. The method can also include introducing gas into one of the two needles 428a, 428b causing a displacement of the sample by the gas. The displaced sample can flow from the sample receptacle 116 through the second needle 428b. The second needle 428b can be in fluidic communication with a filtration module 330 and its components.

A lubricant, such as, for example, a silicone oil, poly(p-xyllene) polymers, parylene, or polyglycol, may be applied to the exterior surface of the needles 428a, 428b during assembly to reduce the force needed to pierce the septum 438 of a sample receptacle 116. Needles that are pre-coated with a lubricant can also be used. The lubricant may also be provided to assist in properly seating the sample receptacle 116 on the needles 428a, 428b, as well as, facilitating needle movement to pierce the septum 438 fully and in the desired location on the septum 438. For example, it can be desirable to pierce the septum 438 in the center to ensure full contact with the fluid contained within the sample receptacle 116.

In embodiments where the configuration includes only one needle 428, rotation and viewing of a sample receptacle 116 surface is permitted for reading of data from the sample receptacle 116 surface after the sample receptacle 116 is inserted into the cartridge 114. In such an embodiment, the framework 432 may include features that allow manual or automated turning of the sample receptacle 116 to permit automated reading of text or other content (for example, barcodes 118 or patient identification labels) off the sample receptacle 116.

Filtration Module

Various embodiments of the diagnostic system 110 contemplate having a filtration module 330, such as that previously described in method 400 and depicted in FIG. 6, in fluidic communication with the sample receptacle 116 and a cartridge 114. Various embodiments of the diagnostic system 110 also contemplate a method of filtering a sample with the filtration module 330 within a cartridge 114. Examples of suitable filtration modules and methods of filtration are described in the '253 application and the '041 PCT application. The filtration module 330 can be designed such that it maintains the compact size and self-contained nature of the cartridge 114.

FIG. 6, as previously described, illustrates an exploded view of an example of a multi-layered filtration module 330 that can be used to filter a biological sample, by passing the biological sample along an example flow path through the filtration module for the biological sample to be filtered. It is contemplated that the filtration module 330 can be configured to have more than or less than the number of layers shown in FIG. 6 depending on the targeted filtrate, the design, and the configuration of the cartridge 114 and/or the configuration of the diagnostic system 110.

Figure 17:
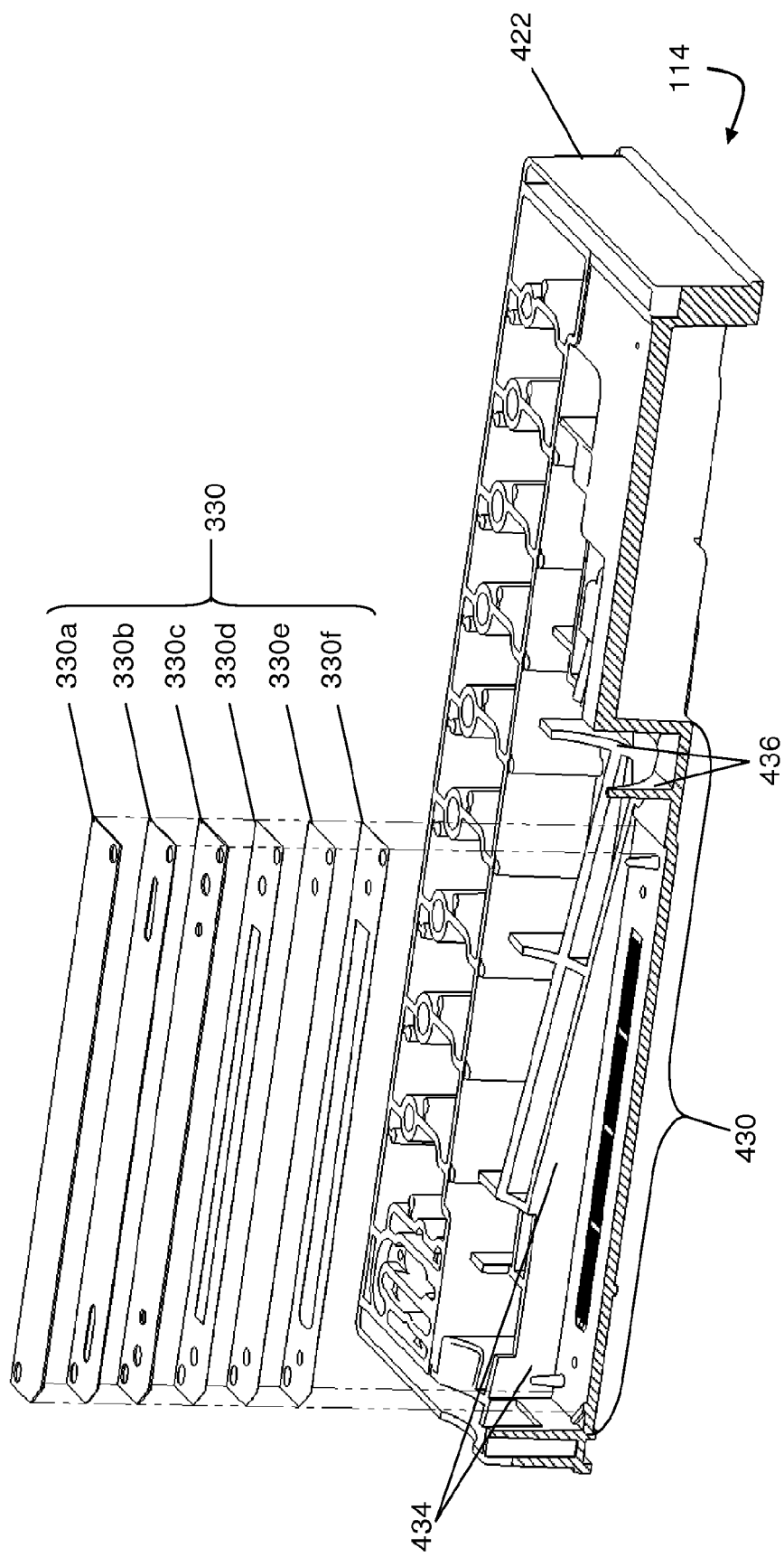
FIG. 17 is an illustration of a cross-section of an exploded view of an example filtration module and a cartridge.

It is further contemplated that the shape of the filtration module 330 can be adapted to fit the design of the cartridge 114 within which it is situated. For example, FIG. 17 provides an exploded view of an example of a multi-layered filtration module 330 depicting the arrangement of the filtration module 330 with a sample receptacle mount 430 within a cartridge 114. The multiple layers that can comprise the filtration module are provided as one embodiment and each are layered 330a-330f in FIG. 17. The multiple layers can be configured to stack together to form the filtration module 330 and can be positioned within the cartridge 114. Additional features, such as guides and supports (not shown), can be used to assist in proper positioning of the filtration module 330 within the cartridge 114. In some embodiments, the filtration module 330 can be positioned below the sample receptacle mount 430.

The filtration module 330 is advantageous because it can be contained within the cartridge 114 and can yield filtered plasma, for example, that is of the same quality as that of centrifuged plasma, meaning that the filtered plasma has the same composition as centrifuged plasma. Additionally, the filtration module 330 can yield a sufficient amount of plasma for the clinical laboratory analysis. The maximum amount of plasma, such as plasma in blood, available from blood is the difference in total volume and hematocrit.

For example, with 4 mL of blood from a patient with 40% hematocrit, the total amount of plasma is 2.4 mL. Typical of all filtration methods, the entire plasma content of blood is not recoverable. The amount of plasma collected relative to the total available plasma is the plasma recovery efficiency. For example, if 1.2 mL of plasma from the available 2.4 mL is collected, then the plasma recovery efficiency is 50%. The filtration module 330 can achieve a plasma recovery efficiency that can match that of centrifugation, as well as an amount sufficient enough to run multiple diagnostic tests within a single cartridge 114.

Reagent Handling Stations (RHS)

Figure 18:
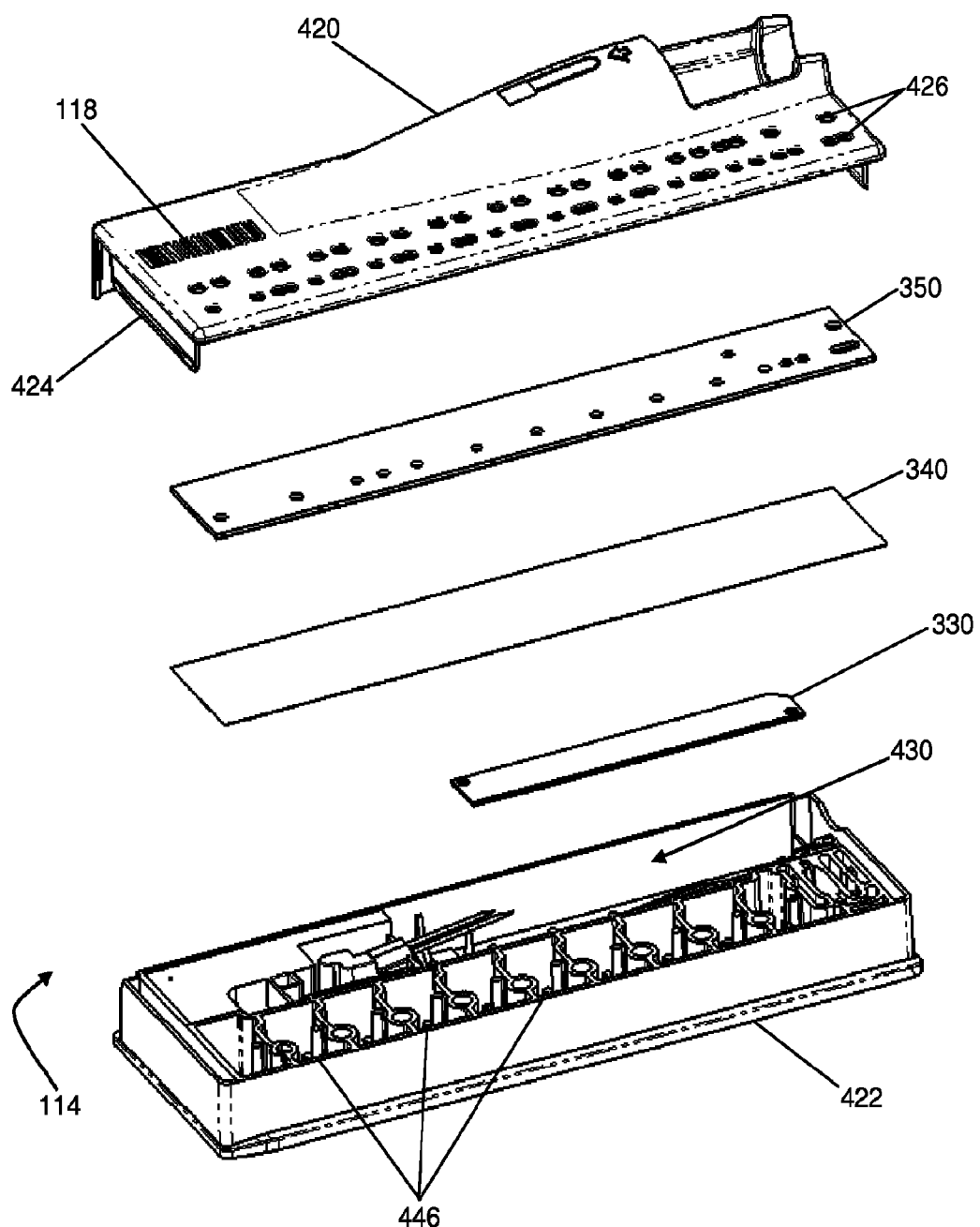
FIG. 18 is an illustration of an exploded perspective view of an example cartridge.

FIG. 18 is an exploded perspective view of an embodiment of a cartridge 114 depicting the cover 420 and the body 422 and multiple layers and seals that will be described in detail in the following sections. FIG. 18 also depicts an embodiment of a unique liquid storage well, or a reagent handling station (RHS) 446, which can be used for the storage of reagents, as a wash station for components, such as probes, and as a waste containment area 1015 on the cartridge 114 during processing of a diagnostic test. Various embodiments of the cartridge 114 contemplate having at least one RHS 446 within the body 422 of the cartridge 114.

Figure 19A:
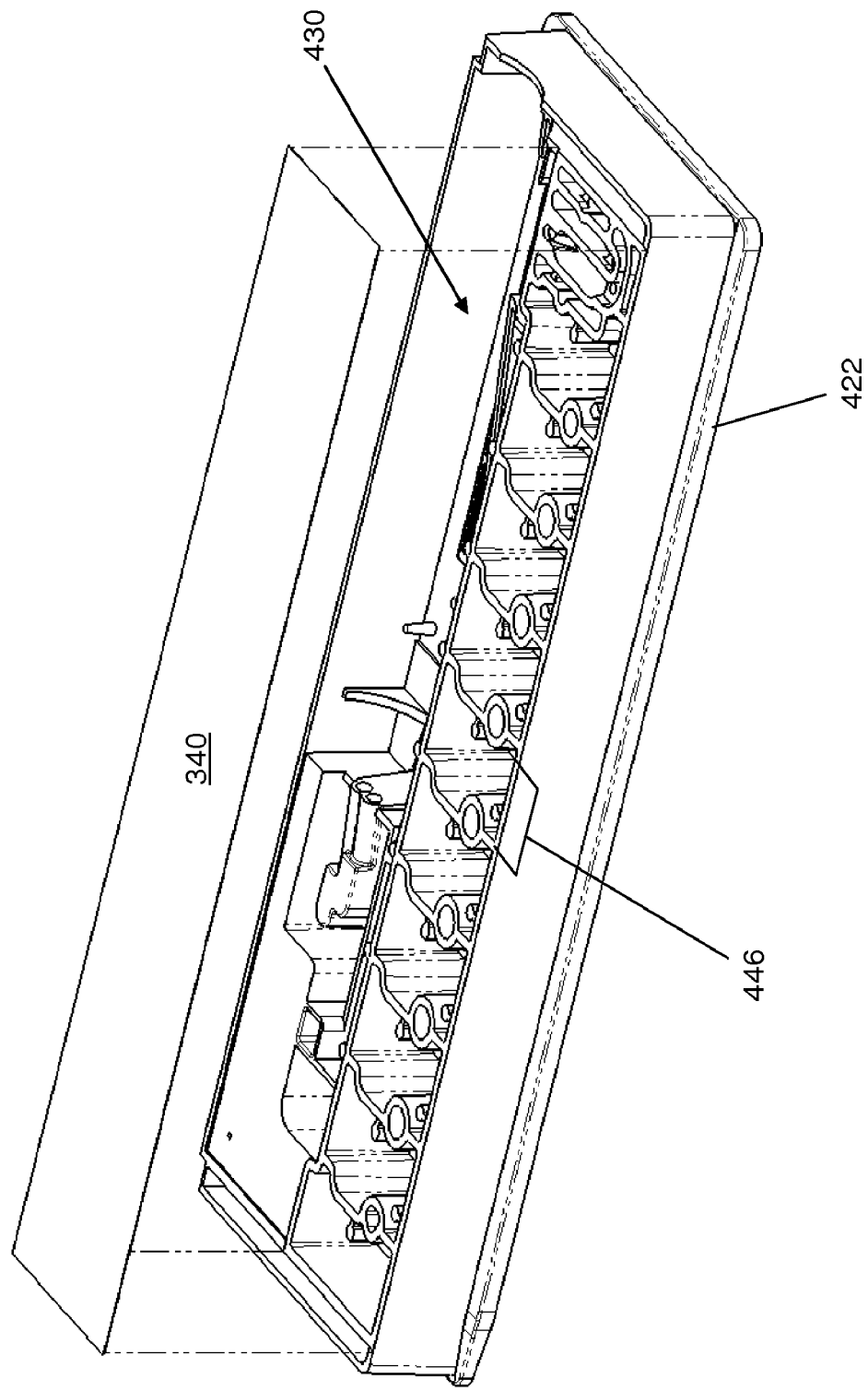
FIG. 19A is an illustration of an exploded perspective view of an example cartridge with multiple reagent handling stations (RHS) and a top seal.
Figure 19B:
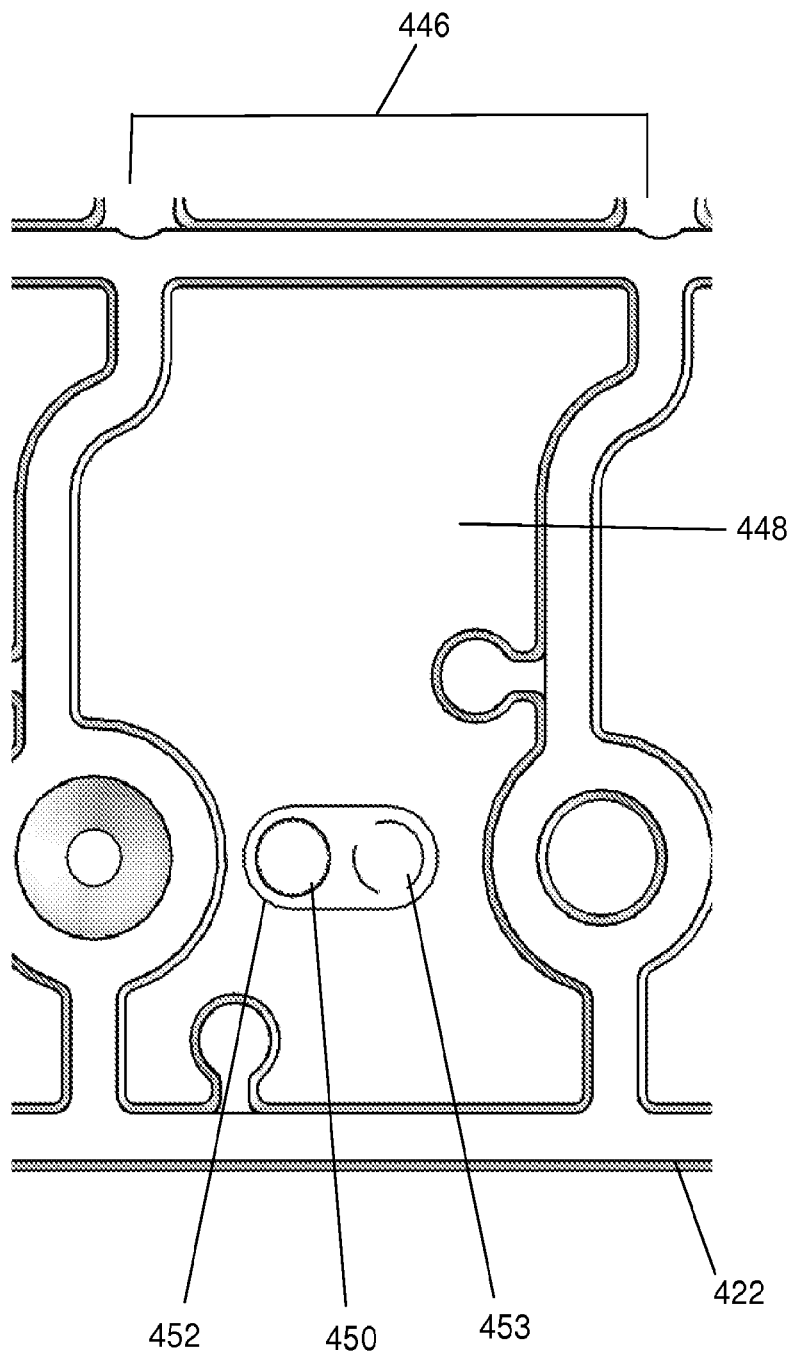
FIG. 19B is an illustration of a top perspective view of a portion of an example cartridge depicting a single RHS.

FIG. 19A depicts an embodiment of a cartridge 114 having at least one RHS 446 and a top seal 340, where multiple RHSs are visible. FIG. 19B provides a detailed top perspective view of a single RHS within a cartridge 114 (marked as 446 in FIG. 19A). The RHS 446 of FIGS. 19A and 19B can be formed within the body 422 and can be configured to facilitate the fluidic connections between the cartridge 114 and the diagnostic instrument 112. FIG. 19B depicts an example RHS 446 which can include a RHS reservoir 448 having a pocket 450, and probe entry sites 452, 453, which could be located on a seal covering the RHS 446, where the seal is not depicted around the probe entry sites 452, 453.

The side portions (e.g., walls) of the RHS reservoir 448 can be designed from low moisture vapor transmission rate (MVTR) materials and can vary in thickness and material. The side portions of the RHS reservoir 448 can be formed within the cartridge body 422 and be made of the same material as the body 422, such as Cyclic Olefin Copolymer (COC) or another material such as other polymers. In some embodiments, the cartridge 114 material is a COC because of the COC's characteristic low Moisture Vapor Transmission Rate (MVTR). For example, the MVTR for Polyplastics TOPAS® 5013, a COC, is 0.00193 g/100 in$^2$/day, which is considered low for the purposes of this disclosure. With such a low MVTR, while some liquid may evaporate during storage, less than 1.2% of liquid reagent will evaporate over a fixed amount of time, in some embodiments. This MVTR level of about 0.016 mL evaporation is negligible when considering the fill capacity of an example RHS reservoir 448.

Liquid drawn from a RHS reservoir 448 can be used to rinse or wash components, such as a first probe's exterior. The liquid can also serve as a source of carrier fluid for the transport of reagents to the detection apparatus of the diagnostic system 110. The RHS reservoir 448 can have a depth greater than the length of a sample probe (not shown) of the diagnostic instrument 112, which can assist in the reduction of the dead volume. The size and shape of the RHS reservoir 448 can vary as long as it can be sealed, e.g., with a foil seal, and there is enough space in the top to vent the liquids to air prior to aspiration. For example, the RHS reservoir 448 may be rectangular, circular, polygonal, or may include rounded or arched sides.

In some embodiments, the RHS reservoir 448 can have a depth of about 0.40 in., about 0.45 in., or about 0.50 in., or depths therebetween, including, about 0.42 in., about 0.43 in., about 0.46 in., about 0.47 in., about 0.48 in. The RHS reservoir 448 can have a total volume of about 1.5 mL, about 1.7 mL, about 2.0 mL, or total volumes therebetween, such as about 1.6 mL and 1.9 mL. In an example embodiment, a RHS reservoir 448 may be about 0.0625 in. in average width and length, and about 0.041 in. in average depth. In another example embodiment, the volume of the RHS reservoir 448 can be about 1.7 mL to the top with a volume of about 1.3 mL. The fill volume may be close to the usable volume but, the fill volume of the RHS reservoir 448 to the top should not match the total volume as the foil layer or top seal 340 may not properly seal if wet by a liquid in the RHS reservoir 448. In an example embodiment, a 0.062 in. diameter probe pocket 450 may be provided to enable liquid to drain to the probe.

The RHS reservoir 448 can be configured to have a low dead volume. In particular, in order to maximize the amount of liquid extracted from the RHS reservoir 448, the depth of the compartment, including any pockets, must be shorter than the reach or extension of a sample probe (not shown) that is used to extract the liquid. For example, the pocket 450 can be positioned at the bottom of the RHS reservoir 448 and have a specific geometry to assist in the extraction of the liquid. The pocket 450 can be located near the location of where the sample probe will enter the RHS 446 and extract the liquid. Thus, as the liquid is being extracted from the RHS reservoir 448, it can also pool or collect in the pocket 450. The sample probe can continue to contact the dwindling remainder volume of liquid thereby maximizing the amount of liquid able to be extracted and reducing the dead volume.

The area of a RHS reservoir 448 may be large enough to allow for at least one probe entry site. For example two probes (not shown) may be provided and accommodated at the probe entry sites 452, 453 from a diagnostic instrument 112. In an example embodiment, the width of a RHS reservoir 448 may be sized to allow for a ±0.013 in. positioning error of the sample probe before it strikes the edge of the probe pocket 450. The probe entry sites 452, 453 can serve to vent the RHS reservoirs 448, and therefore the cartridge 114, to the atmosphere, which can facilitate the fluidic functions of the cartridge 114. Evaporation can be minimized by using a top seal 340 and pierced perforations in the top seal 340. The cartridge 114 can withstand changes in atmospheric pressure when sealed.

In FIG. 19B, the pocket 450 is sufficiently large enough to allow access by the probe and allow for puncturing of a separate perforation (vent) 453 for venting to the atmosphere. Vent 453 requires an air gap beneath the seal to prevent liquid from exiting through the opening. An aspiration location, which can be at probe entry sites 452, 453, can be under a septum to reduce salt accumulation on the probe. A septum (i.e., a septum seal 350) can provide a surface which removes sample from the sample probe by sealing the sample within the RHS reservoir 448 when the probe is removed from the probe entry sites 452, 453 up through the septum. In some embodiments, a septum can be a 0.032 in. thick rubber material (e.g., 30 durometer Silicone).

When a probe from a diagnostic instrument enters the RHS reservoir 448 and draws the reagents into the probe, the reagents can act as a cleaning agent. The fluid motion along the probe can draw particles on both the outside and inside surfaces of the probe up into the diagnostic instrument 112 and eventually to a waste containment area, such as a waste reservoir, within the cartridge 114.

The introduction of air bubbles by moving the diagnostic instrument 112 probe up and down in the vented RHS 446 may allow the introduction of small bubbles. These bubbles may aid in the cleaning of the probe surfaces by increasing the scrubbing action along the probe surfaces. This cleaning can decrease the carryover between diagnostic test reads.

The RHS 446 further may include a multi-layered foil heat seal, top seal 340, described in greater detail in the following disclosure. The top seal 340 can be a multi-layered foil heat seal that may be heat sealed to the top of one or more RHS reservoir 448. The top seal 340, similar to the septum seal 350, can function to help with cleaning the exterior of a probe as the probe traverses the top seal 340. The top seal 340 can facilitate probe cleaning and can reduce carryover between diagnostic readings during operation. The top seal 340 can further facilitate the introduction of air to liquid transitions during liquid draws. The top seal 340 can be comprised of a specially developed foil seal designed to heat seal to thin walls of COC plastic in order to keep the moisture vapor transmission rate low and maintain a minimum size of the device. The thin walls and the seal can also help to maintain thermal uniformity. The top seal 340 can be made of any foil that can form a foil seal, such as Winpak LTD—WINCARE DF10HJ712A Heat Sealing Foil.

Various embodiments contemplate that liquids drawn from the cartridge 114 into the diagnostic instrument 112 may be returned to the cartridge 114 before a diagnostic test run is complete. To minimize the size of the cartridge 114, the RHS 446 can be reused as a waste reservoir for the previously processed liquids, beads, reagents, etc., for the step 500 of method 100. Capillary action can keep the waste materials in the cartridge even upon inversion of the cartridge 114 despite any probe-created perforations. The waste materials may be maintained due to the foil or plastic because the size of the perforations in the foil or plastic being small. For example, a 0.0355" perforation can have a capillary pressure equivalent to 0.71 in.in. of water, which is 1.5× the head pressure from the deepest waste cavity (0.46"), thus not allowing escape of the waste from the cartridge 114.

While the present discussion is largely focused on the use of the RHS 446 with assays, it is not meant to be limiting and is only one example for which this RHS 446 can be used. For example, the RHS 446 can have utility in any long term liquid storage on any plastic disposable device.

Top Seal

Referring to FIG. 18, the cartridge 114 is shown as having various sealing layers, including the top seal 340. Various embodiments of a cartridge 114 contemplate having a lid layer, such as the top seal 340, to seal the portions of the body 422 such as RMS compartments that can hold liquid and dry reagents. It is contemplated that the top seal 340 can be made from more than one layer. For example, the top seal can be comprised of a barrier layer and a laminating element.

The top seal can be joined to the body 422 using a laminating element such as heat seal coating, pressure sensitive adhesive (PSA), pressure sensitive adhesive tape, thermal adhesive, transfer tape, transfer adhesive, double sided tape, tie layer, adhesive film, or similar materials.

The top seal 340 can be die-cut or otherwise configured to have a size and shape that fits and covers only the liquid and dry reagent holding portions of the body 422 so that there is no overhanging material to interfere with cartridge performance.

FIG. 18 provides an embodiment of a body 422 illustrating how a top seal 340 and a septum seal 350 may be fitted to the body 422. FIG. 19A is an illustration of an exploded perspective view of an example cartridge with multiple RHS 446 and a top seal 340. In example embodiments, the top seal 340 and the septum seal may be applied together as a multilayer, or may be applied separately.

The top seal 340 can be made from high barrier materials that can reduce or prevent evaporation of stored liquids under the top seal 340. It is desirable for the top seal 340 to have a very low MVTR. For example, a material that has an MTVR that is at least 2× lower than the material used to form the body 422 will not greatly contribute to any water loss from the liquid being sealed by the top seal 340. Suitable materials for the top seal 340 include, but are not limited to, aluminum foil, aluminum alloy foils, metal alloy foils, high MVTR films, high barrier films, COC films, ACLAR® films (a type of fluorinated-chlorinated resins), films made of fluorinated-chlorinated resins, duplex films, triplex films, WinCare DF10HJ712A (a Universal Sealing Blister Foil from the company WinPak).

Septum Seal

Referring to FIG. 18, an example cartridge 114 may have various sealing layers, including a septum seal 350. Various embodiments of a cartridge 114 contemplate having a multi-layer fluidic septum seal 350 to establish a liquid and air-tight seal of the at least one reagent handling station 446 and to establish a fluidic connection with at least one probe of a diagnostic instrument 112 in the diagnostic system 110.

Figure 20A:
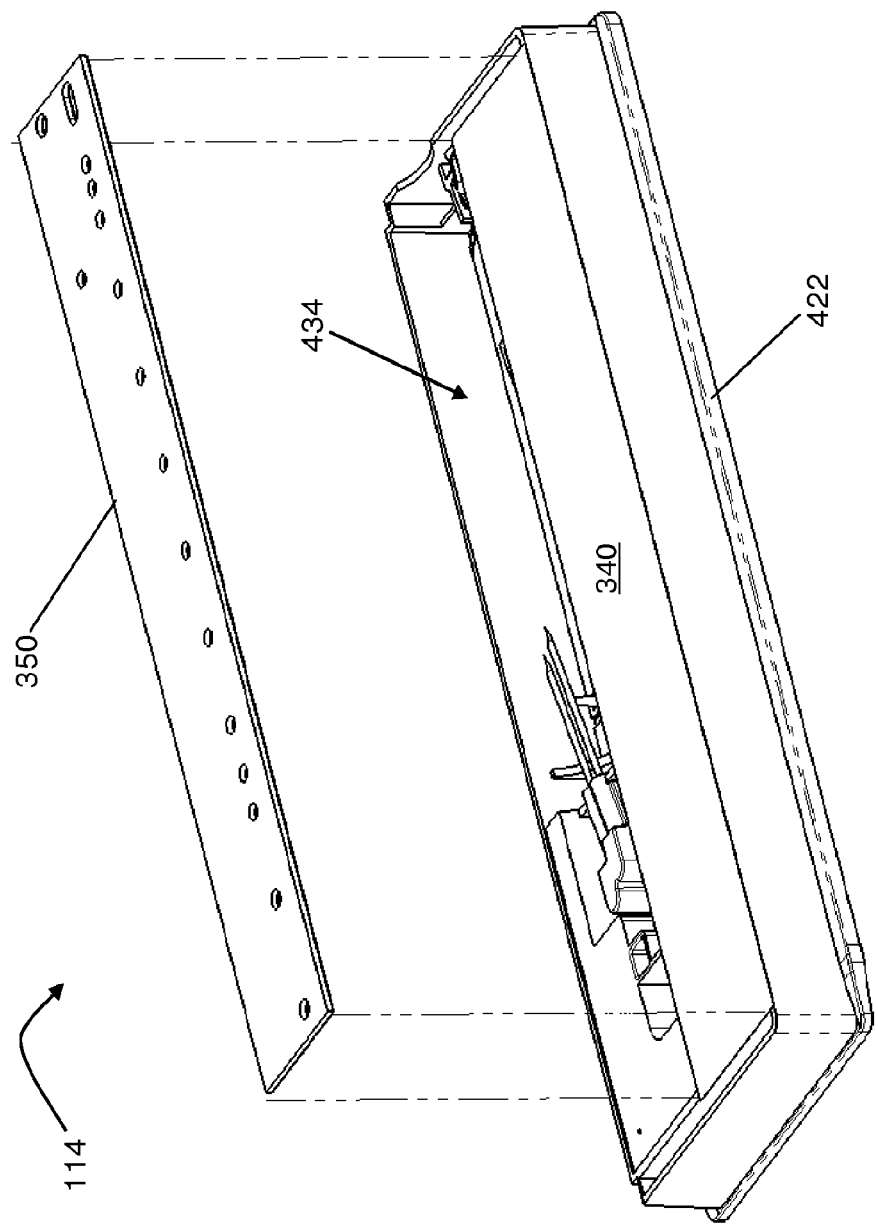
FIG. 20A is an illustration of an exploded perspective view of an example septum seal and cartridge.

FIG. 20A is an illustration of an exploded perspective view of an example septum seal 350 an example cartridge 114. The septum seal 350 can be joined to the top face of the top seal 340 using pressure sensitive adhesive, heat sealing, bonding, or lamination. The septum seal 350 can be a multi-layer film structure that can be designed to connect fluidic elements between the cartridge 114 and the diagnostic instrument 112 using a probe. For example, the septum seal 350 can be used to establish and switch fluidic connections between the cartridge and fluidic control elements, such as a pump, a tubing assembly or fluidic pathway, and at least one probe of a diagnostic instrument. The septum seal 350 can also be a multi-layer film structure that is designed to connect cartridge fluidic elements to the atmosphere using a probe. The septum seal 350 can also serve as a top seal to seal liquid filled wells or reservoirs located on the cartridge 114. The septum seal 350 can also serve as a means to clean the probe free of liquids and solids such as salts.

Figure 20B:
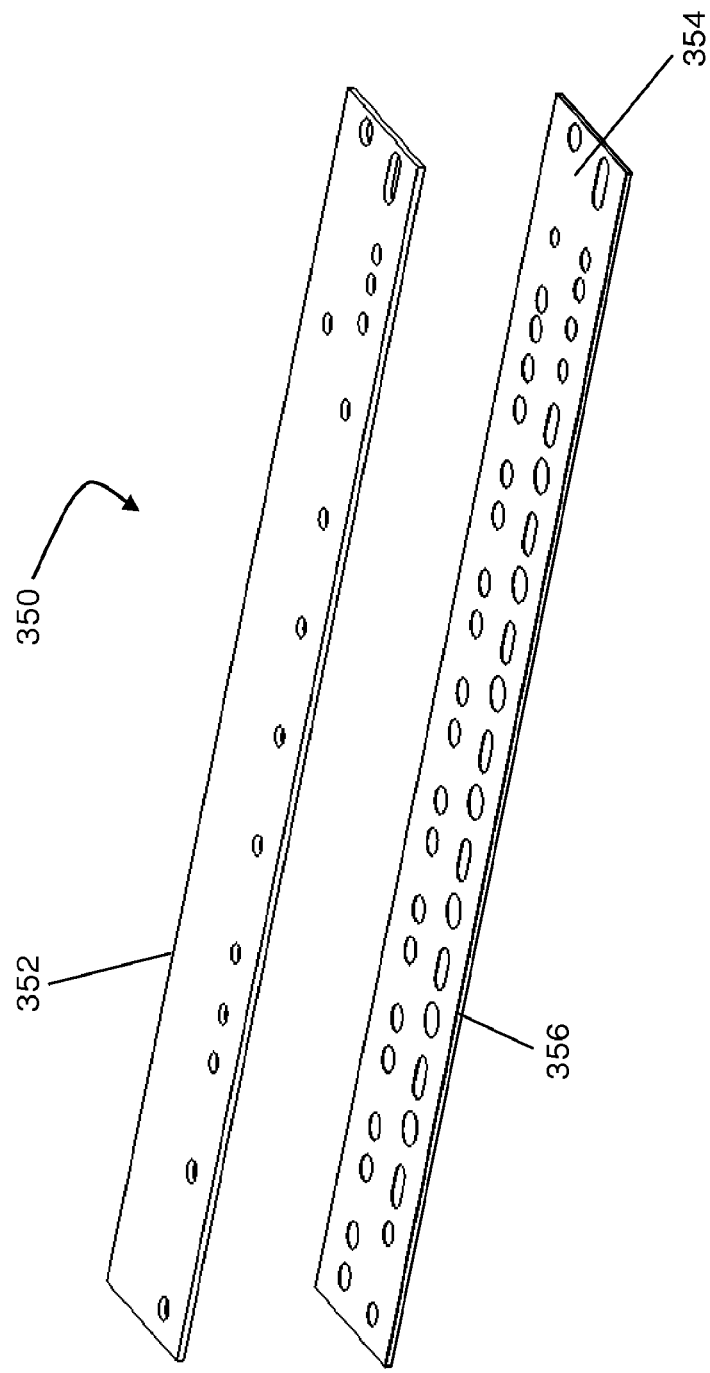
FIG. 20B is an illustration of an exploded perspective view of an example septum seal.

The septum seal 350 can be constructed of multiple layers. FIG. 20B, illustrates an example multiple layer septum seal 350, which may include for example, at least one septum layer 352, at least one laminating element 354, and at least one support layer 356. The septum seal 350 can have various combinations of these layers all joined together to form the multi-layer film structure. The layers can be combined to form different configurations of layers before forming an example completed septum seal 350 as shown in FIG. 20B. However, it is desirable to have at least one septum layer 352 and at least one support layer 356 in a septum seal 350.

Septum layers 352 can be made from a thin partition, film, membrane or similar structure which is pierceable, reversibly stretchable, elastic, reversibly compressible, re-sealing, self-sealing, prevents the exchange of fluids and gases, seals against a probe, and is re-addressable by a probe at the same location. An example septum layer 352 can have one or more probe addressable locations. An example septum layer 352 can be made from a variety of materials that provide these qualities, including, but not limited to, synthetic rubber, silicone rubber, elastomers, fluoroelastomers, natural rubber, copolymers of hexafluoropropylene and vinylidene fluoride, terpolymers of tetrafluoroethylene, vinylidene fluoride and hexafluoropropylene, perfluoromethylvinylether polymers, butyl rubber, or similar materials.

In some embodiments, an example septum layer 352 also can be made of a material that has a hardness of less than or equal to 110 Durometer (Shore A). The septum layer 352 can have a plurality of holes, in at least one row, cut out of the layer in a predetermined pattern that can correspond to the other layers of the septum seal 350, as well as the holes 426 in the cover 420, all of which correlate to the points of contact from the probes of the diagnostic instrument during operation.

The septum layer 352 can have varying thicknesses depending on the materials used for each of the layers within a given septum seal 350. For example, the septum layer can have a thickness of less than or equal to 1/10 in., less than or equal to 1/8 in. or less than or equal to 1/6 in.

Example support layers 356 may be from a film, sheet, foil or similar material which reduce stretch and tension on a septum layer 350, add rigidity to overall structure, add stiffness to overall structure, re-enforce overall structure, have a high flexural modulus, reduce elongation of the septum layer, and may be puncturable. In particular, an example support layer 356 can prevent an example septum layer 352 from breaking and stretching when pierced by a probe, for example. Examples of suitable materials for the support layer 356 can include, but are not limited to, metals such as, aluminum, aluminum alloys, metal alloys, foils, rigid films, plastics sheeting, polytetrafluoroethylene, polyvinyl chloride, polyester, and polymers thereof. In an example embodiment, the support layer 356 can be made from aluminum foil.

The support layer 356 can have varying thicknesses depending on the materials used for each of the layers within a given septum seal 350. For example, the support layer can have a thickness of less than or equal to 7 mils, less than or equal to 6 mils, less than or equal to 5 mils, less than or equal to 4 mils, less than or equal to 3 mils, less than or equal to 2 mils, or less than or equal to 1 mil. The support layer 356 can have a plurality of holes cut out of the support layer 356 in a predetermined pattern. The pattern can correspond to the other layers of the septum seal 350, as well as the holes 426 in the cover 420, and may also correlate to the points of contact from the probes of the instrument 112 during operation.

One purpose of the support layer 356 may be to facilitate the piercing of the septum layer 352 by a probe of the diagnostic instrument 112. The support layer 356 may add stiffness to the underside of the septum layer 352 for the purposes of limiting the stretch of an elastic septum layer 352 during probe entry or withdrawal. Unwanted stretching of an example septum layer 352 can cause significant pressure transients (e.g., positive pressure or vacuum) within the fluidic channels of the cartridge 114. Pressure transients, in turn, may induce unintended or variable fluid motions within the channels, which may disrupt or alter the predetermined positions of the fluid samples.

An example laminating element 354, shown as combined with the support layer 356 underneath the septum layer 352 in FIG. 20B, may include to a thin material used to join or bond layers together. A laminating element 354 may use adhesives as a means to hold together others layers. For example, a laminating element 354 may be a pressure sensitive adhesive (PSA), thermal adhesive, heat seal coating, transfer tape, transfer adhesive, double sided tape, tie layer, adhesive film, or similar materials.

The laminating element 354 can, in some embodiments, contribute to the multilayer film structure the same properties as the support layer 356, in that some laminating elements 354 can add rigidity, add stiffness, re-enforce, and/or reduce elongation. For example, a double-sided tape with a carrier may have support layer 356 properties, where the carrier also provides support in the same manner as the support layer 356. In some embodiments, there may be sufficient stiffness, rigidity, re-enforcement, or reduction of elongation by the double sided tape carrier, that the laminating element 354 may also function and replace support layer 356. For example, a laminating element 354 may include both a double sided tape carrier acting as a support layer 356 and adhesives acting as the laminating element 354.

The laminating element 354 can have a plurality of holes, in at least one row, cut out of the layer in a predetermined pattern that can correspond to the other layers of the septum seal 350, as well as the holes 426 in the cover 420, all of which correlate to the points of contact from the probes of the diagnostic instrument 112 during operation. It is contemplated that where more than one laminating element is used in the septum seal 350, the two laminating elements can be different materials. It is further contemplated that where more than one laminating element is used in the septum seal 350, the two laminating elements can be the same materials.

In certain embodiments, the septum seal 350 can be an element of a closed fluidic path. In certain embodiments, the diagnostic system 110 can employ a closed fluidic path between a diagnostic instrument 112 and a cartridge 114. The closed fluidic path can provide a path through which a sample and necessary reagents can be withdrawn from the cartridge 114, analyzed by the diagnostic instrument 112, and returned to the cartridge 114. In the embodiments, the closed fluidic path may use a substantially single direction of flow.

The septum seal 350 can be designed to be addressable by a probe in one or more locations during operation of the diagnostic system. In some certain embodiments, the septum seal 350 can have a plurality of probe entry sites (formed from and found on each individual layer of the septum seal 350, as described above). These entry probe sites can be located above various internal fluidic channels, wells, fluidic elements, and reservoirs and can be arranged in a plurality of patterns according to cartridge configuration and design.

The septum seal 350 can be designed to be make fluidic connections between the cartridge 114 and the diagnostic instrument 112 when pierced by a probe of the diagnostic instrument 112. As used herein, the phrase "to pierce" means to penetrate through, or make a through hole, or to cut through, or to tear though the septum layer, and then the septum layer self-seals or reseals when the probe is removed. A pierced site is re-usable. The septum seal 350 can form a secure fluid or air passageway between the diagnostic instrument 112 and cartridge 114 using a probe.

The septum seal 350 is designed to connect cartridge fluidic elements to the atmosphere or ambient surroundings by puncture. As used herein, the phrase "to puncture" means to perforate or to make a through hole in the support layer where the hole is irreversibly formed or permanently opened using a probe. Some of these sites may act as vents, which allows ingress of atmospheric air if under vacuum or allowing egress of air if under pressure. Some of these sites allow a probe to address a layer beneath the septum seal 350 without piercing the septum layer 352. There can be at least one, at least two, or a plurality of vents and they can be arranged in various configurations according to a predetermined probe pattern of the corresponding diagnostic instrument. For example, vent configurations can be varied on each layer of the septum seal 350 depending on the configuration of the cartridge and the motion path of the probes.

As described above, the individual layers of an example multi-layer septum seal 350 can be pre-formed into separate layers before being combined into the septum seal. Each of the pre-formed layers can be made from materials that can be sized and formed by conventional die cutting or laser cutting methods. The patterning of the probe sites and vents of the septum seal 350 may be accomplished using conventional die cutting or laser cutting methods. Construction of the septum seal 350 may be accomplished using a conventional rotary press.

In various embodiments, the septum seal 350 can be comprised of four layers, including a septum layer 352, a support layer 356, and two laminating elements 354, each with corresponding pierceable sites and puncturable sites. It is contemplated that all the layers of the septum seal 350 can have the same length and width, for example, about 0.5 in.in. by 5.0 in.in., about 0.6 in.in. by 4.0 in.in., about 0.7 in.in. by 4.5 in.in. and about 0.8 in.in. by 5.0 in.in. In an example embodiment, the layers can be about 0.8 in.in. by 4.9 in.in. It is contemplated that the length and width of the septum seal 350 correspond to the top surface of the cartridge.

In another embodiment, the septum layer 352 can be made of about 0.03 in. thick silicone rubber with hardness of about 30 Durometer (Shore A). The septum layer 352 can have several vents to enable ingress or egress of atmospheric air. The diameter of the vents can be greater than the diameter of the probe. For proper operation, the septum layer 352 is preferably not tensioned or stretched. Unwanted tensioning of the septum layer 352 may result in the pierced site not re-sealing or self-sealing after probe withdrawal.

Bottom Seal

Figure 21A:
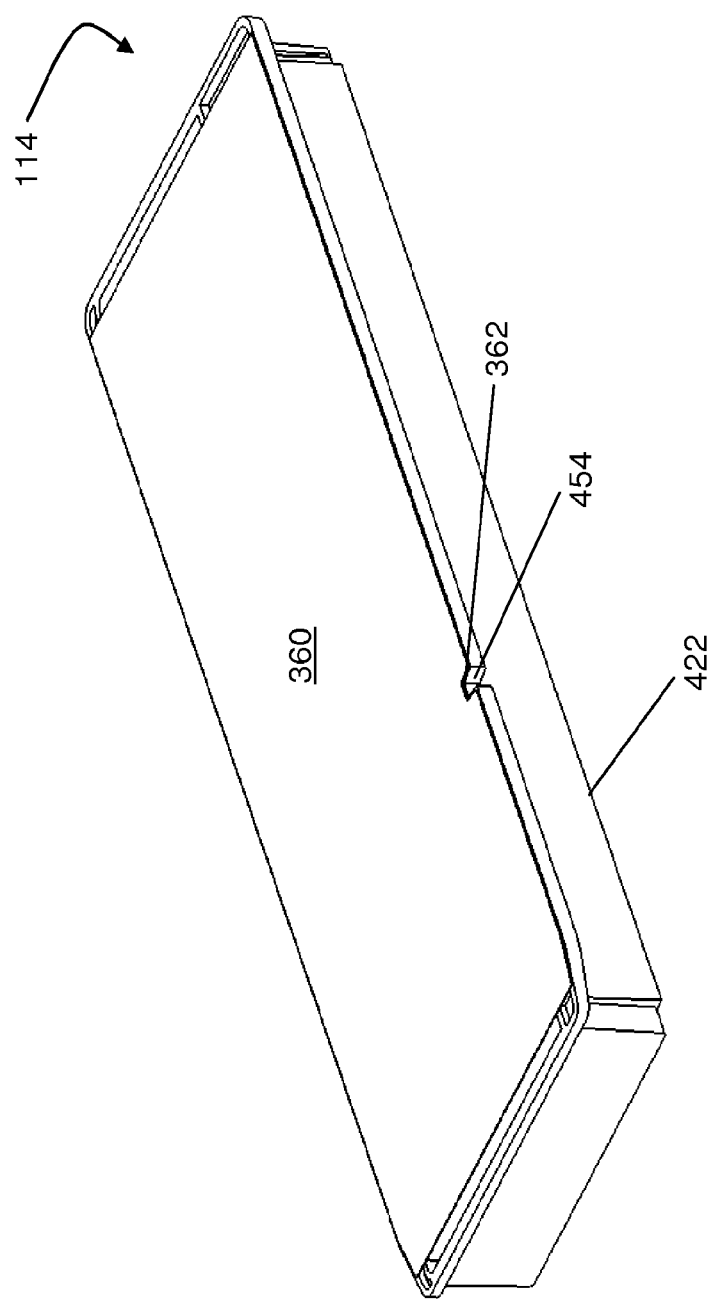
FIG. 21A is an illustration of an perspective view of an example bottom seal on the bottom of a cartridge.
Figure 21B:
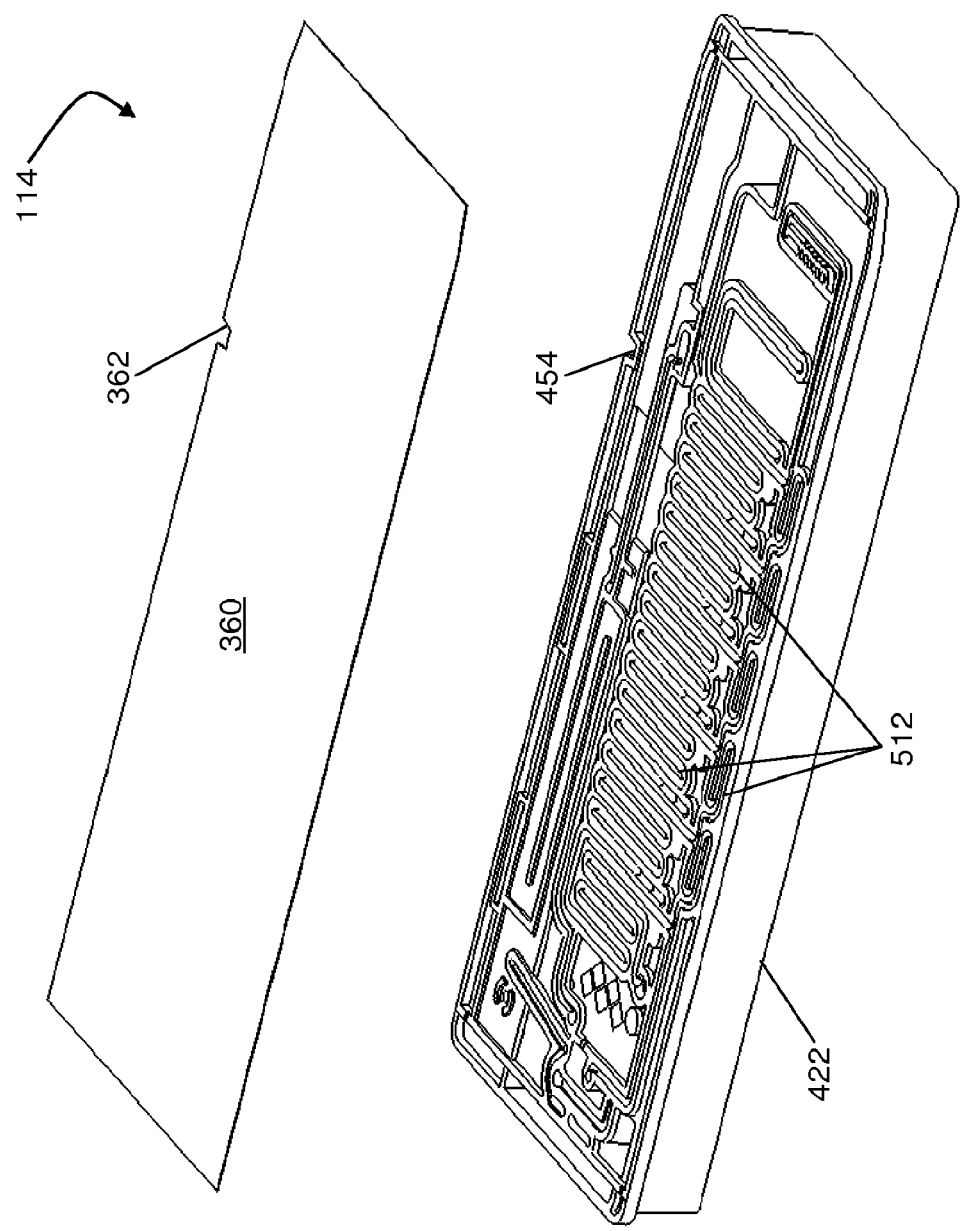
FIG. 21B is an illustration of an exploded perspective view of an example of the bottom of a cartridge with a bottom seal.

FIG. 21A illustrates a perspective view of a bottom of a cartridge 114 having a bottom seal 360 and FIG. 21B is an exploded perspective view of the bottom of the cartridge 114 showing at least one fluidic channel 512 of the cartridge 114 and a bottom seal 360. Various embodiments of a cartridge 114 contemplate having at least one fluidic channel 512 formed from the body 422 and sealed by a bottom seal 360, wherein the bottom seal 360 defines at least a part of the volume of at least one fluidic channel 512.

In various embodiments, the cartridge 114 can be a bottom seal 360 that is a multi-layer, heat-sealable film. The bottom seal 360 can form, in part, a bottom surface of the cartridge 114, as depicted in FIGS. 21A and 21B.

The bottom seal 360 can have characteristics that provide improved cartridge performance such as precision and accuracy. In an example cartridge 114, fluidic channels 512 may be formed and sealed by a bottom seal 360. In particular, the bottom seal 360 encloses at least one volumetric fluidic channel 512 and forms a known, measurable volume. It can be undesirable for the volume to change during the manufacturing of the disposable cartridge 114. In example cartridges 114, specific film materials can be used to make the bottom seal 360 to provide highly accurate fluidic volumetric channels.

Additionally, the multiple layers that comprise the bottom seal 360 may be specifically selected film materials for lamination or joining of the layers and/or die cutting. The selection includes materials that will melt at a temperature below that of the melting temperature of the body 422 material. The bottom seal 360 can also bond or join to the body 422 surface with high seal strength such that the enclosed fluidic channels 512 are sufficiently sealed so as to withstand high pressures or high vacuum levels.

The bottom seal 360 can be cut to various sizes as necessary during assembly. It is desirable to have the bottom seal 360 cut to a particular size and shape to conform, cover and seal the fluidic channels 512 while not extending beyond the edges of the body 422. If the bottom seal 360 overhangs, may interfere with cartridge motion during processing within the diagnostic system 110. The bottom seal 360 can have a notch 362 cut out to correlate to the notch 454 of the body 422. The size and shape of the diameter of the bottom seal 360 can be configured to satisfy individual manufacturing and design requirements and are not meant to be limited by the description of the embodiments described herein. Having a bottom seal 360 that does not extend all the way to the edges of the body 422 also allows the snap fit features 424 of the cover 420 to properly engage the body 422.

In certain embodiments, the bottom seal 360 can be constructed from a combination of a thermal adhesive layer and a support layer. The thermal adhesive layer can be directly coated, formed or joined onto the support layer. Using a heat seal process, the thermal adhesive layer is able to join and seal the support layer to the body 422 to enclose the fluidic channels 512. The thermal adhesive layer thickness is sufficiently thin such that during heat sealing, melt from the thermal adhesive layer does not substantially flow into the fluidic channels and cause unwanted volumetric changes. In particular, flow of melt, i.e., flash, may cause unwanted volumetric changes to the fluidic channels, which can be avoided with a low thickness of the thermal adhesive layer.

The heat seal temperature is a characteristic of the thermal adhesive material of the thermal adhesive layer, and is advantageously lower than the melting point or glass transition temperature of the body 422 material being sealed. For example, in certain embodiments, the heat seal temperature of an example thermal adhesive material can be 113° C., which is a temperature significantly lower than the glass transition temperature of the cyclic olefin copolymer, i.e., 136° C., used for injection molding the body 422. If the heat seal temperature is substantially the same or greater than the melting point or glass transition temperature of the body 422, then during heat sealing, the structure of the fluidic channels 512 may distort due to melting of the body 422 material. Any distortion to the fluidic channels 512 can change the volume which is undesirable. As a consequence, the fluidic channels 512 maintain the volumetric integrity with which each was designed.

The thermal adhesive processing temperature can be adapted to suit the desired manufacturing design, for example, by selecting different materials for the formation of the thermal adhesive layer depending on the type of material used for the body 422. Examples of suitable materials for the thermal adhesive layer include, but are not limited to, copolymers of ethylene and vinyl acetate (EVA), EVA emulsions, such as, polyvinyl acetate copolymers based on vinyl acetate and plastized with vinyl acetate ethylene, vinyl acetate ethylene (VAE) emulsions, VAE copolymer, copolymer adhesives, ethylene methacrylic acid copolymer (EMAA), ethylene acrylic acid copolymer, polyolefin copolymer, ethylene copolymer, propylene copolymer, polyvinyl chloride based thermoplastic resin, polyvinylidene chloride based thermoplastic resin, acrylate and styrene acrylate based thermoplastic resin, acrylate/polyolefin based thermoplastic resin, styrene copolymer based thermoplastic resin, polyester based thermoplastic resin, heat seal lacquer, or other similar materials.

The thermal adhesive layers can be designed to be as thin as possible to conserve space within the cartridge 114 design without sacrificing effectiveness of the cartridge 114. In general, the thermal adhesive layers can have a thickness of less than about 1.5 mil. For example, the thermal adhesive layers can have a thickness ranging from about 0.2 mil to 1.2 mil, about 0.3 mil to about 1.0 mil, about 0.4 mil to about 0.8 mil, or about 0.5 mil to about 0.6 mil. It is contemplated that the thermal adhesive layers can have a thickness of about 1.2 mil, about 1.0 mil, about 0.8 mil, about 0.6 mil, about 0.5 mil, about 0.4 mil, about 0.3 mil, or about 0.2 mil, or any thickness in between these values and less than about 1.5 mil.

Due to the thickness of the thermal adhesive layer, a support layer 356 may be used to provide sufficient stiffness, rigidity, high flexural modulus, and re-enforcement to the bottom seal 360. The support layer can add stiffness to the thin thermal adhesive layer such that the enclosed fluidic channels 512 can have a flat channel surface. As a consequence, the volumes of the fluidic channels can be precise and accurate across many cartridges.

The support layer can be made of a material that does not melt, deflect or substantially deform during the heat sealing process. For example, the support layer can be made of polyethylene terephthalate (PET), polyvinyl chloride (PVC), cyclic olefin copolymer (COC), polyvinylidene chloride (PVDC), polystyrene, polycarbonate (PC), poly(methyl methacrylate) (PMMA), polysulfone, acrylonitrile butadiene styrene (ABS), or other similar materials.

The support layer 356 may be made of materials that are sufficiently stiff and provide high flatness on both surfaces of the combined layers. For example, in certain embodiments, the support and stiffness of the overall bottom seal 360 is derived from the support layer 356 with PET being an example. The use of PET is also advantageous because of the characteristic dimensional stability, high flatness, and high parallelism between surfaces.

The support layer 356 can also be designed to be as thin as possible to conserve space within the overall cartridge 114 design without sacrificing effectiveness of the cartridge 114. The support layer 356 can be thicker and stiffer than the thermal adhesive layer to provide sufficient support and stiffness to the bottom seal 360, while maintaining thinness. Accordingly, the support layers 356 can have a thickness of less than about 5.0 mil. For example, the support layer can have a thickness ranging from about 4.5 mil and about 5.0 mil, from about 4.0 mil to about 4.5 mil, from about 3.0 mil to about 4.0 mil, or from about 2.5 mil to about 3.0 mil or any thickness therebetween. It is contemplated that the support layer can have a thickness of about 5.0 mil, about 4.5 mil, about 4.0 mil, about 3.7 mil, about 3.5 mil, about 3.0 mil, or about 2.5 mil.

When the thermal adhesive and support layers are combined, is the combined layers may have smooth surfaces to ensure that the volume of the fluidic channels 512 is not affected by surface abnormalities of the bottom seal 360. It is may also be desirable to use materials that are dimensionally stable (low shrinkage) and have high parallelism between surfaces. Such materials are preferably also chemically compatible with clinical laboratory specimens, such as blood or plasma.

In certain embodiments, the bottom seal 360 can include an additional tie layer. A tie layer can facilitate the adhesion of the thermal adhesive layer to the support layer. In certain embodiments, for example, a pressure sensitive adhesive (PSA) layer can be used as a tie layer to tie layers, such as the thermal adhesive layer and the support layer. A tie layer can enable dissimilar materials for the thermal adhesive layer and support layer to be used together and joined. The tie layer can be advantageously thin, and can be selected from materials that do not melt or deform during the heat seal process. Examples of suitable materials for the tie layer include but are not limited to PSA materials, polyolefin resins, anhydride modified polyolefin, double side adhesive tapes, or similar materials.

The tie layer is designed to be as thin as possible to conserve space within the overall cartridge 114 design without sacrificing effectiveness of the cartridge 114. The tie layers can have a thickness of less than about 1.5 mil. For example, the tie layers can have a thickness ranging from about 0.2 mil to 1.2 mil, about 0.3 mil to about 1.0 mil, about 0.4 mil to about 0.8 mil, or about 0.5 mil to about 0.6 mil. It is contemplated that the tie layers can have a thickness of about 1.2 mil, about 1.0 mil, about 0.8 mil, about 0.6 mil, about 0.5 mil, about 0.4 mil, about 0.3 mil, or about 0.2 mil, or any thickness in between these values and less than about 1.5 mil.

The materials chosen for the thermal adhesive layer, the support layer, and the tie layer may be optically transparent, optically opaque, or optically translucent. When used, optically transparent or translucent materials can facilitate the functions of the diagnostic system such as, for example, the use of optical sensors within the diagnostic instrument to meter appropriate divisions of fluids within the fluidic channels. The materials chosen for the thermal adhesive layer, the support layer, and the tie layer may be in.osen to have low thermal resistance.

The bottom seal 360 can have a total thickness which is the sum of the individual layers. Additionally, the materials chosen for the bottom seal 360 layers may bond or join to the device surface with high seal strength such that the enclosed fluidic channels are sufficiently sealed so as to withstand high pressures or high vacuum levels.

In some embodiments, the bottom seal 360 can be comprised of materials that are bondable to plastics commonly used for injection molding, including a cyclic olefin copolymer (COC). It is contemplated that when other materials are used for the injection molding of the body 422, the thermal adhesive layer material may be altered as well. In particular, the thermal adhesive layer material composition can depend on the composition of the substrate or body 422, so it can be desired to have a thermal adhesive layer with a lower melting point than the body 422. Examples of suitable combinations of body 422 material and thermal adhesive material include, but are not limited to, the following pairs:

| Body Material | Thermal Adhesive |
| --- | --- |
| cyclic olefin copolymer | ethylene vinyl acetate copolymer |
| polyvinyl chloride | PVC based thermoplastic resin |
| polystyrene | acrylate and styrene acrylate-based thermoplastic resin |
| polypropylene | acrylate/polyolefin-based thermoplastic resin |
| polyethylene | acrylate/polyolefin based thermoplastic resin |
| PET | polyester based thermoplastic resin |

It contemplated that more than one of each layer may be used to construct the bottom seal 360 depending on the materials selected for each layer and the desired properties and thickness of the bottom seal 360. For example, a bottom seal construction may include alternating layers of thermal adhesive layers and tie layers on each side of a support layer.

An embodiment of a bottom seal 360 can be constructed from a thermal adhesive layer comprising a copolymer adhesive with a thickness of about 0.6 mil, a support layer comprising PET with a thickness of about 3.0 mil and a tie layer comprising PSA, with a thickness of about 1.2 mil. Such an example of a bottom seal 360 is able to seal fluidic channels 512 of the body 422 of a cartridge 114, formed by injection molding of a cyclic olefin copolymer with a glass transition temperature of 136° C., such as, for example, TOPAS® 5013.

In another embodiment, the bottom seal 360 can be constructed from two layers joined by lamination and can have a total thickness of about 5.4 mil, which can be the sum thicknesses of the two of the layers. For example, a bottom seal 360 can include thermal adhesive layer of Transilwrap Trans-Kote® PET/MR Laminating Film with a thickness of about 1.2 mil and a support layer of Adhesive Research ARCare 7843 with a thickness of about 4.2 mils for total thickness of 5.4 mils.

The low thickness of the bottom seal 360 permits the materials to be readily die cut. The materials can also be expected to have a low thermal resistance with this low thickness. The materials selected can be optically transparent.

In another embodiment, the bottom seal 360 can be constructed from two layers joined by lamination and can have a total thickness of about 5.4 mil, which is the sum of the layers. For example, a bottom seal 360 can include a thermal adhesive layer with a thickness of about 0.6 mil, a support layer of PET with a thickness of about 0.6 mil, a tie layer made from single-sided PSA tape with a thickness of about 4.2 mil, (e.g., a 1.2 mil adhesive layer and a 3.0 mil PET support layer) for a total thickness of 5.4 mils. The face of the single-sided tape opposite the PSA can be smooth.

Dividing Sample into Aliquots

Figure 22:
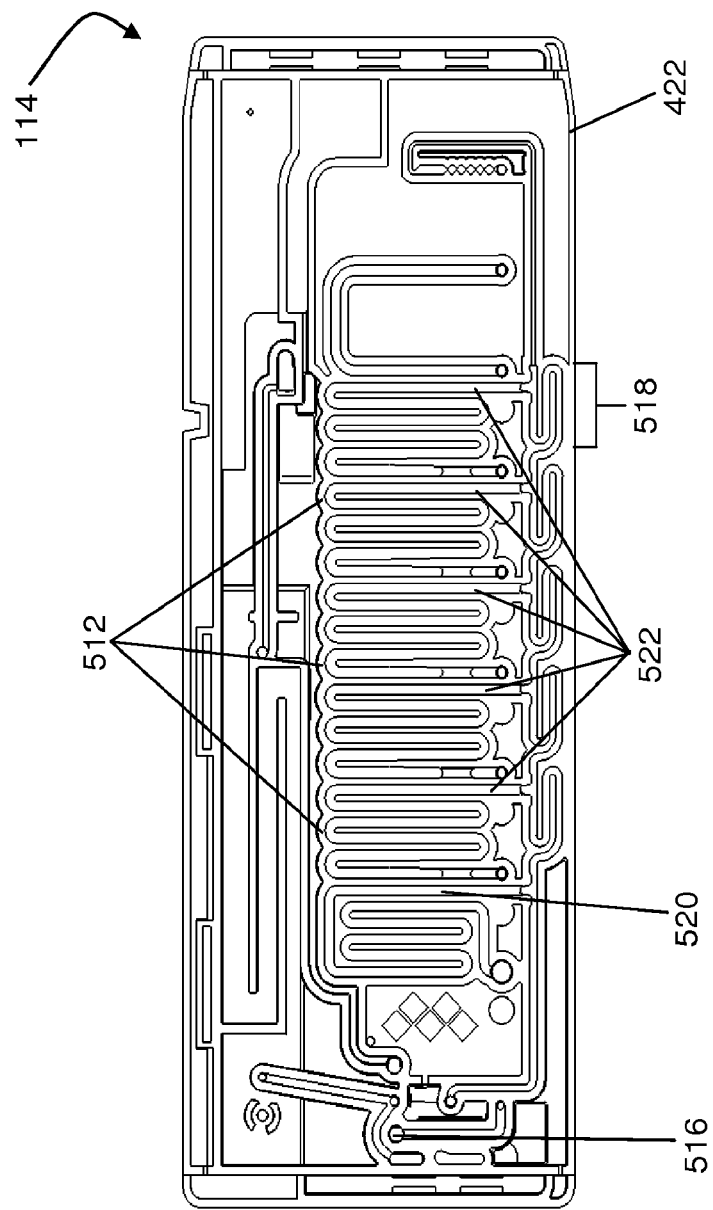
FIG. 22 is an illustration of an bottom view of an example cartridge depicting fluidic channels of a cartridge.

FIG. 22 is a bottom view of a cartridge 114 depicting fluidic channels 512. Various embodiments of a cartridge 114 contemplate having at least one fluidic channel 512 formed from the body 422 and sealed by a bottom seal 360, wherein the bottom seal 360 defines in part the volume of the fluidic channels 512.

Figure 23:
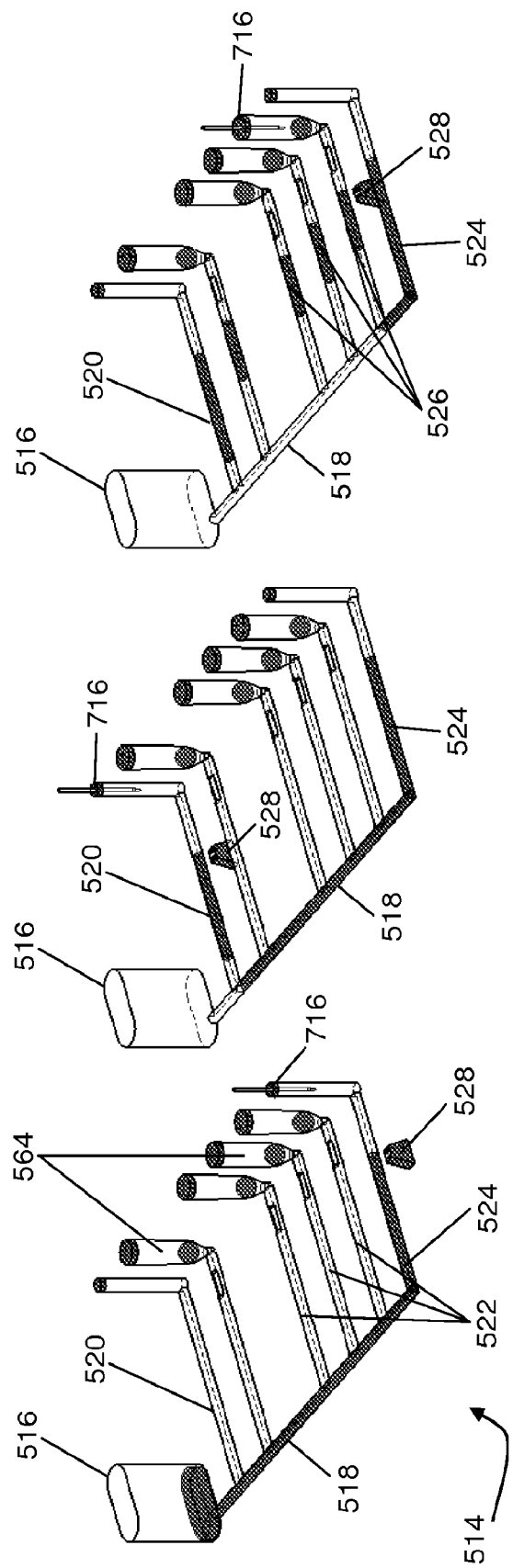
FIG. 23 is an illustration showing an example of sample aliquoted within fluidic channels of a cartridge.

In various embodiments, the method of dividing a sample can include three operations which use the features of an aliquoting mechanism depicted in FIG. 23. FIG. 23 is an illustration of fluidic features used in an aliquot mechanism intended to produce three aliquot volumes, such as, of 25 µL. The aliquot mechanism 514 can be a sub-section of a clinical diagnostic instrument An aliquot method can be precise and accurate independent from a pump accuracy. For example, a first operation can include drawing a sample liquid (shaded) from a sample reservoir 516 (also referred to as a plasma cache or cache) into a primary channel 518. The liquid can be drawn by using a vacuum, which can be generated inside the primary channel 518. The vacuum can be created by a pump connected an end channel pump connecting port 716.

During this operation, other connecting ports may be closed to allow the vacuum to form. When liquid from the sample reaches a primary channel fill mark (not shown), a sensor 528, which addresses the aliquot mechanism 514, can communicate with the pump to stop and release the liquid from the end channel pump connecting port 716. As such, the extent of filling the primary channel 518 can be independent of pump accuracy. The extent of filling the primary channel 518 can depend on the geometry/volume of the primary channel 518.

A second operation can include emptying the remaining sample liquid from the sample reservoir 516 into the secondary channel 520. The liquid can be emptied by using a vacuum generated inside the secondary channel 520. The vacuum can be created by a pump connected to a secondary channel pump connecting port 716. During this operation, the other connecting ports can be closed. The second operation can also be independent of pump accuracy. For example, when a liquid from the sample reaches a secondary channel fill mark (not shown), a sensor 528 which addresses the aliquot mechanism 514, can communicate with the pump to stop and release the liquid from the secondary channel pump connecting port 716. The leftover liquid volume not pulled into the channels can be the excess of sample liquid over total aliquot volume (where total aliquot volume is the aliquot volume multiplied by the number of aliquots).

A third operation can include drawing a segment of liquid from the sample liquid located in the primary channel 518 between receiver channels 522 into a receiver channel 522. The volume of liquid in the primary channel 518 between receiver channels 522 can be the aliquot volume. This can be conducted sequentially for, as an example, three times for each of the three receiver channels 522 (the number of which is dependent on the cartridge design and the diagnostic test being run on the cartridge). For example, this third operation can occur in an embodiment with five secondary channel pump connecting ports 716.

The sequence of drawing aliquot volumes into a receiving channel 522 is conducted in order and starting with the aliquot volume closest to the secondary channel 520 (e.g., from left to right in FIG. 23). This fluid motion can be driven by vacuum generated inside each receiver channel 522 due to a pump being connected to the receiver channel pump connecting port 716. This operation can also be independent of pump accuracy. At the end of the method, all sample liquid that was contained in the sample reservoir 516 may be aliquoted into each of the receiver channels 522 and the secondary channel 520.

The aliquot mechanism 514 can accommodate any type of biological sample such as blood, plasma and urine. In some embodiments of the aliquot mechanism 514, the sample to be aliquoted can be located within a sample reservoir 516. The means for locating the sample into the sample reservoir 512 would be apparent to anyone skilled in the art of assay construction and can be as described herein. The sample reservoir 516 can have a volume ranging from about 125 µL to about 135 µL, about 135 µL to about 150 µL, about 150 µL to about 175 µL, and about 175 µL to about 200 µL. The sample reservoir can have a volume of about 150 µL, about 175 µL, about 200 μL, about 225 μL, or any volume therebetween. In an example embodiment, the sample reservoir 516 can have a volume of about 200 μL. The opening of the sample reservoir 516 can be located on the top surface of the aliquot mechanism 514 and the sample reservoir 516 can be open vented to the ambient atmosphere.

The sample reservoir 516 can be connected to a primary channel 518. The primary channel 518 can have a volume less than the sample reservoir volume. For example, the primary channel 518 can have a volume ranging from about 125 μL to about 135 μL, about 135 μL to about 150 μL, about 150 μL to about 175 μL, and about 175 μL to less than about 200 μL. The primary channel 518 can also have a volume of about 125 μL, about 150 μL, about 175 μL, about 200 μL, or any volume therebetween. In an example embodiment, the primary channel 518 can have a volume of about 150 μL. In one embodiment, the fluidic features can be formed by injection molding fabrication and can be replicated with high precision and accuracy.

The primary channel can be connected to an end channel 524. The end channel 524 can have a volume of about 20 μL, about 25 μL, about 30 μL, or any volume therebetween. In an example embodiment the end channel 524 can have a volume of about 25 μL. The end channel 524 can be connected to a pump connecting port 716. The primary channel 518 can also be connected to three receiver channels 522. The volume of each receiver channel 522 is designed to be greater than the aliquot volume 526 and can be equal to about 50 μL, about 75 μL, about 100 μL, or any volume therebetween. In an example embodiment each receiver channel 522 can have a volume of about 75 μL.

The primary channel 518 can also be connected to a secondary channel 520. External to the aliquot mechanism 514 can be a sensor 528 to detect when a liquid front reaches the primary channel fill mark (not shown). The sensor 528 can be used to detect when a liquid front reaches the secondary channel fill mark (not shown). The volume of the secondary channel 520, based on the fill mark, is designed to be greater than the difference in volume between the sample reservoir 516 and primary channel 518 volume. The secondary channel 520 can have a volume ranging from about 125 μL to about 135 μL, about 135 μL to about 150 μL, about 150 μL to about 175 μL, and about 175 μL to less than about 200 μL. For example, the secondary channel can have a volume of about 125 μL, about 150 μL, about 175 μL, about 200 μL, or any volume therebetween. In an example embodiment the secondary channel 520 can have a volume of about 150 μL.

The secondary channel 520 and each receiver channel 522 can be connected to pump connecting ports 716. The number of pump connecting ports can vary depending on the configuration of the cartridge 114, and may range from 5 to 7 pump connecting ports. For example, in an embodiment, there may be a total of 5 pump connecting ports. The pump connecting ports 716 are normally closed. The fluidic channels, i.e., secondary channel 520, receiver channels 522, and end channel 524, are in fluidic communication with a pumping mechanism through the pump connecting ports 716. Fluid motion between the fluidic channels necessary for the aliquot method can be conducted by applying vacuum pressure from a pump (not depicted). The aliquot volume 526 can be defined as the volume between adjacent receiver channels 522. The number of aliquots can be defined as the number of receiver channels 522.

The sample volume does not require a precise or accurate fill in the sample reservoir 516 but may only refine that its volume exceeds a minimum. For example, the minimum sample reservoir fill can be about 75 μL, about 100 μL, about 125 μL, or any volume therebetween. In an example embodiment the, the minimum sample reservoir fill volume can be about 100 μL.

The aliquot mechanism 514 can be adaptable by increasing or decreasing the number of aliquots accommodated on an aliquot mechanism 514. For example, the number of aliquots can be ≥1, or the total volume may be less than or equal to the sample volume in the sample reservoir 516 divided by the aliquot volume.

The aliquot mechanism 514 can be further adaptable by accommodating different aliquot volumes within a single aliquot mechanism 514. For example, there may be two or more different aliquot volumes within an aliquot mechanism 514.

Mixing Sample

Referring to FIG. 4, method 400 can include mixing a sample with reagents contained within the cartridge 114 in step 408. Various embodiments of the diagnostic system 110 contemplate mixing a sample with reagents, such as lyophilized pellets, stored within the cartridge 114.

Figure 24A:
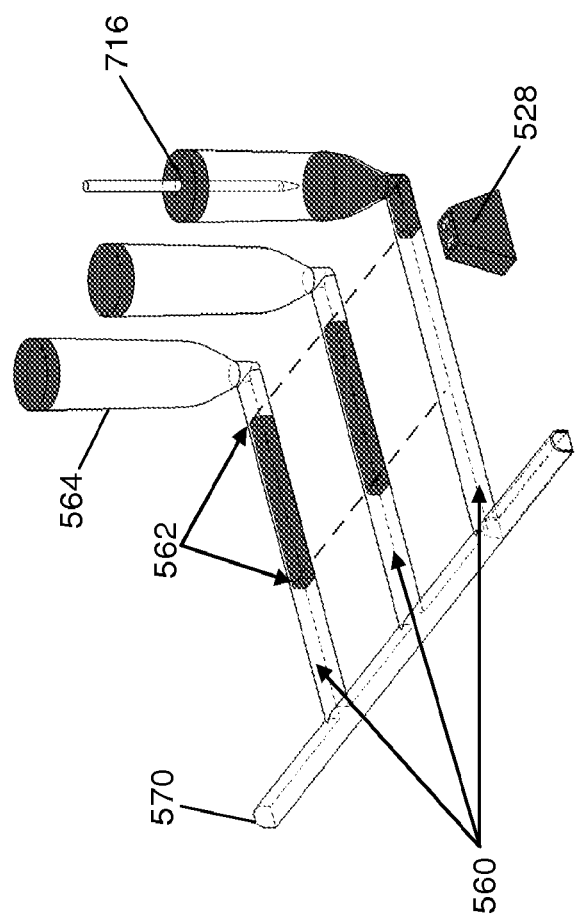
FIG. 24A is an illustration of an example of multiple fluidic channels of a cartridge.

FIG. 24A is an illustration of multiple individual cartridge assay replicates (CARs) 560 to form fluidic channels in a cartridge 114. In various embodiments, the CARs 560 can be the same fluidic channels as those used in the aliquoting method, for example, the primary channels 518, the secondary channels 520, the receiver channels 522, or the end channels 524. FIG. 24A also depicts multiple CARs 560, showing the precise positioning of the sample in an incubation zone 562 by using the optical sensor 528 to detect a liquid-air transition.

In various embodiments, a mixing method can be used to minimize foaming during the rehydration of the reagents or lyophilized pellets. In turn, the minimizing of the foam can minimize the variability between assay replicates as well as between cartridges, thus improving the precision of the diagnostic test. Minimizing foam can be accomplished during rehydration of lyophilized pellets by detecting the leading edge of a sample with an optical sensor 528 and, once detected, slowly introducing the sample to the lyophilized pellet. Obtaining a homogeneous sample before the incubation ensures the accuracy and the precision of an assay by allowing the maximum amount of antigen in a patient sample to bind to the reagents.

Figure 24B:
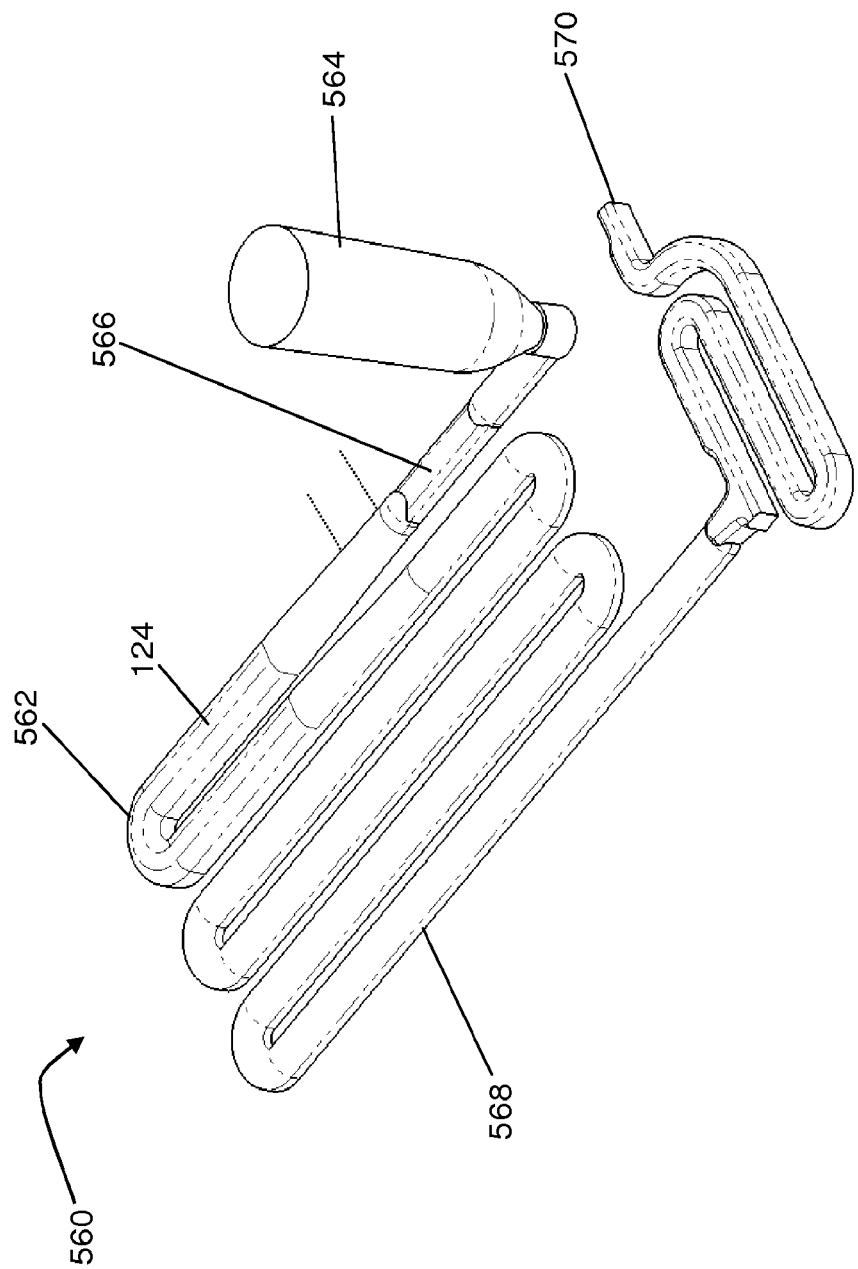
FIG. 24B is an illustration of an example of a single fluidic channel of a cartridge.

FIG. 24B illustrates an example of a CAR 560 within a cartridge 114. Certain embodiments contemplate a cartridge 114 that can have different geometries in the CAR 560 to facilitate some mixing movements, such as a back-and-forth fluidic motion in order to obtain a homogeneous sample before positioning the sample to an incubation zone. Positioning the sample to an identical incubation location for each CAR ensures that the sample in each CAR gets the same degree of incubation. Certain embodiments provide a diagnostic system that can verify the location of the sample by detecting the leading edge of a sample with the optical sensor 528 before positioning the sample to an incubation zone 562 for each assay replicate.

To minimize foaming during the pellet rehydration, the leading edge of the sample can be detected with an optical sensor 528. Once detected, the sample can be slowly introduced to an active mix well 564. To obtain the homogeneous sample, the sample can be moved back and forth across the active mix well 564 bottom and the bead capture zone 566 in order to have the sample fluid pass through different diameters. Fluids that experience diameter changes during flow result in more homogenous mixtures due to the turbulent flow experienced by the fluid because of the diameter changes.

In one embodiment, the active mix well 564 bottom can have a diameter of about 0.05 in., the bead capture zone 566 can have a height of about 0.02 in., and the wash channel can have a height of about 0.04 in. To ensure that the sample is incubated at the identical location in each channel, the leading edge location of the sample is verified with the optical sensor 528 before positioning the sample to the incubation zone 562.

Figure 24C:
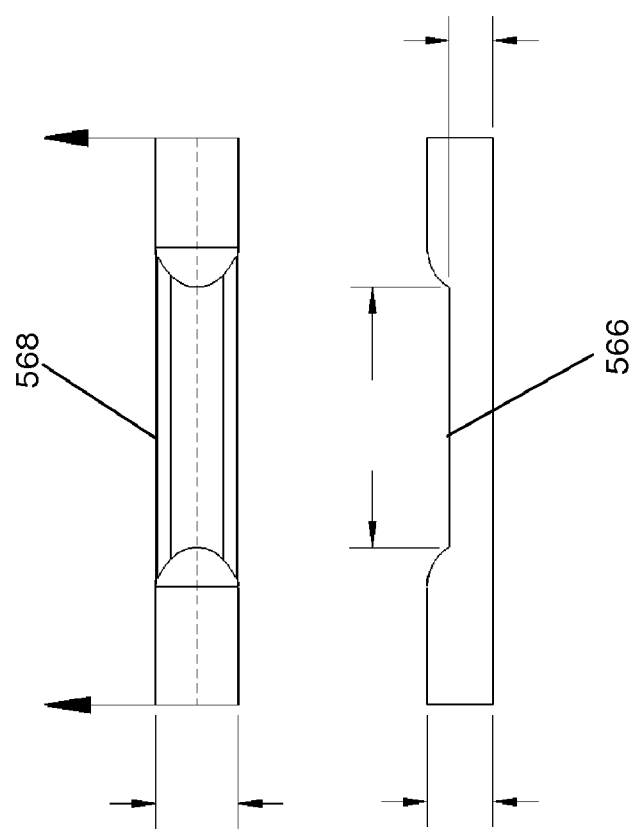
FIG. 24C is an illustration of dimensions of an example of a wash channel and a bead capture zone of an example cartridge.

FIG. 24C shows example dimensions at a bead capture zone 566 (top view shows width of channel; bottom view is a cross-section, showing the height). The width of the channel is identical to the diameter of the bottom of the active mix well 564. In the embodiment depicted, the maximum height of the bead capture zone 566 can be about 0.024 inch, the maximum height of the wash channel 568 can be about 0.04 inch, and the active mix well bottom diameter can be about 0.04 inch. It is contemplated that the height and well bottom diameter can range in sizes and depths depending on the design and configuration of the diagnostic system and these values are not meant to be limiting.

Figure 25:
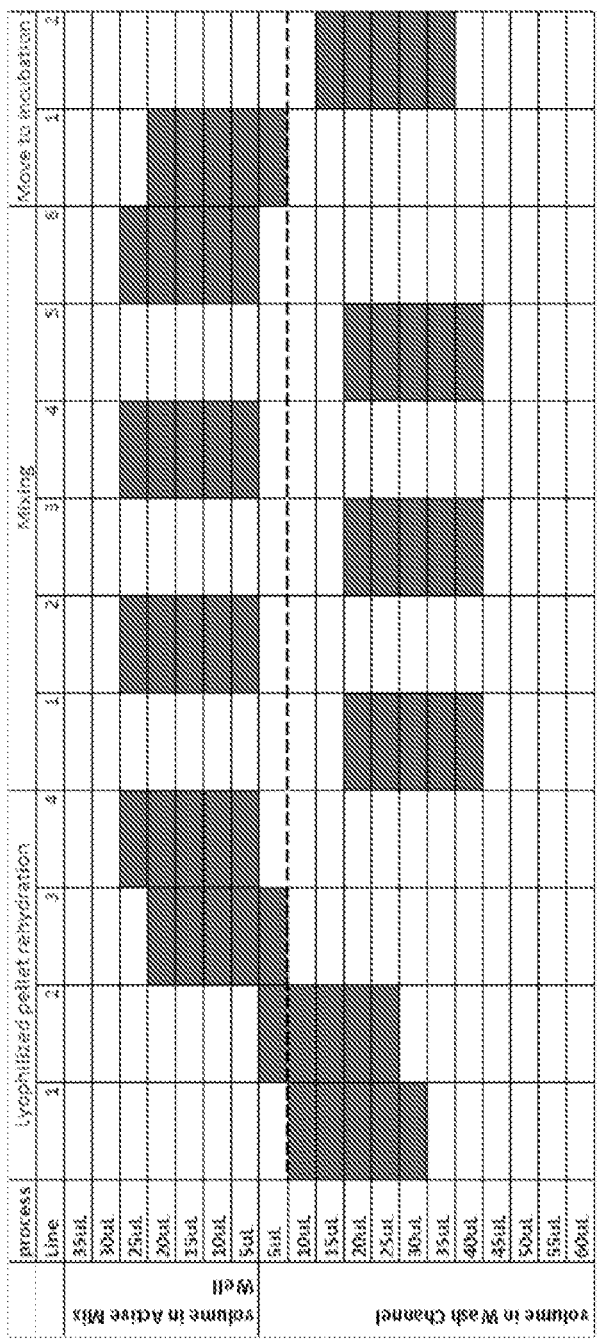
FIG. 25 is a graphical representation of an example of the location of a sample during processing steps of a diagnostic system.

FIG. 25 is a chart of fluidic actions illustrating where a sample (of volume of 25 µl) can be located for each process. The resolution of the fluidic chart is 5 µl. The dotted line in bold between 5 µL and 10 µL in Wash Channel represents the location of Bead Capture Zone. The shaded cells represent the location of a sample (25 µl). There are three operations detailed in the chart that correspond to Tables 1-3 below: Lyophilized pellet rehydration (has 4 steps/"lines"). Mixing (has 6 steps/"lines"). Move to Incubation (has 2 steps/"lines"). The column numbers in the fluidic chart under the operations, correspond to the Steps in Table 1, Table 2, and Table 3 below. For example, during the Mixing operation, the sample (25 µl) can start in a wash channel (15 µl in the wash channel and 10 µl away from the bead capture zone (Step 1 of Mixing process)), and can be moved into an) Active Mix well with the next step (Step 2 of Mixing process)).

Table 1, Table 2, and Table 3 below show a method that can be used for each objective with a detailed description of each process given below each Table. The CAR components mentioned in the description below are identified in FIGS. 24A and 24B. The location of the patient sample in each process is specified in FIG. 25.

TABLE 1

Procedure for Rehydration of Lyophilized Reagents

| Steps | Procedures |
|---|---|
| 1 | Pump Cycle [150, 10, Aspirate, Stop at OS1 (CAR), −100, 50] |
| 2 | Pump Displace [5, 5, Aspirate, Both] |
| 3 | Pump Cycle [30, 5, Aspirate, Stop at OS1 (CAR), 100, 50] |
| 4 | Pump Displace [5, 5, Aspirate, Both] |

Note:
In the commands above, the first parameter in the parenthesis is the desired volume (in µl) to be pumped and the second numerical value is the flow rate (µl/sec) at which the volume will be pumped.

Step 1 from Table 1 commands a pump to aspirate a sample toward the active mix well until an optical sensor detects the leading edge of the sample (an air to liquid transition detected by a sensor measurement difference sited by the fifth parameter "−100" when the sensor measurement changes by −100 my or more, indicates that air to liquid transition has taken place). Step 2 moves the sample further ensuring that the optical sensor is aligned with the sample fully and not just the transition, which enables to measure the correct reference signal for its next detection (liquid to air). Step 3 commands the pump to aspirate the sample toward and into the active mix well rehydrating the lyophilized reagents pellets with the sample until the optical sensor detects the trailing edge of the sample. Notice that Step 3 uses a flow rate of 5 µL/sec whereas the Line 1 utilizes a flow rate of 10 µL/sec. Step 3 introduces the sample slowly into the active mix well in order to minimize foaming while rehydrating the lyophilized reagent pellets. Step 4 ensures that the optical sensor is aligned with air that follows the sample (channel that had been wet by the sample, but has air now) and takes the correct reference signal for its next detection.

TABLE 2

Procedure for Mixing

| Steps | Procedures |
|---|---|
| 1 | Pump Displace [40, 10, Dispense, Both] |
| 2 | Pump Displace [40, 40, Aspirate, Both] |
| 3 | Pump Displace [40, 10, Dispense, Both] |
| 4 | Pump Displace [40, 40, Aspirate, Both] |
| 5 | Pump Displace [40, 10, Dispense, Both] |
| 6 | Pump Displace [40, 10, Aspirate, Both] |
| 7 | Delay [5000] (not shown in the fluidic diagram) |

Step 1 from Table 2 commands the pump to dispense a sample into a wash channel such that the trailing edge of the sample moves past the bead capture zone. Step 2 commands the pump to aspirate and to move the sample across the bead capture zone back into the active mix well. Notice that Step 1 moves the sample at a flow rate of 10 µL/sec whereas Step 2 moves the sample at a flow rate of 40 µL/sec. Slower flow rate while moving the sample from the active mix well into the wash channel (Step 1) was avoided leaving beads on the active mix well wall. Faster flow rate while moving the sample back into the active mix well promoted a proper mixing.

During the mix cycle, a sample moves between an active mix well 564 and a wash channel 568 across a bead capture zone 566 and experiences changes in the cross-sectional area, e.g., from 0.0016 in$^2$ to 0.0011 in$^2$ between the wash channel and the bead capture zone and from 0.0011 in$^2$ to 0.0016 in$^2$ between the bead capture zone and the mix well bottom.

Step 3 and Step 4 repeat the mixing cycle. Step 5 and Step 6 repeat the mixing cycle but differ in that it aspirates the sample back into the active mix well at 10 µL/sec, instead of 40 µL/sec, in order to bring back some of the beads that might have been left in the wash channel during the 40 L/sec aspiration of previous two mixing cycles.

TABLE 3

Procedure for Positioning the Sample to the Incubation Zone

| Steps | Procedures |
|---|---|
| 1 | Pump Cycle [30, 5, Dispense, Stop at OS1 (CAR), −100, 50] |
| 2 | Pump Displace [30, 5, Dispense, Both] |

Step 1 from Table 3 commands a pump to dispense until an optical sensor detects the leading edge of a sample. Step 2 positions the sample to the incubation zone. Notice that a slow flow rate (5 µL/sec) was used to avoid leaving beads on the active mix well wall.

Method for Detecting Air to Liquid and Liquid to Air Transitions in a Fluidic Channel Various embodiments of a diagnostic system 110 contemplate methods of detecting air/liquid boundaries used, for example, in the dividing and mixing methods described above. Certain embodiments provide a method for detecting air to liquid (and liquid to air) boundaries in a fluidic channel, comprising using an optical sensor (can be the same optical sensor 528 now used as a reflective object sensor); emitting light onto a detection spot of a channel with an infrared emitting diode; and detecting the reflective light with a phototransistor, wherein the emitter and detector are side by side housed.

Some embodiments also provide a method for measuring liquid volumes (and air volumes) in a fluidic channel 512, comprising recording the time when an air liquid boundary and liquid air boundary passes a detection spot; calculating the volume of liquid (or air) passing the detection spot based on the flow rate (pump rate, volume velocity) and time.

Some embodiments provide methods for detecting the transition of air liquid and liquid air boundaries in a fluidic sealed channel. Some embodiments use an optical reflective object sensor 528, properly positioned under the fluidic channel where the contents of the channel are moving by controlled means like a pump device. The fluidic channel can be sealed with a clear film, such as, a bottom seal, and it is contemplated that many different transparent and/or translucent materials can be used. The optical sensor 528 can be connected to a signal processing circuitry, generating a signal that is monitored by a microprocessor which timely distinguishes air and liquid by the difference in the amount of reflected light produced by air and liquid.

Figure 26B:
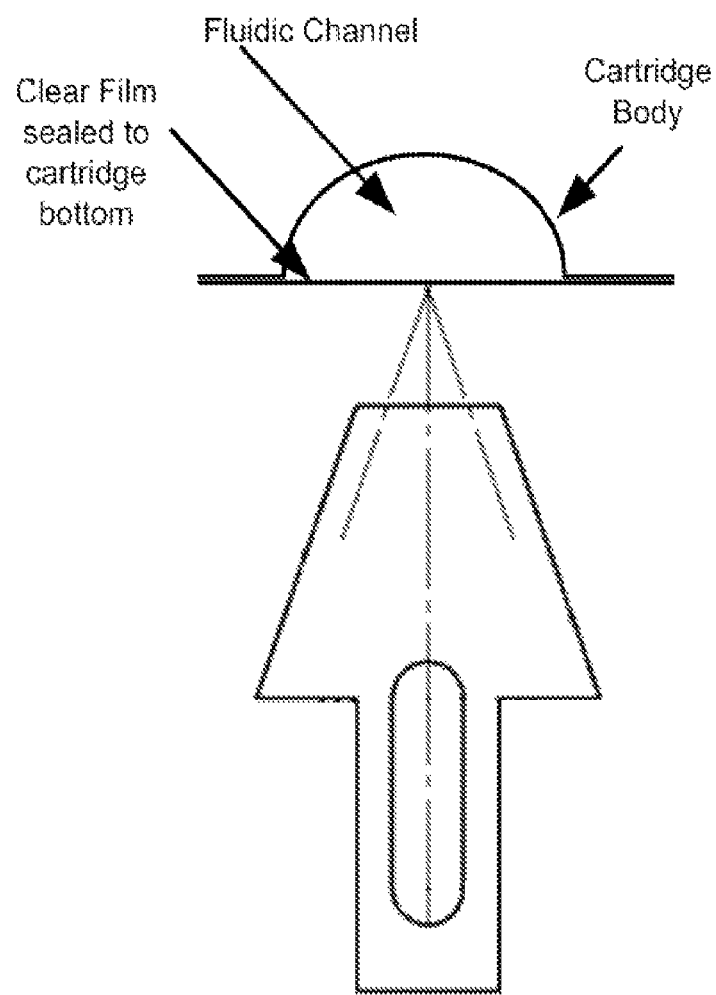
FIG. 26B is an illustration of a cross-section of an example fluidic channel used in a diagnostic system.

The sensor 528 can be an optical sensor. For example, one example sensor 528 may use an infrared emitting diode and a NPN silicon transistor (NPN is one of the two types of bipolar transistors with a layer of P-doped semiconductor (the "base") between two N-doped layers), a portion of which is depicted in FIG. 26A FIG. 26B illustrates a sensor 528 being used to detect state transition (i.e., air-to-liquid, liquid-to-wet, where "wet" is used to define where the content of a channel is air, but the channel had liquid in there before, or wet-to-liquid). An illustration of a cross-section of a fluidic channel is depicted in FIG. 26B. The bottom of the cartridge 14 has a clear film that is sealed to the body of the cartridge, with a sensor positioned to the center of a fluidic channel.

Figure 27:
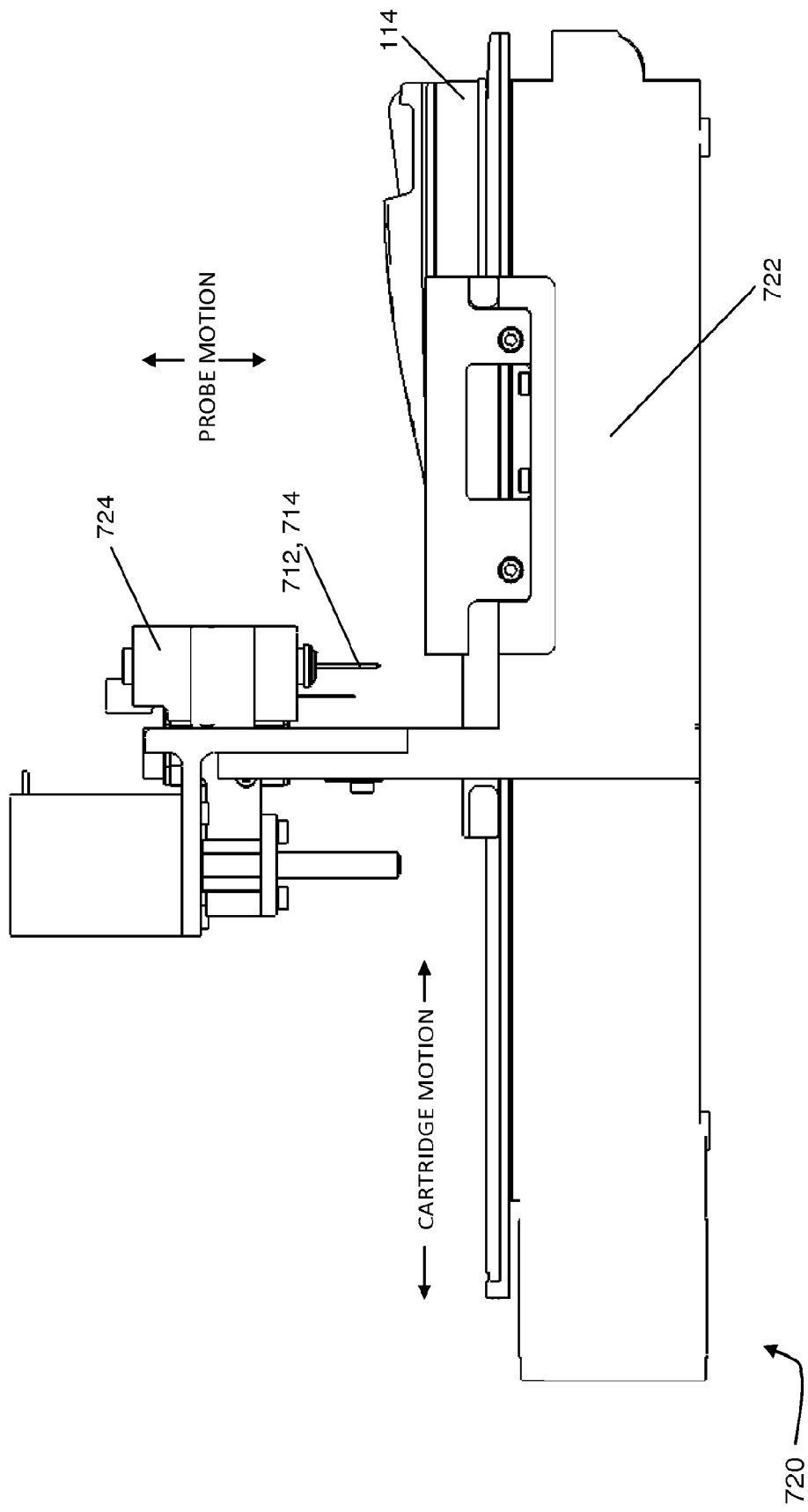
FIG. 27 is a schematic drawing of an example motion assembly used in a diagnostic system.

FIG. 27 illustrates an example diagnostic system 110 that can include a cartridge 114 with multiple channels to conduct similar diagnostics sample preparations or tests. In some embodiments, only one sensor 528 is used or is necessary, and a cartridge motion mechanism 720 can move the cartridge 114 to predetermined positions to align the fluidic channels with the optical sensor 528. The cartridge 114 can be positioned on a cartridge carriage 722, which can have an axis of motion along the horizontal. As the cartridge 114 is moved horizontally, back and forth with the cartridge carriage 722, a probe assembly 724 can move along a vertical axis to facilitate a probe's 712, 714 interaction with the cartridge 114.

Figure 28:
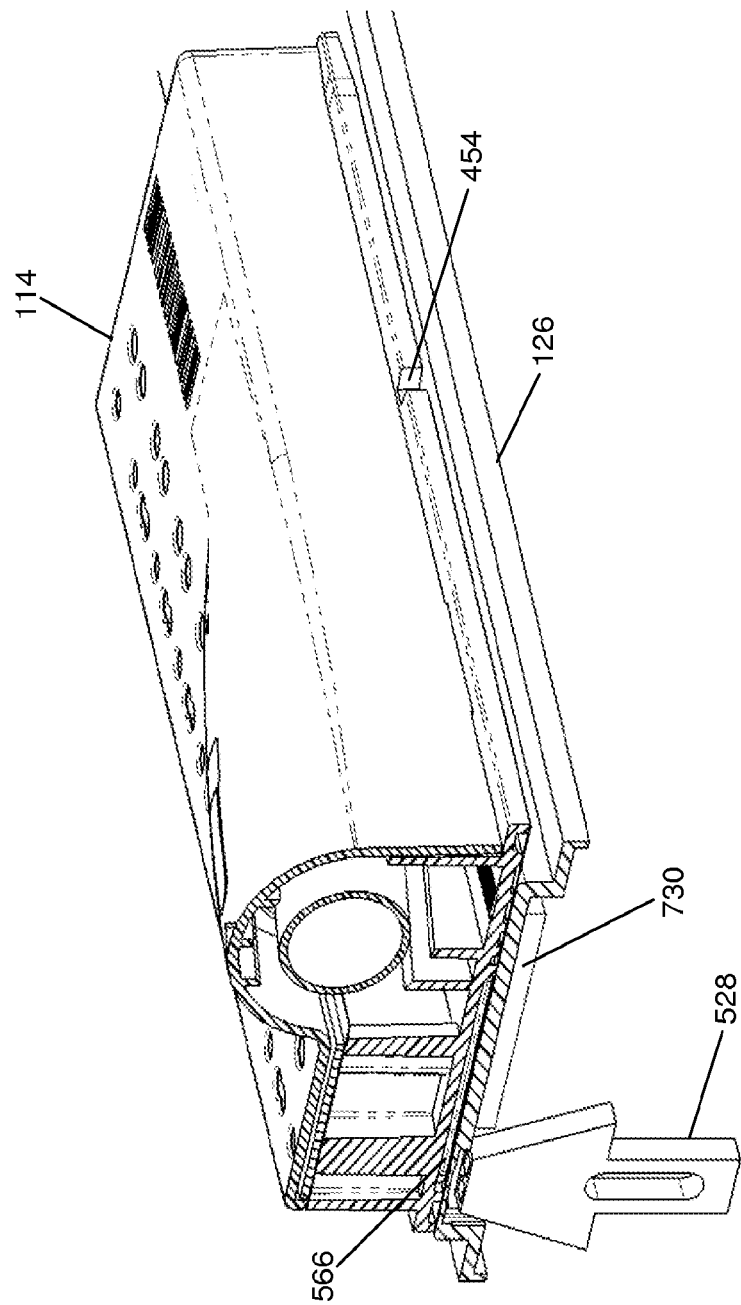
FIG. 28 is an illustration of a perspective view of a cross-section of an example optical sensor in relation to a sectioned view of a cartridge.

FIG. 28 illustrates an example arrangement between an optical sensor 528 and a cartridge 114 position on an incubator 126 of the diagnostic instrument 112. In some embodiments, a cartridge 114 can be placed on an incubator plate 728 and can move on the incubator plate 728 to position the channels at the bottom of the cartridge 114 such that the optical sensor 528 can be aligned near a center portion of the cartridge 114. A printed circuit board 730 under the incubator plate 728 can be provided to control the surrounding electrical components. A cartridge 114 can have the ability to run multiple tests each contained in the fluidic channels. During those tests, the functionality of air/liquid detection can be used to verify the location of the fluid within the fluidic pathways and the volumes of the segments of fluid in the fluidic pathways.

The sensor 528 located at the bottom of the cartridge 114 positioned at the predetermined distance away from the cartridge 114 to allow for monitoring of the contents of the cartridge 114. Monitoring of the contents of the cartridge 114 can be used for verification of volume, detection of presence of undesired air bubbles, verification of the location of the sample, detecting undesired leaks, and/or undesired clogs in the fluidic channels. A typical output from such a sensor 528 monitoring a fluidic channel in a cartridge 114 can be a measure of a volume of liquid which is passed.

Figure 30A:
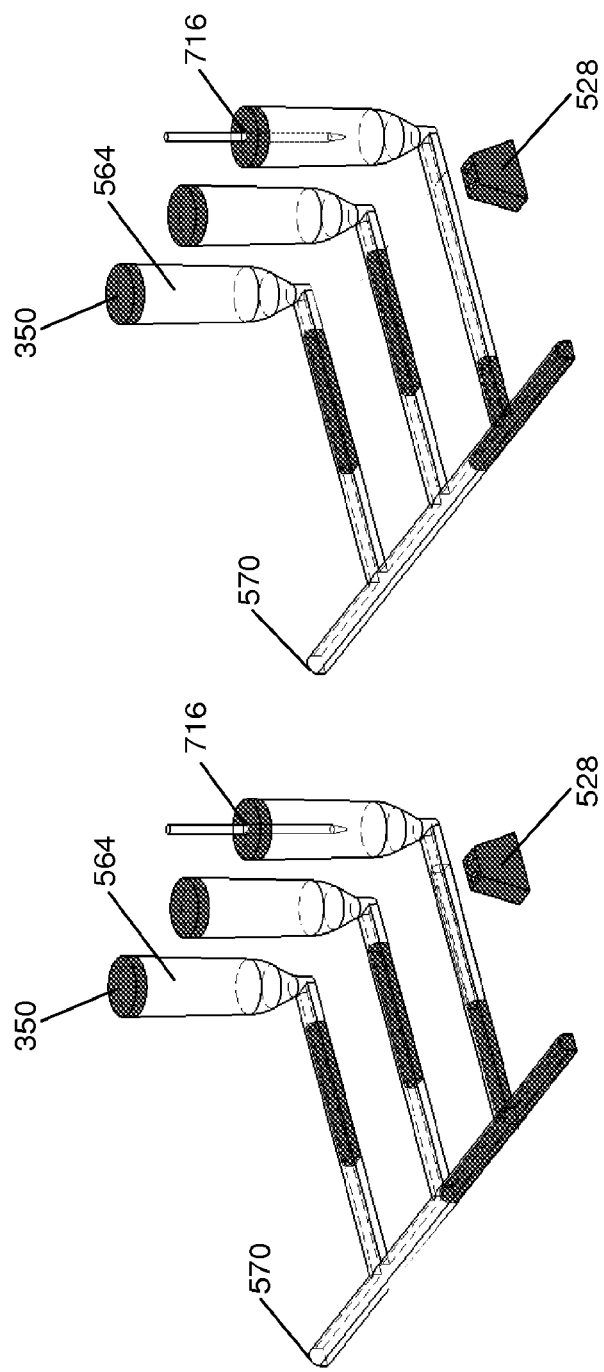
FIG. 30A is a schematic drawing illustrating an example sequence to detect leaks in a fluidics system.
Figure 30B:
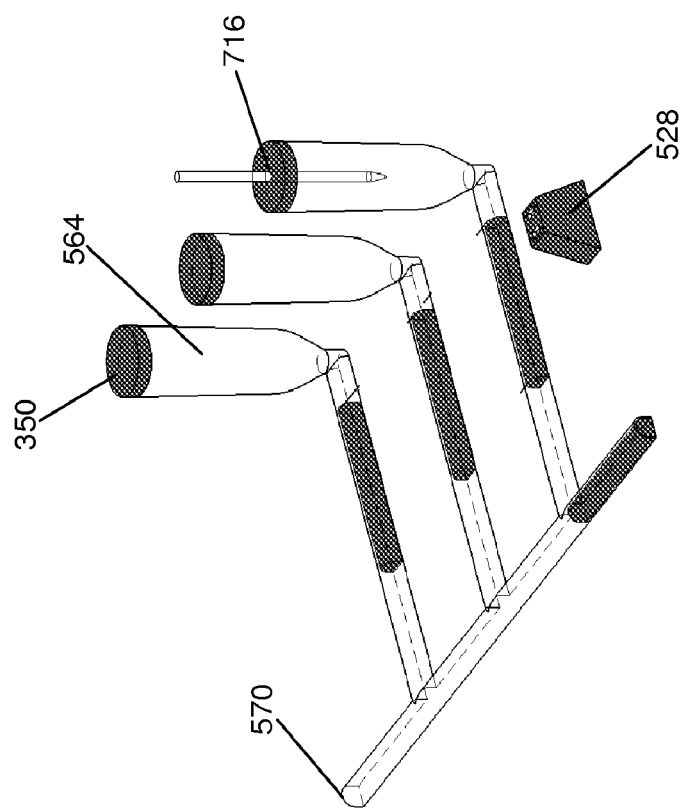
FIG. 30B is a schematic drawing illustrating an example of a when a sample has reached a sensor.
Figure 30C:
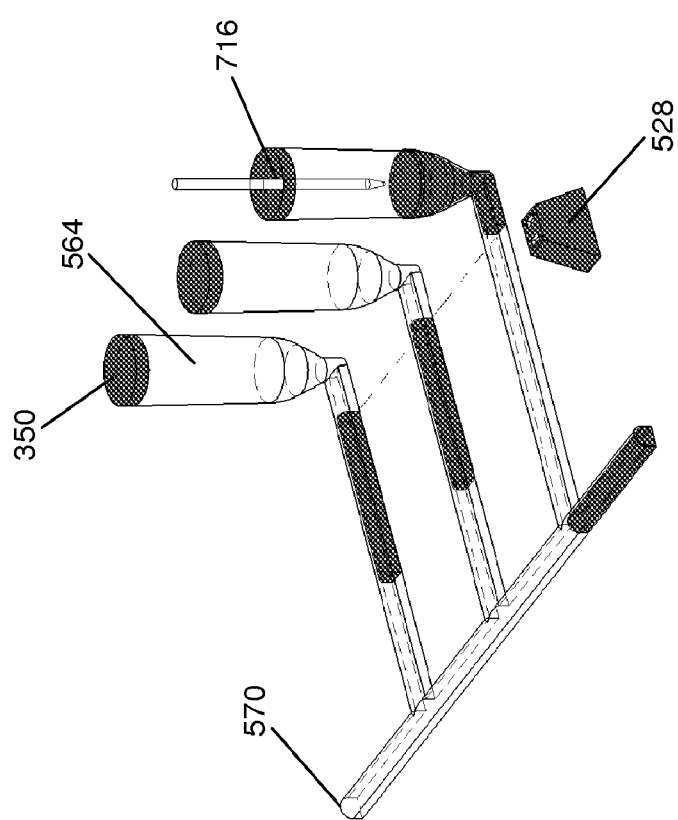
FIG. 30C is a schematic drawing illustrating an example of when a sample has passed a sensor.

FIGS. 30A-30C illustrate an example of a sequence of operations to detect leaks in the fluidic system. This will further be discussed below with respect to Example 2. In some embodiments, the ability to detect air and liquid boundaries can utilize a combination of hardware and software to detect air and clogs in a fluidic system, the presence of leaks and clogs will produce inaccurate results, proper diagnostics will enable the system not to generate any results, rather than wrong results.

The example methods can allow for verification of volume, detection of presence of undesired air bubbles, verification of the location of the sample, detecting undesired leaks, and/or undesired clogs in the fluidic channels, which can be used as a diagnostics mechanism by software to detect undesired behavior with the system that could produce erroneous results if not otherwise detected. Detection of the air to liquid and liquid to air transition can also be used for volume measurement of a liquid volume (more likely a sample that contains the antigen for detection, which the volume is important in measuring precise and accurate concentration) by the use of particular software.

The liquid/air detection methods can be simple and inexpensive methods to detect liquid to air and air to liquid transaction in a sealed fluidic channel. Fluidic volumes can be computed and verified by properly detecting the edges of a liquid volume, e.g., which is being moved by a pump at a constant flow rate. Air bubbles can be identified in otherwise expected liquid volumes, and then can invalidate results obtained from such channel (e.g., if the air bubble is large enough to have compromised the integrity of the volume).

Bead Washing

Referring to FIG. 4, method 400 can include washing the sample-reagent mixture in step 410. Various embodiments of the diagnostic system 110 contemplate washing a sample-reagent mixture 125 within the cartridge 114.

After the aliquoted sample is mixed with the lyophilized (otherwise dry) reagents, and incubation of the mixture has begun, the steps of capturing the beads within the mixture and washing them for detection may occur next. In particular, the diagnostic system provides methods for washing off blood or plasma and free label from beads in a cartridge bead based assay with no human intervention. This can include, but is not limited to, methods for washing off a sample (e.g., patient's blood, plasma or bodily fluids) and methods of freeing label from beads that have a specific antigen and label bound to them.

These methods can increase sensitivity and accuracy by decreasing the noise in the background, as well as not allowing the rest of the matrix (bodily fluids) from exiting the cartridge (which contains the sample and reagents) and entering and possibly contaminating the instrument (performing the detection). The methods achieve a highly effective wash method, by capturing the beads to be washed in a magnetic field, and then passing a liquid-and-air combination over the beads, in a fluidic channel using a very small amount of wash liquid.

In certain embodiments, the methods include steps to remove a patient's blood or plasma from the beads. For example, when beads enter the diagnostic instrument 112 for detection, no detectable remnants of a specific patient sample may remain such as to avoid contaminating the diagnostic instrument 112. In certain other embodiments, the methods include steps to remove the matrix containing free label that has not bound to beads, for example, so that they do not contain relevant information to the measurement, in order to reduce the background signal generated during the detection of the label that has bound to beads. Some embodiments may wash the patient's sample off from the beads, after the binding reaction is completed, while using a very small amount of wash fluid.

Other embodiments use a cartridge-based system where all reagents are housed within the cartridge (e.g., eliminating the need to use an externally connected reagent apparatus to a diagnostic instrument). It is advantageous to keep the volumes to be stored on the cartridge small, in a manner such that the resulting footprints for cartridges and diagnostic instruments are small, such as, for example, in the case of an diagnostic instrument for a point of care setting. One advantage of some of these embodiments is that it eliminates human intervention and it allows for a more precise and accurate measurement hence better diagnostics, by reducing the measurement background.

Figure 31:
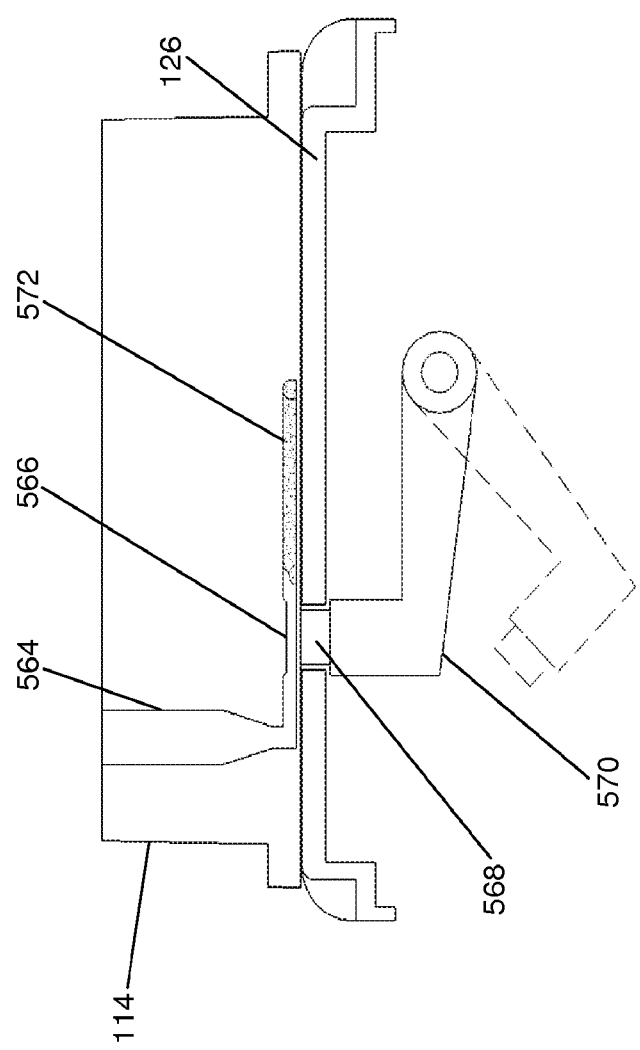
FIG. 31 is an illustration of an example of a mechanism for capturing beads in a sample.

FIG. 31 shows an example of a mechanism that captures beads within a sample within a magnetic field created by a magnet 568 attached to an arm 570 under the cartridge 114. The probe connected to the inlet of the fluidic system can pierce the sealed well creating a sealed connection between the fluidic system and the sample 572. The pump in the fluidic system can create a negative pressure and can move the fluid 572 across a magnet 568 toward the sealed well.

FIG. 24C shows example dimensions of a wash channel 568 and a bead capture zone 566 with the width of the wash channel 568 and the bead capture zone 466 being 0.045 inch, a max height of the bead capture zone 466 being 0.024 inch, a max height of the wash channel 568 being 0.036 inch. In this embodiment, a bead capture zone 466 was designed to have a lower ceiling than the wash channel 568 so that the vertical distance beads travel during the bead capture process is shorter at the bead capture zone than at the wash channel. This promotes more effective bead capturing within a given time. The same feature proving the diameter changes is used to facilitate a turbulent flow in order to help suspend the beads in liquid after they have been washed.

Typically in standard assays, human intervention is used to wash beads that have been used to form immunoassays. Beads in a fluidic sample of measurement external to the "detection instrument" have been washed with buffer in order to remove the free label and other possible contaminants from the beads. These human intervention methods require the transfer of the beads from and to the diagnostic instrument. To minimize human intervention and allow a more precise and accurate measurement, the present disclosure provides a cartridge-based system, in which the sample is washed within the cartridge before isolating the washed sample into the system for measurement.

An example apparatus may use a cartridge 114 that contains a well that is sealed by a septum where the fluidic system connects to it via a probe. The example apparatus can also include a fluidic channel that connects the sealed well to a vented opening, as well as a reservoir for buffer solution. The cartridge can have a thin film bottom sealing the fluidic channels as well as allowing the necessary magnetic field to be applied to capture the beads in the fluid and hold on to them while they are being washed. The apparatus can also include a fluidic system that contains an inlet, an outlet, a detection module, a pump, and tubing connecting these components that can generate fluidic motion in the fluidic channels in a cartridge, as well as aspirate and dispense fluids and air in and out of the cartridge.

In some embodiments of a diagnostic system 110, a probe can pierce a sealed well in a cartridge 114 forming a sealed connection between the sample and a fluidic system attached to the probe. The pump in the fluidic system creates a positive or a negative pressure in order to move the sample in a fluidic channel that connects the pierced well to the vented end 570 in a cartridge. The fluid in the channel contains the sample (e.g., antigens bound between beads and tag labels), unbound tag labels, and matrix (e.g., bodily fluids).

As depicted in FIG. 31, an arm 570 with a magnet 568 can be raised under the cartridge 114 while the fluid 572 moves across a narrow channel (capture zone 566) where the magnet 568 is in contact with the bottom of the cartridge 114. The magnet 568 creates a magnetic field capturing the magnetic beads bound to the antigen within the sample while the sample is moved at a slow rate across the bead capture zone 566. FIG. 31 shows an example of a mechanism that raises an arm with a magnet 568 attached to its end to the bottom of the cartridge 114. FIG. 24C shows a channel with a low ceiling where the bead capturing takes place. A channel with a low ceiling reduces the vertical distance beads need to travel during bead capture process with said capturing mechanism. Once after the beads are captured in an area, the magnet arm is lowered such that the magnet 568 is no longer in contact with the cartridge 114; and the cartridge is moved such that the inlet is above a buffer reservoir. In the buffer reservoir, the fluidic system aspirates a staggered combination of liquid and air and stores them in the tubing. The cartridge 114 is moved back to the location where the beads are captured 566 and, the magnet arm is aligned again with the beads when the magnet 568 is raised and contacts the cartridge bottom. The magnet arm is raised and holds the beads (in the magnetic field) while the staggered combination of liquid and air is dispensed across the captured beads washing the matrix and the unbound tag labels off from the beads.

In certain embodiments, the wash methods can include a sequence of operations in order to capture and wash the beads effectively. For example, the magnet can be raised as the incubated sample, which may contain a patient's blood or plasma mixed and incubated with reagents that contain the beads, flows due to a fluidic system, across a portion of the channel where the magnet makes contact. Using a pump, the reagent pack can be aspirated (consecutive chunks of liquid buffer and air) into the fluidic system (tube) via the probe of the diagnostic instrument. The composition of the pack can influence the cleaning quality. The amount of liquid buffer needed to wash the beads has been determined by the diagnostic system, accomplished by having air and liquid combination in a reagent pack. A liquid air boundary has shown to be very effective in brushing the surface of the beads.

Using the pump and the fluidic system, the reagent pack can be able to flow over into the fluidic channel that is sealed at the probe end and vented on the other side of the patient sample, while the beads remain held to the bottom of the cartridge by the magnet. The above sequence can push the sample away, so that the beads can sit in the clean buffer. The magnet then can be lowered and a series of push pull action is applied in the pump (aspirate dispense) that moves the fluid with the beads back and forth inside the cartridge across the bead capture zone to re-suspend, into clean buffer, beads that had been pulled to the bottom of the cartridge. This provides the washed beads in the clean buffer that now can be aspirated into the fluidic system to be analyzed in the detection module.

Preventing Reuse of a Single Use Device

Figure 32:
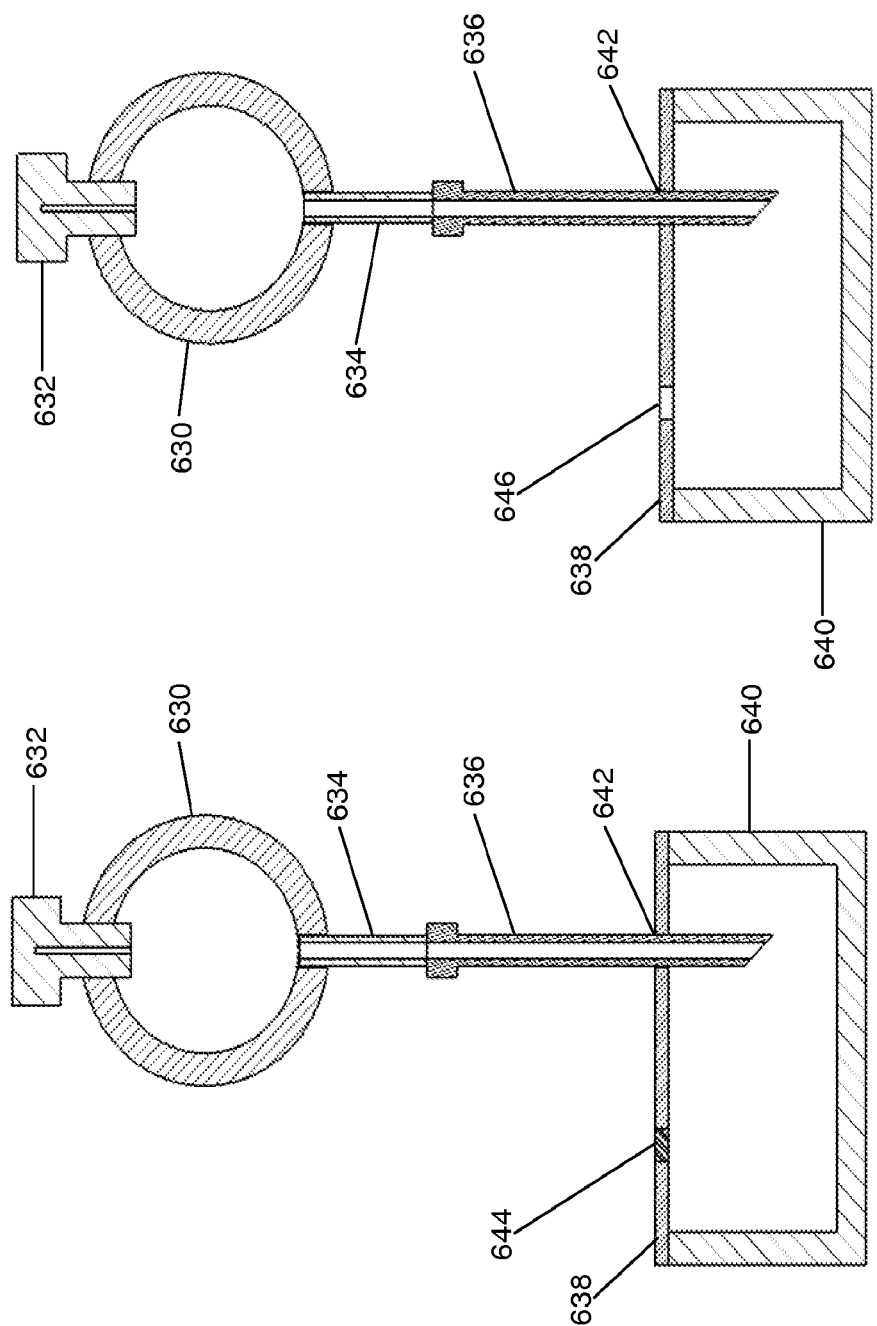
FIG. 32 is an illustration of example vented and unvented diagnostic device.

FIG. 32 is an illustration of an example of the different configurations between a vented and unvented diagnostic system. Various embodiments of diagnostic system 110 contemplate a method of preventing reuse of a cartridge 114. Some embodiments of the diagnostic instrument 112 provide methods to prevent reuse of a single use clinical device (i.e., a cartridge), for example, by detecting fluid flow characteristics that differ between a used and an unused device. This contributes to the prevention of false results incurred by inappropriate use of a used single use clinical device and also prevents the time loss incurred by processing an inappropriate test.

In certain embodiments, detection of a previously used single use clinical device is accomplished by means of a pump used to generate a pressure and a pressure sensor to detect either a vented path that is vented in a used clinical device but not in an unused clinical device or an unvented path that would be unvented in a used clinical device but not in an unused clinical device. This test allows a diagnostic instrument to quickly determine the use status of a clinical device and to disallow processing of a used single use clinical device.

Some embodiments provide methods of detecting a previously used single use clinical device, including detecting a previously used single use clinical device for the purpose of preventing invalid results. Other embodiments provide methods of detecting a previously used single use clinical device by measuring pressure changes and/or methods of generating a positive or negative pressure and detecting the introduction of a previously used single use clinical device by changes in that pressure. Still other embodiments provide methods of detecting a previously used single use clinical device by use of a pump to establish or fail to establish a pressure within the used clinical device for subsequent measurement. Some embodiments provide methods of detecting a previously used single use clinical device by placing a pressure transducer within the fluidic channel that communicates with a device in order to measure a change or lack of change in an established pressure.

In certain embodiments, single use clinical devices have seals, valves, or other features that control fluidic motion to enable processing of results whose fluidic flow state is changed during use; typical of this would be an opened valve or a pierced foil seal. In some embodiments, when the clinical device use is completed, a fluidic pathway configuration of a new device is no longer the same, such as a pierced foil seal or a valve left closed rather than open. By introducing and detecting a pressure in a fluidic pathway that should not be sealed or by failing to introduce a pressure in a fluidic pathway that should be sealed, a used single use clinical device can be detected and rejected as not usable thus preventing invalid results from being presented. FIG. 32 provides an illustration of an example of an unvented device on left and a vented device on right.

Certain embodiments provide methods to prevent reuse of a single use clinical device, for example, (i) by means of a pressure measurement to detect changes in the device brought about during use; (ii) by means of a pressure introduced into the used device and detecting a state only present in a used device; and/or (iii) by means of a pressure transducer to detect an expected pressure introduced into the used device and detecting a state only present in a used device.

FIG. 32 illustrates an embodiment that can include a pump 630 in fluidic communication with a pressure transducer 632, a fluidic pathway, in the form of a tube 634, in communication with a pump chamber and leading to a hollow needle 636, with which it is also in fluidic communication. A needle 636 can be provided to pierce a septum 638 on a single use clinical device 640 thereby creating an airtight seal 642 between the single use clinical device and the outer surface of the needle 636. Air can be inserted into the single use clinical device by the pump after which the pressure in the system can be monitored to determine if the pressure is maintained.

Example: Case 1: Detecting a single use clinical device in which the test chamber is not vented 644 if the single use clinical device is used. Detection of a maintained pressure is indicative of a used single use clinical device whereas detection of a loss of pressure is indicative of an unused single use clinical device.

Example: Case 2: Detecting a single use clinical device in which the test chamber is vented 646 if the single use clinical device is used. Detection of a maintained pressure is indicative of an unused single use clinical device whereas detection of a loss of pressure is indicative of a used single use clinical device.

Undesired reuse of a single use clinical device can be prevented by means of the detection of pressure changes and/or pressure status within the device to determine its use status. In some embodiments, a system is comprised of a pump 630 capable of pressurizing the single use clinical device to a level at which pressure level and pressure change can be detected. A pressure transducer 632 can be used to monitor the pressure within the pressurized fluidic channels of the system. Typically, but not necessarily, a tube 634 can be used to connect the pump 630 to a hollow needle 636, probe or fitment (hereafter called needle, but the present disclosure is not limited to a needle) in fluidic communication to both the pump 630 and the needle 636. The pressure transducer 632 may be situated anywhere within the fluidic pathway. The location of the pressure transducer 632 may be within the pump chamber 632 as long as the chamber is in fluidic communication with the tube 634 and needle 636 during detection. The needle 636 can be placed in fluidic communication with a target chamber of the single use clinical device by a convenient means forming an air-tight connection to the single use clinical device. Pressure can be introduced into the chamber of the single use clinical device 642 by means of the pump 630 or other controlled pressure source and then measured to determine the state of the pressure over some elapsed time.

In certain other embodiments, processing of a single use clinical device can be designed to deliberately leave the device in a fluidic state other than its unused state. A single use clinical device can be further designed to allow an airtight fluidic connection by the needle 636 for a used single use clinical device detection. This may be in the form of a vent which is opened or closed during normal processing or may be a separate feature designed specifically for use detection reasons. If the feature is unvented 644 or closed after use, then pressurization is attempted and then measured, detection of the established pressure indicates a used single use clinical device, whereas detection of a loss of pressure indicates an unused device. If the feature is vented 646 or opened after use, then pressurization is attempted and then measured. Detection of the established pressure indicates an unused single use clinical device, whereas detection of a loss of pressure indicates a used device.

Examples herein are intended to be restricted to a vent and are contemplated to include that any structure such as a valve, a pierced membrane, a broken feature, or activation of a material whose fluid flow properties may be readily changed would serve the same function.

Desiccant System

Figure 33A:
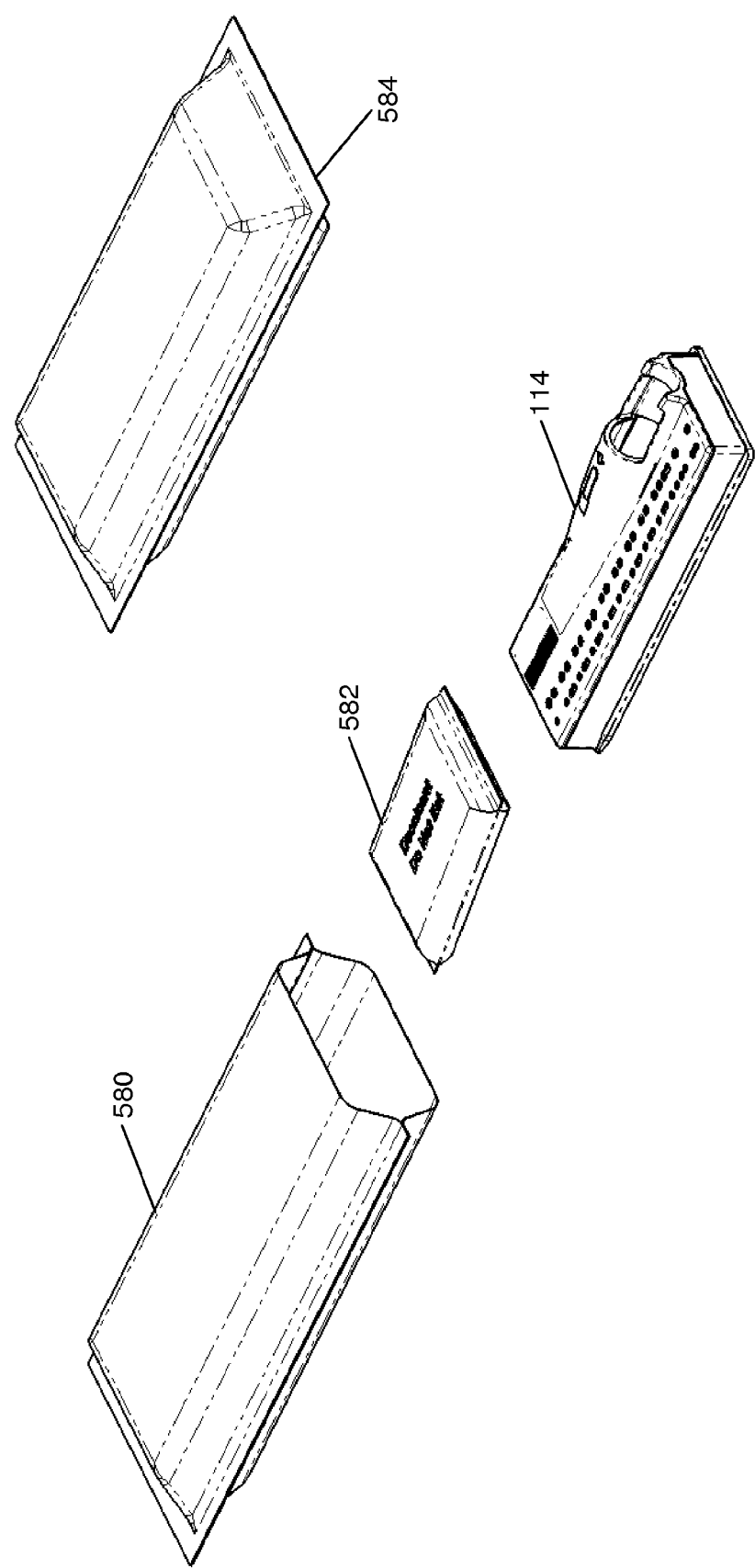
FIG. 33A is an illustration of an exploded perspective view of an example cartridge packaging including a desiccant.

FIG. 33A is an illustration of an example cartridge packaging system, which shows a package 580, a desiccant 582, a cartridge 114, and an airtight packaged cartridge (after sealing) with desiccant 584.

Figure 33B:
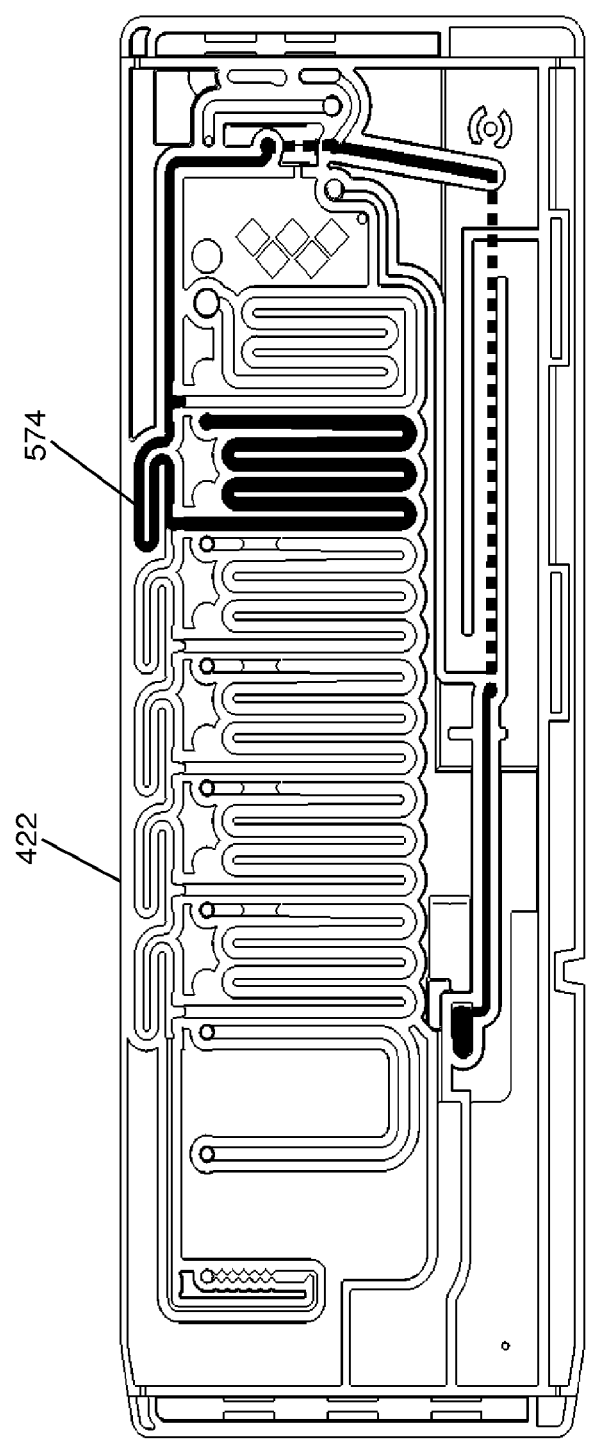
FIG. 33B is an illustration of a bottom view of an example cartridge highlighting a path from the atmosphere to a region on the cartridge.

FIG. 33B shows a path 574 from the ambient air surrounding a cartridge 114 to the nearest dry reagent within the cartridge 114. Various embodiments of a diagnostic system 110 contemplate a desiccant system to for prolonging the shelf-life of a cartridge and maintain the dry quality of dry reagents on the cartridge 114.

In the design of cartridges 114, it may be desirable to lyophilize or dry assay reagents to increase product stability at room temperature storage. It may also be desirable to process the assay with a liquid reagent, for rehydration, washing, or assay processing. In certain embodiments, it can be advantageous to store both the dried reagent on the same device as the liquid reagent. The exposure of dry reagent to moisture from a liquid regent can have the potential to decrease the stability of the dry reagent and thereby decrease shelf life of the cartridge 114. A desiccant can be used to facilitate and maintain the dryness of the dried reagent stored on the cartridge 114.

As used herein, example can include desiccants can include any moisture-absorbent material. Desiccants may induce or maintain a state of dryness by absorbing moisture. Examples of suitable desiccants include, but are not limited to, molecular sieves, silica, calcium sulfate, DRIERITE®, clay, etc. Desiccants can compete with other substances (e.g., assay reagents) in the same ambient air for moisture and can dry or desiccate the other substances.

Examples for using desiccant include providing an improved method for storing both dry reagents and liquid reagents with a desiccant on a cartridge 114. This method is not limited to diagnostic cartridges but lends itself to the aforementioned issues as well. Some embodiments contemplate a method using a desiccant specifically to extend the shelf life of dry reagents on a disposable cartridge that stores both liquid and dry reagents where there is a pathway connecting the dry reagents and moisture vapors from the liquid reagents. For example, some embodiments disclosed herein provide a desiccating system for a cartridge 114 that has both stored liquids and dry reagents which is able to prevent water from being absorbed by the dry reagents and for which the cartridge has an open passageway from the interior location of the dry reagent to exterior where a desiccant is located.

Some embodiments contemplate keeping the dried reagents stable in the presence of liquid for a minimum of two years.

An example cartridge 114 can be made from a Cyclic Olefin Copolymer, e.g., with the Trade name of TOPAS®. The MVTR for TOPAS® grade 5013 is about 0.03 g mm/(m$^2$ day) at 23° C. and 85% RH. The cross-sectional area that water vapor diffuses through is 524 mm$^2$ and the wall thickness is 0.047 in. Therefore, the rate of moisture loss can be calculated to be: [0.03 g mm/(m$^2$ day)]{(524×10$^{-6}$ m$^2$)/(0.047×25.4 mm)}=13.2 µg/day.

Accordingly, it can be predicted based on the calculations above, that to achieve over a 2 year shelf life, a cartridge 114 will release about 87 mg of water. The cartridge 114 can be sealed in a foil package using DRIERITE® as a desiccant to absorb this water. There is a path 574 through a needle that will allow the ambient air (within the foil package) to reach the dry reagents. The amount of DRIERITE®, for example, needed to absorb 87 mg of moisture is 1.3 g. If instead, the 87 mg of water is allowed to reach the dry reagents, such as when no desiccant is used, the shelf life of the cartridge would be greatly shortened.

Diagnostic Instrument Overview

The diagnostic system 110 can include a diagnostic instrument 112, such as that shown in FIG. 5A. Various embodiments of the diagnostic system contemplate that a diagnostic instrument 112 can be compact, portable and contain all mechanical and electrical components necessary to run a diagnostic test in coordination with a cartridge 114. A cartridge 114 holding a biological sample can be introduced into the diagnostic instrument 112 for detection and analysis of the sample within the cartridge 114 by components within the diagnostic instrument 112. The component s and methods associated with the diagnostic instrument 112 will be described in more detail in the following disclosure.

The diagnostic instrument 112 is configured to perform the detection analysis using the highly sensitive and highly specific electrochemiluminescence (ECL) technology to produce precise and accurate diagnostic test results in a point of care clinical setting. The ECL technology has been minimized in size to allow for placement in a POC device for fast, convenient and more effective diagnosis and treatment. The mechanisms and components surrounding the detection analysis will be described in more detail in the following disclosure.

Example diagnostic instruments 112 can be configured to perform steps of a diagnostic test in conjunction with a cartridge 114 with minimal user input and as part of a diagnostic system 110. For example, a cartridge 114 with a sample can be introduced into the diagnostic instrument 112, the diagnostic instrument 112 can perform the diagnostic test on the sample and produce and present results to a user within a short processing period, for example, in as little as 8 to 15 minutes for up to ten different tests. The results can be provided through output devices such as a printer or laboratory information management systems (LIMS). The user is not required to enter much more than some basic patient identification information and/or select the diagnostic function on the diagnostic instrument 112.

It is contemplated that the processing time for an individual cartridge 114 may be longer, for example, up to 20 or 30 minutes, depending on the number of tests being run on the individual cartridge 114. If there are fewer tests to be run then less time may be expected to complete a processing cycle. The number of tests run on an individual cartridge 114 can vary as well. For example, a single cartridge 114 can run one test, two tests, three tests, or five tests, or any number of tests on a single cartridge 114 for a single processing cycle of the diagnostic system 110.

Diagnostic Instrument Industrial Design

The designs of various embodiments of the diagnostic instrument 112 are disclosed in co-pending U.S. Design application Nos. 29/420,956 and 29/420,965, both filed on May 15, 2012, each of which is herein incorporated by reference in its entirety. Images contained within those disclosures use clinical instruments of a diagnostic system, and designs thereof, which relay both the function and form, and the connection between the product, the user, and the environment. Such images represent some embodiments of instrument, which may be similar or different from the instrument 112 disclosed herein.

Diagnostic Components and a Closed Fluidic Path

Figure 5B:
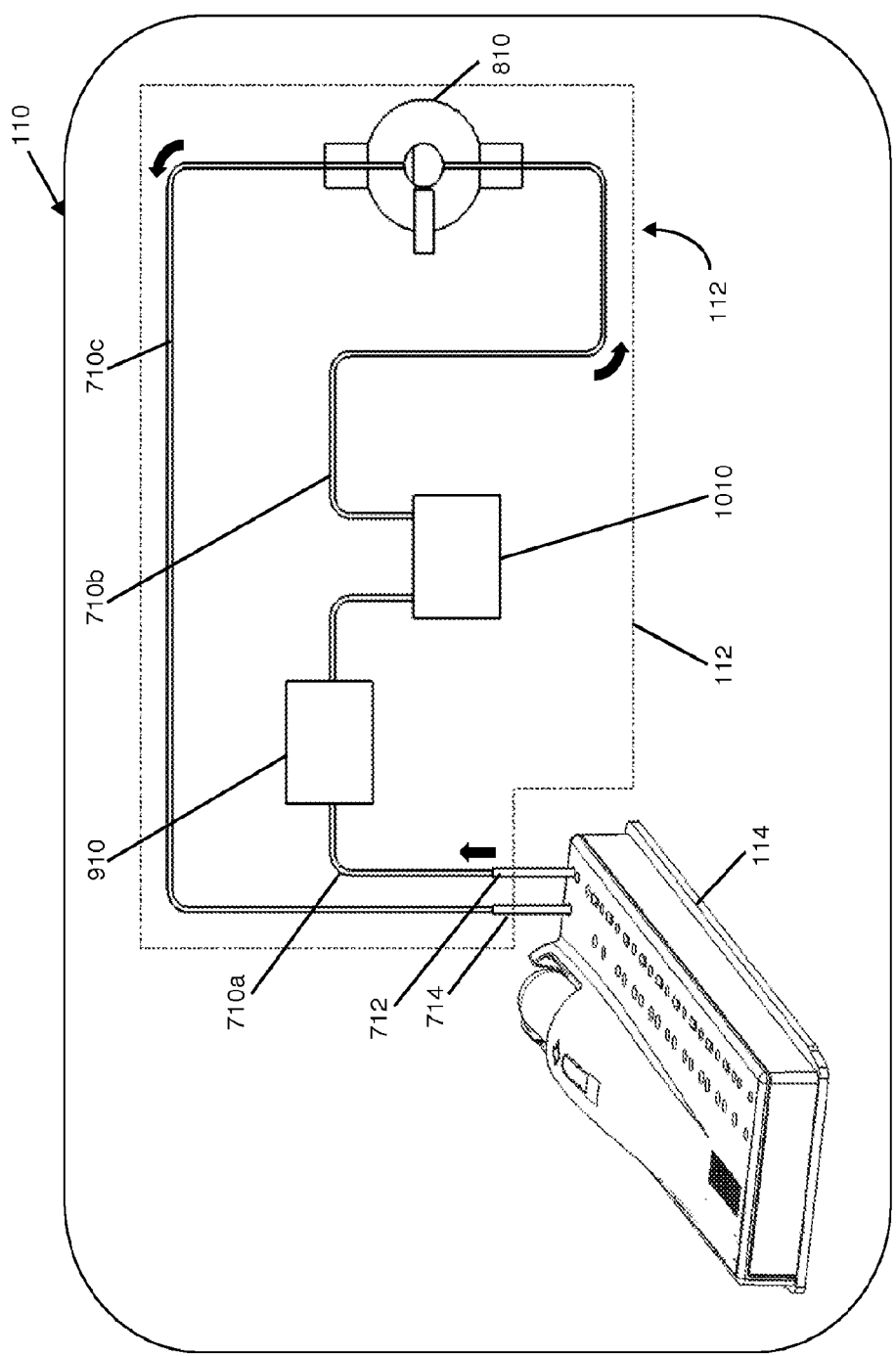
FIG. 5B is an overview illustration of an example closed fluidic path between a diagnostic instrument and a cartridge.

FIG. 5B is an overview illustration of a closed fluidic path 710 (see, e.g., 710a, 710b, 710c) between a diagnostic instrument 112 and a cartridge 114 of a diagnostic system 110. Various embodiments of a diagnostic instrument 112 contemplate having mechanical and electrical components that are connected fluidically to a cartridge 114 by a closed fluidic path 710. For example, the closed fluidic path 710 can fluidically connect a cartridge 114 via a first probe 712 to optional features along the closed fluidic path 710, such as a non-ECL detection module 910 via path 710*a*, at least one ECL detection apparatus 1010, a pump 810 via path 710*b* and returning to the cartridge 114 via path 710*c* and a second probe 714. The closed fluidic path 710 provides a pathway through which diagnostic materials, such as a biological sample and dry and liquid reagents, can be withdrawn from the cartridge 114, and can travel through the diagnostic instrument 112. After processing, the processed reagents and other waste materials can be returned to the cartridge 114 using a substantially single direction of flow (indicated by arrows). This is further discussed with respect to FIG. 35, which includes another example fluid path 710.

Figure 34:
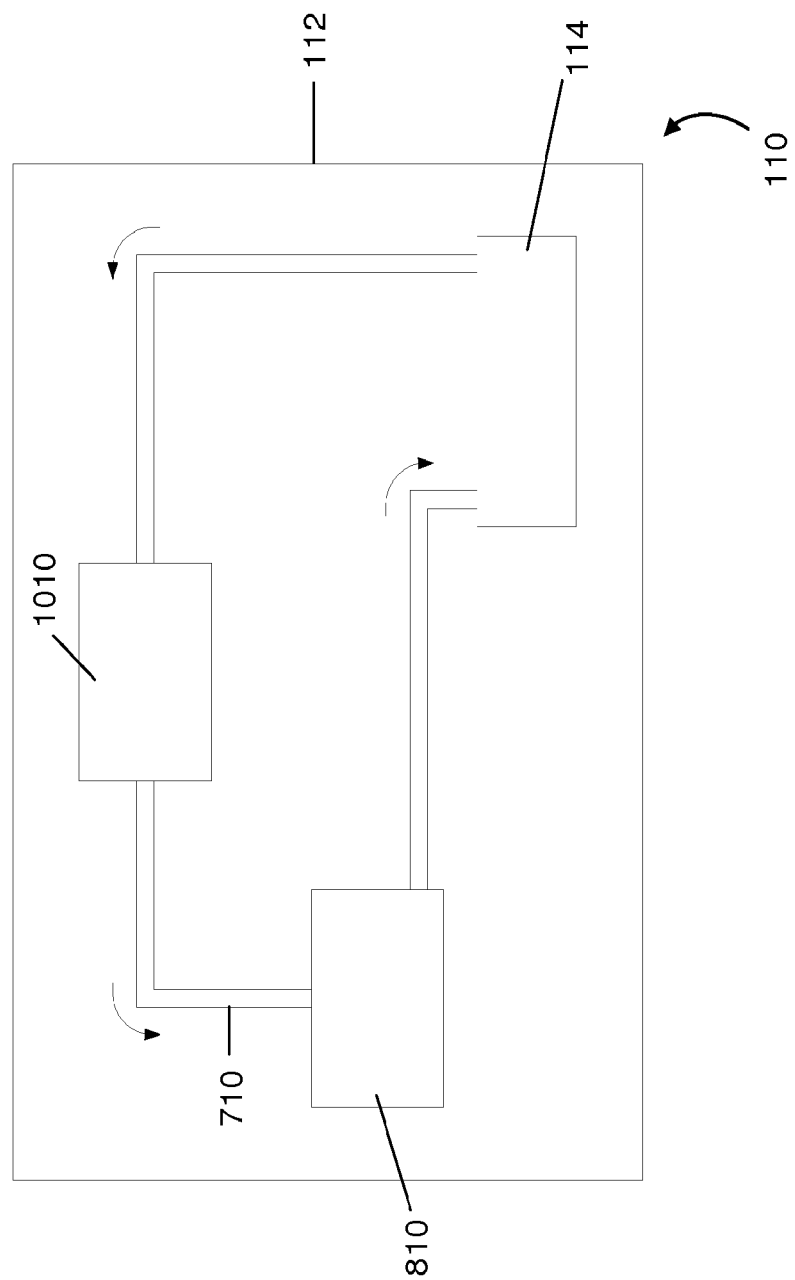
FIG. 34 is an overview illustration of an example closed fluidic path between a diagnostic instrument and a cartridge.
Figure 35:
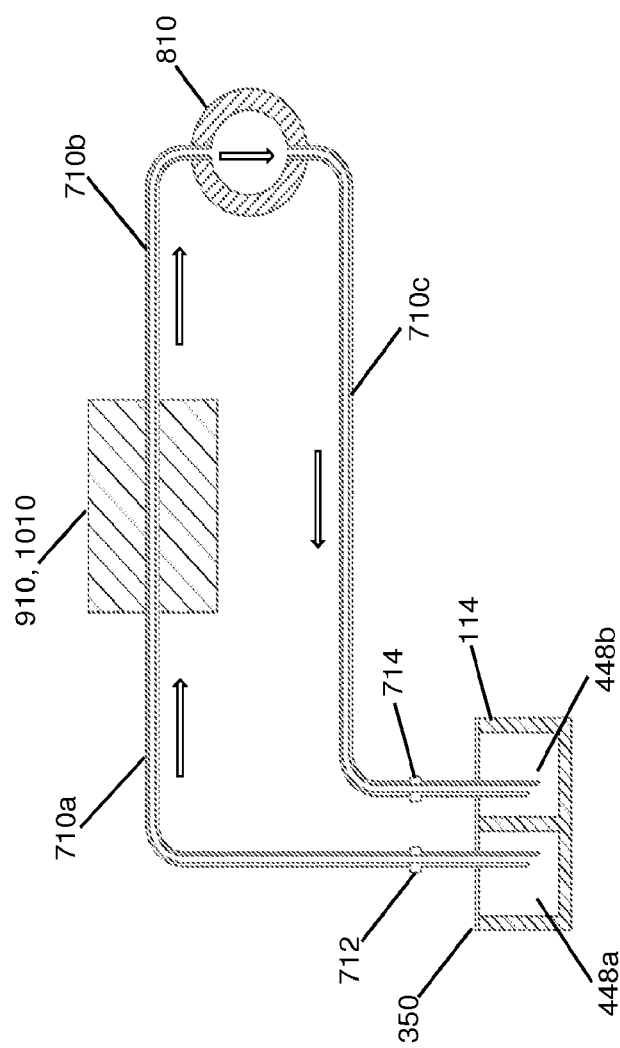
FIG. 35 is an illustration showing a cross-section of an example closed fluidic path between a diagnostic instrument and a cartridge.

FIG. 34 is an overview illustration of an example closed fluidic path between a diagnostic instrument and a cartridge. FIG. 35 is an illustration showing a cross-section of another example of a closed fluidic path 710 between a diagnostic instrument 112 and a cartridge 114. Various embodiments of a diagnostic system 110 contemplate a fluidic connection between a cartridge 114 and a diagnostic instrument 112 where at least two probes 712, 714 of the diagnostic instrument engage a cartridge 114. Part of the closed fluidic path 710*a* can fluidically connect the cartridge 114 to a non-ECL detection module 910 and/or an ECL detection module 1010. Part of the closed fluidic path 710*b* can fluidically connect the detection modules 910, 1010 to a pump 810. Part of the closed fluidic path 710*c* can fluidically connect the pump 810 to the cartridge 114 via probe 714. The components that are connected by the closed fluidic path 710 can be configured in various orders and arrangements depending on the desired design and function of the diagnostic system 110.

The closed fluidic path 710 of the diagnostic system 110 can be configured to begin and end in the cartridge 114 and to have a substantially single direction of flow in a pathway fluidically connecting the diagnostic instrument 112 and the cartridge 114. For example, in some embodiments, the closed fluidic path 710 can originate in the cartridge 114 when the sample is introduced into the cartridge 114 and a septum 438 of the sample receptacle 116 is engaged by the at least one needle (See, e.g., 428 of FIG. 16A) of the cartridge 114. The sample can be drawn through the cartridge 114 along the closed fluidic path 710 and into the diagnostic instrument 112.

in one example as illustrated in FIG. 35, the closed fluidic path can continue from the cartridge 114 to the diagnostic instrument 112 where one of at least two probes, a first probe 712, forms a first probe engagement with the at least one fluidic seal of the cartridge 114, such as the septum seal 350. From this first probe engagement, the first probe 712 fluidically connects to a first reservoir 448*a* (i.e., the reservoir 448 of the RHS 446) of the cartridge 114 to contact reagents stored within the first reservoir 448*a* and withdraw them into the first probe 712. Once the first reservoir 448*a* is emptied of the reagents and/or other contents, it is available for use as a waste reservoir 448*b* or can remain empty.

The first reservoir 448*a* and the waste reservoir 448*b* can be separate reservoirs on the cartridge 114. Alternatively, that the first reservoir 448*a* and the waste reservoir 448*b* can be the same reservoir on the cartridge 114. For example, after a first reservoir 448*a* is emptied of its contents, that same first reservoir 448*a* can be used as a waste reservoir 448*b* for collecting processed reagents and sample. By using previously emptied reservoirs for waste containment the overall volume requirement of the cartridge 114 can be reduced.

Various embodiments of the diagnostic system 110 contemplate a configuration where fluids and liquid and dry reagents used for the diagnostic test can be stored on the cartridge 114 within the at least one reservoir 448, such as the first reservoir 448*a*. The first reservoir 448*a* can contain diagnostic reagents or other materials necessary for test processing. The diagnostic system 110 also can be configured so that at least one reagent and at least one waste material can be stored on the cartridge 114. It is contemplated that fluids or dry or liquid reagents are not stored in the diagnostic instrument 112. It is further contemplated that waste materials are not stored on the diagnostic instrument 112. For example, the waste reservoir 448*b* can receive the waste materials, such as the processed materials, including, for example, at least one of a processed reagent, a blood filtrate, a processed plasma, and a processed sample.

In FIGS. 34 and 35, the closed fluidic path is depicted as three segments, 710*a*, 710*b*, 710*c*; however, any number of segments can be used depending on the desired configuration of components within the diagnostic system 110. The closed fluidic path 710 can be formed from a single material such as tubing or other material suitable for transporting fluids. It is contemplated that the closed fluidic path 710 can be made from more than one material suitable for transporting fluids, in addition to or instead of a first material, such as tubing. It also is contemplated that the closed fluidic path 710 can be formed from one or more different segments that are connected to form the closed fluidic path 710, such as additional components in the cartridge 114 or the instrument 112.

It is contemplated that the closed fluidic path 710 may be formed out of individual components within the diagnostic system 110 and then connected to tubing in-between components. For example, a segment of the closed fluidic path 710 can be formed from the ECL detection module 1010 or the fluidic channels 512 within the cartridge 114. The segments can be joined together to seal the fluids traveling through the closed fluidic path 710. Several suitable materials and mechanisms known in the art can be used to join and seal segments together.

Some embodiments of the closed fluidic path 710 can have a diameter that remains constant or that is variable throughout the pathway, such that the fluid traveling through the pathway can maintain a desired flow rate as facilitated by the pump 810. For example, the closed fluidic path 710 can have a diameter that is the same as a diameter of a probe 712, 714. In the configurations of the closed fluidic path 710 that include more than one segment, the diameters of joining portions can be matched at each junction in order to mitigate potential carryover traps.

Part of the closed fluidic path 710*a* can carry fluids, such as processed sample and reagents from the first probe 712 to a non-ECL detection system 910 and/or to an ECL detection module 1010. The detection within these components 910, 1010 can be performed without the sample or reagents leaving the closed fluidic path 710. If necessary, additional segments of closed fluidic path 710 can be included to connect multiple detection systems. The closed fluidic path 710*b* can carry fluids to a pump 810. The closed fluidic path 710*c* then can carry fluids to the second probe 714, which may be a waste probe. The closed fluidic path 710 terminates when the second (waste) probe 714 forms a probe engagement with the at least one fluidic seal 350 on the cartridge 114 establishing a fluidic communication with the waste reservoir 448*b* within which to deposit the waste materials.

The substantially single direction of flow is depicted by the arrows in FIGS. 34 and 35. The substantially single direction of flow and the closed fluidic configuration can serve to reduce the potential for carryover between tests. For example, unused or unprocessed materials travel through the closed fluidic path before the used or processed materials do, thereby preventing contamination of the unused materials by the processed materials within the same closed fluidic path. After a test is completed, the closed fluidic system can be flushed with a cleansing reagent or lubricant to flush the pathway for following tests, reducing cross-contamination with subsequent tests.

The substantially single direction of flow reduces the potential for carryover between different diagnostic tests such that there is substantially no detectable carryover between diagnostic tests. The substantially single direction of flow also prevents carry over between different cartridges used with the diagnostic system such that there is substantially no detectable carryover between diagnostic tests of different cartridges. Opportunities for carryover can be further reduced by transporting fluids through a single non-branching fluidic path.

In some embodiments, the pump 810 can provide motive force for fluidic motion within the closed fluidic path 710, having a logical entrance and exit for fluidic flow. The opportunity for carryover increases in the pump 810 as the pump likely represents a discontinuity in the geometry of the flow path, therefore maintaining a buffering length of fluidic path between the detection instruments and the pump, greater than the volume of any potential backflow is desirable to prevent carryover. Additional details of the pump 810 components and mechanisms will follow.

Incubator and Incubation Methods

Example incubators 126 can be provided in order to achieve the uniform and controlled temperature of the cartridge during processing. Positioning of the cartridge 114 can be important to the proper function and efficiency of the incubator 126. For example, a majority of the processing of the sample can occur in the fluidic channels 512 of the cartridge 114. In embodiments where the fluidic channels 512 are located near the bottom of the cartridge 114, it is important to position the bottom of the cartridge 114 adjacent to the incubator 126 for optimal exposure to the incubator 126.

As previously discussed, in some embodiments, the sample-reagent mixture 125 can be moved to particular regions of the fluidic channels 512, such as the incubation zone 562 of the CAR 560, as shown in FIG. 24B, where the sample-reagent mixture 125 can be located. In this location, a sample-reagent mixture 125 can be incubated to ensure complete reaction and mixing of the reagents with the antigens in the plasma. The bottom seal 360 can facilitate in part the incubation of the sample-reagent mixture 125 in the fluidic channels 512.

Figure 36:
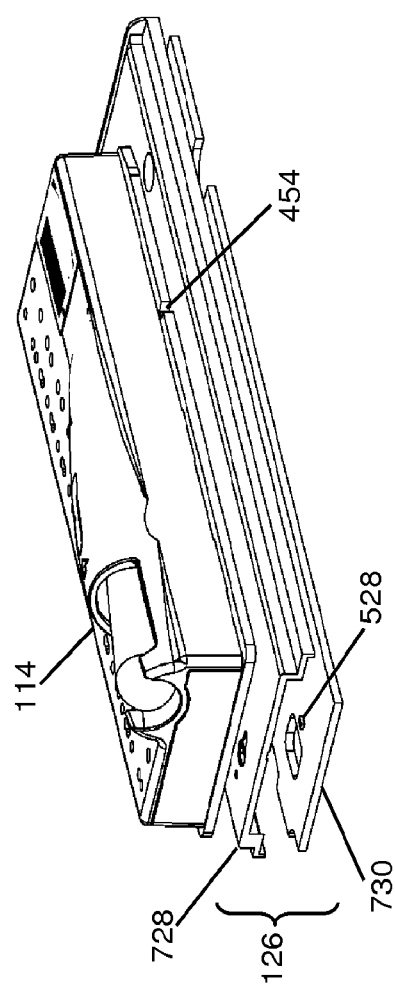
FIG. 36 is an illustration of an perspective view of example components of an example incubation apparatus.

FIG. 36 is an illustration of an example incubator 126 with a cartridge 114. In some embodiments, the incubator 126 can be made up of an incubator plate 728, a heater 730 (also referenced as the PCB), and a sensor 528 that can be integrated into the incubator plate 728 or the heater 730, or at least near the incubator plate 728 and the cartridge 114. The heater (or cooler as needed) 730 can be positioned in such a way as to efficiently and effectively transfer heat to the incubator plate 728 upon which the cartridge 114 can be positioned. The notch 454 on the bottom of the cartridge can assist in properly aligning the cartridge 114 on the incubator 126. The amount of heat generated by and transferred from the heater 730 to the incubator plate 728 can be adjusted according to predetermined parameters, such as the target temperature of a cartridge, the starting temperature of a cartridge, and the rate or time within which it is desired to reach the target temperature of the cartridge.

Referring to FIG. 28, the spatial arrangement between an optical sensor 528 and a cartridge 114 as it is positioned on an incubator 126 of the diagnostic instrument 112 is shown. In some embodiments, a cartridge 114 sits flat on an incubator plate 728 and can move on the incubator plate 728 to position the channels at the bottom of the cartridge 114 such that the optical sensor 528 is aligned at the center of the cartridge channel or is aligned with the incubation zone 562.

In some embodiments, a housing (not depicted) may be used to assist in controlling the temperature around the cartridge 114 and incubator 126 during processing. For example, the housing may be an additional component that forms a tunnel-like encasing around the incubator. The housing may be made from many suitable materials such as, for example, aluminum sheet metal. It is contemplated that the housing can adopt several different configurations, including shape, size and materials, to fit within a given diagnostic system 110.

In some embodiments, the sensor 528 can be located at several varying locations on the heater 730. It is contemplated that more than one sensor may be incorporated into the incubator 126. The sensor 528 can measure the temperature of the incubator plate 728 as it is heated by heater 730 or as its temperature decreases when in contact with a colder cartridge.

The sensor 528 measurements can be monitored by the Central Processing Unit (CPU) (not depicted), and a closed loop proportional-integral-derivative (PID) control can be used to maintain the temperature of the incubator 126 at the target temperature for a period of time. The period of time for incubation of the cartridge 114 can be equal to or less than the time it takes to run a complete diagnostic test on the cartridge 114. In general, the incubation occurs as an initial step in the diagnostic system 110 processing and is used to prepare the plasma sample for diagnostic measurements within the diagnostic instrument 112. Thus, depending on how many tests are being run off of any given cartridge 114, the time period for incubating the cartridge 114 will span at least the time of processing all the tests on a cartridge 114.

For example, the diagnostic instrument 112 can have an incubator 126 that is integral with the motion assembly 720, and which facilitates the incubation of the reaction between targeted antigens in the filtered plasma and beads in the reagents. Typically, such a reaction proceeds well at temperatures between about 25° C. and about 42° C. and for a period of time ranging from about 15 seconds to about ten minutes. However, incubation can occur at hotter or cooler temperatures and for longer or shorter durations of time. It may be desirable to incubate the filtered plasma and reagents at the same temperatures for the same duration of time for all cartridges running the same diagnostic tests. Therefore, the parameters of temperature (incubation) and duration can be predetermined, controlled and altered depending on the reagents being used and the diagnostic test being run on the diagnostic instrument.

The starting temperature of the cartridge 114 can be determined by measuring the temperature with a sensor 528 and a rate of a heater's temperature loss when a cartridge 114 is placed on the heater 730. Usually the cartridge 114 will have a temperature lower than that of the incubator plate 728, and the temperature of the incubator plate 728 will be known prior to positioning the cartridge 114 on the incubator plate 728. For example, the starting temperature of the cartridge can be more than about 5° C., more than about 10° C., or more than about 15° C. colder than the target temperature and/or the temperature of the incubator plate.

Once the starting temperature is known, the heater 730 can supply the amount of heat necessary to incubate the cartridge 114 to the target temperature. The temperature of the heater 730 can be adjusted to control the rate at which the target temperature is reached. For example, depending on the starting temperature of the cartridge 114, and the desired incubation temperature (i.e., the desired temperature at which to incubate the sample-reagent mixture 125, usually 37° C.), adjustments can be made to the various parameters, including changing the time that a higher heater 730 temperature remains applied to the incubator plate 728 to reach the target temperature and/or changing the incubator plate 728 temperature. The adjustments made to the heater temperature facilitate a faster rate at which the cartridge 114 can reach the target temperature, as compared to a cartridge 114 on an incubator 126 without heater adjustments or as compared to keeping the heater temperature constant or set to the target temperature.

Examples 3 and 4, further discussed in the Examples section, provide data on different cartridges 114 that were stored at different temperatures and that were used on the same diagnostic instrument 112. Example 3 describes the incubation quality based on the differences in the starting temperature of the different cartridges.

Example 4 compares boost duration for different cartridges having different starting temperatures, and measuring the incubation quality between the cartridges after their incubation.

Various embodiments of the diagnostic system 110 contemplate methods of temperature control that can facilitate the temperature of the cartridge to reach the target temperature in less time than conventional heating. The method of temperature control can facilitate the temperature of the cartridge to reach the target temperature in less than about 5 minutes, less than about 4.5 minutes, less than about 4 minutes, less than about 3.5 minutes, less than about 3 minutes, less than about 2.5 minutes, less than about 2 minutes, less than about 1.5 minutes, or less than about 1 minute.

In an embodiment, a method of temperature control of a cartridge comprises measuring with a sensor the starting temperature of the cartridge containing a biological sample and at least one reagent; adjusting a set of predetermined pre-incubation parameters depending on the measured starting temperature; heating with a heater the cartridge to a target temperature; maintaining the target temperature for a period of time equal to or less than the time it takes to complete a diagnostic test; intermittently measuring the temperature of the disposable cartridge throughout the segment of time of the diagnostic test to ensure temperature control; and heating at least a portion of the disposable cartridge to the target temperature when the temperature of the disposable cartridge is less than the target temperature.

In certain embodiments, the at least one heater and/or at least one sensor 528 can detect the cartridge temperature. The heater 730 and sensor 528 can be on a PCB, which is integrated into a motion assembly of the diagnostic instrument (not depicted). The same sensor 528 can be used to measure the cartridge 114 temperature and used in the closed loop control to maintain of the temperature of the cartridge 114.

Alternatively, different sensors 528 can be used to measure the cartridge temperature and used in the closed loop control to maintain the temperature of the cartridge 114. The method of incubation can further comprise repeating the incubation method for the duration of the diagnostic test until completion.

FIG. 37. Illustrates example components and feedback control loops of a multi-zone incubator 740. The multi-zone temperature control incubator 740 can operate under independent control loops 734a, 734b. The incubator 740 can achieve uniform and precise incubation of a biological sample within the cartridge 114. The multi-zone temperature control incubator 740 can provide a more uniform temperature control along the body of the cartridge 114 by customizing specific portions or zones of the cartridge for temperature control. This will allow for multiple measurements of the same sample for multiple tests, by allowing a uniform temperature to be maintained among the multiple measurements. Using the multi-zone temperature control incubator 740 can further improve temperature uniformity and precision during processing and operation of the diagnostic system 110.

In general, a multi-zone incubation can help to reduce variability along the length of the cartridge 114 based on the length of a given cartridge 114, and therefore, the number of tests the cartridge 114 accommodate. It is contemplated that the length of an incubator 740 can be at least double that of the length of a given cartridge 114 to allow for maximum movement along the incubator 740 during processing.

In some embodiments, measuring the starting temperature of the cartridge 114 can be achieved when, after a cartridge 114 can be inserted, the heater 730 is momentarily shut off. The rate of the incubator plate's 728 temperature loss can be computed, for example, by monitoring the same sensor 528 that can be used to control the temperature. The rate of temperature loss is related to the rate that heat transfers from the incubator plate 728 to the cartridge 114. The rate that heat transfers from the incubator plate 728 to the cartridge 114 is related to the temperature difference between the incubator plate 728 and cartridge 114. By computing the temperature difference between the incubator plate 728 and cartridge 114 the temperature of the cartridge 114 can be found. Finally, having determined the temperature of the cartridge 114, the duration of the Idle (Boost) Target Temperature can be adjusted accordingly. The incubator can heat up the cartridge 114 by applying a higher incubation temperature set point than a normal incubation temperature set point for a duration of time at a location on the incubator 740.

The diagnostic instrument 112 when there is no cartridge 114 inserted, can maintain the temperature of the incubator plate 728 at an idle target temperature. When a cartridge 114 is inserted into the diagnostic instrument 112 and positioned on the incubator plate 728, the diagnostic instrument 112 can start detecting the temperature of the cartridge 114, by measuring with a sensor 528 the rate of the temperature drop of the incubator plate 728 due to the different temperature of the cartridge 114. The drop rate (calculated by the CPU) can be used to determine the starting temperature of the cartridge 114. The drop rate can then be used to select the duration (from a pre-constructed table or an equation) that the cartridge 114 can be kept on the incubator plate 728 at the Idle (Boost) Target Temperature. This process ensures that the cartridges, regardless of storage temperatures, will have reached a similar temperature by the time the sample is ready to start a reaction with the reagent. Since the cartridge temperature can become the same prior to the beginning of incubation, all cartridges 114 can receive uniform incubation regardless of their individual storage temperatures.

FIG. 37 is an illustration depicting an example of components and feedback control loops of a multi-zone incubation system. A multi-zone incubator, such as that shown in FIG. 37, allows the diagnostic instrument 112 to heat up the cartridge 114 while filtering a sample, for example, without affecting the temperature of the portion of the incubator 126 that is not being cooled off by the cartridge 114. With the single-zone incubator, the incubation plate is controlled by one sensor and one heater. When the cartridge is not moving during processing, such as during filtration, for example, the incubation plate is holding at one constant temperature. This can lead to unequal, unnecessary or excessive heating depending on where the cartridge is positioned on the incubator. With a multi-zoned incubator, however, the different zones are controlled independently of one another to allow for increased temperature control of the cartridge during processing.

The multi-zone incubation can be achieved by having at least two separate heaters and/or coolers 730a, 730b under the incubation plate 728. Each can have its own temperature sensor 528a, 528b. Each can also have its own closed loop control 732a, 732b.

During heat up, the cartridge 114 while filtering blood can be positioned on one of or part of both of the incubation zones 526a, 526b depicted in FIG. 37, and can remain there during filtration for a long period of time, for example, up to about 150 seconds. The multi-zone incubator 740 does not require an added temperature sensor 528 to measure the starting temperature of the cartridge 114 that is coming into the instrument 112 from its storage temperature. The same temperature sensor 528, for example, which can be a thermistor 528a, 528b, can be a portion the feedback control loop controlling the incubator 740 and also can be used for determining the starting temperature of the cartridge 114.

Internal Standard (IS) Module and Method

Various embodiments of the diagnostic system 110 contemplate a non-ECL detection apparatus 910 for use as a failsafe mechanism to ensure the precise and accurate function of the diagnostic system 110. In some embodiments, one such failsafe mechanism can include an internal standard (IS) non-ECL detection apparatus 910 to the diagnostic system 110.

Figure 38A:
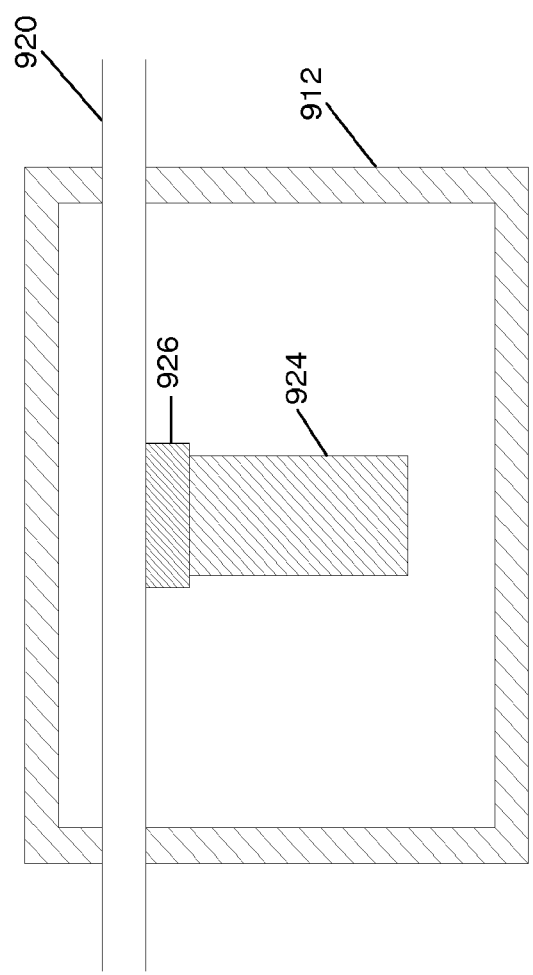
FIG. 38A is a an illustration of an example non-ECL detection apparatus in a diagnostic system.

FIG. 38A is an illustration of an example of an IS, non-ECL detection apparatus 910. The non-ECL detection apparatus 910 can include a housing 912 with a tubing assembly 920 within the housing 912 that can carry a sample to be analyzed. As the sample passes through the housing 912, a laser 924 can be directed through a filter 926 and the laser light can be reflected through the sample. The reflected light can be used to detect the presence of a particular analyte within the sample as it flows through the non-ECL detection apparatus 910. For example, an IS can be used within the detection analysis.

An IS can be a substance that can be added in a constant quantity to samples and calibration standards in an assay or analysis. An IS can be a substance that is very similar, but not identical to the substance of interest in the sample. The effects of assay construction should be the same for the IS as the substance of interest.

One purpose of an IS is to identify failures that might occur during assay construction. As such, the method to implement the IS operates as a failsafe mechanism. Another purpose of an IS to correct for normal variability in assay construction. As such, the method to implement the IS operates as a means to improve precision and accuracy.

Various embodiments of the diagnostic system 110 contemplate a cartridge 114, which can contain all reagents and materials needed to perform a diagnostic test, such as an assay. For diagnostic assays based on ECL detection, one reagent can include beads. This substance can be used in the method to construct a diagnostic assay. In particular, the bead surface is the bound phase for a binding assay. For ECL-based assays, the quantity of label bound to the bead is measured by ECL detection and the ECL signal to concentration. In this aspect, the quantity of beads present during assay construction is critical to the overall performance of the diagnostic instrument 112.

For ECL-based assays, assay construction involves various processing steps. These may include free-bound separations, which generally consist of magnetic collection of the beads and bead wash steps. Any variability in the quantity of beads after such processing is undesired, as this may in some cases reduce precision and accuracy, in other worse cases cause an error in the reported result of the diagnostic assay.

In certain embodiments, fluorescent labeled beads are employed as an IS to prevent errors, and/or improve precision and accuracy in the reported results for ECL-based diagnostic assays.

Further, in certain embodiments, fluorescent labeled beads process identically to ECL labeled beads. As such, any variability experienced by ECL labeled beads are also found within the quantity of fluorescent beads. For example, if during magnetic collection, 95% of the ECL labeled beads in the sample were captured onto a magnet surface, then 95% of the fluorescent beads were likewise captured onto the magnetic surface. Such a process is non-interfering with any other measurements or detection that may occur during the diagnostic test cycle.

In other embodiments, fluorescent labeled beads are employed as an IS to measure bead recovery after assay construction for ECL-based diagnostic assays. Bead recovery is the relative quantity (or percentage) of beads measured compared to the quantity of beads intended to be used in assay construction. For example, if 100,000 beads were initially contained within the diagnostic instrument, and upon completion of assay construction, 95,000 beads were measured, then bead recovery would be 95%.

Bead recovery is derived by comparing the fluorescence signal from the IS to the fluorescence signal from a standardized quantity of fluorescent beads.

Fluorescent beads can be labeled by coating fluorophore onto the bead surface. Coating can involve any different chemical or physical methods. Any one skilled in the art of conjugation can readily coat beads with fluorophore. Further, fluorescent beads can be alternatively labeled by incorporating fluorophore within the interior of the bead. Further the beads can be labeled by both of the above methods.

IS can include fluorescent labeled beads, or fluorescent labeled and ECL labeled beads. For example, a sample may contain a mixture of fluorescent labeled beads and ECL labeled beads. As another example, a sample may contain beads with both a fluorescent label and an ECL label on the same bead.

Example fluorophores can include allophycocyanin (APC) with an absorption maximum of 652 nm and an emission maximum 658 nm. Alternatively, the fluorophore can be Sky Blue (Spherotech) with an absorption maximum of 660 nm and an emission maximum 705 nm.

The beads can be superparamagnetic beads such as Invitrogen™ Dynabeads® M-280 Streptavidin or SPHERO™ Magnetic Particles.

The ECL label can be ruthenium (II) tris(2,2'-bipyridine).

In further embodiments, the diagnostic instrument 112 of the diagnostic system 110 can include a measurement and detection module, called an internal standard (IS) module 910, that can be independent and distinct from an ECL detection module 1010. The ECL detection module 1010 can measure an ECL signal obtained from ECL labeled beads. An IS module and IS do not interfere with the ECL measurement. In other words, the accuracy and precision of other detection methods, such as an ECL detection method, are not affected by the function of the IS module 910 and IS. The IS module 910 may be a device, such as a flow cell, that measures fluorescence. The IS module 910 may perform a non-contact measurement to quantify fluorescence, and hence bead recovery. It is contemplated that the IS module can be in a separate location from the location of the ECL measurement, i.e., separate from the ECL detection module 1010.

IS measurement also can occur at different times during an individual cartridge processing cycle, for example, prior to, after, or at the same time as an ECL measurement during an individual cartridge processing cycle.

No physical contact is made with the sample and inside the tubing assembly that communicates with the IS module 910, except for the application of the laser light as the sample flows through the fluidic pathway or tubing assembly. A fluidic pathway can include any part of the diagnostic system 110 where fluids can flow and is not limited to a tube structure such as the tubing assembly. Thus, this can include the fluidic pathway that can carry the sample through the IS module 910 for detection.

In general, the IS module 910 uses a light source, such as a laser, laser diode, or light emitting diode to excite fluorescent labeled beads present within the sample moving through the IS module. The fluorescent labeled beads emit fluorescent light that can be accurately measured using a light detector such as a photodiode or photomultiplier tube. The measured light fluorescence signal can be compared with the fluorescence signal obtained for a known number of fluorescent labeled beads, and a percentage bead recovery calculated. Examples 5 and 6, discussed below in the Examples section, provide examples of how the IS modules 910 can function as failsafe mechanisms to ensure the precise and accurate function of the diagnostic system 110.

Figure 38B:
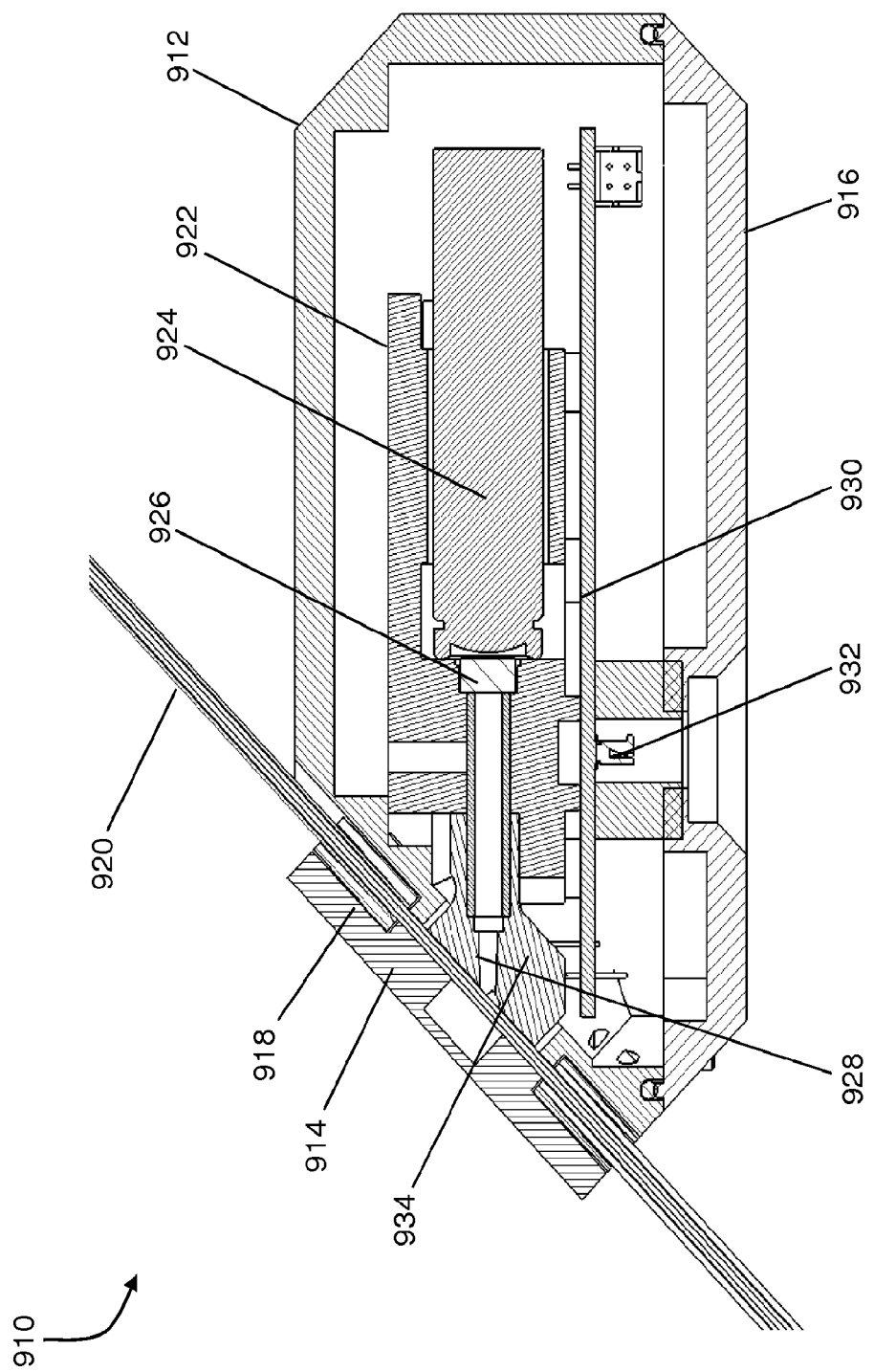
FIG. 38B is an illustration of a cross-section view of an example internal standard (IS) module.
Figure 38D:
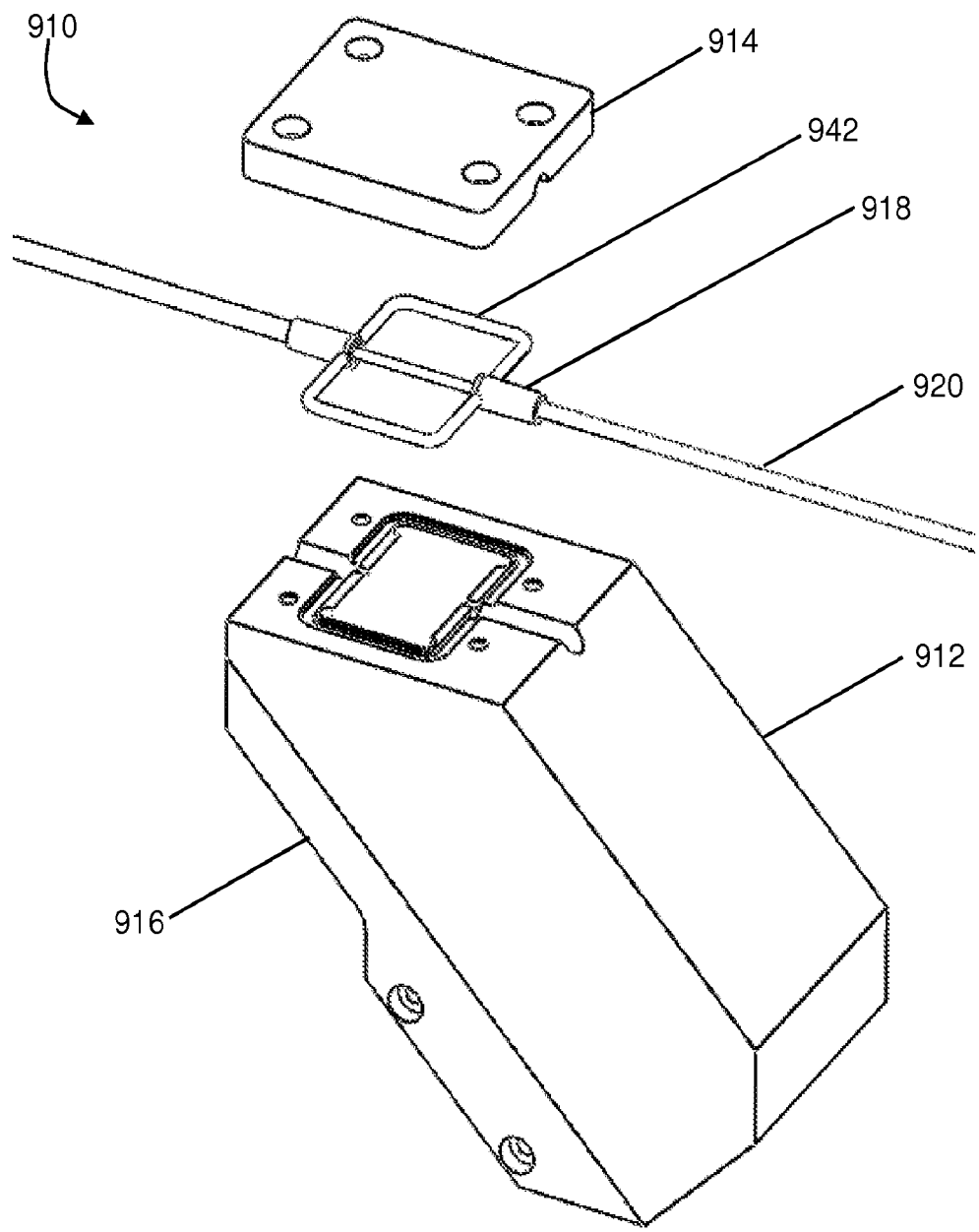
FIG. 38D is an illustration of an exploded perspective view of example internal components of an IS module.
Figure 38E:
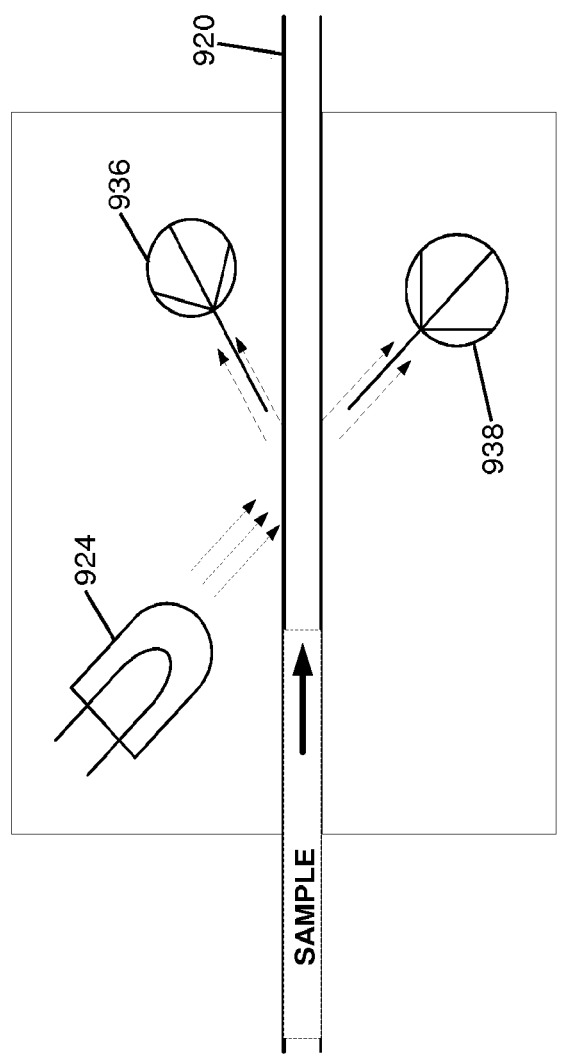
FIG. 38E is an illustration of an example of the transmission and reflection of a light source within an IS module.

Referring to FIGS. 38B-38D, various embodiments of the diagnostic system 110 contemplate a non-ECL detection apparatus, such as an IS module 910, which can be a flow cell having a housing 912 with a tubing assembly 920 and at least one opening 918 in the housing 912 to facilitate the entry and exit of the tubing assembly 920 to and from the IS module 910, as shown in FIGS. 38A-38C. Within the housing 912 of the IS module 910, a laser mount 922 can hold a laser 924 and an excitation filter 926, which can be used to remove light at wavelengths that may interfere with a fluorescence measurement. The laser mount 922 can also have a small aperture (not depicted) at one end through which the laser light can exit as it is guided by a light pipe 928. The light pipe 928 can direct the laser light to a portion of the tubing assembly 920.

The IS module 910 can also include a first photodiode 936 and a second photodiode 938 connected to and powered by a PCB 930. When the laser light is incident the tubing assembly, both the laser light and laser-induced fluorescent light can be detected by the first photodiode 936 and the second 938 photodiodes. Light pipe 928 is secured to laser mount 922 using known fasteners, such as a screw.

The IS module 910 can be formed from housing members including a housing 912, at least one panel 916 and at least one cap 914. The at least one cap 914 also is removable to aid in assembly of the IS module 910. The at least one panel 916 and the at least one cap 914 can be removable and therefore securable to the housing 912 with standard fasteners. The size and shape of the housing 912, panel 916, and cap 914 can vary between different IS modules and depending on the overall diagnostic system 110 design and function.

When present, the at least one cap 914 can be positioned over an uncovered portion of the housing 912 through which the tubing assembly 920 passes. The tubing assembly 920 can be made of a variety of suitable plastic materials. For example, in one embodiment, the tubing assembly 920 can be made from a clear FEP (fluorinated ethylene propylene) with an internal diameter of 0.02". The tubing assembly can be held in place with vacu-tight fittings (not shown) on either side of the housing 912. To prevent light from entering the housing 912, black heat shrink (on the probe side) and black FEP tubing (on the ECL detection side) covers the clear FEP tubing. It is contemplated that other methods can be used to light seal the tubing assembly such as applying an opaque sleeve and coating, painting or tinting the tubing assembly in opaque light blocking materials. The sizing of the aperture 918 in housing 912 correlates to the size of the tubing. In particular, the opening 918 is big enough to allow the tubing assembly 920 to pass through, yet small enough that it can be easily light sealed with a fitting or gasket.

Alternatively, in some embodiments, underneath the at least one cap 914, a gasket 942 can be positioned within a recess of the housing 912. The gasket 942 can be formed to fluidically seal the tubing assembly 920 as it passes through the at least one opening 918 in the housing 912. The gasket 942 also functions to form a light tight seal for the contents of the tubing assembly 920, particularly during the IS measurement.

The housing 912 can be comprised of an opaque material that is sturdy and supportive. Suitable materials include, but are not limited to, aluminum, steel, or brass. The inside surfaces of the housing can be painted black or coated with a seal or tint to absorb stray light that may find a way into the IS module. It is important to have a light tight surrounding to receive an accurate light reading within the IS module.

The light source can be derived from a laser 924. The laser 924 can fit inside a drilled out cylindrical hole of the laser-mount 922, which in turn is positioned in the housing 912, an example of which is shown in FIGS. 38A and 38B. Light from laser 924 can be filtered using excitation filter 926 which can be used to remove light at wavelengths that may interfere with fluorescence measurement. For example, in certain embodiments, before striking the tubing assembly 920, the laser light passes through a 632 nm band pass filter, light pipe 928 and exits the IS module through a round 0.06" aperture. It is contemplated that depending on the fluorophore, different lasers can be used within the IS module. For example, when APC or Sky Blue is the fluorophore, the IS module can employ a 635 nm laser light source.

The PCB 930 can be mounted to the laser mount 922 and can hold the first and second photodiodes 936, 938 (see, e.g., FIGS. 38A and 38B). The first photodiode 936 detects the fluorescent light. The second photodiode 938 measures the power of the laser light. FIG. 38C illustrates example first and second photodiodes 936, 938 that can be mounted on opposite sides of a detector mount 934 attached to the PCB 930. Emission filter 940 can be attached to second photodiode 938, and can be used to remove light of wavelengths that may interfere with the fluorescence measurement. For example, emission filter 940 can be a color glass filter, such as, RG695. The first and second photodiodes 936, 938 are mounted on opposite sides of the detectormount 934 attached to the PCB. Both the fluorescent light as well as the laser light can be detected with photodiodes which converts the light into a measurable electrical signal through connector 932. As the laser light strikes the tubing assembly 920 the first photodiode 936 measures and detects the fluorescent light emitted by the fluorescent beads flowing through the tubing assembly. Concurrently, the second photodiode measures and detects the laser light originating from the tubing assembly.

FIG. 38D provides a depiction of optical path of the laser light within the IS module 910 in an embodiment. The light from laser 924 passes through excitation filter (not shown) and is guided through the light pipe (not shown) onto the tubing assembly 920 containing the sample. The laser light beam is incident the tubing assembly at a 45° angle. The photodiodes are oriented 45 degrees respect to laser beam, and 90° in rotation with respect to each other around the tubing. It is contemplated that non-fluorescence detection methods can be employed within the IS module 910.

ECL Detection Module Overview and Improvements

Figure 39A:
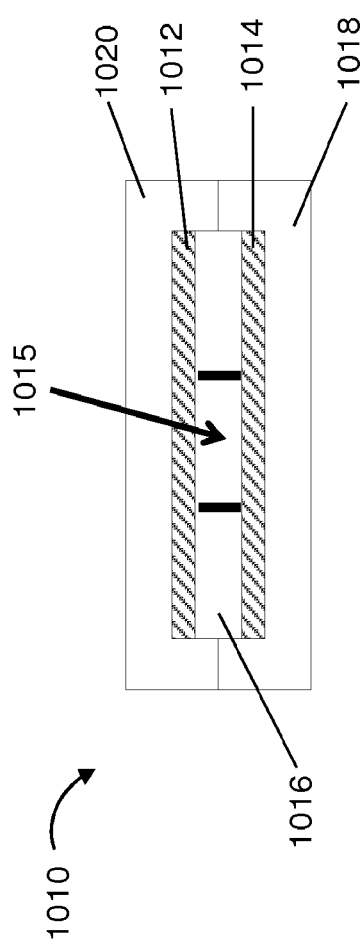
FIG. 39A is an illustration of a cross-section of an example ECL detection apparatus of a diagnostic system.

FIG. 39A is an illustration of a cross-section of an example of an ECL detection apparatus 1010. An ECL detection apparatus 1010 may be included within a diagnostic instrument 112 to detect ECL labels on analytes.

The ECL detection apparatus 1010 can include at least two electrodes 1012, 1014 separated by a gasket 1016 contained within a base 1018 mated with a top 1020. The ECL detection apparatus 1010 can be a flow cell that also includes fluid ports to introduce a fluid for detection and a light source to assist in detecting a targeted analyte within the sample.

In general, an ECL detection apparatus 1010 can include a measurement containment area 1015 with at least two electrodes 1012, 1014, a light detection means and at least two fluid ports to control the ECL reaction, and measure light and control fluid movements.

Typically, an ECL detection module 1010 can operate as a flow cell so it may be necessary for fluids to be introduced and extracted from the measurement containment area 1015 to set up the ECL reaction and flush out processed or used reactants. The measurement containment area 1015 can be a sealed volume with at least two fluid ports that can allow fluids to be pumped in and out of the sealed volume. An ECL reaction can be controlled by the spatial arrangement of the electrodes with an insulator, such as a gasket, so that they remain electrically conductive during the ECL reaction. Electrodes are often made of metal or other opaque substances, and apertures can be cut in them for the detector to observe light from the ECL reaction. Because light detectors can be delicate electronic devices, an optically clear window made of glass, acrylic plastic or other material can be placed between the detector and the measurement containment area 1015 to isolate and protect the electronics from fluids.

In order to introduce or pump fluids through the measurement containment area, the measurement containment area 1015 should be sealed fluid and air tight to prevent air and fluid leakage which could result in fluid or air to bleed into the volume and degrade control of the fluid movements. Air leaks can also cause air bubbles to form within the measurement containment area. Air bubbles can change the electrode surface area exposed to fluid and upset control of the ECL reaction, or can refract light from the ECL reaction and upset light detection.

Figure 39B:
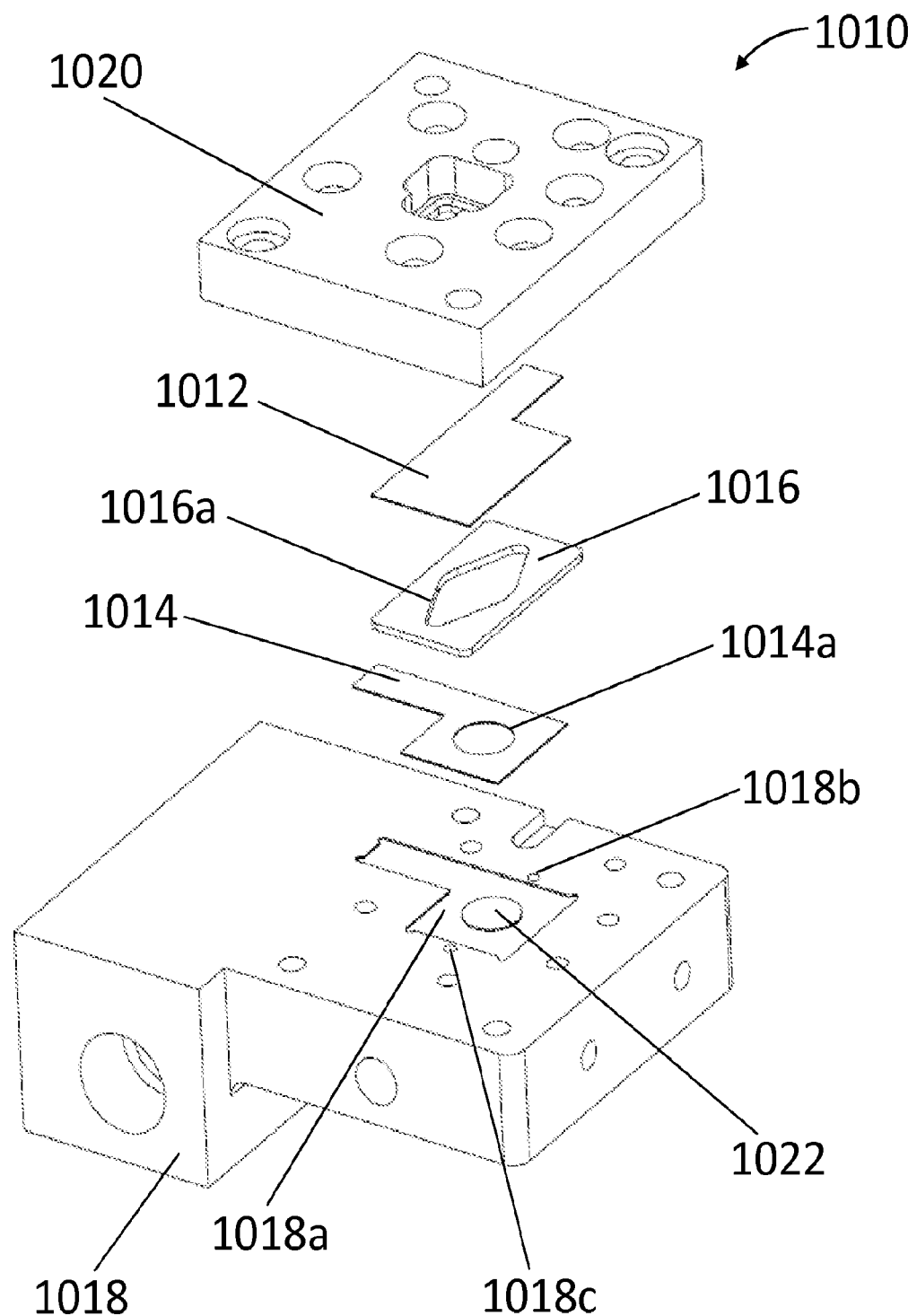
FIG. 39B is an illustration of an exploded view of an example ECL detection apparatus.

FIG. 39B is an illustration of an example ECL detection apparatus 1010. The example ECL detection apparatus 1010 can include at least two flat electrode surfaces 1012, 1014 separated by an insulating gasket 1016 with an aperture 1016a defining a measurement containment area 1015. The perimeter of the aperture volume can be sealed fluid and air tight by gasket 1016. To access this volume, one or both electrodes 1012, 1014 can have openings for at least two fluid ports 1018b, 1018c (permitting fluids to enter and exit the volume and contact the electrodes) and aperture 1014a for the light detector window 1022 (permitting light detection). The at least two fluid ports 1018b, 1018c in the electrodes may also be sealed fluid or air tight. Electrode apertures are commonly sealed by bonding electrodes in place with epoxy cement, acrylic cement or other permanent adhesives.

After bonding, the entire face of the bonded assembly can be ground flush, such that gasket 1016 can seal against a resulting flat planar surface. Typically, these operations are slow and tedious, and the permanent bond prohibits replacing worn or damaged electrodes and other components. Thus, the manufacturability and serviceability of the ECL detection module would be improved by replacing the permanent bonding operations often necessary to seal the light detection and fluid port apertures in electrodes with gaskets or some other repairable means. Such improvements will become apparent in the embodiments discussed herein.

Accurate and precise ECL measurements require the electrode area exposed to fluid and the electrode gap to be closely controlled. The area of the exposed electrode can be determined by the cell gasket cutout. Gaskets are normally made of compliant materials, and compressing the gasket thickness between electrodes will distort the unclamped gasket cutout area, changing the electrode areas exposed to fluid. The accuracy and precision of ECL measurements can be improved if the gasket cutout distortion that results from clamping the gasket were compensated for in the unclamped gasket cutout, such that the clamped gasket cutout area is made precise.

Furthermore, if additional compliant gaskets are used to seal the electrode apertures, compression of these additional gaskets cannot appreciably shift or alter the electrode spacing established for the measurement containment area, otherwise the precision of both the electrode gap and the cell gasket cutout area could significantly decrease. The accuracy and precision of ECL measurements can also be improved if additional compliant gaskets used to seal electrode apertures avoid further compression of the cell gasket and avoid changing the established gap for the measurement containment area.

ECL detection modules 1010 can use sensitive light detectors to detect low level light signals from ECL reactions. ECL detection modules 1010 may often be covered with an opaque case to exclude ambient room light that would otherwise interfere with the low level ECL light signal. The ECL detection module 1010 can use fluid and electrical connections to pass through openings in an opaque case, but these openings must also exclude ambient light from reaching the detector. Light excluding features on the opaque case openings often require bulkhead fittings or connectors mounted to the case wall, or can use grommets, gaskets or other hardware fitted tightly to the case wall and components that pass through the wall.

In addition, commercial tube fittings are primarily designed for fluid transport and electrical connectors are primarily designed for electrical contact, and these often have imperfect light blocking capabilities. In such cases, even thoroughly opaque and light sealed case openings may still leak light into the enclosure through the external tubing or electrical connectors.

An ECL detection module 1010 may be simplified and improved if the opaque case openings for electrical and fluidic connections remained light tight without using bulkhead fittings, grommets, gaskets or other hardware. In addition, light sealing would be further improved if ambient light leaking through the opaque case openings, tubing, tube fittings and wire connections were internally blocked from reaching the detector.

Various embodiments of a diagnostic system 110 contemplate a new and improved ECL detection module 1010 for diagnostic applications. The improvements include, but are not limited to: (I) improvements in the design and use of gasket materials by which a precisely sized measurement containment area 1015 is established in order to increase the accuracy and precision of sample measurements; (II) a novel use of differential compliance to enable mounting and precise spacing of two or more electrodes while also creating feature seals to prevent leaking; and (III) a new method to accomplish light sealing of an enclosure by means of a substantially opaque printed circuit board while at the same time permitting electrical connections and/or the introduction of other components between the inside and outside of the light enclosure; (IV) a new method to accomplish light sealing of an enclosure by using an opaque material beneath enclosure openings, such as, fluidic ports that connect fluidic pathways inside and outside of the light enclosure.

Figure 39C:
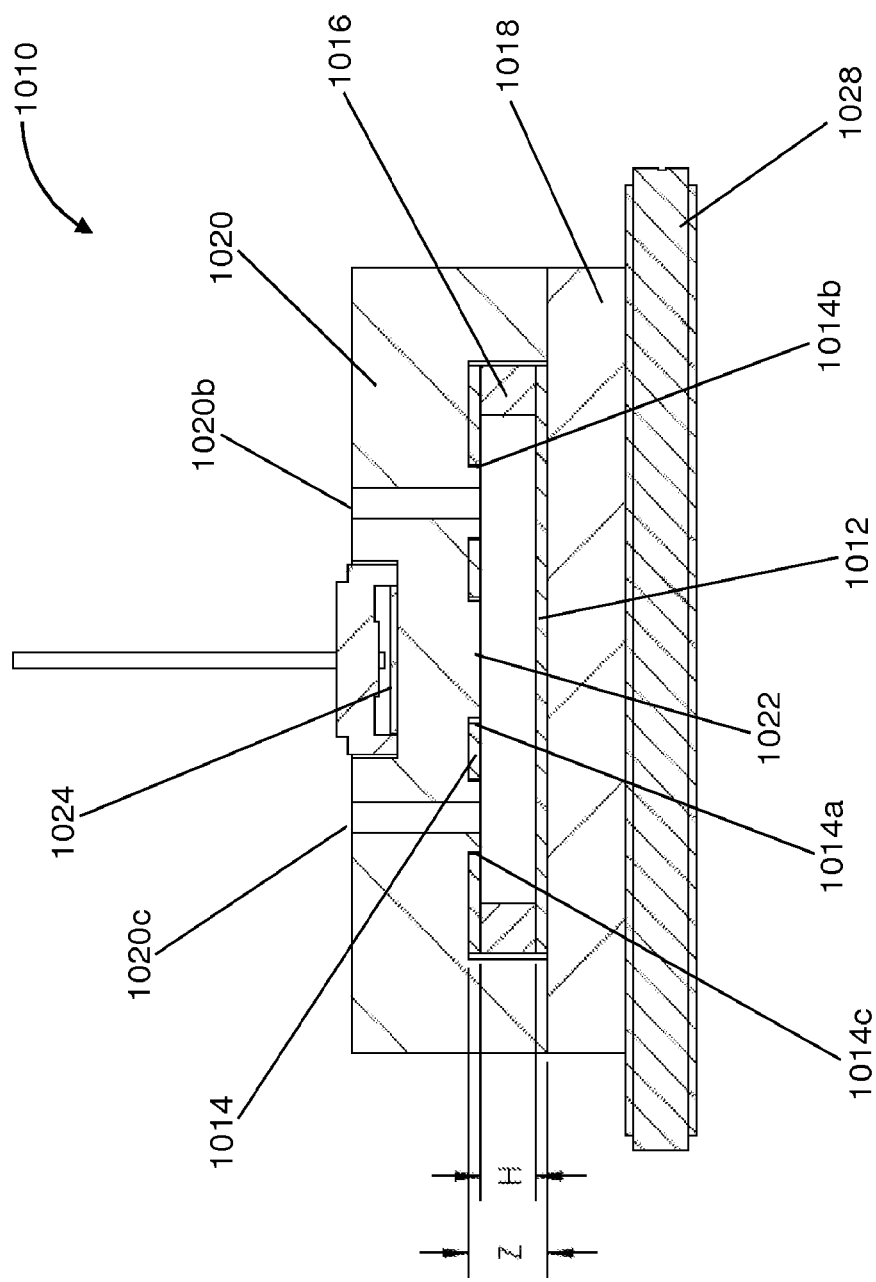
FIGS. 39C-39E are illustrations of cross-sections of example ECL detection modules.
Figure 39D:
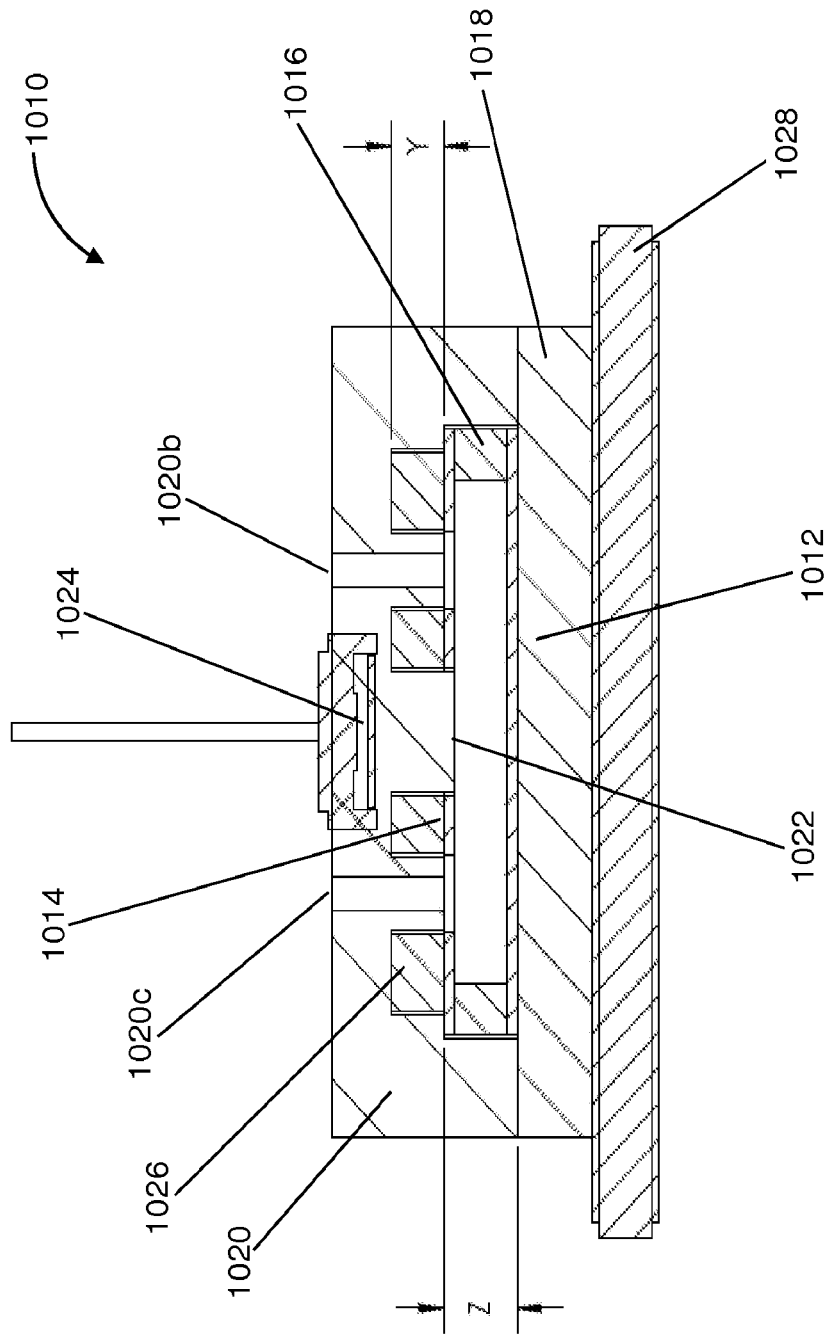
Figure 39E:
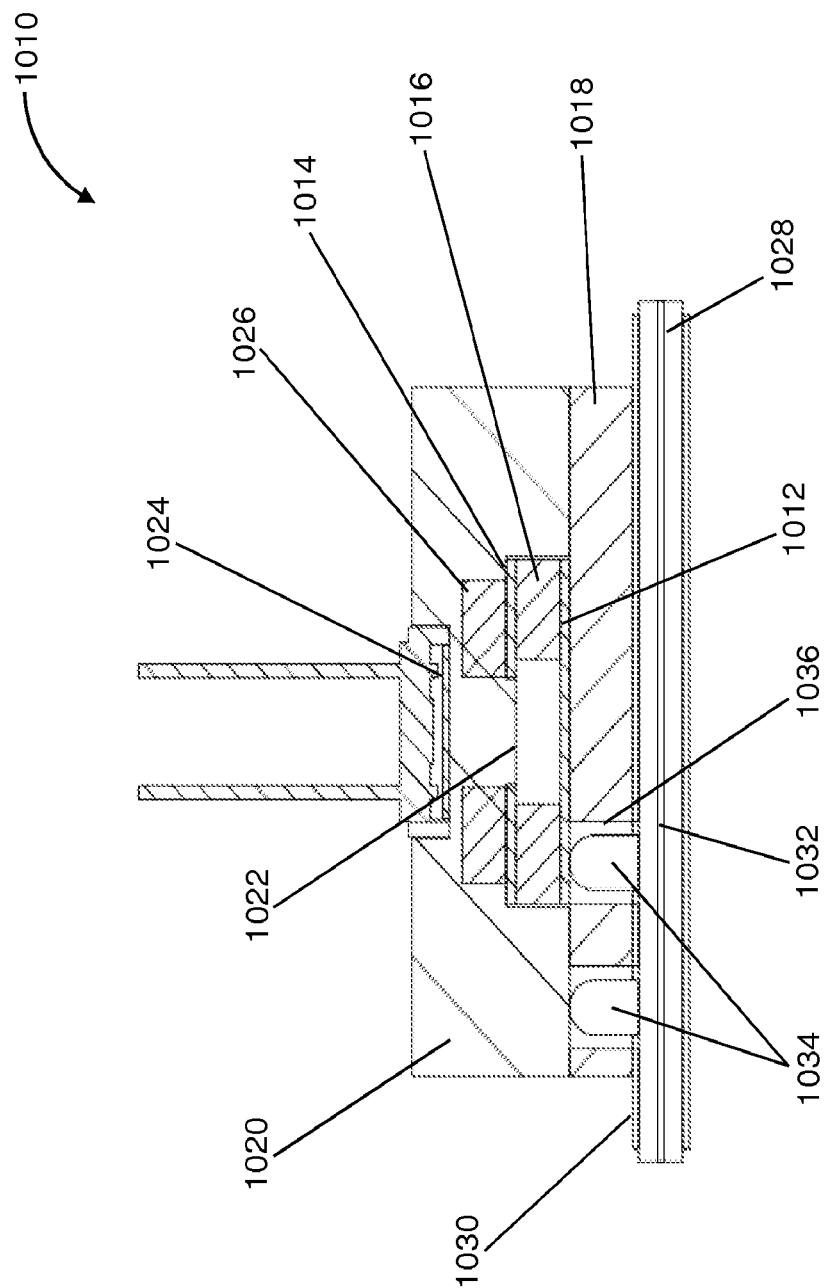

Accordingly, in certain embodiments, the diagnostic system 110 can include an ECL detection module 1010 (which can be a flow cell) with fluidic and electrical connections to the closed fluidic path 710 (See, e.g., FIG. 5B). FIG. 39B is an illustration of an exploded view of an example of an ECL detection module 1010. FIGS. 39C-39E are illustrations of cross-sections of examples of examples of ECL detection modules 1010.

In some embodiments, an ECL detection module 1010 can include an enclosure made of a top 1020 and a base 1018, wherein the upper surface of base 1018 can be flat and form a working surface. The top 1020 can be attached to the working surface of base 1018, thereby forming a cavity of a precise height Z.

The ECL detection module 1010 also can have a first electrode 1012 and a second electrode 1014 that can be stacked upon each other and separated by a first gasket 1016. The base 1018 can support the first electrode 1012 and the electrode/gasket stack. The first gasket 1016 can be sufficiently thick and compliant to require forceful closure of top 1020 onto base 1018 and press electrodes 1012, 1014 firmly against the cavity walls, thereby creating a precise predetermined separation gap H between the first and second electrodes 1012, 1014.

As can be understood by one of skill in the art, a change in compliance can be associated with a change in thickness or a change in hardness between two different materials, or a change in geometry of the compressed area between two different materials or two of the same materials. Thus, the term compliant can refer to the displacement of material for a given load and it can also refer to the softness of a material wherein a material can be more compliant due to the material being softer.

A cut out opening 1014a in the second electrode 1014 can permit light to pass through the second electrode 1014 during the ECL measurement. The cut out 1014a in the second electrode 1014 aligns with a transparent window 1022 in the top 1020, such that light from the ECL reaction can be measured by a photodetector 1024. Fluids must enter and exit the measurement containment area 1015 to setup the ECL reactions and flush the cell of prior reactants. FIG. 39C shows fluid inlet and outlet ports 1020b and 1020c aligned to two additional apertures 1014b and 1014c in electrode 1014. The ECL detection module also includes a printed circuit board 1028 that is positioned next to the base 1018 and connects the components within the ECL detection module electrically.

The first and the second electrodes 1012, 1014 can be made from a variety of conductive noble metals, including, but not limited to, platinum, gold, iridium, palladium, osmium, and alloys thereof. The first and second electrodes 1012, 1014 may also be made of conductive non-metals, such as carbon. The top 1020 can be made from a variety of durable materials, including, but not limited to, acrylic, polyether ether ketone and acetal polymers. The base 1018 can be made from a variety of durable materials, including, but not limited to aluminum, copper and stainless steel.

Figure 39F:
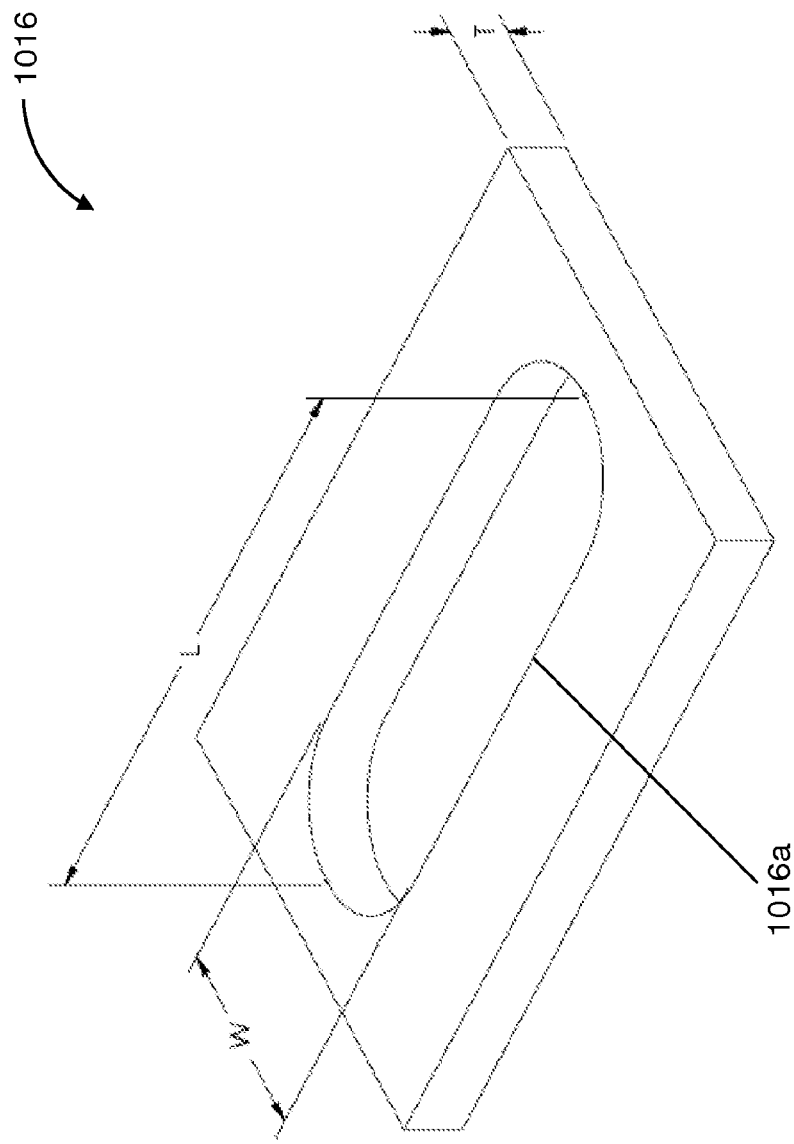
FIG. 39F is an illustration of an example gasket having an elongated cutout.

FIG. 39F is an illustration of an example of a gasket 1016 having an elongated cutout 1016a. When a gasket 1016 is clamped between the electrodes 1012 and 1014, the elongated cutout 1016a can create a measurement containment area 1015 (i.e., the ECL reaction chamber). The measurement containment area 1015 may be sealed liquid tight and airtight by a gasket that is made from a compliant material that seals against the electrode 1012, 1014 surfaces. Accordingly, gaskets can be made from a variety of compliant materials including, but not limited to, perfluoroelastomers such as Chemraz 631 or Kalrez 2037, fluoroelastomers, nitrile and silicone rubbers, and polymers such as polytetrafluoroethylene (PTFE) and polychlorotrifluoroethylene (PCTFE). Electrode surfaces are only exposed to chemical fluids within the gasket cutout 1016a, and consequently only this portion of the electrode surfaces are active during ECL reactions.

Consistent ECL reactions and measurements among instruments can utilize the measurement containment area 1015 geometry and electrode spacing to be uniform and precise from flow cell to flow cell. When the gasket 1016 thickness T is compressed between the electrodes, the gasket opening 1016a can distort laterally and dimensions L and W can be diminished from the uncompressed state. Thus, it is necessary to control both the gasket thickness compression and the gasket opening distortion to achieve precise flow cell geometry and electrode spacing. The cavity pocket depth Z in FIG. 39C can be precision machined in base 1018 to ensure uniform spacing between the electrodes 1012, 1014 and consistent clamping of gaskets. In addition, the thickness of electrodes 1012, 1014 can be made to precision tolerances.

Compliant materials, when compressed across their thickness, can be spread laterally. Thus, cut-out 1016a can close down if gasket 1016 is clamped between the electrodes 1012, 1014. Limiting the final clamped dimension of cut-out 1016a requires tight control of the gasket thickness, and can minimize variations of the measurement containment area 1015 geometry. Compliant materials used to create gaskets are often fabricated from sheets or slabs that are molded, extruded, calendered or cut into appropriate thicknesses by slicing or skiving. However, the gasket thickness precision is generally inferior to the tolerances of other rigid components used in the system.

Gaskets of varying thicknesses cut to the same inside profile 1016a will, when compressed, result in different-sized internal areas, which can in turn result in undesirable ECL signal variations when used in an ECL detection module. It is desirable to improve the measurement containment area 1015 geometry precision by sizing the gasket cutout 1016a in proportion to the thickness of the gasket, such that when the first gasket is constrained to a fixed compression distance, the desired size measurement containment area 1015 can be achieved. Sizing the inside profile 1016a based on the thickness of the gasket raw material, while taking the compressive characteristics of the material into account, can result in maintaining the compressed gasket cutout area to an acceptable tolerance.

Accordingly, the precise, predetermined size of the separation gap H can provide a desired level of accuracy of an ECL measurement. The compliant gasket provides expansive force to maintain a precise distance between the electrodes as is required in order to obtain precise ECL measurements. As ECL measurements depend on both the distance H between the electrodes and the area of the exposed portion of the electrodes, the cutout in the gasket that forms the measurement containment area 1015 must be precise. In order to establish a precise electrode exposure area after compression of the first gasket 1016 (as shown in FIGS. 39C and 39D), the size of the cutout that will form the measurement containment area 1015 is adjusted based on the thickness T of the raw material of the first gasket and the compressive characteristics of the raw material.

FIG. 39C illustrates an example first gasket 1016 that can seal a perimeter of a measurement containment area 1015 against the electrodes 1012, 1014, but no seal is shown around the window aperture 1014*a* or fluid port apertures 1014*b* or 1014*c* in electrode 1014. These areas can be sealed by cementing the second electrode into the body with epoxy, acrylic or other permanent adhesives. The adhering process is slow, messy, difficult and time consuming. In addition, the cemented joints erode away during flow cell use, causing the second electrode 1014 to delaminate or develop leaks and servicing or replacement of individual components is made difficult or impossible. Some embodiments do not require adhesives to create the fluidic seals within the ECL detection module 1010. These embodiments can also maintain the precise positioning of the components relative to each other as is required to make an ECL detection module 1010 precise and accurate.

FIG. 39D illustrates an example second gasket 1026 that can back at least one of the electrodes in order to establish fluidic sealing. The second gasket 1026 can be more compliant than and have a lower compressive force than the first gasket 1016 so as not to change the separation gap H set for the first and second electrodes 1012, 1014 by the first gasket 1016. This second gasket 1026 eliminates the requirement to adhere the electrodes to the enclosure with adhesives such as epoxy, improving the ease of assembly, the reliability and longevity of the seal and makes servicing components practical.

The light levels generated by ECL are low and photodetector 1024 is very sensitive to light. Thus, in certain embodiments an opaque case (not shown) may enclose the detection area in part, with the base 1018 to exclude ambient light that would otherwise interfere with detection of the internal low level ECL light signals. The opaque case and base 1018 can have openings for the required fluidic and electrical connections to the flow cell, and these openings must also exclude ambient light.

For example, the fluidic openings can be present on top of the ECL detection module 1010. The fluidic tubing and fittings that fit to these openings can be designed to transport fluids, and often have limited ability to block ambient light. Ambient light travelling through the fluidic tubing and connections may enter the ECL detection module 1010 through the openings, and the opaque top half of flow cell base 1018 blocks this light from reaching the detector.

FIG. 39E illustrates an example of an opaque enclosure of an ECL detection module can further include at least one opening 1036 to permit electrical connections to be introduced into the enclosure. The electrical connections 1034 are provided by the PCB 1028. The PCB 1028 may be made from an inherently opaque material, or can have an opaque coating 1030, such as solder mask or screen printed layers, on its surface to prevent light leakage into the enclosure through the at least one opening 1036. Examples of opaque materials and opaque coatings include black glass fiber/epoxy laminates and black matte liquid photo-imageable solder masks meeting IPC SM 840 Qualification and Performance Standards for permanent solder mask. The printed circuit board 1028 can also include an internal or external conductor layer which can further block undesired light entry.

FIG. 39F illustrates an example first gasket 1016 formed from a raw material of nominal thickness having a thickness tolerance of ±0.002 in. This depicted first gasket requires that a different size L×W cutout be made for each 0.001 in. of thickness variation in order to achieve adequate precision of the compressed cutout area. Alternately, the L×W cutout dimensions could vary continuously with the gasket material thickness deviation from nominal thickness. Gasket material characteristics and thickness tolerances range widely, and the particular design requirements of the measurement device will determine how the gasket cutout dimensions must be adjusted to achieve adequate precision of the clamped, in situ gasket cutout area.

There are various configurations that can be used when constructing an ECL detection module 1010 and those described herein and depicted in the figures are merely for illustrative purposes and not meant to be limiting. It is contemplated that some of the configurations may be combinations of all or part of the embodiments described herein. Some of the various embodiments include an ECL detection module 1010 comprising an enclosure having a top 1020 and a base 1018. A stack is formed within the enclosure with a first electrode 1012, a second electrode 1014 and a first gasket 1016 sandwiched between the electrodes.

A cavity or gap formed by the pieces of the enclosure can define the desired gap (Z) in which to house the electrode/gasket stack, thereby establishing the distance between the electrodes. The first gasket 1016, made of compliant material, can have a thickness greater than the desired distance between the first and second electrodes 1012, 1014. A measurement containment area 1015 of precise size can be defined by a cutout 1016*a* once the first gasket 1016 is compressed. The first gasket 1016 can be fabricated with a cutout 1016*a* that has been sized such that the known compression height (Z) of the electrode/gasket stack and gasket raw material thickness will produce a measurement containment area 1015 of the desired size when compressed. The size of the measurement containment area 1015 is determined by many factors including, but not limited to, the thickness of the raw material of the first gasket 1016 and the compressive characteristics of that raw material; the cutout geometry and body pocket depth Z. A transparent window for ECL detection may be provided through an opening in the second electrode 1014.

Another embodiment provides an ECL detection module 1010 that can include an enclosure having a top 1020 and a base 1018. A first electrode 1012 forms a stack with a second electrode 1014 with a first gasket 1016 sandwiched between them within the enclosure. A cavity or gap can be formed by a pocket in the top 1020, which defines in part the desired gap (Z) in which to house the electrode/gasket stack, thereby establishing the distance between the first and second electrodes 1012, 1014. The second electrode 1014 can have cutout openings for ECL detection and two fluidic ports. A second cavity in the top houses a second gasket 1026, which has openings for two fluidic ports 1020*b*, 1020*c* and a transparent window 1022 for ECL detection in top 1020. The second gasket 1026 fluidically seals the cutout openings in the second electrode 1014. The compressive characteristics of the first and second gaskets 1016, 1026 along with the height of the gaps (Y) and (Z) are selected such that the compressive force of the second gasket 1026 is adequate to create the desired fluidic seals without displacing the second electrode 1014, and thereby maintains the desired gap between the first and second electrodes 1012, 1014 created by the first gasket 1016.

Still another embodiment provides an ECL detection module 1010 that can include an enclosure having a top 1020 and a base 1018. A first electrode 1012 can form a stack with a second electrode 1014 with a first gasket 1016 sandwiched between them within the enclosure. A cavity or gap can be formed by a pocket in the top 1020, which defines in part the desired gap (Z) in which to house the electrode/gasket stack, thereby establishing the distance between the first and second electrodes 1012, 1014. A second cavity in the top houses a second gasket 1026 which forms fluidic seals to two fluidic passages. A transparent window 1022 for ECL detection may be provided through an opening in the second electrode 1014 and the second gasket 1026. Additional gaskets (not shown) behind the second electrode 1014 may be used to create additional fluidic seals under the same constraints as the second gasket 1026. The compressive characteristics of the first and second gaskets 1016, 1026 along with the height of the gaps (Y) and (Z) are selected such that the compressive force of the second gasket and/or additional gaskets are adequate to create the desired fluidic seals without displacing the second electrode and thereby changing the desired gap between the first and second electrodes created by the first gasket.

Still another embodiment provides an ECL detection module 1010 that can include an enclosure having a top 1020 and a base 1018, and a first electrode 1012 and a second electrode 1014 stacked upon each other with a first gasket 1016 sandwiched between the electrodes. The first gasket 1016 can provide a mechanism to maintain relative positions between the components within the enclosure. At least one opening 1036 in the base can provide for connections of electrical connectors 1034 or other components between the exterior of the enclosure and components within the enclosure. At least one of the electrical connectors 1034 can establish electrical contact with the first electrode 1012. A printed circuit board 1028 can form a portion of the light tight enclosure, specifically around the at least one opening 1036. An inner conductor layer 1032 within the printed circuit board 1028 can create a substantial barrier to undesired light, as does screen printed layers 1030 on the surfaces of the printed circuit board 1028.

Still another embodiment provides an ECL detection module 1010 that can include an enclosure having a top 1020 and a base 1018, where it is a light tight enclosure and a portion of the enclosure is established by a printed circuit board 1028 used to make electrical connections between components within and outside of the enclosure. A first electrode 1012 and a second electrode 1014 are stacked upon each other with a first gasket 1016 sandwiched between the electrodes. The printed circuit board 1028 can be made of material that is inherently opaque or have one or both of (a) a light shield in the form of either an internal or surface conductor layer, and (b) a light shield in the form of a polymeric layer on either or both of the printed circuit board faces where the polymeric layer is substantially opaque. The resulting enclosure is light sealed while allowing electrical connections through the openings in the enclosure.

ECL detection can be a quick and sensitive technique. It has been described in detail in the following U.S. Pat. Nos. 5,714,089, 6,165,729, 6,316,607, 6,312,896, 6,808,939, 6,881,589, 6,881,536, and 7,553,448, all of which are herein incorporated in their entirety. It is contemplated that a label is an ECL label that may be bound to a magnetic bead, and the presence of the bound labeled molecule is detected by ECL. ECL signals are generated by a redox reaction between an ECL label with a substrate. In certain embodiments the electrochemiluminescence label is a ruthenium-containing reagent. One example of a suitable ECL label is Tris(bypyridine)ruthenium(II) [Ru(bipy)3]2+, also referred to as TAG. In certain other embodiments, the substrate is tripropylamine (TPA). Some advantages of the method of using ECL-based assays is they are rapid and sensitive. Example 7 provides data on assay results obtained from using an ECL detection module 1010.

Pump Instrument Improvements

Referring to FIG. 5B, a diagnostic system 110 can include a pump 810. Various embodiments of the diagnostic system 110 contemplate a pump 810 that can be integral in many of the functions of the diagnostic system 110.

Figure 40:
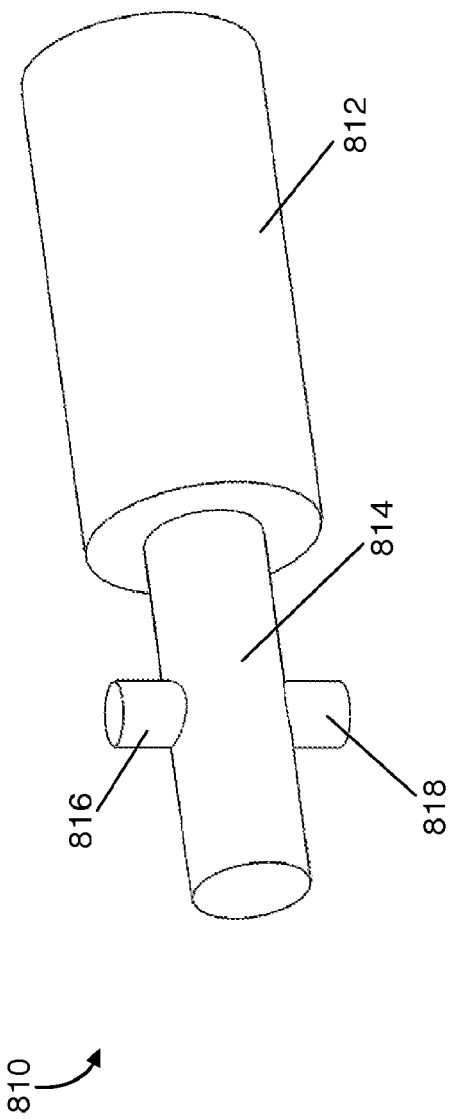
FIG. 40 is an illustration of an example pump of a diagnostic system.

FIG. 40 is an illustration of an example of a pump 810 of a diagnostic system 110. The pump 810 can include a cylinder 812 with a piston 814 and an inlet 816 and an outlet port 818. Improvements can be made to a basic cylinder piston fluidic pump to minimize communication of gases and liquids between the inlet and outlet ports of a dual-action piston pump (e.g., a pump in which the piston serves to move fluids into and out of the chamber and also serves as the means of establishing communication between the chamber and one of two or more ports by means of both linear and rotational action). Because of the properties of the updated design, improvements are realized in the precision and accuracy of aspiration and dispensing to and from the pump.

Figure 41B:
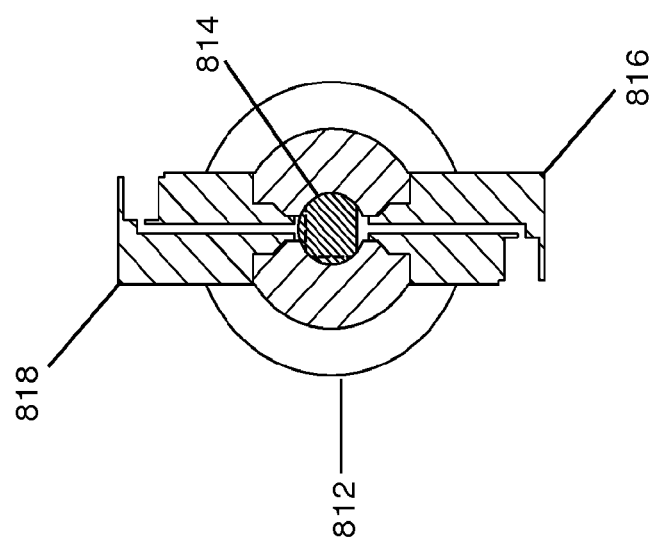
FIG. 41B is an illustration of a cross-section of the pump of FIG. 41A.
Figure 41C:
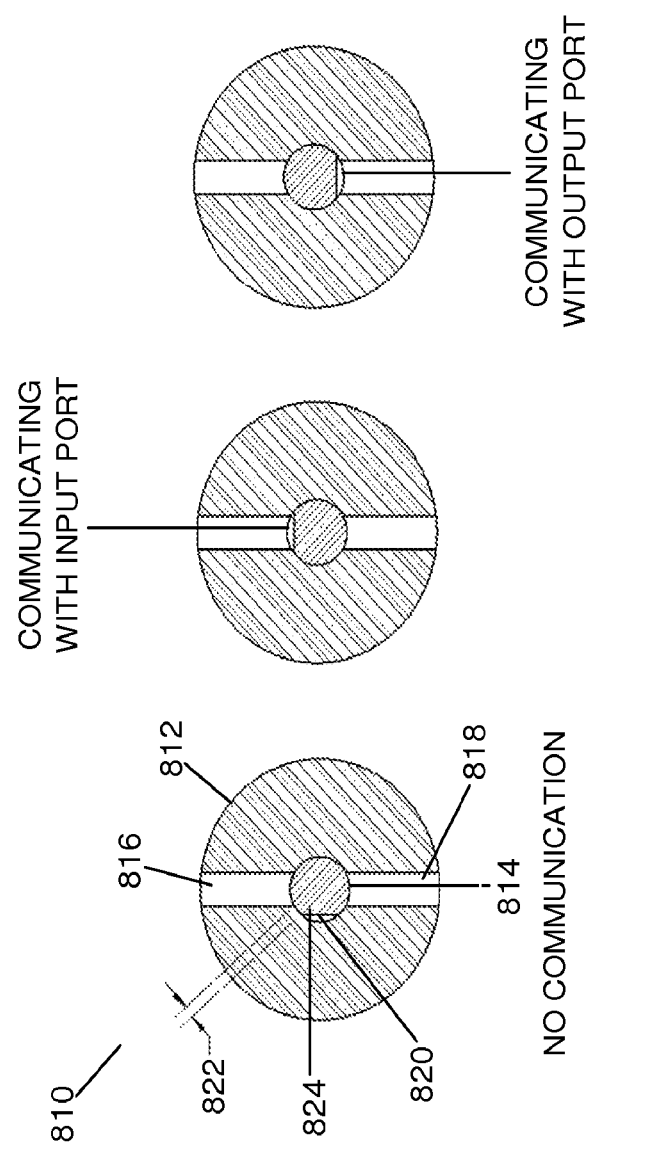
FIG. 41C is an illustration of a series of cross-section views of example fluidic communications of a pump.

FIG. 41A is an illustration of an example of a pump 810 in a diagnostic system 110. FIG. 41B is an illustration of a cross-section of the pump 810 of FIG. 41A. FIG. 41C is an illustration of a series of cross-section views of an example of fluidic communications of a pump 810. The pump 810 can include the cylinder 812, and a bore within the cylinder 812 that can house the piston 814 that serves as a fluid containment chamber 824 during pumping. The piston 814 can be cylindrical with the exception of a flat surface. The piston 814 can be rotated such that its flat surface points to the inlet port 816, the outlet port 818, or neither port. Both the cylinder 812 and the piston 814 can be constructed of a suitable material such as a plastic, ceramic or metal, for example, zirconia ceramic. The piston 814 can alternatively be made of a material with a close thermal expansion coefficient to prevent binding due to differential thermal expansion. The bore and piston 814 can be sized to produce a clearance small enough to prevent liquid leakage but large enough to allow free movement of the piston 814 within the cylinder 812. The portion of the cylinder bore which is not occupied by the piston 814 creates a fluid containment chamber 824. Motors controlled by firmware drive the piston linear motion (to aspirate or dispense) and rotational motion (to connect to a port, acting as the valve). The electronics or printed circuit board (PCB) in FIG. 41A houses a nonvolatile memory which is used to store measured backlash for each individual pump.

At least one fluidic pathway, including input port(s) 816 or output port(s) 818, can pierce the wall of the cylinder 812 to establish communication channels into and out of the cylinder 812. The input port 816 and the output port 818 can be situated diametrically opposed to each other within the cylinder wall. A flat 820 is sized and formed onto one side of the piston 814, so that when facing a fluidic pathway of choice, a fluidic communication is established between the fluid containment chamber 824 and the selected fluidic pathway while blocking communication to the other fluidic pathway(s).

The piston 814 is sealed to the cylinder 812 by close tolerance matching between itself and the cylinder 812 with a nominal clearance ranging from about 1.75 microns to about 2.75, such as, for example, about 2 microns, or about 2.5 microns. A close fit created by this configuration creates a substantially watertight seal between the cylinder 812 and piston 814. Once the gap between the piston 814 and the cylinder 812 is wetted, the seal becomes airtight. The terminal end of the piston 814, the end which faces into the chamber, is flatted on one side along between about 0.6 in.in. and about 0.75 in.in. of its length.

The flat 820 allows communication between the port 816 or 818 that the flat 820 faces and the fluid containment chamber 824. The small wetted gap between the non-flatted side of the piston 814 and the cylinder wall can produce a seal preventing communication of fluid between the fluid containment chamber 824 and that port effectively closing it. As a pressure differential develops between the fluid containment chamber 824 and the closed port, the wetting fluid between the piston 814 and cylinder 812 becomes inadequate to prevent some leakage to the closed port. Decreasing the width of the flat 820 increases the distance between the fluid containment chamber 824 and the closed port thereby preventing or reducing the undesired communication. Using the above design configuration the pump can aspirate or dispense out of either port without undesired communication with the opposite port.

The sealing distance 822 between the input port 816 or output port 818 on a commercially available pump 810 may be as small as 0.006 in.in. depending on the orientation of the flat 820. In one embodiment, reduction of the size of the flat 820 increases the sealing distance 822 to 0.044 in.in. improving sealing by a factor of about 7.33. In the some embodiments, rotational positioning of the flatted piston 814 is about ±0.002 in.in. allowing the sealing distance 822 to be as small as 0.004 in.in., in which case the sealing improves by a factor of about 10.5 with the reduced width flat 820. It is contemplated that the sealing distance 822 can be up to about 0.09 in.in. with an improvement of about 22.25. It is further contemplated that the flat size could be further reduced, limited only by the requirement that the cross-section of the flat 820 is not smaller than the cross-section of the port, for example, 816 or 818, in order to not cause pressure restrictions within the pump chamber.

The flat size is governed by several driving factors including (a) the flat 820 being sized to create a path between the selected fluidic pathway and the fluid containment chamber 824 that has a cross-section that is greater than or equal to the cross-section of the fluidic pathway so as not to restrict fluid flow; and/or (b) the flat 820 being sized to maximize the seal distance between the edges of the flat and the unselected fluidic pathway(s) so as to prevent undesired communication of fluids.

The stroke of the piston 814 can be limited so that the non-flatted portion opposite the flat 820 fails to reach an unselected fluidic pathway to prevent else unrestricted, undesired communication between the fluidic pathways from occurring. It is contemplated that there may be certain circumstances where this communication may be permitted or desired, for example, with a flush of the fluidic system during decontamination.

Due to the geometry of the parts described above, it can be possible to position the flat 820 of the piston 814 within the cylinder 812, such that is not in communication with any port 816, 818. This arrangement permits creating a pressure differential between the fluid containment chamber 824 and a non-connected port, preferably while there is a compliant medium (such as air) in the chamber. Subsequent establishment of communication with a port will generate a burst of fluid motion into or out of the chamber depending on the polarity of the pressure. Such bursts can be used for manifold fluidic motion purposes such as dislodging debris or unclogging fluidic pathways.

Methods for Calculating and/or Compensating for Backlash in a Fluidic Pump

Figure 42:
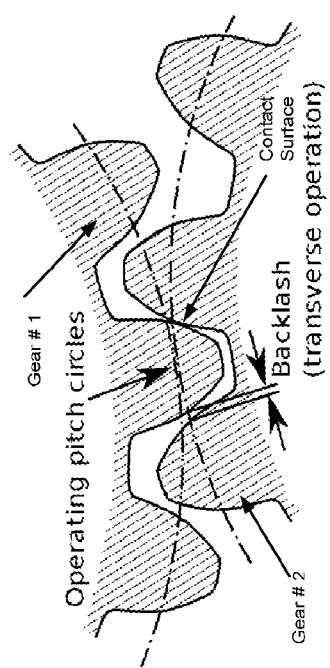
FIG. 42 is an illustration of an example mechanism depicting backlash.

FIG. 42 is an illustration of a mechanism depicting backlash. Electromechanically driven fluidic pumps, and in particular, positive pressure piston pumps, have backlash. Backlash in mechanical systems sometimes called lash or play, and is characterized by a clearance region between mating components, or an amount of lost motion due to clearance or slackness when a movement is reversed and contact is re-established.

For example, when a direction of the pump is changed from aspirate to dispense or dispense to aspirate, an electromechanical system can drive a piston 814 to start driving the piston 814 in the opposite direction, but the actual engagement of the mechanism where the piston 814 will actually move in the opposite direction may be delayed for the backlash amount.

As another example, in a pair of gears 4210, 4220 backlash 4230 is the amount of clearance between mated gear teeth 4210, 4220. In FIG. 42, a first gear 4210 and a second gear 4220 are provided. First gear 4210 contacts second gear 4220 at a contact surface 4240. When the first gear 4210 changes direction and starts moving clockwise, for the distance of the motion that is equal to the backlash amount 4230, second gear 4220 may not move. Second gear 4220 may start moving once the first gear 4210 has moved the backlash amount 4230 and starts making contact with the second gear 4230.

A pump 810 can have multiple mechanical interfaces, including but not limited to gears and couplings, any or all of which may contribute to the total backlash 4230 between the motor and the piston 814. When the direction of the pump 810 is changed from aspirate (taking fluid/air in) to dispense (pushing fluid/air out) or dispense to aspirate, the electromechanical system that drives the piston 814 will start driving the piston 814 in the opposite direction, but the actual engagement of the mechanism where the piston 814 will actually move in the opposite direction may be delayed for the backlash amount 4230.

Measuring the backlash amount and adding the backlash amount to the desired volume to compensate for the backlash is a common approach used to compensate for the backlash. However, systems have relied on indirect measurement of the motion of the piston, rather than the direct. Indirect measurements are likely to be less accurate than direct measurements.

FIG. 41B illustrates a pump/piston arrangement that has no valves. As illustrated, the ports can be sealed off in order to facilitate the measurement of the backlash. Motors controlled by firmware drive the piston linear motion (to aspirate or dispense) and rotational motion (to connect to a port, acting as the valve). The printed circuit board (PCB) in FIG. 41A houses a nonvolatile memory which is used to store measured backlash for each individual pump.

Various embodiments of the diagnostic system 110 contemplate methods for measuring and, optionally, then compensating for the amount of backlash from motor driven fluid pumps. These methods achieve a highly accurate backlash measurement, by monitoring the changes in pressure occurring in the pump chamber when changing directions, processing the data in firmware and calculating the amount of backlash, and then using the calculated backlash under regular operation when direction is changed. The pressure measurement system described herein is sensitive to detect a pressure change in the chamber for the smallest pump motion, therefore the backlash measurement is very accurate. Indeed, driving the backlash amount from pressure changes is highly accurate and superior to existing methods since it is a direct measure of the fluid that is pumped when the piston direction is changed. Also provided in the present disclosure is an integrated electronics housing a non-volatile memory packaged with the pump, eliminating the need to recalculate backlash when a pump assembly is replaced in an existing instrument.

Some embodiments provide a method to calculate accurate pump backlash. Accurately measured and compensated backlash can yield to accurate volumes pumped even after changing the direction of pumping. Some embodiments retain the calculated backlash with the pump in electronic memory instrument, such that when a pump is replaced in the diagnostic instrument in the field, the measurement does not have to be repeated, which will save time and make it easier to do field repairs. Example 9 describes the effects of compensating for the amount of backlash in a pump and showing the improvements made after compensation.

Some embodiments provide a fluid pump 810 for use in high performance systems, such as in diagnostic systems, using micro fluidics and volumes in the micro liter range, where moving fluidics directly or moving air in a closed system in order to move fluidics and position the fluidics accurately while changing direction having a piston movable in a chamber for drawing air or fluid into, pressurizing, and delivering the pressurized air or fluid from the chamber. For example, in FIG. 41A, a pressure transducer 826 can be used, directly connected to and measuring the chamber pressure. Electronics 828 can be used to process the signal generated by the pressure transducer 826 and feed it to a microprocessor. The pump motion can be driven by firmware. The firmware can convert the requested volume to be pumped into electrical signals, which through driver electronics and mechanicals, drive the piston.

An embodiment provides a method of backlash calculation wherein the pump inlet and outlet can be closed such that the chamber is connected to neither the inlet nor the outlet (or if a syringed type piston, only the inlet). The piston can be moved in one direction, and since the chamber is closed, pressure (or vacuum) can build up in the chamber. Once this is established, the motion can be stopped, and a pressure measurement can then be stored by the system. The direction can be changed and the system can be driven to move the piston in the opposite direction while monitoring the pressure. This motion can be as resolute as possible. The pressure does not change direction until the backlash amount is moved and until the piston has actually started moving in the opposite direction. The amount of volume pumped until the pressure change in the other direction occurs is the backlash measured. The data to determine the backlash can be analyzed by the microprocessor that is generating the sequences to move the pump to enable the measurement. The microprocessor then will store the measured backlash onto a non-volatile memory being housed by the electronics that are packaged with the pump. Every subsequent request of the pump motion will compensate by moving the piston more than the requested amount by the backlash amount, only for the first pump motion after a direction change.

In an example of an automated implementation of the backlash measurement it can be assumed that (a) a valve or other means exists such that the pump chamber can be either vented to the ambient environment (open) or sealed (closed) under the control of firmware; (b) the pump piston can be moved within the chamber under the control of firmware; and (c) a pressure transducer exists such that the pressure in the chamber can be sampled periodically by firmware. The procedure consists of three phases: 1) setup, 2) data capture, and 3) analysis.

The setup phase moves the piston to a desired initial location and vents the chamber such that the initial pressure is ambient (zero). The procedure in one embodiment includes the following steps: (1) Set the valve to the "open" position; (2) Set the piston to the initial location (near the fully aspirated position); (3) Pause to allow the chamber reach ambient pressure; and (4) Set the valve to the "closed" position.

During the data capture phase, pressure samples are captured and stored into memory at a fixed rate while the piston is moved through a sequence of operations. This sequence in one embodiment is (1) Repeat the following for N iterations; (2) Move the piston x distance in the dispense direction; and (3) Move the piston x distance in the aspirate direction. Each operation in this sequence can commence immediately following the completion of the previous operation.

Figure 43A:
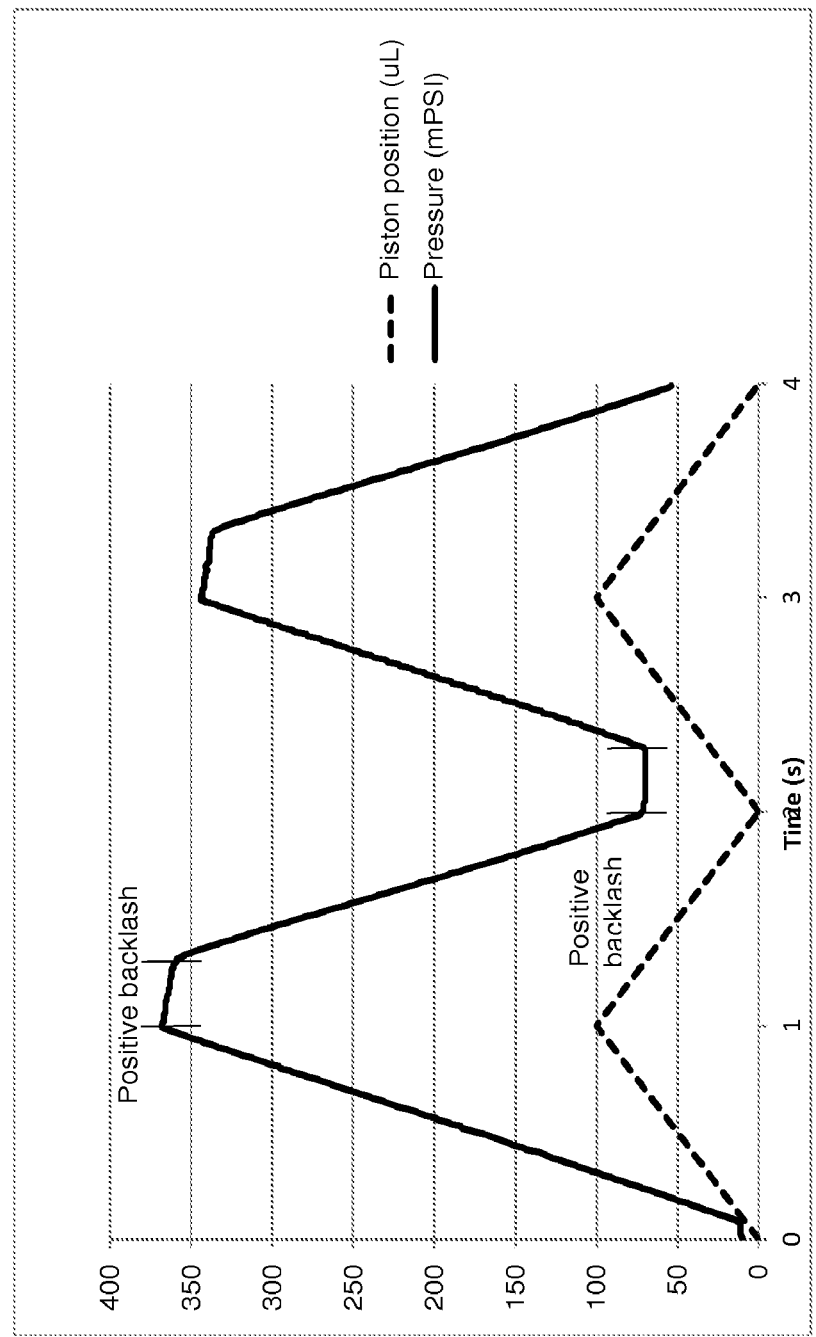
FIG. 43A is a graphical representation of an example of varying piston positions and resulting pressures of a pump system.
Figure 43B:
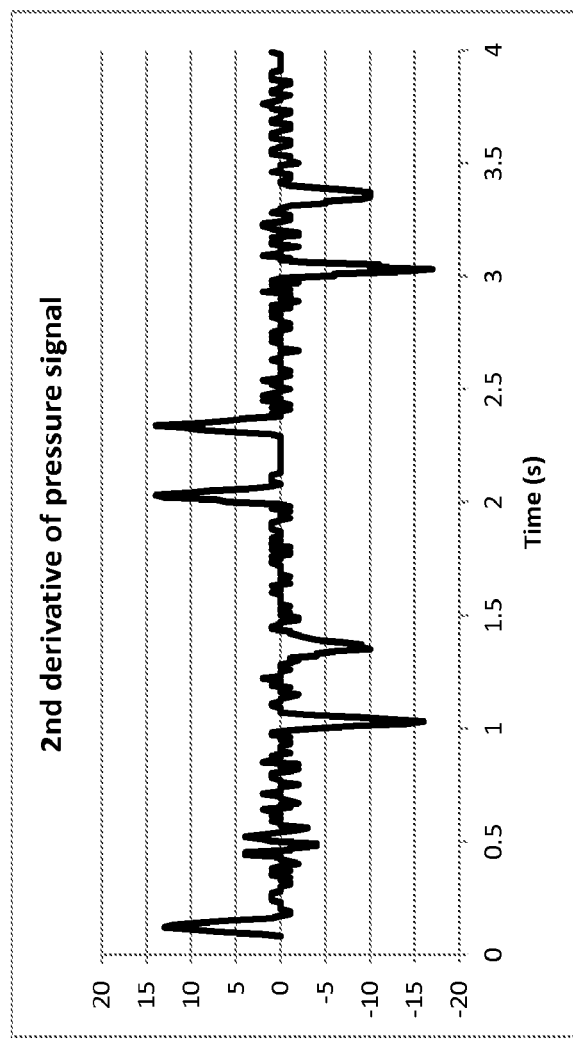
FIG. 43B is a graphical representation of an example of the second derivative of the pressure signal in FIG. 43A.

During the analysis phase, the captured pressure data is processed to produce the desired output: the pump backlash. FIG. 43A shows a pressure measurement data for an example pump. The piston position plot shows the expected piston position if the backlash was equal to zero (ideal pump). Starting at time t=[1, 2, 3] seconds, there are time periods in which the motor driving the piston is moving but the pressure is not changing at the expected rate. The duration of one of these periods (in seconds) multiplied by the flow rate (in μL/s) equals the backlash (in μL). The duration of each backlash period is the distance between the locations where there is a step change in the slope of the pressure signal. These locations can be easily obtained by taking the second derivative of the pressure signal and looking for local maxima. A plot of the second derivative of the pressure signal in FIG. 43A is shown in FIG. 43B. The pressure signal measured in FIG. 43B can be used to calculate the backlash correction by getting maximum/minimum marks on derivative graph and then translating those values to firmware to direct pump how to compensate. For N cycles, 2*N backlash measurements are produced. These can be averaged to produce a single value that is used to compensate for backlash during pump operations.

Further detailing the analysis of the pressure signal in FIG. 43A, the procedure is as follows. 1) Compute the second derivative of the pressure signal to produce the output shown in FIG. 43B. The first derivative is found by computing (PD1(n)=P(n)−P(n−1)) for each n where P is the pressure, PD1 is the pressure first derivative, and n is the sample number. The second derivative is produced by computing (PD2(n)=PD1(n)−(PD1(n−1)) for each n where PD2 is the pressure second derivative. 2) In the second derivative data, find the first two negative local maxima that exceed a given threshold. 3) The time difference between these two maxima is Δt1. 4) Starting after the second negative local maximum, find the next two positive local maxima that exceed the threshold. 5) The time difference between these two maxima is Δt2. 6) Starting after the second positive local maximum, find the next two negative local maxima that exceed the threshold. 7) The time difference between these two maxima is Δt3. 8) Compute the average of the three Δt measurements. 9) Multiply this averaged value by the flow rate (in μL/s) to produce the measured backlash value (in μL).

If the pressure signal contains random noise which is significant compared to the slope of the pressure changes, computing the second derivative using the above procedure may not produce clearly distinguishable local maxima. In this situation, a remedy is to compute the derivative as (D(n)=X(n)−X(n−m)) where D is the derivative output, X is the input data, n is the sample index, and m is a constant offset >1. m is selected as the lowest integer that produces clearly distinguishable local maxima. During normal operation, backlash compensation is performed by firmware in response to commands to move the pump piston. When the piston is commanded to move opposite the last direction, the backlash distance is added to the commanded distance and the motor is driven by this amount. This causes the piston to move the desired distance and displace the desired volume.

Commonly a pump will be commanded to aspirate a given volume at a given flow rate. For relatively low flow rates, the backlash compensation period may be large enough to cause the actual flow rate to be significantly lower than the commanded flow rate, even though the total volume is correct. In such a case, it is desirable (because it will be faster and save time) to compensate for the backlash using a higher velocity than the commanded flow rate and then switch to the commanded flow rate. Also in this case, the pump can be made to perform in the same way as a pump with no backlash at all flow rates.

FIG. 41A illustrates an embodiment of a pump 810. The central processing unit (CPU) 830 of a microprocessor which performs the backlash measurement uses one sensor input and three control outputs. As shown in FIG. 41A, the input (1) connects to the pressure transducer to collect the pressure data used to measure the backlash. Output (2) controls the piston rotation and is used to control whether the chamber is vented to ambient pressure or sealed. Output (3) connects to the nonvolatile memory and is used to store the computed backlash. Output (4) controls the piston linear motion and is used to move the piston in an iterative dispense/aspirate sequence while the pressure data is collected.

In still other embodiments, as an alternative to measuring the backlash as an independent activity, the backlash can be measured and compensated for every time there is a change in direction while running the pump. The measurement method can be the same as previously described. In particular, the pressure of the pump would be monitored while pumping in the direction requested. When the reverse direction pumping is requested, the pump would be directed to move in the reverse direction, while monitoring the pressure at the same time. The pressure should not change while the pump is experiencing the backlash amount. That amount can be measured via monitoring of the pressure transducer, and then that can be added on to the requested volume in order to compensate for the backlash.

Advantages to this alternative method include that in some pumps, the backlash amount experienced may be different and may depend on where the piston location is. That is, in a pump that has a total volume of 1000 µl, if the direction is changed after having pumped 800 µl, the backlash amount may be different than if 500 µl was pumped instead. Measuring the backlash amount independently can only occur at certain piston positions. Compensating for the backlash at any piston position with the measured backlash amount will not be as accurate (if the pump has backlash that depends on piston position). Measuring the backlash every time the pump changes direction (no matter what the piston position is), and compensating with the measured backlash can be more accurate and will not depend on the piston position.

Pump Storage Fluid

Various embodiments of a diagnostic system 110 contemplate a pump storage fluid stored on the cartridge 114 for use in-between diagnostic tests. Pump designs based on close-fitting ceramic-on-ceramic piston and cylinder sets (such as IVEK's rotary/reciprocating Metering Pumps) are highly susceptible to freezing, seizing or stiction. During periods of non-use, residual liquid inside the pump (dead volume) may evaporate if allowed to dry out (open to ambient) and leave behind solids. These solids, while possibly very low in concentration or mass, may increase significantly the friction between the piston and cylinder. Under such conditions, the piston motion becomes frozen. This may require complete disassembly and cleanup of the pump. Additionally, this may cause mechanical breakdown of the coupling mechanism between the piston and motor.

A pump storage fluid can prevent and/or inhibit the formation of solids between a piston and cylinder by, for example, not evaporating and/or by solubilizing any residual salt or solids present in the dead volume of a pump. This non-volatile liquid can act as a lubricant for the seal or tight fitting piston and cylinder set of a pump within the diagnostic instrument. Stiction can be avoided because lubricant persistently fills the gap between the piston and cylinder. In this manor the pump storage fluid prevents the pump seals or tight fitting piston and cylinder set from drying out and therefore prevents freezing, seizing, or stiction. The pump storage fluid is also referred to as pump storage liquid and pump prime fluid.

The pump storage fluid can be used to provide a clinical laboratory instrument which is free of normal user maintenance or free of or has reduced mechanical breakdown (related to the pump) is an improvement. Normal user maintenance that may be eliminated includes operations that service a pump such as requiring the instrument operator to flush liquids and/or empty waste containers. Eliminating user maintenance saves operator time, and therefore lower costs. Eliminating components from an instrument such as liquid loops from an instrument reduces costs.

Additionally, the present disclosure provides a pump storage fluid which enables the pump to recover from storage without wetting the seals or tight fitting piston and cylinder set. The minimum amount of pump storage fluid required to protect a pump can be very low, e.g. 1 nL. The pump storage fluid can be present in an amount ranging from about 1 nL to about 2 nL, from about 1 nL to about 1.5 nL, or from about 1.5 nL to about 2 nL. The minimum amount of pump storage fluid required to protect the pump depends on the gap volume between the piston and cylinder set. For example, a one in. diameter piston and one in. length chamber with a 2 micron gap between piston and cylinder has a gap volume of 4 µL. This is the minimum amount of pump storage fluid required to protect such a pump.

The pump storage fluid can be stored on the cartridge of the diagnostic system and used at the end of the each cartridge run. After proper application of a pump storage fluid of the invention, the pump does not require a liquid loop, and can be allowed to dry out (e.g., pump internal volume open to ambient) without risk of freezing, seizing or stiction. Upon re-start, the pump rapidly returns to its original performance. (See Example 10).

IVEK Corp. produces and sells ceramic positive displacement pumps with adequate volume metering precision and accuracy. The pumps are valve-less with close-fitting ceramic-on-ceramic piston and cylinder set. IVEK Corp. states in its use instructions that ceramic piston/cylinder sets are sensitive to neglect and may freeze if allowed to dry. Further, IVEK Corp. recommends the pump to remain wet at all times by means of liquid loop. If allowed to dry out, disassembly and cleaning of the pump is usually necessary. These manufacturer's storage options/requirements render its pump unsuitable for a clinical instrument designed for no or little user maintenance.

In some embodiments, a pump storage fluid of the invention contains a non-volatile, water soluble, salt solubilizing liquid that lubricates close-fitting ceramic-on-ceramic piston and cylinder set pumps. In some embodiments, a pump storage fluid is comprised of 30% by weight of diethylene glycol, 69.99% by weight of water, and 0.0013% by weight of PROCLIN® 200 (anti-microbial agent).

In some embodiments, a pump storage fluid is comprised of a lubricant such as diethylene glycol. The lubricant can comprise an ethylene glycol, including, but not limited to, ethylene glycol, diethylene glycol, triethylene glycol, tetraethylene glycol, polyethylene glycol or any combinations thereof. In some embodiment the lubricant can comprise a propylene glycol, including, but limited to propylene glycol, dipropylene glycol, tripropylene glycol, tetrapropylene glycol, polypropylene glycol or any combinations thereof. In some embodiments, a lubricant is comprised of glycerine. The lubricant can comprise both glycerine and glycols. In some embodiments, a pump storage fluid comprises between 5 and 95% by weight of lubricant. The pump storage fluid can contain water to reduce viscosity. The pump storage fluid can contain at least one anti-microbial agent or does not contain an anti-microbial agent.

In one embodiment, a pump storage fluid has at least one of the following properties: (1) Liquid at the operating temperature; (2) Low vapor pressure—does not evaporate; (3) Water soluble—readily flushed out of pump; (4) Solvent for residual salts or other solids within the pump dead volume; (5) Low surface tension—wets and fills gap between piston and cylinder; (6) Low viscosity—does not slow down fluid motions; (7) Chemically stable when inside pump or stored in intermediate containers; (8) Does not react with fluids for decontamination; (9) Chemically compatible with exposed materials; and (10) Does not interfere with adjacent operations. In some embodiments, a pump storage fluid has all of the above properties.

Some embodiments enable the use of a piston and cylinder type pump in a clinical instrument which has no installed liquids such as priming fluids, waste, wash liquids, cleaning liquids, or liquid loops. Some embodiments prevent unwanted freezing, seizing, or stiction of a piston and cylinder type pump, e.g., for up to six months, up to 9 months or up to 1 year periods of non-use. Some embodiments prevent unwanted freezing or seizing of a piston and cylinder type pump by the use of a pump storage fluid. Some embodiments provide a storage liquid for the pump which is chemically compatible with the parent instrument including the pump. Some embodiments provide a storage liquid which is chemically compatible with its intermediate storage container, e.g., a plastic clinical instrument. Some embodiments provide a storage liquid which also is suitable for priming a piston and cylinder type pump. Some embodiments provide a storage liquid which is operable at small volumes such as 1 nL.

Failsafe Mechanisms

Various embodiments of the diagnostic system 110 contemplate failsafe mechanisms that can prevent a user from selecting a mismatched cartridge for the selected diagnostic test, prevent use of an already used cartridge or a cartridge with a broken fluidic seal, or prevent processing of cartridges after undue delays from the start of a diagnostic test.

Referring to FIG. 5A, the diagnostic system 110 can include for an external scanner 122, such as that depicted in FIG. 5A, that can be used to read one or more of the optical machine-readable labels 118, such as a bar code. In some embodiments, the user can scan optical machine-readable labels 118 on the sample receptacle 116, the cartridge 114 and/or the packaging or packaging inserts prior to introducing the cartridge 114 into the diagnostic instrument 112. With that information stored, and after the user introduces the cartridge 114 into the diagnostic instrument 112, the diagnostic instrument 112 can detect whether the cartridge 114 that the user introduced into the diagnostic instrument 112 was the identical cartridge 114 that the user intended to run in the diagnostic instrument 112.

Other embodiments provide a mechanism to detect whether a cartridge 114 has expired after it has been removed from its package, and scanned by the user. For those cartridges that have an opened package expiry limit, the optical machine-readable labels 118 can provide information about the expiration dates for a given cartridge 114 and once scanned, the diagnostic instrument 112 can detect whether the said time has expired or not, when the user inserts the cartridge 114 into the diagnostic instrument 112. The diagnostic instrument 112 can alert the user to not proceed with the test if the cartridge 114 is expired. The alerts to the users can be transmitted through the user interface 122 or can be an audible warning signal.

The diagnostic instrument 112 can be equipped with a computer code scanner, such as a barcode scanner, or an external scanner 120, that can scan the cartridge(s) outside of the diagnostic instrument 112, and a computer system running software that interacts with the barcode system and with the user through a display (not shown). In some embodiments, a cartridge 114 is removed from a protective package, and scanned by the diagnostic instrument 112. The diagnostic instrument 112 upon scanning and decoding the bar coded information will direct the software appropriately to display the cartridge information read from the barcode.

Figure 44:
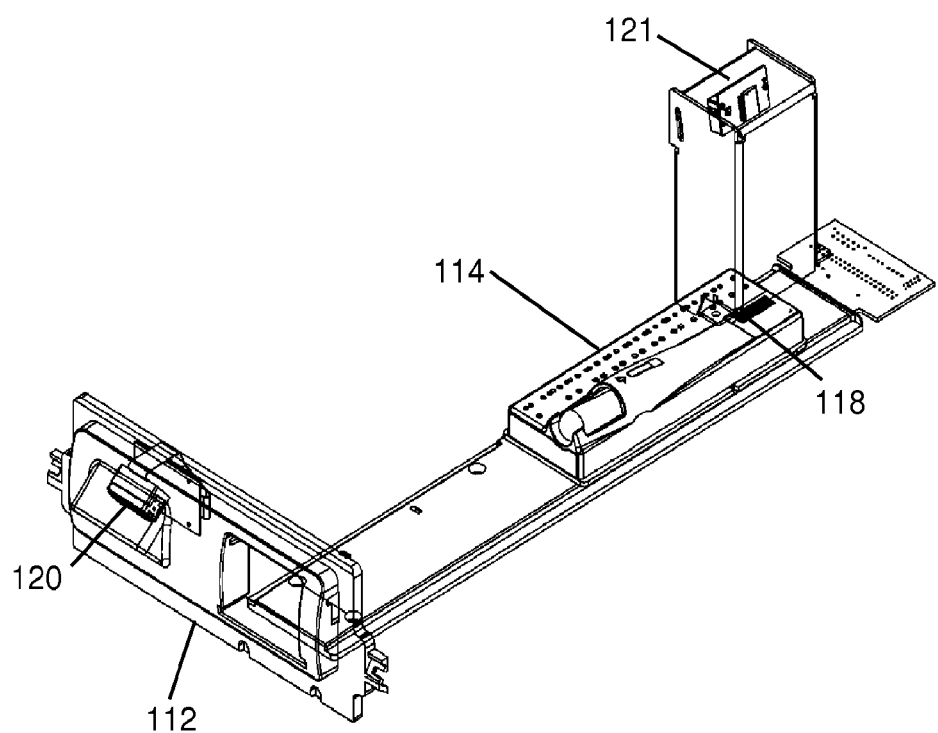
FIG. 44 is an illustration of example external and internal scanners of a diagnostic system.

FIG. 44 is an illustration of an example failsafe mechanism capable of verifying that a cartridge 114 introduced into a diagnostic instrument 112 is used within a recommended time limit after a first scan of the cartridge 114 outside the diagnostic instrument 112. In some embodiments, the diagnostic system 110 can include the use of a secondary barcode reader, or an internal scanner 121, that can be situated inside the diagnostic instrument 112, and can be aligned to read optical machine-readable labels on the disposable cartridge 114, e.g., to compare via software with the previously read optical machine-readable label (from outside) before starting the processing of the cartridge 114. This operation can be done without user input or awareness, except when an inconsistency is detected with the cartridge that is scanned outside and with the one scanned inside, at which time the user is alerted.

In various embodiments, a software timer can be used to measure the time from an initial scan of a cartridge to a second scan inside the diagnostic instrument. The software timer can be checked to ensure that the cartridge has been used within a recommended time limit after the first scan.

Instrument Software Steps

Figure 45:
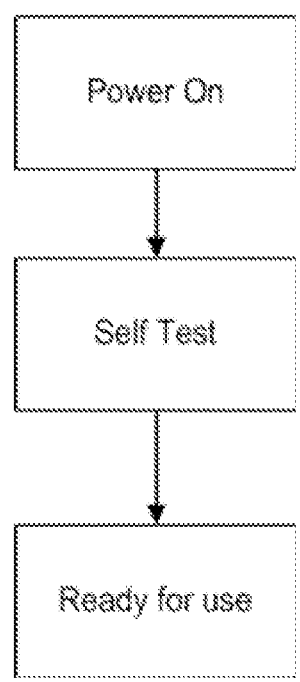
FIG. 45 is a flow chart for an example startup sequence.

Various embodiments of the diagnostic system 110 contemplate software programs that can control the electrical functions of the diagnostic system 110. Simple software guided workflows can be used, such as a simple start-up sequence set forth in FIG. 45. In some embodiments, upon daily power-up and prior to running each sample, a system completes a self-test and system is ready for use upon successful completion of these routines.

The operational specification describes the sequence of events that must occur in the course of a test cycle. For assaying an enzyme in a sample of blood or blood derivative, this specification discloses the following method: introducing the sample into a cartridge, metering of a portion of the sample, moving the metered sample with reagent at the analysis location, positioning the reacted sample at a sensor, and detecting the product of the reaction using a sensor.

The performance specification sets the criteria for parameters such as the range of results that will be reported, the necessary accuracy and precision of the test, and the acceptable operating conditions. The test results must match the sensitivity and range of the commonly accepted coagulation tests and must do so with comparable or better precision. Furthermore, as a point-of-care instrument may be operated by non-technically trained personnel, the instrument software must detect any cartridge errors that do occur.

Figure 46A:
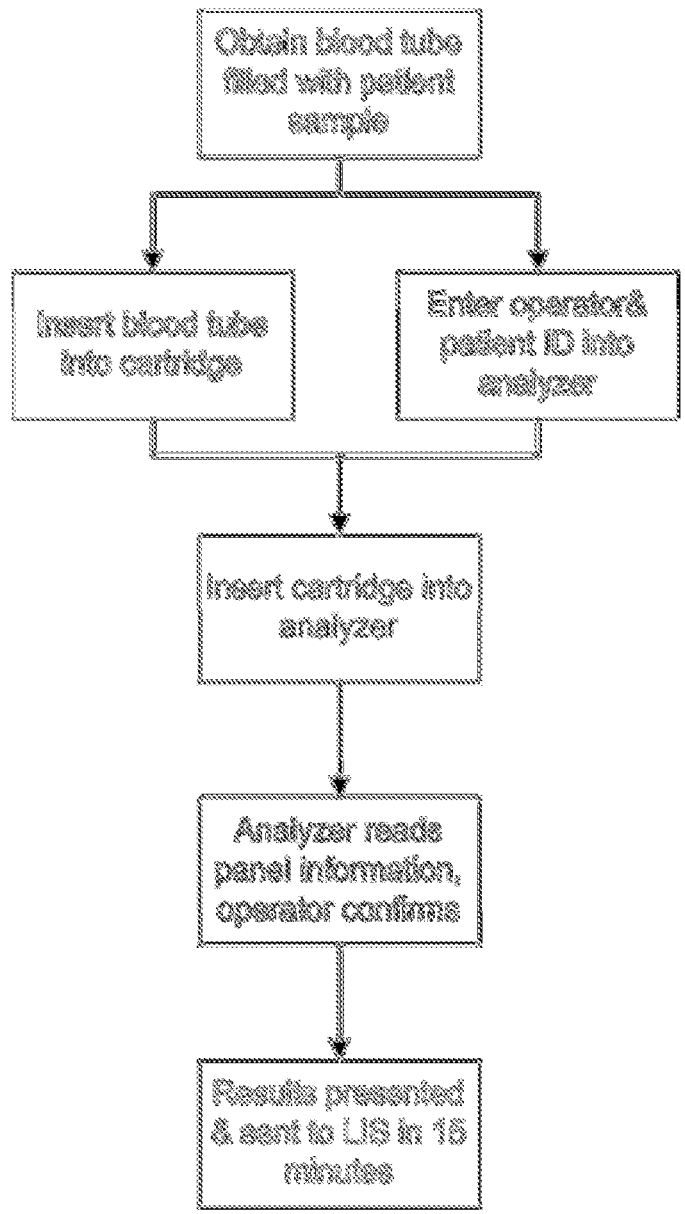
FIG. 46A is a flow chart for an example instrument-driven work flow.
Figure 46B:
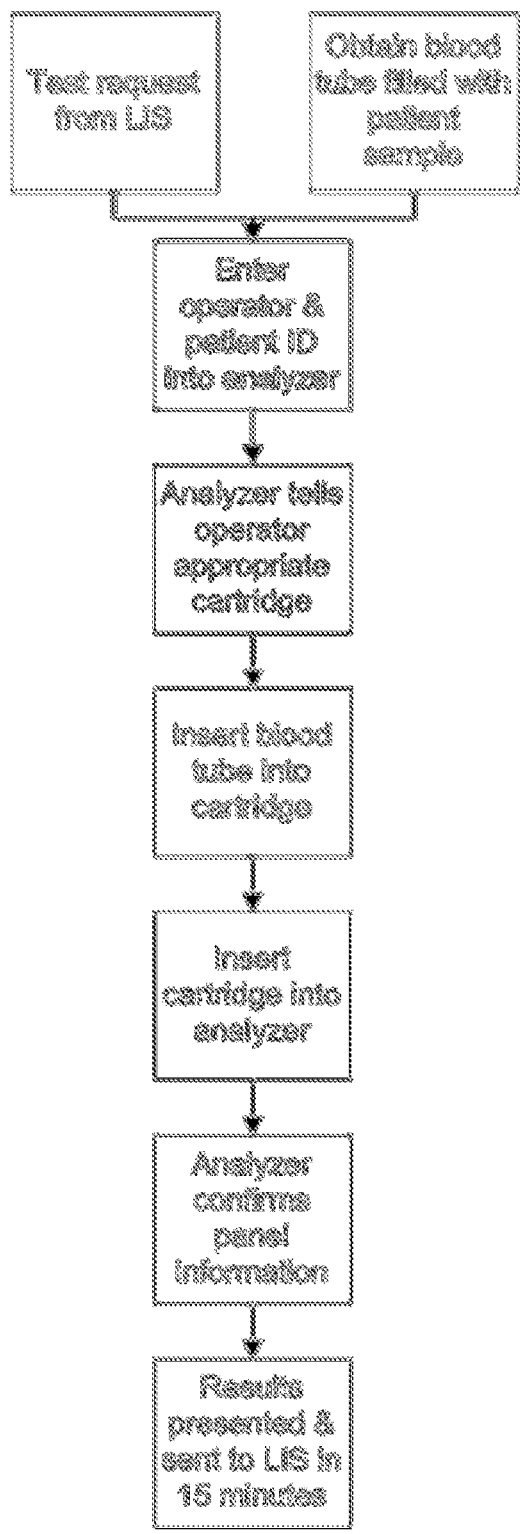
FIG. 46B is a flow chart for an example laboratory information system (LIS)-driven work flow.

Additional steps for testing venous wperforationperforation blood patient samples are shown in FIGS. 46A and 46B. Other sequences and options are possible and the following should be considered only as examples. An operator can draw blood into a blood tube using standard practices. In the instrument-driven mode, the operator (in either order) inserts the blood tube into the cartridge and enters the patient ID and operator ID into the diagnostic instrument. The operator can then insert the cartridge into the diagnostic instrument. The diagnostic instrument, after reading the panel information from the cartridge, may ask the operator to confirm the panel. Afterwards, the sample is processed and results are presented, for example, in roughly 15 minutes. In the laboratory information system (LIS)-driven mode, the diagnostic instrument is told the panel on the cartridge and the patient ID from the LIS. The diagnostic instrument, after the operator enters the patient ID, tells the operator which cartridge to use. The operator inserts the blood tube into that cartridge and inserts it into the diagnostic instrument. The diagnostic instrument confirms the correct cartridge is used, processes the sample, and presents the results.

All publications, patents and patent applications mentioned in this disclosure are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online.

Citation or discussion of a reference herein shall not be construed as an admission that such is prior art to the present invention.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." The use of the term/phrase "and/or" when used with a list means one or more of the listed items may be utilized, e.g., it is not limited to one or all of the elements.

As used herein the transitional term "comprising" is open-ended. A claim using this term can contain elements in addition to those recited in such claim. Thus, for example, the claims can read on methods that also include other steps not specifically recited therein, as long as the recited elements or their equivalent are present.

The following examples are merely illustrative and not intended to be limiting.

EXAMPLES

Example 1

Computing the Volume of a Liquid

Figure 29:
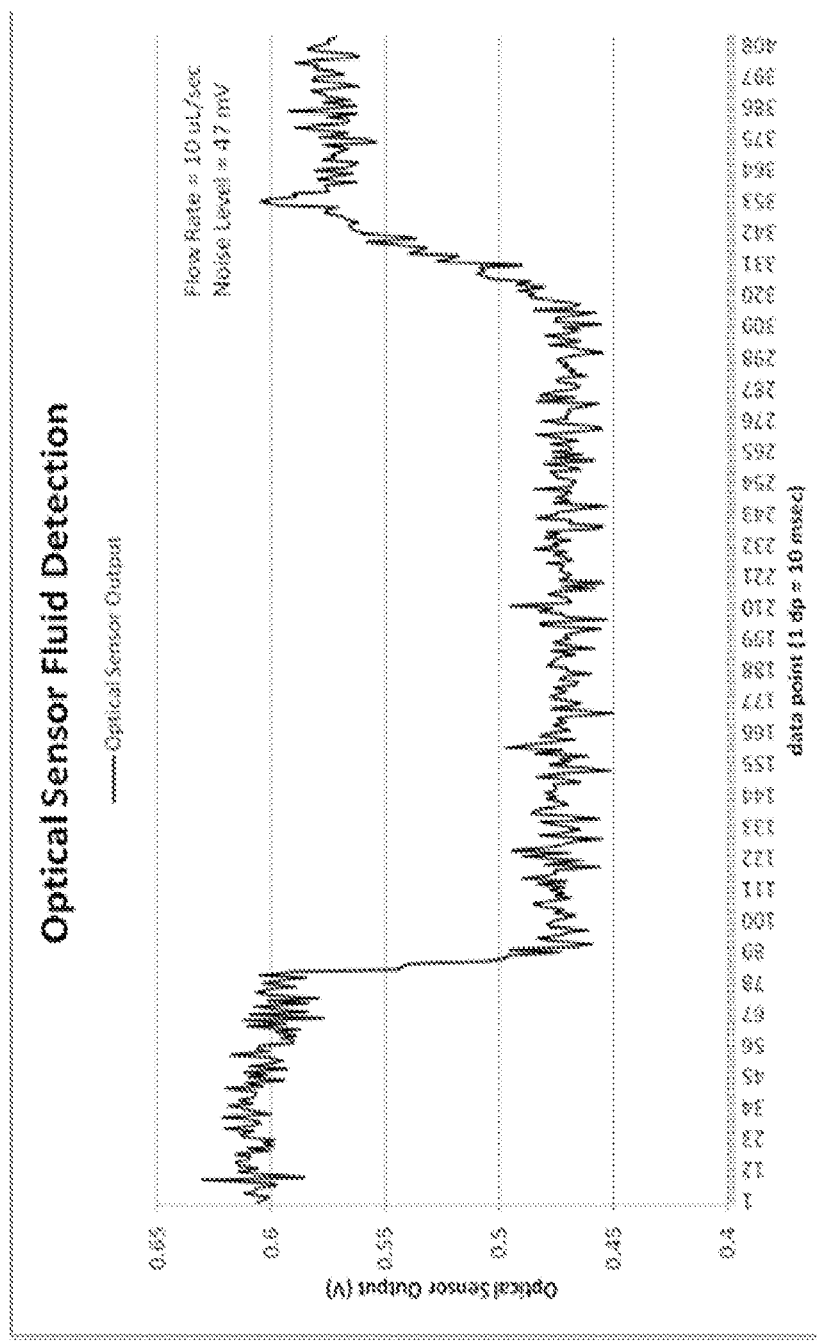
FIG. 29 is a graphical representation of an example of a moving liquid slug detected by a sensor.

FIG. 29 illustrates a typical output from a system monitoring the fluidic channel where a volume of liquid is passed. In FIG. 29, the horizontal axis is time (each data point is 10 milliseconds (ms)) and the vertical axis is the analog sensor output in volts. There is a 130 mV difference between the high (representing AIR in the system) and the low (representing LIQUID) in the system. There is a 110 mV difference between the low (representing LIQUID) and the high (after data point 342, representing WET). The noise level on the signal is about 47 mV, which is low enough to enable clear distinction of air and liquid in the channels.

A sensor output was used to compute the volume of the liquid, by computing the time that the liquid was present and multiplying by the pump's flow rate during the fluid motion. Also, the fact that there were no interruptions in the "low" signal (e.g., remains low, does not go up to the 0.6 V level) indicated that there were no air bubbles in the fluid volume. In this example above, air and liquid boundaries happened twice, one at about time point=81 and the other at about 318 (in this example where the flow rate was 10 µL/sec, liquid volume deleted was then 318−81=237 data points where each was 10 ms, making the total volume detected 23.7 µl.

Example 2

Detecting Leaks in a Fluidic System

FIG. 30A illustrates an example of a sequence of operations to detect leaks in the fluidic system. On a disposable cartridge where the patient sample was divided into aliquots of equal amounts each was processed independently in a multiple test cartridge (a cartridge that can run multiple tests with the same patient's sample). Sample Vs was aspirated into the channel, via the probe at the probe entry site 716. The sample volume was aspirated through a probe at the probe entry site 716 sealed to a septum 350, into the desired channel. The software reset a timer (T0) and commanded the pump to aspirate at a fixed flow rate (Fr) while monitoring the optical sensor's output until an air to liquid boundary was detected (FIG. 30B), as soon as it was detected the firmware made a copy of the current timer (T1).

The pump continued aspirating the sample, and as soon as a liquid to air transition was detected, the software made the copy of the timer (T2), after which the pump was stopped (FIG. 30C, depicting that sample passed the sensor and enabled volume measurement).

The following are examples of calculations that were used to determine clogs, leaks and/or verification and when desired correction of volumes.

Vx=(T1−T0)*Fr will be compared to Va, Vx>Va will indicate a leak. If Vx>>Va may indicate a clog in between pump and the probe.

Vy=(T2−T1)*Fr will be compared to Vs to verify the accuracy of the aliquot.

Example 3

Figure 47:
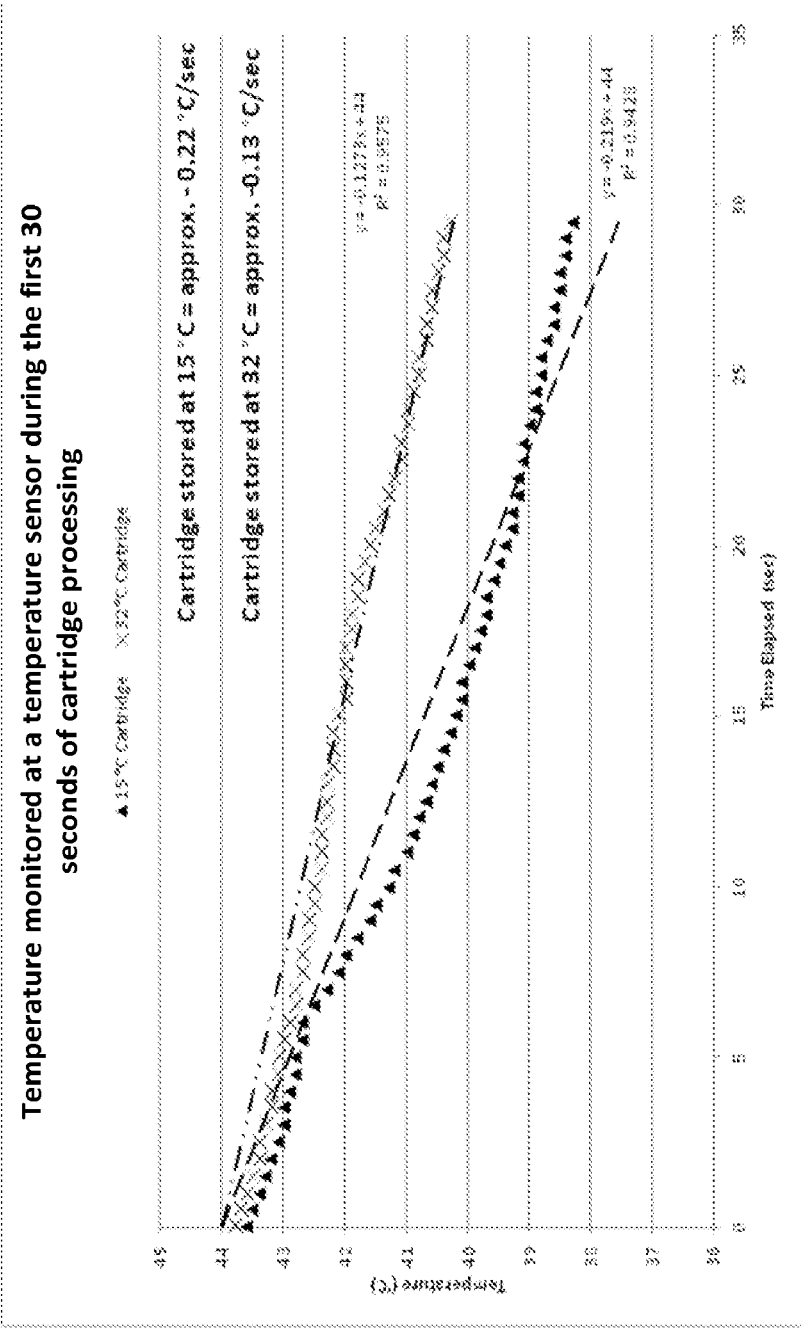
FIG. 47 is a graphical representation of an example of temperature monitored for two cartridges in Example 3 and 4.

Detecting Cartridges Stored at Different Temperatures and Applying Different Incubation Set Temperatures for Cartridges Stored at Different Temperatures Cartridges stored at two different temperatures were differentiated by monitoring the temperature at a temperature sensor and evaluating the temperature loss over the first 30 seconds of cartridge processing. FIG. 47 is a graphical representation of the temperature monitored at a temperature sensor for two different cartridges stored at two different temperatures. When cartridges at two different storage conditions are detected, the instrument can apply different parameter values for the incubation.

Table 4 below shows a scenario when different incubation set temperatures were applied for the cartridges stored at two different storage temperatures. Table 4 below shows the set temperatures used for this example.

TABLE 4

| | Incubation Temperature Set Points | |
|---|---|---|
| Test No. | For 15° C. Cartridge | For 32° C. Cartridge |
| A | 40.5° C. | 40.5° C. |
| B | 40.5° C. | 39° C. |

Notice that, for Test A, both cartridges stored at 15° C. and 32° C. were incubated at the same incubator temperature set point. For Test B, cartridges stored at 15° C. and 32° C. were incubated at different incubator temperature set points. The chart below shows the differences in the incubation quality (average temperature during the incubation) between the cartridge stored at 15° C. and the cartridge stored at 32° C. for each sample for Test A and Test B. Note that this particular cartridge in this example had 7 samples available. The difference in the incubation quality shown in the chart below is the difference in average temperatures during incubation between the cartridge stored at 15° C. and the cartridge stored at 32° C. The lower difference in the incubation quality was desirable; the sample should be incubated identically independent from the cartridge's storage temperature.

Figure 48:
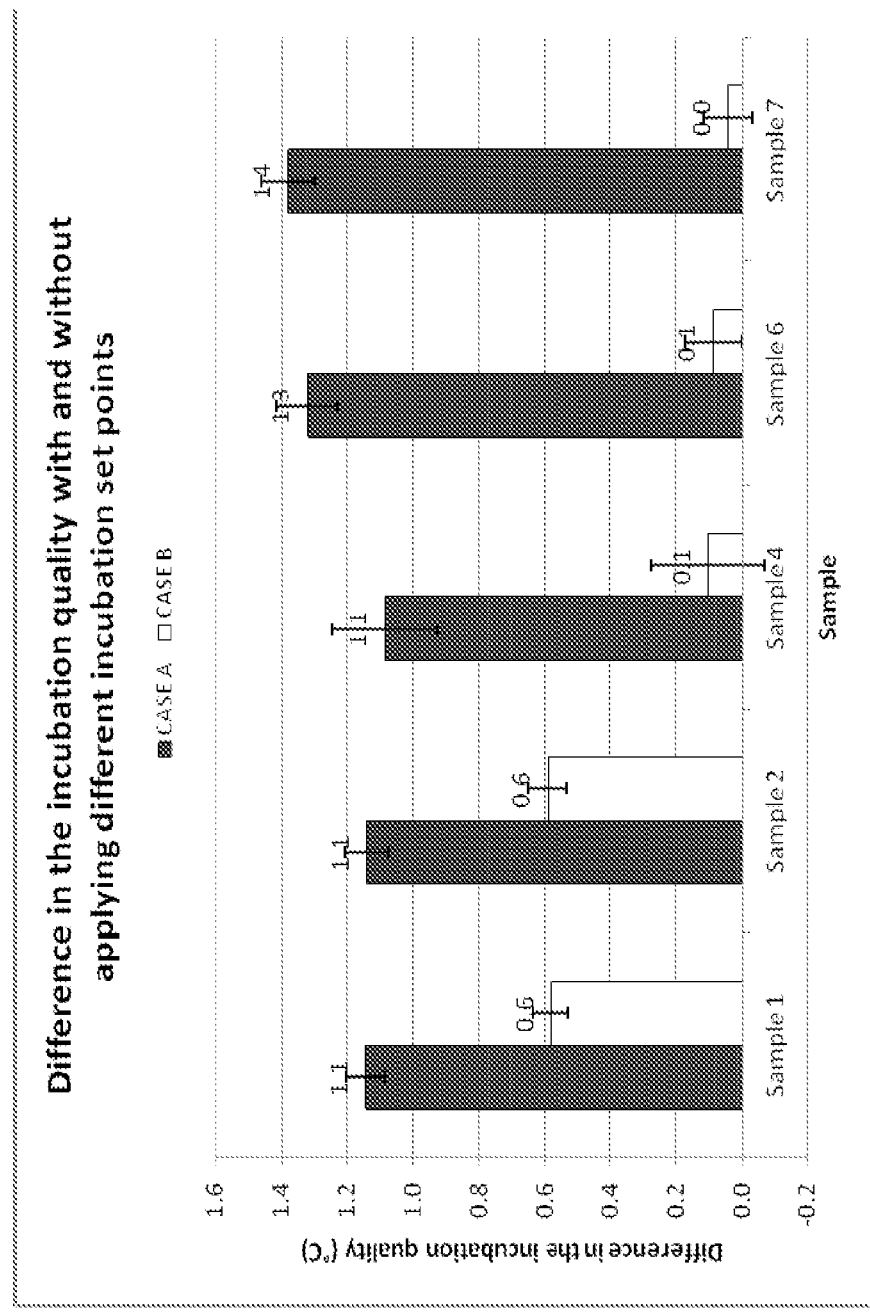
FIG. 48 is a graphical representation illustrating an example of the difference in the incubation quality with and without applying different incubation set points in Example 3.

FIG. 48 is a graphical representation illustrating the difference in the incubation quality with and without applying different incubation set points. Without applying different temperature set points for cartridges stored at different temperatures, the difference in the incubation quality ranges between 1.1° C. and 1.4° C. When applying different temperature set points for cartridges stored at different temperatures, the difference in the incubation quality ranges between 0° C. and 0.6° C.

Example 4

Applying Different Boost Durations for Cartridges Stored at Different Temperatures The example below shows a scenario when cartridges stored at different temperatures were initially heated up for different durations. The initial heating up process was defined as boost in this example. Table 5 below shows different boost durations used for this example. The boost used in this example uses a 4° C. higher incubation temperature set point (44.5° C.) than the normal incubation temperature set point (40.5° C.) for 30 seconds or 330 seconds at the cartridge location during the blood filtration operation.

TABLE 5

| | Boost Duration | |
|---|---|---|
| Test No. | For 15° C. Cartridge | For 32° C. Cartridge |
| A | 30 sec | 30 sec |
| B | 30 sec | 30 sec |

Notice that, for Test A, both cartridges stored at 15° C. and 32° C. had the same boost duration. For Test B, cartridges stored at 15° C. and 32° C. had different boost durations. The chart below shows the differences in the incubation quality (average temperature during incubation) between the cartridge stored at 15° C. and the cartridge stored at 32° C. for each sample for Test A and Test B. Note that this particular cartridge in this example had 7 samples available. The difference in the incubation quality shown in the chart below is the difference in average temperatures during incubation between the cartridge stored at 15° C. and the cartridge stored at 32° C. The lower difference in the incubation quality was desirable; the sample should be incubated identically independent from the cartridge's storage temperature.

Figure 49:
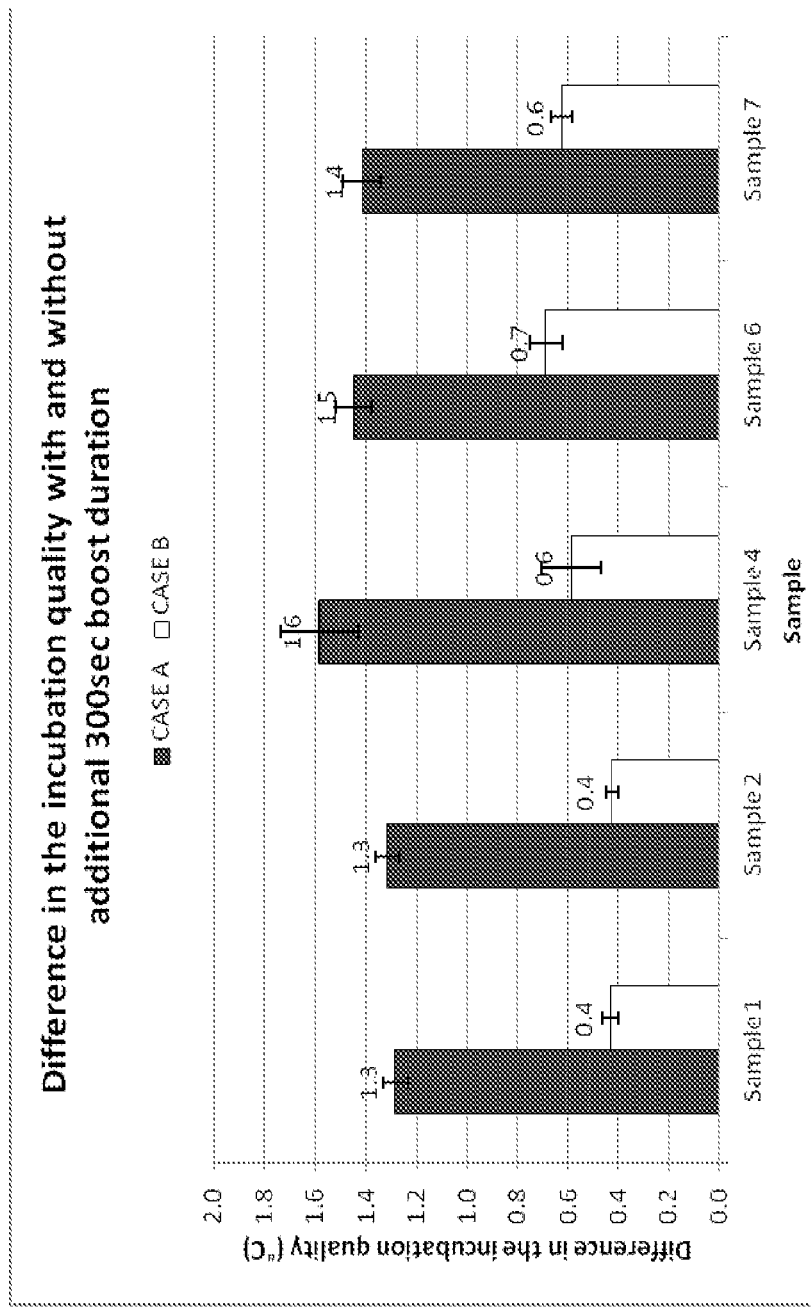
FIG. 49 is a graphical representation illustrating an example of differences in incubation quality in Example 4.

FIG. 49 is a graphical representation illustrating differences in incubation quality with and without additional boost duration. Without applying different boost durations for cartridges stored at different temperatures, the difference in the incubation quality ranges between 1.3° C. and 1.6° C. When applying different boost durations for cartridges stored at different temperatures, the difference in the incubation quality ranges between 0.4° C. and 0.6° C.

Example 5

Internal Standard (IS)

A standardized quantity of 24,038 fluorescent beads yielded a fluorescent signal of 189,395. These fluorescent beads were processed as an IS in two test trials, with the following results in Table 6:

TABLE 6

| | Test #1 | Test #2 |
|---|---|---|
| Fluorescent signal | 149,608 | 167,056 |
| Number of beads | 18,989 | 21,203 |
| Bead Recovery | 79.0% | 88.2% |

In a test where the predetermined cutoff point for Failsafe mechanism is 85%, the run from test #2 did result in a PASS condition, when run from test #12 resulted in a FAIL condition.

Example 6

Use of IS as Failsafe to Detect False Negative Result

A standardized quantity of fluorescent labeled beads was added to assay reagents for a 5-fluorouracil assay. The reagents were incorporated onto a cartridge as part of a diagnostic system. Replicate measurements were made on a sample, where the sample was a 5-fluorouracil standard at 2000 ng/mL. The fluorescence signal and ECL signal results for four replicates are given in Table 7.

TABLE 7

| Test Number | ECL | Fluorescence |
|---|---|---|
| 1 | 91775 | 81771 |
| 2 | 58521 | 49400 |
| 3 | 81484 | 79203 |
| 4 | 99932 | 78649 |

With the exception of test number 2, the ECL signal demonstrated consistent results, i.e. the precision was 10% CV for the three replicates. The fluorescent signal also demonstrated very consistent results, i.e. the precision was 2% CV for the three replicates.

The fluorescence signal for test number 2 was low, i.e. 49400 or 36% decreased from the fluorescent mean. The corresponding ECL signal for test number 2 was falsely low, i.e. 58521 or 38% decreased from the ECL mean. This indicated that the IS was able to detect as false negative ECL reading.

Example 7

ECL Detection of Assay

A prototype system was designed and built for evaluation. The prototype system consisted of a Wellstat Alpha 1 POC instrument with molded cartridges containing 5-FU specific reagents such as assay compositions. Example assay compositions may include a biomarker that can attach to a targeted analyte. For example, 5-Fluorouracil (5-FU) is widely used in cancer patients to treat tumors including, but not limited to, colorectal, head and neck, stomach and breast carcinomas. 5-FU is most often administered systemically, but is also applied topically to treat some forms of pre-cancerous and cancerous skin disorders. In the case of 5-FU overdoses, a reagent with a biomarker specifically designed to attach to 5-FU may be provided. Further discussion of the biomarker for 5-FU may be found in PCT Application No. PCT/US12/67353, which is hereby incorporated in its entirety by reference.

The system was evaluated for detecting 5-FU in plasma and whole blood. The evaluation consisted of measuring the following characteristics (or metrics) commonly assessed in diagnostic assays: Assay Dynamic Range, Analytical Sensitivity (LDL), Accuracy and Assay Precision, Spiked Recovery in the Whole Blood, and Carryover.

A. Assay Dynamic Range—Analytical Sensitivity

Assay Dynamic Range and Analytical Sensitivity (LDL) was determined by running four (4) calibrators (known amount of 5-FU) with values of 0.0, 25, 1,000, and 10,000 ng/mL in plasma. They were run in 3 replicates.

Based on a standard curve generated from running the above mentioned calibrators, the 5-FU assay LDL was determined to be 3.96 and the dynamic range was determined to be 3.96-10,000 ng/mL. This means that the system is be able to measure any concentration in the above mentioned range.

B. Accuracy and Assay Precision

Accuracy was assessed by using three (3) test samples (delipidated/defibrinated human plasma) spiked at three (3) different concentrations (100, 2,000, and 8,000 ng/mL) of 5-FU. Each sample was be analyzed in ten (10) replicates.

Precision measured for the three concentrations ranged from 3.3% to 14%. The accuracy of measured concentrations ranged from 7%-27%.

C. Spiked Recovery in Blood

Whole human blood (30 mL per 5-FU concentration) was spiked with 5-FU at three (3) different concentrations (50, 1,000, and 4,000 ng/mL). To ensure complete mixing of the spiked 5-FU in the blood, the vacutainer containing blood was mixed by inversion on a rotator for five (5) minutes at room temperature. The spiked blood was analyzed within two (2) hours of spiking.

The % recovery for the 1000 & 4000 ng/ml were calculated to be 85 and 89% respectively.

D. Carryover

Analyte carry over was evaluated by measuring a high concentration sample (10,000 ng/mL 5-FU) in a cartridge followed by a low concentration sample (0.0 ng/mL 5-FU) in a cartridge. This was tested a total of five (5) times in a single day.

Signal carry over was evaluated by measuring a low concentration sample (0.0 ng/mL 5-FU) in a cartridge followed by a high concentration sample (10,000 ng/mL 5-FU) in a cartridge. This was tested a total of five (5) times in a single day.

Results indicated that there was no analyte carryover based on the fact that Cal 1 5-FU concentration values remained at or near 0 for all five samples. No signal carryover was evident based on Cal 4 concentrations at 100±6% of the expected 10000 ng/mL concentration. Significant analyte carryover would result in a reduction of ECL counts with Cal 1, which in actuality had a 3.5% increase in ECL counts over the Calibrator 1 controls. Significant signal carryover would result in an increase of ECL counts with Cal 4, while the assay results show a 7% decrease from the Calibrator 4 controls.

Example 8

Measurement of Backlash

Currently pump backlash can be measured by isolating the chamber (from the inlet and outlet ports) and moving the piston to aspirate and dispense at a constant velocity while capturing pressure data. The amount of distance that the motor is in motion while the pressure is not changing directly translates to the pump backlash at that location.

Firmware compensates for this backlash by moving the pump linear motor an additional distance (equal to the measured backlash) when the piston is commanded to move in the opposite direction from its last displacement. It is desirable to have an independent verification of this functionality. For this reason, a test was devised to verify proper operation by measuring the mass of the displaced liquid and infer to the volume.

A pump with a built-in valve had inlet and outlet ports. The pump had a chamber that can hold 400 µl of liquid. The pump could be connected to either the inlet port or to the outlet port by a command. The pump could aspirate (draw liquid in) or dispense (push liquid out) to either one of the ports that it was connected. The piston position that was fully dispensed (meaning it had 0 µl in its chamber) was considered the home position for the pump.

An analytical balance was used to weigh the liquid. Pump storage liquid was used as the liquid to pump and measure, because its evaporation rate was lower than water and it would reduce the weight measurement error. A container partially filled with pump storage fluid was placed on the balance, and tubing which connected to the pump inlet port was suspended in the liquid such that the tube was not in contact with any wall of the container.

The pump was thoroughly flushed to remove all air from the system. The piston flat was positioned toward the inlet port (meaning the pump was fluidically connected to the inlet port which was connected to the tubing that was connected to the pump storage liquid in the container on the analytical balance). The piston was homed (fully dispensed), then aspirated 110 µl, then dispensed 10 µl at 10 µl/s. This moved the piston's position 100 µL from home, with the last direction being dispense and the last velocity being 10 µL/s. The balance is tared and the pump was commanded to dispense 10 µl at 10 µl/s. The change in weight was recorded. Since the last piston direction before the test, was dispense (same as the test direction), the change in volume measured after the dispense stroke was expected to be 10 µL regardless of the backlash. This measurement was therefore called the dispense control. This measurement was 10.3 µl.

The balance was tared again, the piston was aspirated by 10 µL (forcing the direction change), and the change in weight was again recorded. This procedure was executed with the backlash compensation disabled and also executed when the backlash compensation was enabled.

For the aspirate direction, the change in volume was expected to be (10 μL—backlash) with backlash compensation disabled and 10 μL with it enabled. 6.6 μl was measured when backlash was not compensated and 9.9 μl was measured when backlash was compensated.

The balance was tared again, the piston was again aspirated by 10 μl (with no direction change), and the change in weight was again recorded. Since the last piston direction before the test, was aspirate (same as the test direction), the change in volume measured after the aspirate stroke was expected to be 10 μL regardless of the backlash. This measurement was therefore called the aspirate control. This measurement was 9.9 μl.

The balance was tared again, this time the piston was dispensed by 10 μL (forcing the direction change from aspirate to dispense), and the change in weight was again recorded. This procedure was executed with backlash compensation disabled and also executed when the backlash compensation was enabled. For the dispense direction, the change in volume was expected to be (10 μL—backlash) with backlash compensation disabled and 10 μL with it enabled. 7.0 μl was measured when backlash was not compensated and 10.0 μl was measured when backlash was compensated.

The density of the pump storage liquid sample was measured to be 1.039 g/mL. This value was used to convert the measured weight into volume. The pump under test was 1_350194_008. Before running the verification, the backlash was measured using the pressure method in 4 trials. The results were [3.3 μL, 3.2 μL, 3.1 μL, 3.1 μL]. Based on these four measurements, backlash was determined to be 3.2 μL.

Table 8 below provides the change in volume (in μL) as measured by the analytical balance for both dispense and aspirate strokes of the test. Since the backlash was 3.2 μL, it was expected that the change in volume for the aspirate stroke would be 6.8 μL with backlash compensation disabled. 7.6 μL was actually measured, which is within the allowed measurement error. For the dispense stroke with backlash compensation enabled, it was expected that the change in volume would be 10 μL and it was actually 10 μL,

TABLE 8

Control Measurement when there is no direction changing

| Measured Volume (μl) | Aspirate 10 μl | Dispense 10 μl |
|---|---|---|
| No Direction Change | 9.6 | 9.9 |

TABLE 9

Test Measurement when there is direction changing with and without backlash compensation

| | Measured Volume (μl) | | | |
|---|---|---|---|---|
| | Aspirate 10 μl after dispense | | Dispense 10 μl after aspirate | |
| | backlash not compensated | backlash compensated | backlash not compensated | backlash compensated |
| Direction Change | 6.6 | 9.9 | 7.0 | 10.0 |

Based on this test run, the displacement error in the aspirate direction improved from 34% to 1%. In the dispense direction the displacement error improved from 30% to 0%. Thus, when applying the backlash correction, accuracy was improved.

Example 9

Real-Time Backlash Measurement and Compensation

A test was completed to illustrate how pump backlash could be measured and compensated for as part of the normal operation of the pump. If the pressure at the pump chamber was stable at the start of a displacement operation, and there was sufficient fluidic resistance between the active pump port and atmosphere, a pressure change occurred when the piston motion began. The pump motor distance traveled before this pressure change was detected was the amount of backlash.

A length of 0.040" tubing was partially filled with water, which provided resistance such that a pressure change occurred when the piston moved. The pump chamber was air filled. The piston was moved to 100 μL from home and rotated to the inlet port. The last direction of the pump motion was aspirate. 5 seconds of pressure data was captured at 100 samples per second. Negative velocity represented the dispense direction, and positive velocity corresponded to the aspirate direction.

During the 5 second cycle, the event timeline was as follows.

At t=1 s, the pump motor was started in the dispense direction at 10 μL/s.

At t=1.3 s, the pump piston started to move. This was detected by the slope of the pressure signal going positive. Because the piston did not move for 0.3 s while the pump motor was moving, the backlash was determined to be (0.3 s)(10 μL/s)=3 μL.

Because it was desired to displace a total volume of 10 μL, the pump motor continued to move at 10 μL/s from t=1.3 s to t=2.3 s.

At t=2.3 s the pump motor stopped. At this point the pump motor had moved 13 μL and the piston had dispensed 10 μL.

From t=2.3 s to t=3.3 s the pump was idle, allowing the pressure to stabilize.

At t=3.3 s, the pump motor started moving in the aspirate direction at 10 μL/s.

At t=3.6 s, the pump piston started to move. This was detected by the slope of the pressure signal going negative. Because the piston did not move for 0.3 s while the pump motor was moving, the backlash was again determined to be (0.3 s)(10 μL/s)=3 μL.

Because it was desired to displace a total volume of 10 μL, the pump motor continued to move at 10 μL/s from t=3.6 s to t=4.6 s.

At t=4.6 s the pump motor stopped. At this point the pump motor had moved 13 μL and the piston had aspirated 10 μL.

Table 10 summarizes the pump linear motor travel distance and actual piston travel for the dispense and aspirate cases in the above operation.

TABLE 10

Distance and displacement for pump operation at direction change with real-time backlash measurement enabled

| Dispense 10 µl after aspirate | | Aspriate 10 µl after dispense | |
|---|---|---|---|
| Pump motor distance | Piston displacement | Pump motor distance | Piston displacement |
| 13 µL | 10 µL | 13 µL | 10 µL |

Currently pump backlash is measured by isolating the chamber and moving the piston back and forth at a constant velocity which capturing pressure data. The amount of time that the motor is in motion while the pressure is not changing directly translates to the pump backlash at that location.

Firmware compensates for this backlash by moving the pump linear motor an additional distance (equal to the backlash) when the piston is commanded to move in the opposite direction as its last displacement. The correct operation of this compensation mechanism can be verified by confirming using the same pressure method that the backlash is near zero once compensation is enabled. It is desirable however to have an independent verification of this functionality. For this reason, a test was devised to verify proper operation by measuring the mass of the displaced liquid.

An analytical balance was used to weigh the liquid. Pump storage fluid was used because its evaporation rate is lower than water. A container partially filled with Pump storage fluid was placed on the balance, and tubing which connects to the pump waste port was suspended in the liquid such that the tube was not in contact with any wall of the container.

The pump was thoroughly flushed to remove all air from the system. The piston flat was positioned toward the waste port. The piston was moved to the position 100 µL from home, with the last direction being dispense and the last velocity being 10 µL/s. Subsequent motion was at 10 µL/s, which was the velocity at which the backlash was measured using the pressure method.

The balance was tared, the piston was dispensed 10 µL, and the change in weight was recorded. The balance was tared again, the piston was aspirated by 10 µL, and the change in weight was again recorded. This procedure was executed with backlash compensation disabled and enabled.

Since the last piston direction before the test was dispense, the change in volume measured after the dispense stroke was expected to be 10 µL regardless of the backlash. For the aspirate direction, the change in volume was expected to be (10 µL—backlash) with backlash compensation disabled and 10 µL with it enabled.

The density of the pump storage fluid sample was measured to be 1.039 g/mL. This value was used to convert the measured weight into volume. The pump under test was 1_350194_008. Before running the verification, the backlash was measured using the pressure method in 4 trials. The results were [3.3 µL, 3.2 µL, 3.1 µL, 3.1 µL]. Based on these four measurements, backlash was determined to be 3.2 µL.

Table 11 below provides the change in volume (in µL) as measured by the analytical balance for both dispense and aspirate strokes of the test. Since the backlash was 3.2 µL, it was expected that the change in volume for the aspirate stroke would be 6.8 µL with backlash compensation disabled. 6.6 µL was actually measured, which is within the allowed measurement error. For the aspirate stroke with backlash compensation enabled, it was expected that the change in volume would be 10 µL and it was actually 9.9 µL, which was also within the allowed measurement error.

TABLE 11

| Backlash compensation in firmware (µL) | Disabled | Enabled |
|---|---|---|
| Δvol dispense (µL) | 9.6 | 9.3 |
| Δvol aspirate (µL) | −6.6 | −9.9 |

Based on this test run, the displacement error in the aspirate direction improved from −34% to −1%. Thus, when applying the backlash correction, accuracy was improved. Without backlash correction the pump aspirated 6.6 µl when it was desired to aspirate 10 µl. With the backlash correction applied the pump aspirated 9.9 µl, which is an improvement.

Example 9

Pump Storage Fluid

To prepare a pump for storage it is flushed with a pump storage fluid. The following example demonstrates how flushing is accomplished. An example of a routine procedure for preparing a pump (IVEK Linear B size pump module mfg. part #032106-7007) for storage is to first draw air into the pump to remove working fluid (such as aqueous solution with surfactant, amines, salts, and buffer components). Significant working fluid remains in the pump as dead volume is approximately 75 µL in this example. Pump storage fluid, composed of 30% diethylene glycol in water, is then drawn into pump so as to exchange with the residual working fluid. Significant quantities of salts from the working fluid remain inside the pump due to its dead volume. The operation must draw (1 mL) in sufficient pump storage fluid to get enough lubricant into the gap between the piston and cylinder. Lastly, the pump is flushed with air to remove the pump storage fluid. A significant amount of pump storage fluid, and specifically diethylene glycol lubricant remains inside the pump's piston cylinder gap. The preparation for storage operation takes 45 seconds. The quantity of lubricant is sufficient to protect the pump for at least six months at 30° C.

What is claimed is:

1. A method of performing a diagnostic test in a diagnostic system, comprising:
introducing a sample into a cartridge of the diagnostic system, the cartridge comprising:
structural members;
a body and a cover, wherein the body and the cover mate together;
at least one reagent handling station formed from the body;
a septum seal between the body and the cover configured to establish a liquid and air-tight seal for the at least one reagent handling station and capable of establishing a fluidic connection with at least one probe of a diagnostic instrument in the diagnostic system;
a bottom seal adjacent to the body;
at least one fluidic channel formed from the body and sealed by the bottom seal, wherein the bottom seal defines in part the volume of the at least one fluidic channel; and
a mounting apparatus for mounting a sample container to the cartridge, the mounting apparatus comprising:
a framework comprising at least one of the structural members of the cartridge; and
at least one needle capable of establishing a fluidic connection between the cartridge and the sample container when the at least one needle pierces a septum of the sample container, wherein the framework is configured to guide the sample container into a position such that the sample container is capable of being fixed at an angle ranging from about 45° to about 5° from a horizontal axis of the cartridge;

introducing the cartridge of the diagnostic system into the diagnostic instrument of the diagnostic system, the diagnostic instrument comprising:

a non-electrochemiluminescence (ECL) detection system;

the at least one probe further comprising a first probe and a waste probe;

the first probe fluidically connected to the non-ECL detection system by at least one fluidic tube;

an ECL detection system fluidically connected to the non-ECL detection system by the at least one fluidic tube;

a pump fluidically connected to the ECL detection system by at least one fluidic tube and fluidically connected to the waste probe by at least one fluidic tube;

mixing the sample with at least one reagent to form a detectable complex, wherein the at least one reagent is stored on the cartridge;

analyzing the detectable complex with the ECL detection system of the diagnostic instrument; and providing detection results through a user interface on the diagnostic instrument.

2. The method of claim 1, further comprising:
incubating with an incubator in the diagnostic instrument the sample-reagent mixture capable of forming the detectable complex within the cartridge.

3. The method of claim 1, further comprising:
washing the sample-reagent mixture capable of forming the detectable complex to obtain the detectable complex.

4. The method of claim 1, wherein the at least one reagent comprises a lyophilized pellet.

5. The method of claim 1, wherein the at least one reagent comprises at least one of a bead, a lyophilized pellet, a buffer, or a detectable label.

6. The method of claim 1, wherein the at least one fluidic channel comprises a sample reservoir, a primary channel, a secondary channel, and at least one receiver channel.

7. The method of claim 6, further comprising dividing the sample within the cartridge, the dividing comprising:

drawing a first volume of the sample from the sample reservoir of the cartridge into the primary channel of the cartridge;

detecting with an optical sensor of the diagnostic instrument when the primary channel is filled with a first predetermined volume;

emptying any remaining sample from the sample reservoir not used to fill the primary channel into the secondary channel by detecting with the optical sensor of the diagnostic instrument a liquid air boundary;

drawing a second volume of the sample from the primary channel into the at least one receiver channel;

detecting with an optical sensor of the diagnostic instrument when the at least one receiver channel is filled with a second predetermined volume; and repeating the process until each of the at least one receiver channels holds the second predetermined volume of the sample, wherein each of the steps performed are independent of pump accuracy.

8. The method of claim 7, wherein the sample reservoir has a volume which is greater than or equal to the total aliquot volume.

9. The method of claim 7, wherein the sample reservoir has a volume chosen from about 125 µL to about 135 µL, about 135 µL to about 150 µL, about 150 µL to about 175 µL, and about 175 µL to about 200 µL.

10. The method of claim 7, wherein the sample reservoir has a volume of about 200 µL.

11. The method of claim 7, wherein the primary channel has a volume less than the sample reservoir.

12. The method of claim 7, wherein the primary channel has a volume chosen from about 125 µL to about 135 µL, about 135 µL to about 150 µL, about 150 µL to about 175 µL, and about 175 µL to less than about 200 µL.

13. The method of claim 7, wherein the primary channel has a volume of about 150 µL.

14. The method of claim 7, wherein the secondary channel has a volume less than the sample reservoir.

15. The method of claim 7, wherein the secondary channel has a volume chosen from about 125 µL to about 135 µL, about 135 µL to about 150 µL, about 150 µL to about 175 µL, and about 175 µL to less than about 200 µL.

16. The method of claim 7, wherein the secondary channel has a volume of about 150 µL.

17. The method of claim 7, wherein the secondary channel has a volume greater than the difference in volume between the sample reservoir and the primary channel volumes.

18. The method of claim 7, wherein each of the primary channel, the secondary channel and the receiver channels is fluidically connected to a pump of a diagnostic instrument using a probe pierced through a septum seal.

19. The method of claim 1, wherein the at least one reagent comprises an assay reagent and a lyophilized reagent.

20. The method of claim 19, wherein the mixing step comprises:

drawing the sample within the at least one fluidic channel;

detecting an air liquid transition of the sample using an optical sensor of the diagnostic system, wherein the at least one fluidic channel is fluidically connected to the pump of the diagnostic system;

drawing the sample into a first well containing the assay reagent, wherein the first well is fluidically connected to the pump of the diagnostic system;

wetting in a mixing well the lyophilized reagent with the sample to form a sample mixture within the mixing well of the cartridge; and mixing the sample mixture with the assay reagent to form a testing sample in a testing sample well of the cartridge.

21. The method of claim 20, wherein the mixing further comprises back and forth motions of the pump of the diagnostic system.

22. The method of claim 21, wherein the back and forth motion of the pump produces a flow of the sample mixture of greater than 5 microliters per second.

23. The method of claim 20, wherein the testing sample is substantially free of foam.

24. The method of claim 20, further comprising moving the testing sample in the cartridge into an incubation zone in the diagnostic system.

25. The method of claim 20, further comprising:
moving the testing sample in the cartridge into an incubation zone in the diagnostic system; and
incubating the testing sample in the cartridge at a temperature greater than 1° C. and for a period of time greater than one second.

26. The method of claim 20, further comprising:
moving the testing sample in the cartridge into an incubation zone in the diagnostic system using the pump; and sensing an air liquid boundary using the optical sensor of the diagnostic system.

27. The method of claim 20, further comprising:
providing the testing sample to the diagnostic instrument to be analyzed, the providing step comprising:
   moving the testing sample from the testing sample well to a third well of the cartridge;
   introducing the at least one probe of the diagnostic system into the third well of the cartridge; and
   moving the testing sample into the diagnostic instrument of the diagnostic system using the at least one probe.

28. The method of claim 27, wherein introducing the at least one probe comprises piercing the septum seal of the cartridge using the at least one probe.

29. The method of claim 27, wherein the providing step is repeated one or more times corresponding to the number of testing sample wells when there are two or more testing sample wells.

30. The method of claim 20, wherein each of the steps performed in the method are independent of pump accuracy.

31. The method of claim 20, wherein drawing the sample comprises metering the sample using a metering device.

32. The method of claim 20, further comprising:
filtering plasma out of blood, wherein the plasma is the sample before drawing the sample within the at least one fluidic channel.

33. The method of claim 20, further comprising:
measuring the volume of the testing sample within the at least one fluidic channel using the pump of the diagnostic system; and
detecting a first air liquid transition and a second liquid air transition using the optical sensor of the diagnostic system.

34. The method of claim 20, further comprising a washing step after the mixing step.

35. The method of claim 1, further comprising incubating the sample-reagent mixture within the cartridge, the incubating comprising:
   in a first zone of an incubator, measuring with a first sensor a starting temperature of a portion of the cartridge containing the sample and the at least one reagent, wherein the cartridge is shorter in length than the length of the incubator and the portion of the cartridge only contacts the first zone of the incubator;
   comparing the starting temperature of the portion of the cartridge to a first target temperature;
   heating with a first heater the portion of the cartridge to the first target temperature;
   maintaining the first target temperature of a portion of the cartridge using a closed loop control for a period of time; and
   in a second zone of the incubator, measuring with a second sensor a starting temperature of a second portion of the cartridge containing the sample and at least one reagent, wherein the second portion of the cartridge only contacts the second zone of the incubator;
   comparing the starting temperature of the second portion of the cartridge to a second target temperature;
   heating with a second heater the second portion of the cartridge to the second target temperature; and
   maintaining the target temperature of the second portion of the cartridge using a second closed loop control for a period of time.

36. The method of claim 1, further comprising washing the sample-reagent mixture to obtain the detectable complex, the washing comprising:
   drawing the sample-reagent mixture containing a detectable complex into the at least one fluidic channel using the pump of the diagnostic instrument, wherein the at least one fluidic channel is fluidically connected to the pump;
   detecting an air liquid transition of the sample-reagent mixture using the optical sensor of the diagnostic instrument;
   contacting a magnet to a portion of the at least one fluidic channel configured to capture the detectable complex from the sample-reagent mixture at the portion of the at least one fluidic channel;
   separating with the magnet the detectable complex from the sample-reagent mixture; and
   washing away the sample-reagent mixture from the captured detectable complex.

37. The method of claim 36, the at least one fluidic channel comprising at least one difference in a cross sectional area between the at least one fluidic channel and the at least one reagent handling station.

38. The method claim of 37, wherein the at least one difference in the cross sectional area ranges from about 0.0016 in$^2$ to about 0.0011 in$^2$.

39. The method of claim 36, further comprising:
   aspirating a wash liquid pack from the at least one probe fluidically connected to the pump of the diagnostic system, wherein the wash liquid pack comprises segments of liquid buffer and air, and wherein the wash liquid pack comprises cleaning qualities;
   dispensing the wash liquid pack over the portion of the at least one fluidic channel with captured beads contacted by the magnet; and
   removing the magnet from the portion of the at least one fluidic channel.

40. The method of claim 39, wherein the wash liquid pack volume is less than 100 microliters.

41. The method of claim 39, wherein the wash liquid pack comprises a liquid-and-air combination.

42. The method of claim 39, wherein the wash liquid pack comprises alternating liquid segments and air segments within the at least one fluidic channel of the cartridge.

43. The method of claim 39, wherein the at least one portion of fluidic channel comprises a bead capture zone.

44. The method of claim 43, wherein the detectable complexes make up greater than 99% of the volume within the bead capture zone after washing.

45. The method of claim 1, further comprising analyzing with a non-ECL detection system, the analyzing with a non-ECL detection system comprising:
   illuminating the detectable complex flowing through a closed fluidic pathway of the diagnostic instrument, wherein the detectable complex comprises a known amount of fluorescent beads and ECL beads;
   measuring fluorescence from the fluorescent beads; and
   processing the measured fluorescence signal to calculate ECL bead recovery by comparing the measured fluorescence signal to a fluorescence signal from a standardized quantity of fluorescent beads.

46. The diagnostic system of claim 45, further comprising an assay composition comprising a mixture of at least one of a fluorescent labeled bead and at least one of an electrochemiluminescence (ECL) labeled bead.

47. The assay composition of claim 46, wherein beads can be both fluorescently labeled and ECL labeled.

48. The method of claim 1, wherein the providing detection results comprises:

converting the data from the analysis of the detectable complex into a user-friendly format; and
outputting the data through a user interface of the diagnostic instrument.

49. The method of claim 1, further comprising: extracting blood from the sample container, comprising:
positioning the sample container containing the sample on the cartridge, the at least one needle of the cartridge comprising:
at least two needles to establish a fluidic connection between the cartridge and sample container when the at least two needles pierce a septum of the sample container, wherein the framework guides the sample container into position such that the sample container is at an angle ranging from about less than 45° to about 5° from the horizontal; and
introducing gas into one of the at least two needles causing a displacement of the blood by the gas, wherein the displaced blood flows from the sample container through a second of the at least two needles.

50. The method of claim 49, wherein the second of the at least two needles is in fluidic communication with a filtration module.

51. The method of claim 49, wherein the second of the at least two needles is in fluidic communication with a filtration module, a fluidic channel, and a sample reservoir, where an optical sensor of the diagnostic instrument detects an air liquid boundary when the sample reservoir is filled.

52. The method of claim 1, wherein the ECL detection system comprises:
an ECL detection module comprising:
an enclosure having a top and a base, wherein the surface of the base is flat and capable of forming a working surface, and the top is attached to the base capable of forming the bottom of the enclosure thereby forming a cavity having a height;
a first electrode; a second electrode; and a first gasket, wherein the first electrode and the second electrode are stacked and separated by the first gasket, wherein the base supports the first electrode, and wherein the first gasket has a compressible thickness that is capable of creating a predetermined separation gap between the first and second electrodes;
a transparent window formed out of the second electrode to facilitate ECL detection; and
a printed circuit board, wherein the printed circuit board is positioned next to the base of the ECL detection module, electrically connecting components within the ECL detection system.

53. The method of claim 1, the diagnostic instrument further comprising:
a motion assembly having two axes configured to fluidically connect to the first probe and the waste probe of the diagnostic instrument.

54. The method of claim 1, wherein the non-ECL detection system comprises:
an apparatus for measuring bead recovery, comprising:
a housing;
the at least one fluidic tube located within the housing in fluidic communication with the ECL detection system;
a fluorescence excitation source; and
a fluorescence light detector, wherein the fluorescence excitation source is capable of emitting light such that the light reflects off of or is transmitted by the detectable complex flowing through the at least one fluidic tube in the housing,
wherein the detectable complex passes through a closed fluidic pathway originating in the cartridge to a closed fluidic pathway of the diagnostic instrument and back to the cartridge, such that substantially all of the fluid is collected in the cartridge, and
wherein the fluorescence light detector is capable of measuring the amount of light reflected off of or transmitted by the detectable complex in the fluid to determine whether an acceptable level of the detectable complex is present in the fluid indicating a positive detectable complex recovery measurement.

55. A method of performing a diagnostic test in a diagnostic system having a closed fluidic pathway, comprising:
introducing a sample into a cartridge of the diagnostic system, the cartridge comprising:
at least one needle;
at least one reservoir;
at least one fluidic seal; and
at least one fluidic channel,
introducing the cartridge into a diagnostic instrument of the diagnostic system, the diagnostic instrument comprising:
at least two probes;
a diagnostic fluidic pathway;
a non-electrochemiluminescence (ECL) detection system;
an ECL detection system fluidically connected to the non-ECL detection system; and
a pump, wherein the closed fluidic pathway of the diagnostic system comprises the diagnostic fluidic pathway of the diagnostic instrument and the at least one fluidic channel of the cartridge and begins at the at least one needle of the cartridge, passes through the diagnostic instrument, and ends at the at least one reservoir of the cartridge, and is capable of providing fluid from the cartridge to the diagnostic instrument;
mixing the sample with at least one reagent to form a detectable complex, wherein the at least one reagent is stored on the cartridge;
analyzing the detectable complex with the ECL detection system of the diagnostic instrument; and
providing detection results through a user interface on the diagnostic instrument.

\* \* \* \* \*